United States Patent
Chiou

(10) Patent No.: US 12,053,247 B1
(45) Date of Patent: Aug. 6, 2024

(54) SYSTEM FOR MULTI-DIRECTIONAL TRACKING OF HEAD MOUNTED DISPLAYS FOR REAL-TIME AUGMENTED REALITY GUIDANCE OF SURGICAL PROCEDURES

(71) Applicant: OnPoint Medical, Inc., Bedford, MA (US)

(72) Inventor: Chuang-Jang Chiou, Bedford, MA (US)

(73) Assignee: OnPoint Medical, Inc., Franconia, NH (US)

( * ) Notice: Subject to any disclaimer, the term of this patent is extended or adjusted under 35 U.S.C. 154(b) by 32 days.

(21) Appl. No.: 17/457,769

(22) Filed: Dec. 6, 2021

Related U.S. Application Data

(60) Provisional application No. 63/121,293, filed on Dec. 4, 2020.

(51) Int. Cl.
  *A61B 34/20* (2016.01)
  *A61B 90/00* (2016.01)
  (Continued)

(52) U.S. Cl.
  CPC .............. *A61B 34/20* (2016.02); *A61B 90/37* (2016.02); *G06F 3/011* (2013.01); *G06T 7/20* (2013.01);
  (Continued)

(58) Field of Classification Search
  CPC ... A61B 34/20; A61B 90/37; A61B 2090/372; G06T 7/70; G06T 7/20; G06T 2207/30208; G06F 3/011
  See application file for complete search history.

(56) References Cited

U.S. PATENT DOCUMENTS

| | | | |
|---|---|---|---|
| 5,526,812 A | 6/1996 | Dumoulin et al. |
| 5,676,673 A | 10/1997 | Ferre et al. |
| | (Continued) | |

FOREIGN PATENT DOCUMENTS

| | | |
|---|---|---|
| EP | 1028659 | 2/2004 |
| GB | 2498833 | 12/2016 |
| | (Continued) | |

OTHER PUBLICATIONS

Abe et al., "A Novel 3D Guidance System Using Augmented Reality for Percutaneous Vertebroplasty", Journal of Neurological Spine, vol. 19, pp. 492-501, Oct. 2013.
(Continued)

*Primary Examiner* — Christopher Koharski
*Assistant Examiner* — Michael S Kellogg
(74) *Attorney, Agent, or Firm* — Greenberg Traurig, LLP; Natalie Salem; Barry Schindler

(57) ABSTRACT

Aspects of the present disclosure relate to systems, devices and methods for tracking a head mounted display for generating a virtual display superimposed onto a patient during a surgical procedure. The head mounted display (HMD) is tracked using a first fiducial marker, sub-array or array integrated or attached to the HMD over a first movement range and using a second fiducial marker, sub-array or array integrated or attached to the HMD over a second movement range. The system is configured to superimpose and maintain a virtual display onto the patient over a head movement range that is greater than the first or the second movement range.

20 Claims, 24 Drawing Sheets

(51) Int. Cl.
  *G06F 3/01*  (2006.01)
  *G06T 7/20*  (2017.01)
  *G06T 7/70*  (2017.01)
(52) U.S. Cl.
  CPC .......... *G06T 7/70* (2017.01); *A61B 2090/372* (2016.02); *G06T 2207/30208* (2013.01)

(56) References Cited

U.S. PATENT DOCUMENTS

| | | | |
|---|---|---|---|
| 5,800,352 | A | 9/1998 | Ferre et al. |
| 5,803,089 | A | 9/1998 | Ferre et al. |
| 5,829,444 | A | 11/1998 | Ferre et al. |
| 5,873,822 | A | 2/1999 | Ferre et al. |
| D415,146 | S | 10/1999 | Hori |
| 5,967,980 | A | 10/1999 | Ferre et al. |
| 6,175,756 | B1 | 1/2001 | Ferre et al. |
| 6,341,231 | B1 | 1/2002 | Ferre et al. |
| 6,396,497 | B1 | 5/2002 | Reichlen |
| 6,445,943 | B1 | 9/2002 | Ferre et al. |
| 6,599,247 | B1 | 7/2003 | Stetten |
| 6,714,810 | B2 | 3/2004 | Grzeszczuk et al. |
| 7,130,676 | B2 | 10/2006 | Barrick |
| 7,774,044 | B2 | 8/2010 | Sauer et al. |
| 7,812,815 | B2 | 10/2010 | Banerjee et al. |
| 8,320,612 | B2 | 11/2012 | Knobel et al. |
| 8,730,266 | B2 | 5/2014 | Brown et al. |
| 8,989,843 | B2 | 3/2015 | Chien |
| 9,068,820 | B2 | 6/2015 | Kosmecki et al. |
| 9,068,824 | B2 | 6/2015 | Findeisen et al. |
| 9,123,155 | B2 | 9/2015 | Cunningham et al. |
| 9,183,560 | B2 | 11/2015 | Abelow |
| 9,215,293 | B2 | 12/2015 | Miller |
| 9,299,138 | B2 | 3/2016 | Zellner et al. |
| 9,310,559 | B2 | 4/2016 | Macnamara |
| 9,311,284 | B2 | 4/2016 | Warila et al. |
| 9,389,424 | B1 | 7/2016 | Schowengerdt |
| 9,417,452 | B2 | 8/2016 | Schowengerdt et al. |
| 9,429,752 | B2 | 8/2016 | Schowengerdt et al. |
| 9,503,681 | B1 | 11/2016 | Popescu et al. |
| 9,547,940 | B1 | 1/2017 | Sun et al. |
| 9,582,717 | B2 | 2/2017 | Lee et al. |
| 9,792,721 | B2 | 10/2017 | Kosmecki et al. |
| 9,861,446 | B2 | 1/2018 | Lang |
| 9,980,780 | B2 | 5/2018 | Lang |
| 10,078,221 | B2 | 9/2018 | Pilkinton et al. |
| 10,136,952 | B2 | 11/2018 | Couture et al. |
| 10,154,239 | B2 | 12/2018 | Casas |
| 10,159,530 | B2 | 12/2018 | Lang |
| 10,278,777 | B1 | 5/2019 | Lang |
| 10,292,768 | B2 | 5/2019 | Lang |
| 10,368,947 | B2 | 8/2019 | Lang |
| 10,405,927 | B1 | 9/2019 | Lang |
| 10,603,113 | B2 | 3/2020 | Lang |
| 10,743,939 | B1 | 8/2020 | Lang |
| 10,799,296 | B2 | 10/2020 | Lang |
| 10,823,960 | B1* | 11/2020 | Cho ........................ G06F 18/22 |
| 10,849,693 | B2 | 12/2020 | Lang |
| 11,013,560 | B2 | 5/2021 | Lang |
| 11,172,990 | B2 | 11/2021 | Lang |
| 11,311,341 | B2 | 4/2022 | Lang |
| 11,348,257 | B2 | 5/2022 | Lang |
| 2001/0041838 | A1 | 11/2001 | Holupka et al. |
| 2002/0082498 | A1 | 6/2002 | Wendt et al. |
| 2002/0016349 | A1 | 11/2002 | Sauer |
| 2005/0113846 | A1 | 5/2005 | Carson |
| 2005/0215879 | A1 | 9/2005 | Chuanggui |
| 2005/0028146 | A1 | 12/2005 | Marquart et al. |
| 2005/0267353 | A1 | 12/2005 | Marquart et al. |
| 2005/0281465 | A1 | 12/2005 | Marquart et al. |
| 2006/0142739 | A1 | 6/2006 | Disilestro et al. |
| 2007/0015999 | A1 | 1/2007 | Heldreth et al. |
| 2007/0035511 | A1 | 2/2007 | Banerjee et al. |
| 2007/0038944 | A1 | 2/2007 | Carignano et al. |
| 2007/0236514 | A1 | 10/2007 | Agusanto et al. |
| 2007/0276234 | A1 | 11/2007 | Shahidi |
| 2008/0269596 | A1 | 10/2008 | Revie et al. |
| 2009/0068620 | A1 | 3/2009 | Knobel et al. |
| 2009/0089081 | A1 | 4/2009 | Haddad |
| 2009/0138019 | A1 | 5/2009 | Wasielewski |
| 2009/0267805 | A1 | 10/2009 | Jin et al. |
| 2011/0190637 | A1 | 8/2011 | Knobel et al. |
| 2013/0093829 | A1 | 4/2013 | Rosenblatt et al. |
| 2013/0096373 | A1 | 4/2013 | Chabanas et al. |
| 2013/0116574 | A1 | 5/2013 | Knobel et al. |
| 2013/0169683 | A1 | 7/2013 | Perez et al. |
| 2013/0261503 | A1 | 10/2013 | Sherman et al. |
| 2013/0261504 | A1 | 10/2013 | Claypool et al. |
| 2013/0261633 | A1 | 10/2013 | Thornberry |
| 2013/0296682 | A1 | 11/2013 | Clavin et al. |
| 2013/0326364 | A1 | 12/2013 | Latta et al. |
| 2014/0081659 | A1 | 3/2014 | Nawana et al. |
| 2014/0085203 | A1 | 3/2014 | Kobayashi |
| 2014/0088941 | A1 | 3/2014 | Banerjee et al. |
| 2014/0118335 | A1 | 5/2014 | Gurman |
| 2014/0135746 | A1 | 5/2014 | Schoepp |
| 2014/0198190 | A1 | 7/2014 | Okumu |
| 2014/0218366 | A1 | 8/2014 | Kosmecki et al. |
| 2014/0275760 | A1 | 9/2014 | Lee et al. |
| 2014/0303491 | A1 | 10/2014 | Shekhar et al. |
| 2014/0334670 | A1 | 11/2014 | Guigues et al. |
| 2015/0100067 | A1 | 4/2015 | Cavanagh et al. |
| 2015/0206218 | A1 | 7/2015 | Banerjee et al. |
| 2015/0310668 | A1 | 10/2015 | Ellerbrock |
| 2015/0366628 | A1 | 12/2015 | Ingmanson |
| 2016/0163105 | A1 | 6/2016 | Hong et al. |
| 2016/0182877 | A1 | 6/2016 | DeLuca |
| 2016/0191887 | A1 | 6/2016 | Casas |
| 2016/0206379 | A1 | 7/2016 | Flett et al. |
| 2016/0220105 | A1 | 8/2016 | Duret |
| 2016/0225192 | A1* | 8/2016 | Jones ...................... G06F 3/012 |
| 2016/0228193 | A1 | 8/2016 | Moctezuma de la Barrera et al. |
| 2016/0287337 | A1 | 10/2016 | Aram et al. |
| 2016/0324580 | A1 | 11/2016 | Esterberg |
| 2016/0331467 | A1 | 11/2016 | Slamin et al. |
| 2016/0381256 | A1 | 12/2016 | Aguirre-Valencia |
| 2017/0027651 | A1 | 2/2017 | Esterberg |
| 2017/0035517 | A1 | 2/2017 | Geri et al. |
| 2017/0071673 | A1 | 3/2017 | Ferro et al. |
| 2017/0108930 | A1 | 4/2017 | Banerjee et al. |
| 2017/0160549 | A1 | 6/2017 | Badiali et al. |
| 2017/0178375 | A1 | 6/2017 | Benishti et al. |
| 2017/0202633 | A1 | 7/2017 | Liu |
| 2017/0231714 | A1 | 8/2017 | Kosmecki et al. |
| 2017/0258526 | A1 | 9/2017 | Lang |
| 2017/0312032 | A1 | 11/2017 | Amanatullah et al. |
| 2018/0049622 | A1 | 2/2018 | Ryan et al. |
| 2018/0116728 | A1 | 5/2018 | Lang |
| 2018/0125584 | A1 | 5/2018 | Lang |
| 2018/0256256 | A1 | 9/2018 | May et al. |
| 2018/0263704 | A1 | 9/2018 | Lang |
| 2019/0000564 | A1 | 1/2019 | Navab et al. |
| 2019/0070012 | A1 | 3/2019 | Leemrijse et al. |
| 2019/0094993 | A1* | 3/2019 | Kim .................... G06F 3/03545 |
| 2019/0110842 | A1 | 4/2019 | Lang |
| 2019/0192226 | A1 | 6/2019 | Lang |
| 2019/0216452 | A1 | 7/2019 | Nawana et al. |
| 2019/0262078 | A1 | 8/2019 | Lang |
| 2019/0380784 | A1 | 12/2019 | Lang |
| 2020/0060767 | A1 | 2/2020 | Lang |
| 2020/0078680 | A1* | 3/2020 | Simpkinson ............ G06T 11/00 |
| 2020/0246074 | A1 | 8/2020 | Lang |
| 2020/0305980 | A1 | 10/2020 | Lang |
| 2021/0022808 | A1 | 1/2021 | Lang |
| 2021/0106386 | A1 | 4/2021 | Lang |
| 2021/0267691 | A1 | 9/2021 | Lang |

FOREIGN PATENT DOCUMENTS

| | | |
|---|---|---|
| WO | WO1993025157 | 12/1993 |
| WO | WO 2005088539 | 9/2005 |
| WO | WO 2010034117 | 4/2010 |
| WO | WO 2014057352 | 4/2014 |
| WO | WO 2015110859 | 7/2015 |
| WO | WO 2015145395 | 10/2015 |

(56) References Cited

FOREIGN PATENT DOCUMENTS

| WO | WO 2016028828 | 2/2016 |
|---|---|---|
| WO | WO 2016162789 | 10/2016 |
| WO | WO 2016195401 | 12/2016 |
| WO | WO 2016207628 | 12/2016 |
| WO | WO 2017160651 | 9/2017 |
| WO | WO 2018085417 | 5/2018 |
| WO | WO 2018085691 | 5/2018 |
| WO | WO 2018132804 | 7/2018 |
| WO | WO 2018052966 | 10/2018 |

OTHER PUBLICATIONS

Aguerreche L. et al., "Reconfigurable Tangible Devices for 3D Virtual Object Manipulation by Single or Multiple Users." VRST 2010, Nov. 2010, Hong Kong, Hong Kong SAR China. inria-00534095.
Aichert et al., "Image-Based Tracking of the Teeth for Orthodontic Augmented Reality", Medical Image Computing and Computer-Assisted Intervention, Lecture Notes in Computer Science, vol. 7511, Springer, pp. 601-608, 2012.
Anderson et al., "Virtual annotations of the surgical field through an augmented reality transparent display", The Visual Computer, vol. 32, Issue 11, pp. 1481-1498, Nov. 2016.
Armstrong et al., "A Heads-Up Display for Diabetic Limb Salvage Surgery: A View Through the Google Looking Glass"; Journal of Diabetes Science and Technology 2014, vol. 8(5) 951-956.
Azura, R., "A survey of augmented reality." Teleoperators and Virtual Environments, vol. 6, Issue 4, Aug. 1997, pp. 355-385.
Bajura, M., et al., "Merging Virtual Objects with the Real World: Seeing Ultrasound Imagery Within the Patient.", In Proceedings of SIGGRAPH '92, 1992, New York: ACM Press, pp. 203-210.
Baker et al., "The Emergence of Augmented Reality in Orthopaedic Surgery and Education", The Orthopaedic Journal at Harvard Medical School, vol. 16, pp. 8-16, Jun. 2015.
Bauer et al., "Joint ToF Image Denoising and Registration with a CT Surface in Radiation Therapy", Scale Space and Variational Methods in Computer Vision, Lecture Notes in Computer Science, Springer, vol. 6667, pp. 98-109.
Bauer et al., "Multi-Modal Surface Registration for Markerless Initial Patient Setup in Radiation Therapy Using Microsoft's Kinect Sensor", 2011 IEEE International Conference on Computer Vision Workshops (ICCV Workshops), Barcelona, Nov. 2011, pp. 1175-1181, Jan. 16, 2012.
Bauer et al., "Real-Time Range Imaging in Health Care: A Survey", Time-of-Flight and Depth Imaging, Sensors, Algorithms, and Applications. Lecture Notes in Computer Science, vol. 8200, pp. 228-254, 2017.
Bauer, Sebastian, Doctoral Thesis, "Rigid and Non-Rigid Surface Registration for Range Imaging Applications in Medicine", urn:nbn:de:bvb:29-opus4-54665, Nov. 27, 2014.
Benford, S. et al., "User embodiment in collaborative virtual environments", Proceedings of the SIGCHI conference on Human factors in computing systems, CHI '95, pp. 242-249, 1995.
Besl PJ, McKay ND. 2, 1992. A method for registration of 3-D shapes. IEEE Trans PAMI, vol. 14, pp. 239-256.
Bichlmeier C., et al. "Contextual Anatomic Mimesis Hybrid In-Situ Visualization Method for Improving Multi-Sensory Depth Perception in Medical Augmented Reality.", IEEE 2007, 2007 6th IEEE and ACM International Symposium on Mixed and Augmented Reality.
Bichlmeier et al., "Virtually Extended Surgical Drilling Device: Virtual Mirror for Navigated Spine Surgery"; MICCAI 2007, Part I, LNCS 4791, pp. 434-441.
Billinghurst, et al., "The MagicBook: A Transitional AR Interface.", Computers and Graphics, Nov. 2001, pp. 745-753.
Billinghurst, M., et al., "Collaborative Mixed Reality", First International Symposium on Mixed Reality (ISMR '99). Mixed Reality—Merging Real and Virtual Worlds, pp. 261-284. Berlin: Springer Verlag.
Billinghurst, M., et al., "Collaborative Mixed Reality.", Communications of the ACM 2002, vol. 45 Issue 7, pp. 64-70 (2002).
Billinghurst, M., et al., "Experiments with Face to Face Collaborative AR Interfaces.", Virtual Reality Journal, vol. 4, No. 2, (2002).
Birkfellner et al., "A Head-Mounted Operating Binocular for Augmented Reality Visualization in Medicine—Design and Initial Evaluation", IEEE Transactions on Medical Imaging, vol. 21, No. 8, pp. 991-997, Aug. 2002.
Birkfellner et al., "Computer-enhanced stereoscopic vision in a head-mounted operating binocular", Physics in Medicine & Biology, vol. 48, No. 3, pp. 49-57, Feb. 7, 2003.
Birkfellner et al., "In-Vitro Assessment of a Registration Protocol for Image Guided Implant Dentistry", Clinical Oral Implants Research, vol. 12, Issue 1, pp. 69-78, Feb. 2001.
Blackwell et al., "An Image Overlay System for Medical Data Visualization", Medical Image Analysis vol. 4, pp. 67-72, 2000.
Blackwell et al., "Augmented Reality and Its Future in Orthopaedics", Clinical Orthopaedics & Related Research, vol. 354, pp. 111-122, Sep. 1998.
Bruker Nano Surfaces, 3D Optical Microscopy for Orthopedic Implants; Jun. 17, 2016.
Castillo et al., "Augmented Reality for Assistance of Total Knee Replacement", Journal of Electrical and Computer Engineering, vol. 2016, Article 9358369, pp. 1-6, 2016.
Catani et al., "Knee Surgery Using Computer Assisted Surgery and Robotics", Springer Heidelberg Publishing, Book, pp. 1-221, 2013.
Chandak, "MEMS Based Wireless Controlled Robot with Voice and Video Camera"; International Journal of Scientific & Engineering Research, vol. 5, Issue 4, Apr. 2014.
Charbonnier et al., "Real Virtuality: Perspectives offered by the combination of Virtual Reality headsets and Motion Capture", Artanim, Real Virtuality White Paper, Aug. 23, 2015.
Chen et al., "Development of a surgical navigation system based on augmented reality using an optical see-through head-mounted display"; Journal of Biomedical Informatics 55 (2015) 124-131.
Cruz-Neira C. et al., "The cave: audio visual experience automatic virtual environment.", Commun. ACM, vol. 35, No. 6, pp. 64-72, Jun. 1992.
Cui et al., "KinectAvatar: Fully Automatic Body Capture Using a Single Kinect", ACCV'12 Proceedings of the 11th International Conference on Computer Vision—vol. 2, pp. 133-147, Nov. 2012.
Daniel and Ramos, "Augmented Reality for Assistance of Total Knee Replacement", Journal of Electrical and Computer Engineering, vol. 2016, Article ID 9358369, Hindawi Publishing Corporation.
Davies et al., "Computer Assisted Orthopaedic Surgery", 8th Annual Meeting of CAOS—International Proceedings, Apr. 2008.
DeLambert et al., "Electromagnetic Tracking for Registration and Navigation in Endovascular Aneurysm Repair: A Phantom Study" European Journal of Vascular and Endovascular Surgery, vol. 43, pp. 684-689, 2012.
Draelos, Mark, "The Kinect Up Close: Modifications for Short-Range Depth Imaging", NC State Theses and Dissertations, pp. 1-88, Mar. 26, 2012.
Elmi-Terander et al., "Surgical Navigation Technology Based on Augmented Reality and Integrated 3D Intraoperative Imaging"; Spine Surgery, vol. 41, No. 21, pp. E1303-1311, 2016.
Ferrari et al., "Video See-Through in the Clinical Practice", 1st International Workshop on Engineering Interactive Computing Systems for Medicine and Health Care, EICS4Med. vol. 727, pp. 19-24, 2011.
Fischer et al., "Medical Augmented Reality Based on Commercial Image Guided Surgery", European Association for Computer Graphics, Proceedings of the 10th Eurographics Symposium on Virtual Environments, pp. 83-86, Jun. 2004.
Fitzmaurice, G., et al., "Bricks: Laying the Foundations for Graspable User Interfaces.", Proceedings of Conference on Human Factors in Computing Systems (CHI '95), Denver, Colorado, ACM Press, 442-449, (1995).
Flusser et al., "Image Fusion: Principles, Methods and Applications", Tutorial EISIPCO 2007 Lecture Notes.
Fritz et al., "Augmented Reality Visualization with Image Overlay for MRI-Guided Intervention: Accuracy for Lumbar Spinal Proce-

(56) References Cited

OTHER PUBLICATIONS dures with a 1.5-T MRI System", Vascular and Interventional Radiology, AJR: 198, Mar. 2012.

Fritz et al., "Augmented Reality Visualization with Use of Image Overlay Technology for MR Imaging—guided Interventions: Assessment of Performance in Cadaceric Shoulder and Hip Arthrography at 1.5T"; Radiology: vol. 265, No. 1, Oct. 2012, pp. 254-259.

Garon, Mathieu; Boulet, Pierre-Olivier; Doiron, Jean-Philippe; Beaulieu, Luc; Lalonde, Jean-François (2016): Real-time High Resolution 3D Data on the HoloLens. In: International Symposium on Mixed and Augmented Reality (ISMAR).

Garrido-Jurado, S.; Muñoz-Salinas, R.; Madrid-Cuevas, F. J.; Marín-Jiménez, M. J. (2014): Automatic generation and detection of highly reliable fiducial markers under occlusion. In: Pattern Recognition 47 (6), S. 2280-2292. DOI: 10.1016/j.patcog.2014.01.005.

Gavaghan et al., "Augmented Reality Image Overlay Projection for Image Guided Open Liver Ablation of Metastatic Liver Cancer"; C.A. Linte et al. (Eds.): AE-CAI 2011, LNCS, pp. 36-46, 2012.

Gee A, et al., "Processing and visualizing three-dimensional ultrasound data.", The British Journal of Radiology, vol. 77, S186-S193, (2004).

George et al., "Low Cost Augmented Reality for Training of MRI-Guided Needle Biopsy of the Spine", Medicine Meets Virtual Reality 16, pp. 138-140, IOS Press, 2008.

Germano et al., Advanced Techniques in Image-Guided Brain and Spine Surgery, Thieme Medical Publishers, Incorporated, 2002.

Gonzalez, Smart Multi-Level Tool for Remote Patient Monitoring Based on a Wireless Sensor Network and Mobile Augmented Reality, Sensors, Sep. 2014; 14(9): 17212-17234.

Gorbert, M. et al., "Triangles: Tangible Interface for Manipulation and Exploration of Digital Information Topography.", Proceedings of CHI '98, Apr. 18-23, 1998, © 1998 ACM.

Gromov et al., "What is the optimal alignment of the tibial and femoral components in knee arthroplasty?: An overview of the literature"; Acta Orthopaedica 2014; 85(5): 480-487.

Hayashibe et al., "Surgical Navigation Display System Using Volume Rendering of Intraoperatively Scanned CT Images", Computer Aided Surgery, vol. 11, No. 5, pp. 240-246, Sep. 2006.

Hinterstoisser, S. Holzer S.; Cagniart, C.; Ilic, S.; Konolige, K.; Navab, N.; Lepetit, V. (2011b): Multimodal Templates for Real-Time Detection of Texture-less Objects in Heavily Cluttered Scenes.

Hinterstoisser, S.; Cagniart, C.; Ilic, S.; Sturm, P.; Navab, N.; Fua, P.; Lepetit, V. (2012a): Gradient Response Maps for Real-Time Detection of Texture-Less Objects. In: IEEE Transactions on Pattern Analysis and Machine Intelligence.

Hinterstoisser, S.; Lepetit, V.; Benhimane, S.; Fua, P.; Navab, N. (2011a): Learning Real-Time Perspective Patch Rectification. In: International Journal of Computer Vision (IJCV), Springer. DOI: 10.1007/s11263-010-0379-x.

Hinterstoisser, S.; Lepetit, V.; Ilic, S.; Holzer, S.; Bradski, G.; Konolige, K.; Navab, N. (2012b): Model Based Training, Detection and Pose Estimation of Texture-Less 3D Objects in Heavily Cluttered Scenes.

Hoff, "Fusion of Data from Head-Mounted and Fixed Sensors"; First International Workshop on Augmented Reality, 1, 1998, pp. 1-15.

Holographic weapon sight—Wikipedia https://en.wikipedia.org/wiki/Holographic_weapon_sight retrieved on Nov. 22, 2016.

Hu et al., "A Convenient Method of Video See-through Augmented Reality Based on Image-Guided Surgery System", Internet Computing for Engineering and Science, 2013 Seventh International Conference on Internet Computing for Engineering and Science, Shanghai, pp. 100-103, Dec. 12, 2013.

Hua et al., "A 3D Integral Imaging Optical See-Through Head-Mounted Display", Optical Society of America, vol. 22, No. 11, pp. 1-8, Jun. 2, 2014.

Ishii, H., et al., "Iterative Design of Seamless Collaboration Media.", Communications of the ACM, vol. 37, No. 8, Aug. 1994, pp. 83-97.

Ji et al., "Real-Time Eye, Gaze, and Face Pose Tracking for Monitoring Driver Vigilance"; Real-Time Imaging 8, pp. 357-377, 2002.

Jiang et al., "A Robust Automated Markerless Registration Framework for Neurosurgery Navigation", The International Journal of Medical Robotics and Computer Assisted Surgery, vol. 11, pp. 436-447, Oct. 19, 2014.

Jolesz, Ferenc A., "Intraoperative Imaging and Image-Guided Therapy", Springer Science & Business Media, 893 pages, Jan. 14, 2014.

Kanade et al., "Simulation, Planning, and Execution of Computer-Assisted Surgery", Proceedings of the NSF Grand Challenges Workshop, 1996.

Kato, H.; Billinghurst, M. (1999): Marker tracking and HMD calibration for a video-based augmented reality conferencing system. In: Augmented Reality, 1999. (IWAR '99) Proceedings. 2nd IEEE and ACM International Workshop on, S. 85-94.

Kersten-Oertel et al., "The State of the Art of Visualization in Mixed Reality Image Guided Surgery", Computerized Medical Imaging and Graphics, vol. 37, pp. 98-112, Jan. 2013.

Kim et al., "Registration Accuracy Enhancement of a Surgical Navigation System for Anterior Cruciate Ligament Reconstruction: A Phantom and Cadaveric Study", The Knee, vol. 24, pp. 329-339, 2017.

Kolodzey et al., "Wearable technology in the operating room: a systematic review"; GMJ Innov 2017; 3:55-63.

Kumar et al., "A Portable Wireless Head Movement Controlled Human-Computer Interface for People with Disabilities", International Journal of Advanced Research in Electrical, Electronics and Instrumentation Engineering, vol. 3, Issue 7, Jul. 2014.

Kutter et al., "Real-time Volume Rendering for High Quality Visualization in Augmented Reality", International Workshop on Augmented Environments for Medical Imaging including Augmented Reality in Computer-aided Surgery (AMI-ARCS 2008), New York, MICCAI Society, Sep. 2008.

Lamata et al., "Augmented Reality for Minimally Invasive Surgery: Overview and Some Recent Advances"; Augmented Reality, Jan. 2010.

Liao et al., "3-D Augmented Reality for MRI-Guided Surgery Using Integral Videography Autostereoscopic Image Overlay", IEEE Transactions on Biomedical Engineering, vol. 57, No. 6, pp. 1476-1486, Jun. 2010.

Liao et al., "Surgical Navigation by Autostereoscopic Image Overlay of Integral Videography", IEEE Transactions on Information Technology in Biomedicine, vol. 8, No. 2, pp. 114-121, Jun. 2004.

Lievin et al., "Stereoscopic Augmented Reality System for Computer-Assisted Surgery", International Congress Series, vol. 1230, pp. 107-111, Jun. 2001.

Lindert et al., "The use of a head-mounted display for visualization in neuroendoscopy", Computer Aided Surgery, 2004; 9(6): 251-256.

Linte et al., "On Mixed Reality Environments for Minimally Invasive Therapy Guidance: Systems Architecture, Successes and Challenges in their Implementation from Laboratory to Clinic", Comput Med Imaging Graph, Mar. 2013; 37(2): 83-97, DOI: 10.1016/j.compmedimag.2012.12.002.

Liu et al., "An Optical See-Through Head Mounted Display with Addressable Focal Planes" IEEE International Symposium on Mixed and Augmented Reality, Cambridge, UK, pp. 33-42, Oct. 3, 2008.

Lorensen WE, Cline HE. [ed.], in M.C. Stone. 1987. Marching cubes: A high resolution 3d surface construction algorithm. Proceedings of SIGGRAPH 87. pp. 163-169.

Maier-Hein et al., "Optical Techniques for 3D Surface Reconstruction in Computer-Assisted Laparoscopic Surgery", Medical Image Analysis, vol. 17, pp. 974-996, May 3, 2013.

Maier-Hein, L. et al., "Towards Mobile Augmented Reality for On-Patient Visualization of Medical Images.", Bildverarbeitung für die Medizin 2011: Algorithmen—Systeme—Anwendungen Proceedings des Workshops vom 20.—Mar. 22, 2011 in Lübeck (pp. 389-393).

Masamune et al., "An Image Overlay System with Enhanced Reality for Percutaneous Therapy Performed Inside CT Scanner", Medical Image Computing and Computer-Assisted Intervention, Lecture Notes in Computer Science, vol. 2489, pp. 77-84, Oct. 2002.

(56) References Cited

OTHER PUBLICATIONS

Maurer et al., "Augmented-Reality Visualization of Brain Structures with Stereo and Kinetic Depth Cues: System Description and Initial Evaluation with Head Phantom", Proceedings, vol. 4319, Medical Imaging 2001: Visualization, Display, and Image-Guided Procedures, pp. 445-456, May 28, 2001.
Medeiros D. et al., "Proposal and evaluation of a tablet-based tool for 3D virtual environments.", SBC Journal on 3D Interactive Systems, vol. 4, No. 2, pp. 30-40, (2013).
Melzer, "Head-Mounted Displays", The Avionics Handbook, 2001.
Menozzi et al., "Development of Vision-Aided Navigation for a Wearable Outdoor Augmented Reality System", IEEE Plans, Position Location and Navigation Symposium, Article No. 6851442, pp. 760-772, 2014.
MicroVision 2015 Annual Report and Proxy Statement for 2016 Annual Meeting of Shareholders.
Moore et al., "Image Guidance for Spinal Facet Injections Using Tracked Ultrasound", MICCAI 2009, Part I, LNCS 5761, pp. 516-523 2009.
Muller et al., "Automatic Multi-Modal ToF/CT Organ Surface Registration", Bildverarbeitung für die Medizin, pp. 154-158, Mar. 2011.
Newcombe, R. A.; Izadi, S.; Hilliges, O.; Molyneaux, D.; Kim, D.; Davison, A. J. et al. (2011): KinectFusion. Real-time dense surface mapping and tracking. In: 2011 10th IEEE International Symposium on Mixed and Augmented Reality, S. 127-136.
Nicolau, "Augmented Reality in Laparoscopic Surgical Oncology.", Surgical Oncology, vol. 20, pp. 89-201 (2011).
Nikou et al., "Augmented Reality Imaging Technology for Orthopaedic Surgery", Operative Techniques in Orthopaedics, vol. 10, No. 1 Jan. 2000: pp. 82-86.
Noonan et al., "The Design and Initial Calibration of an Optical Tracking System Using the Microsoft Kinect", IEEE Nuclear Science Symposium Conference Record, pp. 3614-3617, Oct. 2011.
Okamura, Allison, "Tracking and Surgical Navigation, Registration", Stanford Lecture 8: ME 328: Medical Robotics, pp. 1-19, Spring 2013.
Ortega et al., "Usefulness of a head mounted monitor device for viewing intraoperative fluoroscopy during orthopaedic procedures", Arch Orthop Trauma Surg (2008) 128:1123-1126.
Paprosky et al., "Intellijoint HIP: a 3D mini-optical navigation tool for improving intraoperative accuracy during total hip arthroplasty"; Med Devices (Auckl). 2016; 9: 401-408.
Pauly et al., "Machine Learning-Based Augmented Reality for Improved Surgical Scene Understanding", Computerized Medical Imaging and Graphics, vol. 1280, pp. 1-6, Jun. 2014.
Peters et al., "Image-Guided Interventions, Technology and Applications", Springer Science and Business Media, 576 pages, 2018.
Ponce et al., "Emerging Technology in Surgical Education: Combining Real-Time Augmented Reality and Wearable Computing Devices", The Cutting Edge, Nov. 2014, vol. 37, No. 11.
Qian, Long; Azimi, Ehsan; Kazanzides, Peter; Navab, Nassir (2017): Comprehensive Tracker Based Display Calibration for Holographic Optical See-Through Head-Mounted Display.
Ren et al., "Marker-Based Surgical Instrument Tracking Using Dual Kinect Sensors", IEEE Transactions on Automation Science and Engineering, vol. 11, No. 3, pp. 921-924, Jul. 2014.
Rhodes, "A brief history of wearable computing", MIT Wearable Computing Project.
Rinaldi et al., "Computer-Guided Applications for Dental Implants, Bone Grafting, and Reconstructive Surgery", Elsevier Inc., 556 pages, 2016.
Robinett et al., "A Computational Model for the Stereoscopic Optics of a Head-Mounted Display", Proceedings vol. 1457, Stereoscopic Displays and Applications II, pp. 140-160, 1991.
Rolland et al., "A Comparison of Optical and Video See-through Head-mounted Displays", Proceedings vol. 2351, Telemanipulator and Telepresence Technologies, pp. 293-307, Dec. 21, 1995.
Rolland et al., "Optical Versus Video See-Through Head-Mounted Displays in Medical Visualization", Presence: Teleoperators and Virtual Environments, vol. 9, Issue 3, pp. 287-309, Jun. 2000.
Rosenthal et al., "Augmented Reality Guidance for Needle Biopsies: A Randomized, Controlled Trial in Phantoms"; MICCAI 2001, LNCS 2208: 240-248.
Rosman et al., "Articulated Motion Segmentation of Point Clouds by Group-Valued Regularization", Eurographics Workshop on 3D Object Retrieval, EG 3DOR, pp. 77-84, May 2012.
Salmi Jamali, S. et al., "Utilising Mobile-Augmented Reality for Learning Human Anatomy.", 7th World Conference on Educational Sciences, (WCES-2015), Feb. 5-7, 2015, Novotel Athens Convention Center, Athens, Greece.
Sanko, "Microvision's Nomad Augmented Vision System: The How and the Why"; SID Pacific Northwest Chapter Meeting, Jun. 11, 2003.
Sauer et al., "An Augmented Reality Navigation System with a Single-Camera Tracker: System Design and Needle Biopsy Phantom Trial", Proceedings of the 5th International Conference on Medical Image Computing and Computer-Assisted Intervention—Part II, pp. 116-124, Sep. 2002.
Sauer et al., "Augmented Workspace: Designing an AR Testbed", Proceedings IEEE and ACM International Symposium on Augmented Reality, pp. 47-53, Munich 2000.
Schramm, Kinect: The Company Behind the Tech Explains How it Works, Jun. 19, 2010, https://www.engadget.com/2010/06/19/kinect-how-it-works-from-the-company-behind-the-tech/?guccounter=1&guce_referrer=aHR0cHM6Ly93d3cuZ29vZ2xlLmNvbS8&guce_referrer_sig=AQAAAKHcnRaFMexHHXiiRrcGjKYjWQ2VJGsMA556eCVncvte7f0VM4aN3GpWj1WqU3RfCnTwHcTbxmibv1Iz_TUFgILvsRhShqXDrSM63OcvvjlSzpUoBvsC2LsOmHqf-zifqdYelctf0D0MDM78YhH-u7w9JUfxuLDGVUxUi9hDQLZo.
Scuderi et al., "Total Knee Arthroplasty with a Novel Navigation System Within the Surgical Field", Orthopedic Clinics, vol. 45, Issue 2, pp. 167-173, Apr. 2014.
Shen et al., "3D Augmented Reality with Integral Imaging Display", Proceedings of SPIE—The International Society for Optical Engineering, vol. 9867, Article No. 98670Y, Apr. 2016.
Sherstyuk et al., "Dynamic Eye Convergence for Head-Mounted Displays Improves User Performance in Virtual Environments", Proceedings of the ACM SIGGRAPH Symposium on Interactive 3D Graphics and Games, pp. 23-30, Mar. 2012.
State et al., "Stereo Imagery from the UNC Augmented Reality System for Breast Biopsy Guidance", MMVR 2003.
Tan, D. J.; Tombari, F.; Ilic, S.; Navab, N. (2015): A Versatile Learning-Based 3D Temporal Tracker. Scalable, Robust, Online. In: 2015 IEEE International Conference on Computer Vision (ICCV), S. 693-701.
Technische Universitat Munchen, A Look into the Body—Augmented Reality in Computer Aided Surgery, Department of Informatics, Research-Highlights.
Tong et al., "Scanning 3D Full Human Bodies Using Kinects", IEEE Transactions on Visualization and Computer Graphics, vol. 18, Issue 4, pp. 643-650, Apr. 1, 2012.
Traub, J., Stefan, P., Heining, S.M., Sielhorst, T., Riquarts, C., Eulerz, E., Navab, N. (2006): Hybrid Navigation Interface for Orthopedic and Trauma Surgery. R. Larsen, M. Nielsen, and J. Sporring (Eds.): MICCAI 2006, LNCS 4190, pp. 373-380.
Trevisan et al., "Towards Markerless Augmented Medical Visualization", AMI-ARCS, pp. 57-66, 2004.
Vagvolgyi et al., "Video to CT Registration for Image Overlay on Solid Organs", Procedural Augmented Reality in Medical Imaging and Augmented Reality in Computer-Aided Surgery (AMIARCS) pp. 78-86, 2008.
2008. Vercauteren et al., "Real Time Autonomous Video Image Registration for Endomicroscopy: Fighting the Compromises", Three-Dimensional and Multidimensional Microscopy: Image Acquisition and Processing XV., vol. 6861, pp. 68610C. International Society for Optics and Photonics, Feb. 12, 2008.
Vogt et al., "Reality Augmentation for Medical Procedures: System Architecture, Single Camera Marker Tracking, and System Evaluation", International Journal of Computer Vision, vol. 70, No. 2, pp. 179-190, 2006.

(56) References Cited

OTHER PUBLICATIONS

Vogt, Sebastian, "Real-Time Augmented Reality for Image-Guided Interventions", PhD Thesis, Nürnberg: Der Technischen Fakultät der Universität Erlangen, 2009.

Wang et al., "3D Modeling from Wide Baseline Range Scans Using Contour Coherence", Proceedings of the IEEE Conference on Computer Vision and Pattern Recognition, pp. 4018-4025, 2014.

Wang et al., "Augmented Reality 3D Displays with Micro Integral Imaging"; Journal of Display Technology, Oct. 2014.

Wang et al., "Augmented Reality Navigation with Automatic Marker-Free Image Registration Using 3-D Image Overlay for Dental Surgery", IEEE Transactions on Biomedical Engineering, vol. 61, No. 4, pp. 1295-1304, Apr. 2014.

Wang H. et al., "Precision insertion of percutaneous sacroiliac screws using a novel augmented reality-based navigation system: a pilot study"., Intl. Orthop. (SICOT) 2016, 40: 1941-1947.

Watsen, K., et al., "A Handheld Computer as an Interaction Device to a Virtual Environment.", Proceedings of the International Projection Technologies Workshop, Stuttgart, Germany, May 10-11, 1999.

Weiss et al., "Augmented Reality Visualization Using Image-Overlay for MR-Guided Interventions: System Description, Feasibility, and Initial Evaluation in a Spine Phantom", Musculoskeletal Imaging, AJR:196, Mar. 2011, DOI:10.2214/AJR.10.5038.

Wellner, P., "Interacting with Paper on the DigitalDesk.", Communications of the ACM. 36, 7, 87-96, (1993).

Wilson et al., "Validation of Three-Dimensional Models of the Distal Femur Created from Surgical Navigation Point Cloud Data"; CAOS 2015.

Xiaojun et al., "Development of a Surgical Navigation System Based on Augmented Reality Using an Optical See-Through Head-Mounted Display", Journal of Biomedical Informatics, vol. 55, pp. 124-131, 2015.

Yamazaki, K. et al., "Gesture Laser and Gesture Laser Car-Development of an Embodied Space to Support Remote Instruction.", In Bodker, S., Kyng, M. and Schmidt, K. (eds.), Proceedings of the Sixth European Conference on Computer Supported Cooperative Work—ECSC W'99, Sep. 12-16, Copenhagen, Denmark. Kluwer Academic Publishers, Dordrecht.

Yang H. et al., "Exploring collaborative navigation.", Proceedings of the 4th international conference on Collaborative virtual environments, CVE, pp. 135-142, (2002).

Ye et al., "Accurate 3D Pose Estimation from a Single Depth Image", IEEE International Conference on Computer Vision (ICCV), pp. 731-738, Nov. 2011.

Yoon et al., "Technical Feasibility and Safety of an Intraoperative Head-Up Display Device During Spine Instrumentation", The International Journal of Medical Robotics and Computer Assisted Surgery, vol. 13, No. 3, pp. 1-9, Sep. 2017.

\* cited by examiner

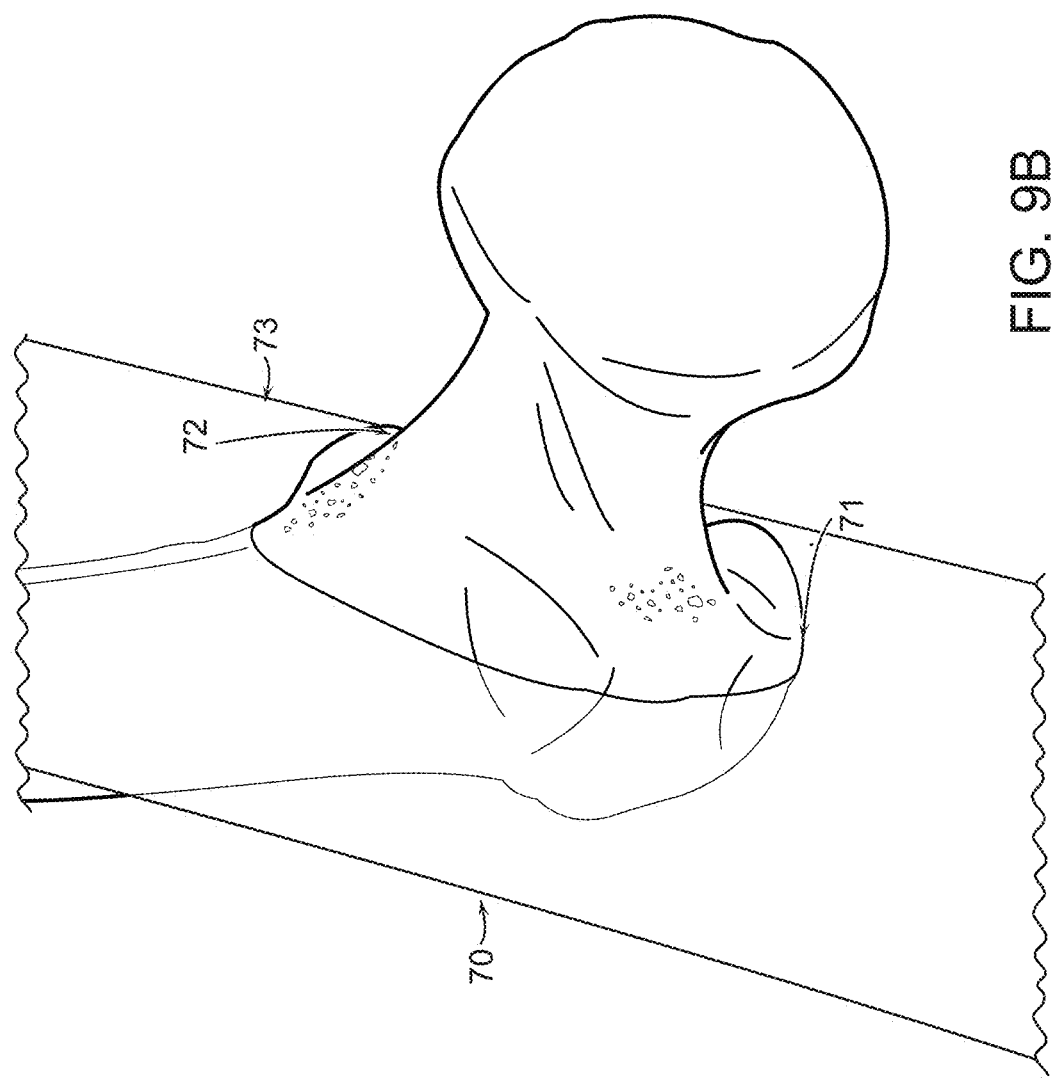

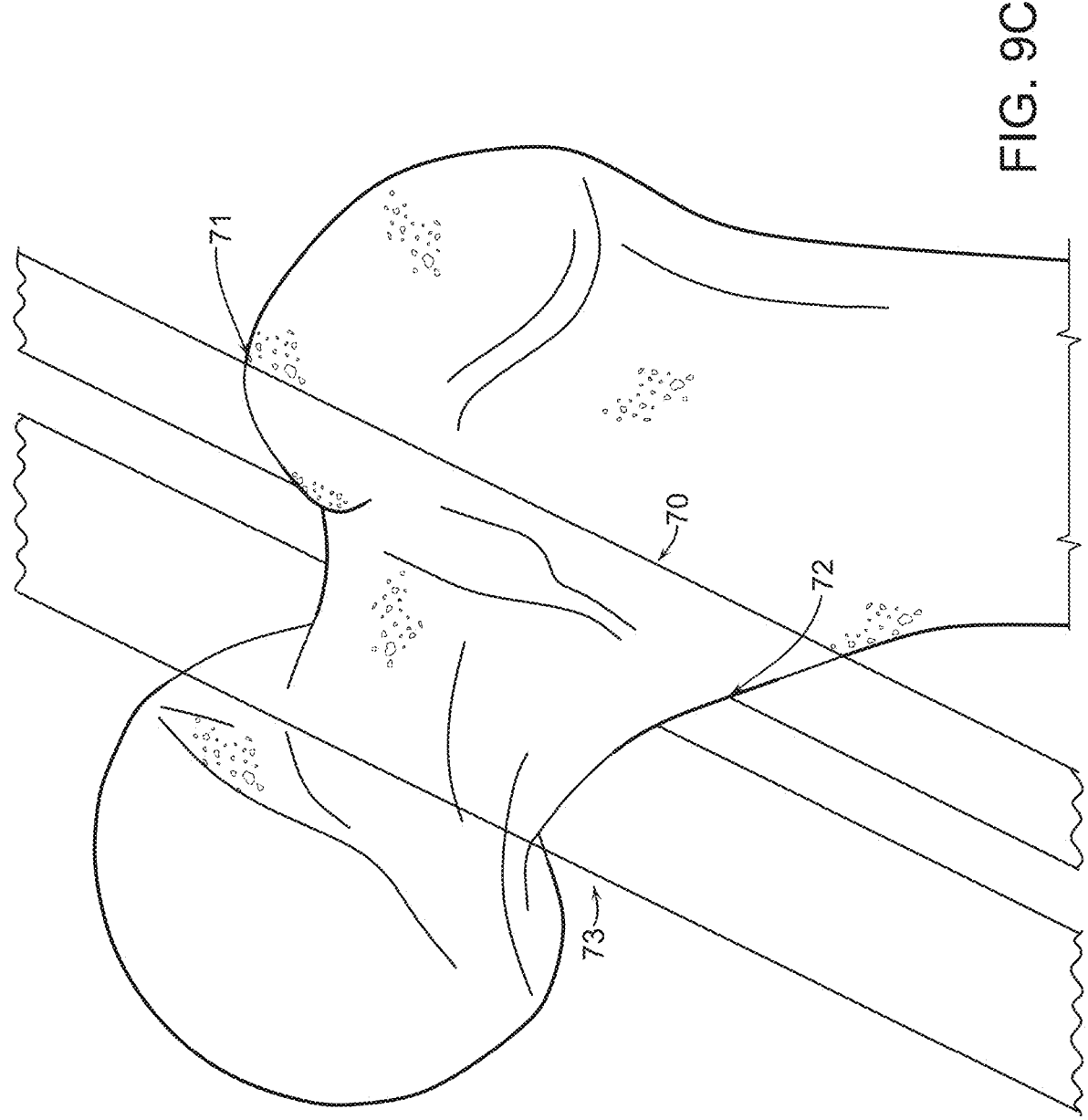

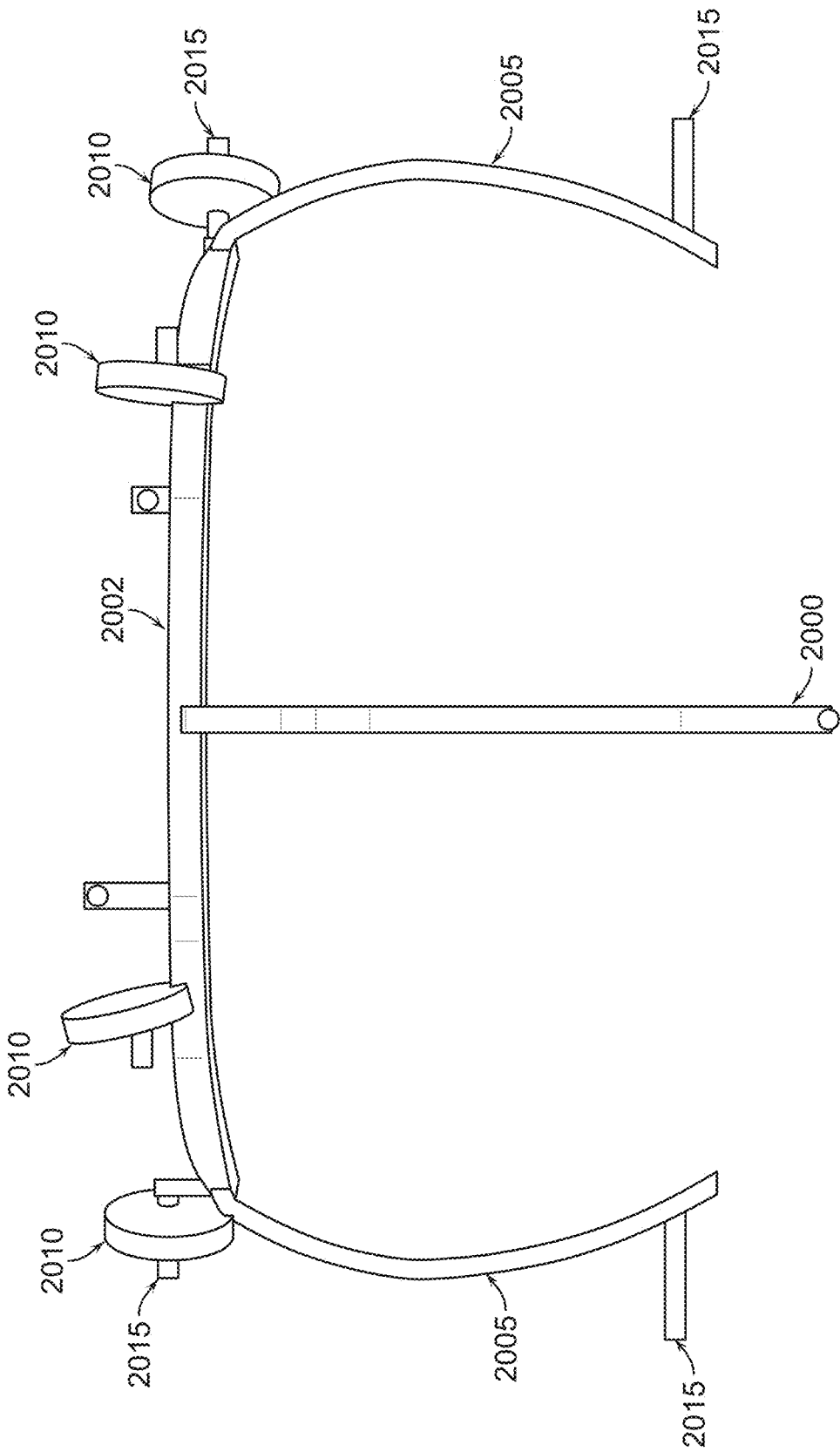

SYSTEM FOR MULTI-DIRECTIONAL TRACKING OF HEAD MOUNTED DISPLAYS FOR REAL-TIME AUGMENTED REALITY GUIDANCE OF SURGICAL PROCEDURES

RELATED APPLICATION(S)

This application claims the benefit of and the priority to U.S. Provisional Application Ser. No. 63/121,293, filed Dec. 4, 2020, the entire content of which is hereby incorporated by reference in its entirety.

TECHNICAL FIELD

Aspects of the present disclosure relate to systems, devices and methods for performing a surgical step or surgical procedure with visual guidance using a head mounted display.

BACKGROUND

With computer assisted surgery, e.g. surgical navigation or robotics, pre-operative imaging studies of the patient can be used. The imaging studies can be displayed in the OR on an external computer monitor and the patient's anatomy can be registered in relationship to the information displayed on the computer monitor. Since the surgical field is in a different location and has a different view coordinate system for the surgeon's eyes than the external computer monitor, hand-eye coordination can be challenging for the surgeon.

SUMMARY

Aspects of the present disclosure relate to a system for guiding a physical surgical tool, instrument, implant or device in a surgical procedure of a patient, the system comprising a head mounted display, at least one computer processor, at least one camera first fiducial marker, a first sub-array of fiducial markers or a first array of fiducial markers having a first location, first orientation, or first location and orientation, wherein the first fiducial marker, first sub-array of fiducial markers or first array of fiducial markers is attached to or integrated into the head mounted display, and a second fiducial marker, a second sub-array of fiducial markers or a second array of fiducial markers having a second location, orientation, or location and orientation, wherein the second fiducial marker, second sub-array of fiducial markers or second array of fiducial markers is attached to or integrated into the head mounted display, wherein the first and the second location, the first and the second orientation, or the first and the second location and orientation are different, wherein the system is configured to track the first fiducial marker, first sub-array or first array over a first movement range of the head mounted display with the at least one camera, wherein the system is configured to track the second fiducial marker, second sub-array or second array over a second movement range of the head mounted display with the at least one camera, and wherein the first movement range and the second movement range are different.

In some embodiments, the system is configured to generate a composite movement range of the head mounted display formed by a combination of the first movement range and the second movement range tracked by the system, wherein the composite movement range is greater than the first movement range or the second movement range. In some embodiments, the first movement range determines a first trackable range of viewing directions of the head mounted display, wherein the second movement range determines a second trackable range of viewing directions of the head mounted display, and wherein the composite movement range determines a total trackable range of viewing directions of the head mounted display. In some embodiments, the system is configured to generate a virtual display of a tool, instrument, guide, implant, device, 3D model of at least one anatomic structure or combination thereof, by the head mounted display, superimposed onto the at least one anatomic structure of the patient within the tracked composite movement range of the head mounted display.

In some embodiments, the first fiducial marker, first sub-array or first array has a first dimension, shape, geometry, or geometric pattern or combination thereof, wherein the second fiducial marker, second sub-array or second array has a second dimension, shape, geometry, or geometric pattern or combination thereof, and wherein the first dimension, shape, geometry, or geometric pattern or combination thereof is different from the second dimension, shape, geometry, or geometric pattern or combination thereof. In some embodiments, the system is configured to recognize the first dimension, shape, geometry, or geometric pattern or combination thereof and track it as part of the first fiducial marker, sub-array or array, wherein the system is configured to recognize the second dimension, shape, geometry, or geometric pattern or combination thereof and track it as part of the second fiducial marker, sub-array or array.

In some embodiments, the first movement range is overlapping with the second movement range. In other embodiments, the first movement range and the second movement range are not overlapping.

In some embodiments, the movement of the head mounted display comprises a movement in x direction, y direction, z direction, a rotation, or a combination thereof. In some embodiments, the first movement range of the first fiducial marker, first sub-array or first array is different from the second movement range of the second fiducial marker, second sub-array or second array in at least a x direction, a y direction, a z direction, a rotation, or a combination thereof.

In some embodiments, the first movement range comprises a range of −10 to +10 degrees, −20 to +20 degrees, −30 to +30 degrees, −40 to +40 degrees, −50 to +50 degrees, −60 to +60 degrees, −70 to +70 degrees, −80 to +80 degrees, −90 to +90 degrees, −100 to +100 degrees, −110 to +110 degrees, or value or range therebetween in up or down, left or right, forward or backward movement, rotation, or a combination thereof of the head mounted display in relationship to an initial or a predetermined viewing direction of the head mounted display or in relationship to a neutral position of a surgeon's head or neck, a predetermined position of the surgeon's head or neck, an anatomic structure of the patient, a fiducial marker attached to the patient, a sub-array of fiducial markers attached to the patient, an array of fiducial makers attached to the patient, an OR table, a fixed structure in an operating room, the camera, or a combination thereof.

In some embodiments, the first movement range comprises a range of −10 to +10 mm, −20 to +20 m, −30 to +30 mm, −40 to +40 m, −50 to +50 mm, −60 to +60 mm, −70 to +70 mm, −80 to +80 mm, −90 to +90 mm, −100 to +100 mm, −120 to +120 mm, −130 to +130 mm, −150 to +150 mm, −200 to +200 mm, −300 to +300 mm, −400 to +400 mm, −500 to +500 mm, −600 to +600 mm, or value or range therebetween in up or down, left or right, forward or backward movement, rotation, or a combination thereof of the head mounted display in relationship to an initial or a predetermined viewing direction of the head mounted display or in relationship to a neutral position of the surgeon's head or neck, a predetermined position of the surgeon's head or neck, an anatomic structure of the patient, a fiducial marker attached to the patient, a sub-array of fiducial markers attached to the patient, an array of fiducial makers attached to the patient, an OR table, a fixed structure in the operating room, the camera, or a combination thereof.

In some embodiments, the second movement range comprises a range of −10 to +10 degrees, −20 to +20 degrees, −30 to +30 degrees, −40 to +40 degrees, −50 to +50 degrees, −60 to +60 degrees, −70 to +70 degrees, −80 to +80 degrees, −90 to +90 degrees, −100 to +100 degrees, −110 to +110 degrees, or value or range therebetween in up or down, left or right, forward or backward movement, rotation, or a combination thereof of the head mounted display in relationship to an initial or a predetermined viewing direction of the head mounted display or in relationship to a neutral position of the surgeon's head or neck, a predetermined position of the surgeon's head or neck, an anatomic structure of the patient, a fiducial marker attached to the patient, a sub-array of fiducial markers attached to the patient, an array of fiducial makers attached to the patient, an OR table, a fixed structure in the operating room, the camera, or a combination thereof.

In some embodiments, the second movement range comprises a range of −10 to +10 mm, −20 to +20 m, −30 to +30 mm, −40 to +40 m, −50 to +50 mm, −60 to +60 mm, −70 to +70 mm, −80 to +80 mm, −90 to +90 mm, −100 to +100 mm, −120 to +120 mm, −130 to +130 mm, −150 to +150 mm, −200 to +200 mm, −300 to +300 mm, −400 to +400 mm, −500 to +500 mm, −600 to +600 mm, or value or range therebetween in up or down, left or right, forward or backward movement, rotation, or a combination thereof of the head mounted display in relationship to an initial or a predetermined viewing direction of the head mounted display or in relationship to a neutral position of the surgeon's head or neck, a predetermined position of the surgeon's head or neck, an anatomic structure of the patient, a fiducial marker attached to the patient, a sub-array of fiducial markers attached to the patient, an array of fiducial makers attached to the patient, an OR table, a fixed structure in the operating room, the camera, or a combination thereof.

In some embodiments, at least a portion of the first fiducial marker, first sub-array or first array is separated from at least a portion of the second fiducial marker, second sub-array or second array by a disk, shield or barrier. In some embodiments, the disk, shield or barrier is configured to avoid overlap of the at least a portion of the first fiducial marker, first sub-array or first array with the at least a portion of the second fiducial marker, second sub-array or second array in a line of sight of the at least one camera.

In some embodiments, a disk, shield or barrier is positioned between at least a portion of the first fiducial marker, first sub-array or first array and at least a portion of the second fiducial marker, second sub-array or second array. In some embodiments, the disk, shield or barrier is configured to avoid overlap of the at least a portion of the first fiducial marker, first sub-array or first array with the at least a portion of the second fiducial marker, second sub-array or second array in the line of sight of the at least one camera.

In some embodiments, the at least one camera is configured to detect visible light, infrared light, or visible light and infrared light.

In some embodiments, the at least one camera is part of a surgical navigation system, or wherein the at least one camera is part of a surgical robot, or wherein the at least one camera is part of a surgical navigation system and a surgical robot.

In some embodiments, the at least one camera is integrated or attached to the head mounted display, or wherein the at least one camera is separate from the head mounted display.

In some embodiments, the at least one camera is integrated or attached to a first head mounted display, and wherein the at least one camera integrated or attached to the first head mounted display is configured to track the first fiducial marker, first sub-array or first array integrated into or attached to a second head mounted display. In some embodiments, wherein the at least one camera integrated or attached to the first head mounted display is configured to track the second fiducial marker, second sub-array or second array integrated into or attached to the second head mounted display, or wherein the at least one camera integrated or attached to the first head mounted display is configured to track the first fiducial marker, first sub-array or first array integrated into or attached to a second head mounted display and wherein the at least one camera integrated or attached to the first head mounted display is configured to track the second fiducial marker, second sub-array or second array integrated into or attached to the second head mounted display.

In some embodiments, the first fiducial marker, the second fiducial marker, or the first fiducial marker and the second fiducial marker comprise at least one optical marker, geometric pattern, bar code, QR code, retroreflective marker, active marker, passive marker, RF marker, infrared marker, LED or a combination thereof.

In some embodiments, the first subarray, the second subarray, or the first subarray and the second subarray comprise at least one fiducial marker.

In some embodiments, the first array or the second array comprise at least one fiducial marker.

In some embodiments, the first array or the second array comprise at least one subarray or wherein the first array or the second array comprise at least one fiducial marker and at least one subarray.

In some embodiments, the system comprises a third fiducial marker, third sub-array or third array integrated into or attached to the head mounted display at a third location, orientation, or location and orientation, and the system is configured to track the third fiducial marker, third sub-array or third array over a third movement range of the head mounted display with the at least one camera, wherein the third movement range is at least in part different from the first movement range and the second movement range.

In some embodiments, the first sub-array, the second sub-array, or the first and second sub-array comprises a facet. In some embodiments, the first array, the second array, or the first array and second array comprise two or more facets.

In some embodiments, the first array, the second array, or the first array and second array is multi-faceted.

BRIEF DESCRIPTION OF THE DRAWINGS

Illustrative, non-limiting example embodiments will be more clearly understood from the following detailed description taken in conjunction with the accompanying drawings.

FIGS. 9A, 9B and 9C are illustrative examples of arbitrary virtual planes in the hip and a femoral neck cut plane according to some embodiments of the present disclosure.

FIGS. 12A, 12B, 12C, 12D, 12E, 12F and 12G are non-limiting examples of various fiducial marker, sub-array or array configurations trackable, e.g. a first, second, third fiducial marker, sub-array or array configuration, trackable by at least one camera through a first, second, third movement range of an HMD. Various disks, shields, or barriers for reducing overlap of fiducial markers, sub-arrays or arrays within the line of sight of the camera are also shown.

DETAILED DESCRIPTION

Figure 1:
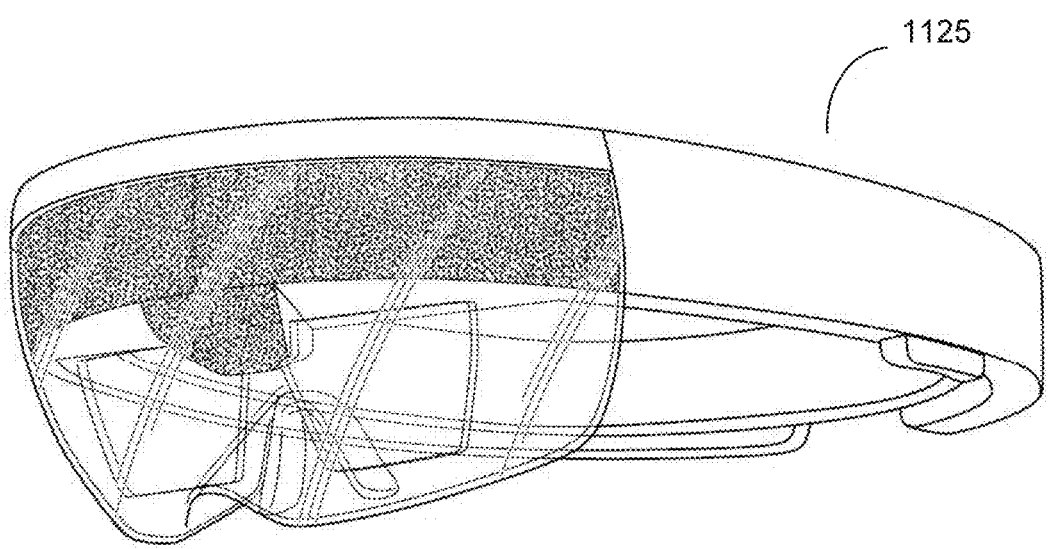
FIG. 1 is an non-limiting example of a see through optical head mounted display according to some embodiments of the present disclosure.

Aspects of the present disclosure provide, among other things, systems, devices and methods for a simultaneous visualization of live data of the patient and digital representations of virtual data such as virtual cuts and/or virtual surgical guides including cut blocks or drilling guides through an head mounted display (HMD). In some embodiments, the system can include one or more HMD, one or more processor and one or more user interfaces. In some embodiments, the surgical site including live data of the patient, the HMD, and the virtual data are registered in a common coordinate system. In some embodiments, the virtual data are superimposed onto and aligned with the live data of the patient. In some embodiments, the head mounted display is a see-through HMD. Unlike virtual reality head systems that blend out live data, the HMD allows the surgeon to see the live data of the patient through the HMD, e.g. the surgical field, while at the same time observing virtual data of the patient and/or virtual surgical instruments or implants with a predetermined position and/or orientation using the display of the HMD unit.

In some embodiments, an operator such as a surgeon can look through an HMD observing physical data or information on a patient, e.g. a surgical site or changes induced on a surgical site, while pre-existing data of the patient are superimposed onto the physical visual representation of the live patient. Systems, methods and techniques to improve the accuracy of the display of the virtual data superimposed onto the live data of the patient are described in International Patent Application No. PCT/US2018/012459, which is incorporated herein by reference in its entirety.

Methods and systems of registration and cross-referencing including registration and cross-referencing surgical sites and one or more HMDs such as the ones described in PCT International Application Serial Nos. PCT/US2017/021859, PCT/US2018/13774 and PCT/US2019/015522 can be used. Methods and systems of displaying virtual data in various surgical, medical or dental applications using one or more HMDs such as the ones described in PCT International Application Serial Nos. PCT/US2017/021859, PCT/US2018/13774 and PCT/US2019/015522. These applications are hereby incorporated by reference in their entireties.

Aspects of the present disclosure relate to systems, devices and methods for performing a surgical step or surgical procedure with visual guidance using an head mounted display. In some embodiments, the head mounted display can be a see through head mounted display, e.g. an optical see through head mounted display, for example for augmented reality (AR) applications. In some embodiments, the head mounted display can be a non-see through head mounted display, e.g. video see through type, for virtual reality applications, optionally with video display including video streaming of live data from the patient, e.g. video feed from a camera integrated into, attached to, or separate from the head mounted display. The head mounted display can provide surgical guidance in a mixed reality environment. Various embodiments are described for adjusting the focal plane or focal point or selecting the focal plane or focal point for displaying virtual structures, objects, instruments, implants (e.g. implant components) or device using, for example, the distance between the head mounted display and the surgical site, e.g. an uncut or a cut bone in a joint replacement, a vertebral body or spinal element in a spinal procedure, a vessel or vascular structure in a cardiovascular, neurovascular, or general vascular procedure, or a tooth or gum in a dental procedure, or in any other surgical procedures, e.g. brain surgery, thoracic surgery, pelvic surgery, breast surgery etc.

Some aspects of the disclosure relate to a system for performing a surgical procedure, the system comprising: a processor; a see through head mounted display; and a marker attached to a patient, wherein the system is configured to generate a 3D stereoscopic view of a virtual surgical guide, wherein the virtual surgical guide is a placement indicator at one or more predetermined coordinates indicating a predetermined position, predetermined orientation or combination thereof for aligning a physical surgical tool or a physical surgical instrument, wherein the system is configured to display the 3D stereoscopic view by the see through head mounted display onto the patient, wherein the processor is configured to determine a distance between the one or more predetermined coordinates of the virtual surgical guide and the see through head mounted display, wherein the one or more predetermined coordinates of the virtual surgical guide are referenced to or based on the marker, wherein the processor is configured to adjust at least one focal plane, focal point, or combination thereof of the display of the 3D stereoscopic view based on the determined distance.

In some embodiments, the system comprises one or more markers. In some embodiments, the marker is configured to reflect or emit light with a wavelength between 380 nm and 700 nm. In some embodiments, the marker is configured to reflect or emit light with a wavelength greater than 700 nm. In some embodiments, the marker is a radiofrequency marker, or wherein the marker is an optical marker, wherein the optical marker includes a geometric pattern.

In some embodiments, the one or more markers comprise at least one marker attached to the patient, at least one marker attached to the see through head mounted display, at least one marker attached to a structure in the operating room or any combination thereof.

In some embodiments, the system is configured to determine one or more coordinates using one or more cameras.

In some embodiments, the one or more cameras detect light with a wavelength between 380 nm and 700 nm. In some embodiments, the one or more cameras detect light with a wavelength above 700 nm.

In some embodiments, the system comprises at least one camera integrated into or attached to the see through head mounted display. In some embodiments, at least one camera is separate from the head mounted display. In some embodiments, the one or more cameras are configured to determine the position, orientation, or position and orientation of the marker. In some embodiments, the one or more cameras are configured to determine one or more coordinates of the marker. In some embodiments, the one or more cameras are configured to track the one or more coordinates of the marker during movement of the marker. In some embodiments, the one or more cameras are configured to determine one or more coordinates of the see through head mounted display.

In some embodiments, the system is configured to track the one or more coordinates of the see through head mounted display during movement of the patient, the see through head mounted display, or the patient and the see through head mounted display.

In some embodiments, the system comprises one or more processors. In some embodiments, the one or more processors are configured to generate the 3D stereoscopic view of the virtual surgical guide. In some embodiments, the one or more processors are configured to determine the distance between the one or more predetermined coordinates of the virtual surgical guide and the see through head mounted display. In some embodiments, the one or more processors are configured to track one or more coordinates of at least one or more markers, one or more see through head mounted displays, or combinations thereof during movement of the patient, the see through head mounted display or the patient and the see through head mounted display. In some embodiments, the one or more processors are configured to determine the distance between the one or more predetermined coordinates of the virtual surgical guide and the see through head mounted display during movement of the marker, movement of the see through head mounted display, or movement of the marker and the see through head mounted display, and wherein the one or more processors are configured to adjust the at least one focal plane, focal point, or combination thereof based on the change in the determined distance.

In some embodiments, the one or more processors are configured to adjust the at least one focal plane, focal point or combination thereof intermittently. In some embodiments, the one or more processors are configured to adjust the at least one focal plane, focal point or combination thereof continuously.

In some embodiments, the physical surgical tool or physical surgical instrument is configured to effect a tissue removal in the patient. The tissue removal can be a removal of bone or a removal of cartilage or a removal of bone and cartilage.

In some embodiments, the system comprises one or more see through head mounted displays. The one or more see through head mounted displays can comprise one or more combiners and/or one or more waveguides. The one or more see through head mounted displays can comprise one or more mirrors.

In some embodiments, the one or more see through head mounted displays comprise a first display unit for the left eye and a second display unit for the right eye. In some embodiments, the one or more see through head mounted displays comprise a stack of one or more planar or non-planar display units. The one or more planar or non-planar display units comprise at least one of a combiner, a mirror, a waveguide, or combinations thereof. In some embodiments, the at least one focal plane, focal point or combination thereof matching the determined distance coincides with at least one of the planar or non-planar display units in the stack. In some embodiments, the stack of one or more planar or non-planar display units display a range of focal planes, focal points or combination thereof and wherein the range of focal planes, focal points or combination thereof includes a focal plane, focal point or combination thereof near the determined distance.

In some embodiments, the one or more see through head mounted displays comprise at least one active optical element for adjustment of the at least one focal plane, focal point or combination thereof. The system comprises one or more mechanical, electrical, electromagnetic, piezoelectric adjustment effectors, or combinations thereof, and wherein the mechanical, electrical, electromagnetic, piezoelectric adjustment effectors, or combination thereof are configured to move at least a portion of the at least one active optical element to adjust the at least one focal plane, focal point or combination thereof. In some embodiments, the movement of the at least portion of the at least one active optical element comprises at least one translation, rotation, pivoting, or combination thereof of the of the at least portion of the at least one active optical element. In some embodiments, the at least one active optical element comprises a deformable lens or a deformable mirror or combinations thereof.

In some embodiments, the virtual surgical guide is a virtual path, a virtual trajectory, a virtual surgical tool, a virtual surgical instrument, a virtual cut block, a virtual trial implant, a virtual implant component, a virtual implant, a virtual device, a predetermined start point, a predetermined start position, a predetermined start orientation or alignment, a predetermined intermediate point, a predetermined intermediate position, a predetermined intermediate orientation or alignment, a predetermined end point, a predetermined end position, a predetermined end orientation or alignment, a predetermined plane, a predetermined cut plane, a predetermined depth marker, a predetermined stop, a predetermined angle or orientation or rotation marker, a predetermined axis, or a predetermined tissue change or alteration.

Aspects of the disclosure relate to a system for performing a surgical procedure in a patient, the system comprising: a processor; a see through head mounted display; and a marker attached to a patient, wherein the see through head mounted display comprises a first display unit for the left eye and a second display unit for the right eye, wherein the system is configured to generate a first view of a virtual surgical guide for the first display unit and a second view of the virtual surgical guide for the second display unit, wherein the virtual surgical guide is a placement indicator at one or more predetermined coordinates indicating a predetermined position, predetermined orientation or combination thereof for aligning a physical surgical tool or a physical surgical instrument, wherein the system is configured to generate using the first view and using the second view a 3D stereoscopic view of the virtual surgical guide based on the one or more predetermined coordinates, wherein the system is configured to display the 3D stereoscopic view by the see through head mounted display onto the patient, wherein the system is configured to determine a distance between the one or more predetermined coordinates and the see through head mounted display, wherein the one or more predetermined coordinates are referenced to or based on the marker, wherein the system is configured to adjust the convergence between the first and second views displayed by the first display unit and the second display unit of the virtual surgical guide based on the determined distance.

In some embodiments, the system comprises one or more processors, one or more markers, one or more see through head mounted display or combinations thereof. In some embodiments, the one or more processors are configured to generate the 3D stereoscopic view of the virtual surgical guide. In some embodiments, the one or more processors are configured to determine the distance between the one or more predetermined coordinates of the virtual surgical guide and the see through head mounted display. In some embodiments, the one or more processors are configured to track one or more coordinates of one or more fiducial markers, one or more subarrays, one or more arrays, one or more see through head mounted displays, or combinations thereof during movement of the patient, movement of the see through head mounted display or movement of the patient and the see through head mounted display. The one or more fiducial markers, one or more subarrays, one or more arrays can be attached to the patient and/or can be integrated into or attached to the head mounted display. In some embodiments, the one or more processors are configured to determine the distance between the one or more predetermined coordinates of the virtual surgical guide and the see through head mounted display during movement of the marker, movement of the see through head mounted display, or movement of the marker and the see through head mounted display, and wherein the one or more processors are configured to adjust the convergence based on a change in the determined distance. In some embodiments, the one or more processors are configured to adjust the convergence intermittently. In some embodiments, the one or more processors are configured to adjust the convergence continuously.

In some embodiments, the system comprises one or more see through head mounted displays. The one or more see through head mounted displays can comprise one or more combiners and/or one or more waveguides. The one or more see through head mounted displays can comprise one or more mirrors.

In some embodiments, the one or more see through head mounted displays comprise a stack of planar or non-planar display units. The one or more planar or non-planar display units comprise at least one combiner, a mirror, a waveguide, or combinations thereof.

In some embodiments, the one or more see through head mounted displays comprise at least one active optical element to adjust the convergence. In some embodiments, the system comprises one or more mechanical, electrical, electromagnetic, piezoelectric adjustment effectors, or combination thereof and wherein the mechanical, electrical, electromagnetic, piezoelectric adjustment effectors, or combination thereof are configured to move at least a portion of the at least one active optical element to adjust the convergence. The movement can comprise a translation, rotation, pivoting, or combination thereof of the at least one active optical element. In some embodiments, the at least one active optical element comprises a deformable lens or a deformable mirror or combinations thereof.

In some embodiments, the convergence between the first and second views is adjusted by adjusting a size, dimension, position, orientation or combination thereof of the first and second views on the first and second display units based on the determined distance.

In some embodiments, the virtual surgical guide is a virtual path, a virtual trajectory, a virtual surgical tool, a virtual surgical instrument, a virtual cut block, a virtual trial implant, a virtual implant component, a virtual implant, a virtual device, a predetermined start point, a predetermined start position, a predetermined start orientation or alignment, a predetermined intermediate point, a predetermined intermediate position, a predetermined intermediate orientation or alignment, a predetermined end point, a predetermined end position, a predetermined end orientation or alignment, a predetermined plane, a predetermined cut plane, a predetermined depth marker, a predetermined stop, a predetermined angle or orientation or rotation marker, a predetermined axis, or a predetermined tissue change or alteration.

In some embodiments, the system is configured to determine one or more coordinates using one or more cameras. The one or more cameras can detect light with a wavelength between 380 nm and 700 nm or with a wavelength above 700 nm.

In some embodiments, at least one camera integrated into or attached to the see through head mounted display. In some embodiments, at least one camera is separate from the head mounted display.

In some embodiments, the one or more cameras are configured to determine the position, orientation, or position and orientation of a fiducial marker, sub-array, or array. In some embodiments, the one or more cameras are configured to determine one or more coordinates of the fiducial marker, sub-array or array.

In some embodiments, the system is configured to track the one or more coordinates of the marker during movement of the marker.

In some embodiments, the one or more cameras are configured to determine one or more coordinates of the see through head mounted display.

In some embodiments, the system is configured to track the one or more coordinates of the see through head mounted display during movement of the patient, movement of the see through head mounted display, or movement of the patient and the see through head mounted display.

In some embodiments, the physical surgical tool or physical surgical instrument is configured to effect a tissue removal in the patient. In some embodiments, the tissue removal is a removal of bone or a removal of cartilage or a removal of bone and cartilage.

In some embodiments, the marker is configured to reflect or emit light with a wavelength between 380 nm and 700 nm. In some embodiments, the marker is configured to reflect or emit light with a wavelength greater than 700 nm. In some embodiments, the marker is a radiofrequency marker, or wherein the marker is an optical marker, wherein the optical marker includes a geometric pattern.

In some embodiments, the system comprises one or more fiducial markers, sub-arrays, and/or arrays. In some embodiments, the one or more fiducial markers, sub-arrays, and/or arrays comprise at least one fiducial marker, sub-array, and/or array attached to the patient, at least one fiducial marker, sub-array, and/or array attached to the head mounted display, at least one fiducial marker, sub-array, and/or array attached to a structure in the operating room or any combination thereof.

Aspects of the present disclosure describe novel systems, devices and methods for performing a surgical step or surgical procedure with visual guidance using a head mounted display, e.g. by displaying virtual representations of one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration, on a live patient. In some embodiments, the head mounted (HMD) is a see through head mounted display (HMD). In some embodiments, an optical see through HMD is used. In some embodiments, a video see through HMD can be used, for example with a camera integrated into, attached to, or separate from the HMD, generating video feed.

In some embodiments, one or more head mounted display (HMD) can be used wirelessly.

Bluetooth

In some embodiments, the device can comprise a Bluetooth transmitter and/or receiver.

Bluetooth can be a packet-based protocol with a master/slave architecture. One master can communicate with multiple slaves in a piconet. A master Bluetooth device can communicate with multiple devices in a piconet. The devices can switch roles, by agreement, and the slave can become the master (for example, a headset initiating a connection to a phone necessarily begins as master—as an initiator of the connection—but may subsequently operate as the slave).

Bluetooth can be a layer protocol architecture comprising core protocols, cable replacement protocols, telephony control protocols, and adopted protocols.

The device can, in some embodiments, employ high-speed Bluetooth protocols.

The device can comprise an interface between a server and the device using a Bluetooth device. The interface can be HCl (Host Controller Interface).

The Host Controller Interface can provide a command interface for the controller and for the link manager, which can allow access to the hardware status and control certain registers. This interface can provide an access layer for all Bluetooth devices. The HCl layer of the machine can exchange commands and data with the HCl firmware present in the Bluetooth device. The HCl can, in some embodiments, automatically discover other Bluetooth devices that are within the coverage radius.

The hardware that constitutes a Bluetooth device, including the Bluetooth device that can optionally be within the device, can include two parts: a radio device, responsible for modulating and transmitting the signal and a digital controller. These specific parts can, in some embodiments, be physically separate and can in other embodiments be physically together.

The digital controller can, in some embodiments, be CPU. In some embodiments, the CPU can run a Link Controller; and interfaces with the host device, such as the Host Controller Interface. The Link Controller can be responsible for the processing of the baseband and the management of ARQ and physical layer FEC protocols. The CPU can, in some embodiments, handle the transfer functions (both asynchronous and synchronous), audio coding, and data encryption. The CPU of the device is, in some embodiments, responsible for performing the instructions related to the Bluetooth of the host device, in order to simplify its operation. For the performance of specific instructions related to the Bluetooth of the host device, the CPU can run software called Link Manager that has the function of communicating with other devices through the LMP protocol.

The Link Manager can, in some embodiments, establish the connection between devices. For example, the Link Manager can establish the connection between the device, either between the drill or saw handle and saw battery or integrated within the drill or saw and the server.

The Link Manager can be responsible for the establishment, authentication and configuration of the link. The Link Manager can furthermore find other managers and communicates with them due to the management protocol of the LMP link.

The Link Manager Protocol can comprise a number of PDUs (Protocol Data Units) that can be sent from one device to another. The following is a list of supported services:
1) Transmission and reception of data.
2) Name request
3) Request of the link addresses.
4) Establishment of the connection.
5) Authentication.
6) Negotiation of link mode and connection establishment.

The system, when in discoverable mode, can transmit the following information on demand:
1) Device name
2) Device class
3) List of services 4) Technical information (for example: device features, manufacturer, Bluetooth specification used, clock offset)

The system can have a unique 48-bit address. The system can have a friendly Bluetooth name, which can be set by the user. This name can appear when another user scans for devices and in lists of paired devices.

During pairing between the server and the system attached to or integrated into the saw or drill, the two can establish a relationship by creating a shared secret or a link key. If both devices store the same link key, they are paired or bonded.

The following are pairing mechanisms that can be used in some embodiments of the present disclosure:
1) Legacy pairing, wherein each device must enter a PIN code; pairing is only successful if both devices enter the same PIN code. Legacy has the following authentication mechanisms:
   a. Limited input devices, wherein the devices have a fixed PIN, for example "1111" or "2222", that are hard-coded into the device
   b. Numeric input devices, wherein the user can enter a numeric value up to 16 digits in length
   c. Alpha-numeric input devices wherein the user can enter full UTF-8 text as a PIN code
2) Secure Simple Pairing (SSP), using a public key cryptography, and certain modifications can help protect against man in the middle, or MITM attacks. SSP has the following authentication mechanisms:
   a. Just works: This method functions with no user interaction. However, the device may prompt the user to confirm the pairing process.
   b. Numeric comparison: The devices being paired display a 6-digit numeric code. The user can compare the numbers to ensure they are the exact same. If the comparison succeeds, the user(s) can confirm pairing on the device(s) that can accept an input. This method provides MITM protection, assuming the user confirms on both devices and actually performs the comparison properly.
   c. Passkey Entry: This mechanism can be used between a device with a display and a device with numeric keypad entry (such as a keyboard), or two devices with numeric keypad entry. In the first case, the display presents a 6-digit numeric code to the user, who then enters the code on the keypad. In the second case, the user of each device enters the same 6-digit number.
   d. Out of band (OOB): This method uses an external means of communication, such as near-field communication (NFC) to exchange information used in the pairing process. Pairing is completed using the Bluetooth radio, but requires information from the OOB mechanism.

In some embodiments, the device comprises a Bluetooth transmitter and/or receiver wherein the Bluetooth transmitter and/or receiver is configured to work in conjunction with an augmented reality surgical guidance system, a surgical navigation system, a robot, a robotic system, and/or a handheld robot.

In some embodiments, the Bluetooth transmitter and/or receiver and the established connection between the Bluetooth transmitter and/or receiver and the augmented reality surgical guidance system, surgical navigation system, robot, robotic system, and/or handheld robot can work in conjunction with one or more on/off switches and/or one or more potentiometers, e.g. digital potentiometers, and/or one or more rheostats and/or one or more actuators to regulate the speed of the movement of a saw blade or movement of a drill bit or to provide haptic feedback.

For example, in cases where the augmented reality surgical guidance system, surgical navigation system, robot, robotic system, and/or handheld robot detects a movement of the drill or saw deviating from the intended surgical axis, target, target area, target volume, tissue resection target, area, volume (e.g. bone or tissue removal or resection, e.g. with a bone drill or bone saw) by a specific distance in any direction in one or more dimensions the augmented reality surgical guidance system, surgical navigation system, robot, robotic system, and/or handheld robot can transmit information to the Bluetooth receiver which can regulate the Bluetooth switch, including both a transmitter and receiver, to activate an on/off switch and/or a potentiometer, e.g. digital, and/or a rheostat and/or a specific actuator for haptic feedback. In cases where the augmented reality surgical guidance system, surgical navigation system, robot, robotic system, and/or handheld robot detects a movement of the drill or saw that approaches, for example, a specific anatomical structure or safe zone, the augmented reality surgical guidance system, surgical navigation system, robot, robotic system, and/or handheld robot can similarly work in conjunction with the Bluetooth switch within the device attached to the drill or saw to adjust, control, and/or regulate an on/off switch and/or a potentiometer and/or a rheostat and/or a specific actuator for haptic feedback. The same concept can similarly work for turning on or increasing the speed of the movement of the saw blade or the drill bit or other power tool or instrument when approaching certain anatomic structures.

The Bluetooth switch, Bluetooth receiver, and/or Bluetooth transmitter can, in some embodiments, employ low latency Bluetooth in order to provide instant saw or drill speed regulation or instant haptic feedback.

WiFi

In some embodiments, the device comprises a WiFi transmitter and/or receiver.

In some embodiments, the device can comprise WiFi capability. Different versions of WiFi can be used including but not limited to: 802.11a, 802.11b, 802.11g, 802.11n (Wi-Fi 4[40]), 802.11h, 802.11i, 802.11-2007, 802.11-2012, 802.11ac (Wi-Fi 5[40]), 802.11ad, 802.11af, 802.11-2016, 802.11ah, 802.11ai, 802.11aj, 802.11aq, 802.11ax (Wi-Fi 6[40]), and 802.11ay.

In some embodiments, the device comprises a WiFi transmitter and/or receiver wherein the WiFi transmitter and/or receiver is configured to work in conjunction with a surgical guidance system.

In some embodiments, the system can include routers that can be configured for intranet and internet connections.

In some embodiments, the system can utilize several distinct radio frequency ranges. For example, the system utilizes the 802.11 standard, it can include distinct radio frequencies ranges for use in Wi-FI communications such as: 900 MHZ, 2.4 GHz, 5 GHZ, 5.9 GHZ, and 60 GHz bands. Each frequency or range can have a multitude of channels.

In some embodiments, the system and/or device's Wi-Fi can be part of the IEEE 802 protocol family. In some embodiments, the system and/or device can comprise one or more transmitters. WiFi transmitters are low power devices.

In some embodiments, the system and/or device can comprise one or more antennas. The system and/or device can comprise an access point compliant with 802.11b and/or 802.11g. Using the stock omnidirectional antenna can have a range of 100 m (0.062 mi). The identical radio with an external semi parabolic antenna (15 dB gain) with a similarly equipped receiver at the far end can have a range over 20 miles.

In some embodiments, the system and/or device can comprise multiple-input and multiple-output. The system and/or device including but not limited to standards such as IEEE 802.11n and IEEE 802.11ac, can comprise multiple antennas for extended range and higher speeds.

In some embodiments, the WiFi can comprise Local Area Networks (LAN).

In some embodiments, the device can include one or more access points. A wireless access point can connect a group of wireless devices to an adjacent wired LAN.

In some embodiments, the device can include one or more wireless adapters. Wireless adapters can allow devices to connect to a wireless network.

In some embodiments, the device can include one or more routers. Wireless routers can integrate a Wireless Access Point, Ethernet switch, and internal router firmware application that provides IProuting, NAT, and DNS forwarding through an integrated WAN-interface.

In some embodiments, the device can include one or more wireless network bridges. Wireless network bridges can act to connect two networks to form a single network at the data-link layer over Wi-Fi. The main standard is the wireless distribution system (WDS). Wireless bridging can connect a wired network to a wireless network.

In some embodiments, the device can include one or more security features. Security features can be any security standard known in the art.

In some embodiments, the WiFi transmitter and/or receiver and the established connection between the WiFi transmitter and/or receiver and the augmented reality surgical guidance system can work in conjunction with one or more on/off switches and/or one or more potentiometers and/or one or more rheostats and/or one or more actuators to regulate the oscillation of a saw blade or movement of a drill bit or to provide haptic feedback.

For example, in cases where the augmented reality surgical guidance system detects a movement of the drill or saw or other power tool or instrument deviating from the intended cut/drill surgical axis, the surgical guidance system can regulate the WiFi switch, including both a transmitter and receiver, to activate an on/off switch and/or a potentiometer, e.g. digital, and/or a rheostat and/or a specific actuator for haptic feedback. In cases where the surgical guidance system detects a movement of the drill or saw or other power tool or instrument that approaches, for example, a specific anatomical structure or safe zone, the surgical guidance system can similarly work in conjunction with the WiFi switch within the device attached to the drill or saw or other power tool or instrument to activate an on/off switch and/or a potentiometer and/or a rheostat and/or a specific actuator for haptic feedback. The same concept can similarly work for turning on or increasing the speed of the movement of the saw blade or the drill bit or other power tool or instrument when approaching certain anatomic structures.

LiFi

In some embodiments, the device comprises a LiFi transmitter and/or receiver.

In some embodiments, the device can comprise LiFi capability. LiFi can use light from light-emitting diodes (LEDs) as a medium to deliver networked, mobile, high-speed communication.

In some embodiments, the system can comprise visible light communications (VLC). VLC works by switching the current to the LEDs off and on at very high speeds.

In some embodiments, the system can comprise Bg-Fi. Bg-Fi can be a Li-Fi system consisting of an application for a mobile device, and a simple consumer product device, with color sensor, microcontroller, and embedded software. Light from the mobile device display communicates to the color sensor on the consumer product, which converts the light into digital information. Light emitting diodes enable the consumer product to communicate synchronously with the mobile device.

In some embodiments, the Li-Fi system can be wireless and can use 802.11 protocols. In some embodiments, the LiFi system can use ultraviolet, infrared and visible light communication. One part of the visible light communication can be designed from communication protocols established by the IEEE 802 workgroup. The IEEE 802.15.7 standard can, in some embodiments, define the physical layer (PHY) and media access control (MAC) layer. The modulation formats recognized for PHY I and PHY II are on-off keying (OOK) and variable pulse position modulation (VPPM). The Manchester coding used for the PHY I and PHY II layers can include the clock inside the transmitted data by representing a logic 0 with an OOK symbol "01" and a logic 1 with an OOK symbol "10", all with a DC component. The DC component avoids light extinction in case of an extended run of logic 0's.

The use of LiFi provides additional benefits as the light waves are unlikely to affect or hinder the efficiency of a medical procedure or medical devices.

In some embodiments, the device can comprise a LiFi transmitter and/or receiver wherein the LiFi transmitter and/or receiver is configured to work in conjunction with a surgical guidance system. Aspects of the disclosure can be applied to knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery. In some embodiments, one or more head mounted displays can display virtual data, e.g. virtual surgical guides, for knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery.

In some embodiments, one or more head mounted displays can be used to display volume data or surface data, e.g. of a patient, of imaging studies, of graphical representation and/or CAD files.

Aspects of the disclosure relate to a system or device comprising at least one head mounted display, the device being configured to generate a virtual surgical guide. In some embodiments, the virtual surgical guide is a three-dimensional representation in digital format which corresponds to at least one of a portion of a physical surgical guide, a placement indicator of a physical surgical guide, or a combination thereof. In some embodiments, the at least one head mounted display is configured to display the virtual surgical guide superimposed onto a physical joint based at least in part on coordinates of a predetermined position of the virtual surgical guide, and the virtual surgical guide is configured to align the physical surgical guide or a physical saw blade with the virtual surgical guide to guide a bone cut of the joint.

In some embodiments, the at least one head mounted display is configured to display the virtual surgical guide superimposed onto a physical joint based at least in part on coordinates of a predetermined position of the virtual surgical guide, and the virtual surgical guide is configured to align the physical surgical guide or a physical saw drill, pin, burr, mill, reamer, broach, or impactor with the virtual surgical guide to guide a drilling, pinning, burring, milling, reaming, broach or impacting of the joint.

In some embodiments, the at least one head mounted display is configured to display the virtual surgical guide superimposed onto a physical spine based at least in part on coordinates of a predetermined position of the virtual surgical guide, and the virtual surgical guide is configured to align the physical surgical guide or a physical tool or physical instrument with the virtual surgical guide to guide an awl, a drill, a pin, a tap, a screwdriver or other instrument or tool.

In some embodiments, the system or device comprises one, two, three or more head mounted displays.

In some embodiments, the virtual surgical guide is configured to guide a bone cut in a knee replacement, hip replacement, shoulder joint replacement or ankle joint replacement.

In some embodiments, the virtual surgical guide includes a virtual slot for a virtual or a physical saw blade.

In some embodiments, the virtual surgical guide includes a planar area for aligning a virtual or a physical saw blade.

In some embodiments, the virtual surgical guide includes two or more virtual guide holes or paths for aligning two or more physical drills or pins.

In some embodiments, the predetermined position of the virtual surgical guide includes anatomical information, and/or alignment information of the joint. For example, the anatomic and/or alignment information of the joint can be based on at least one of coordinates of the joint, an anatomical axis of the joint, a biomechanical axis of the joint, a mechanical axis, or combinations thereof.

In some embodiments, the at least one head mounted display is configured to align the virtual surgical guide based on a predetermined limb alignment. For example, the predetermined limb alignment can be a normal mechanical axis alignment of a leg.

In some embodiments, the at least one head mounted display is configured to align the virtual surgical guide based on a predetermined femoral or tibial component rotation. In some embodiments, the at least one head mounted display is configured to align the virtual surgical guide based on a predetermined flexion of a femoral component or a predetermined slope of a tibial component.

In some embodiments, the virtual surgical guide is configured to guide a proximal femoral bone cut based on a predetermined leg length.

In some embodiments, the virtual surgical guide is configured to guide a bone cut of a distal tibia or a talus in an ankle joint replacement and the at least one head mounted display is configured to align the virtual surgical guide based on a predetermined ankle alignment, wherein the predetermined ankle alignment includes a coronal plane implant component alignment, a sagittal plane implant component alignment, an axial plane component alignment, an implant component rotation or combinations thereof.

In some embodiments, the virtual surgical guide is configured to guide a bone cut of a proximal humerus in a shoulder joint replacement and the at least one head mounted display is configured to align the virtual surgical guide based on a predetermined humeral implant component alignment, wherein the humeral implant component alignment includes a coronal plane implant component alignment, a sagittal plane implant component alignment, an axial plane component alignment, an implant component, or combinations thereof.

In some embodiments, the predetermined position of the surgical guide is based on a pre-operative or intra-operative imaging study, one or more intra-operative measurements, intra-operative data or combinations thereof.

Aspects of the disclosure relate to a system or device comprising two or more head mounted displays for two or more users, wherein the device is configured to generate a virtual surgical guide, wherein the virtual surgical guide is a three-dimensional representation in digital format which corresponds to at least one of a portion of a physical surgical guide, a placement indicator of a physical surgical guide, or a combination thereof, wherein the head mounted display is configured to display the virtual surgical guide superimposed onto a physical joint based at least in part on coordinates of a predetermined position of the virtual surgical guide, and wherein the virtual surgical guide is configured for aligning the physical surgical guide or a saw blade to guide a bone cut of the joint.

Aspects of the disclosure relate to a system or device comprising at least one head mounted display and a virtual bone cut plane, wherein the virtual bone cut plane is configured to guide a bone cut of a joint, wherein the virtual bone cut plane corresponds to at least one portion of a bone cut plane, and wherein the head mounted display is configured to display the virtual bone cut plane superimposed onto a physical joint based at least in part on coordinates of a predetermined position of the virtual bone cut plane. In some embodiments, the virtual bone cut plane is configured to guide a bone cut in a predetermined *varus* or *valgus* orientation or in a predetermined tibial slope or in a predetermined femoral flexion of an implant component or in a predetermined leg length.

Aspects of the disclosure relate to a method of preparing a joint for a prosthesis in a patient.

In some embodiments, the method comprises registering one or more head mounted displays worn by a surgeon or surgical assistant in a coordinate system, obtaining one or more intra-operative measurements from the patient's physical joint to determine one or more intra-operative coordinates, registering the one or more intra-operative coordinates from the patient's physical joint in the coordinate system, generating a virtual surgical guide, determining a predetermined position and/or orientation of the virtual surgical guide based on the one or more intra-operative measurements, displaying and superimposing the virtual surgical guide, using the one or more head mounted displays, onto the physical joint based at least in part on coordinates of the predetermined position of the virtual surgical guide, and aligning the physical surgical guide or a physical saw blade with the virtual surgical guide to guide a bone cut of the joint.

In some embodiments, the one or more head mounted displays are registered in a common coordinate system. In some embodiments, the common coordinate system is a shared coordinate system.

In some embodiments, the virtual surgical guide is configured to guide a bone cut in a knee replacement, hip replacement, shoulder joint replacement or ankle joint replacement.

In some embodiments, the predetermined position of the virtual surgical guide determines a tibial slope for implantation of one or more tibial implant components in a knee replacement.

In some embodiments, the predetermined position of the virtual surgical guide determines an angle of *varus* or *valgus* correction for a femoral and/or a tibial component in a knee replacement.

In some embodiments, the virtual surgical guide corresponds to a physical distal femoral guide or cut block and the predetermined position of the virtual surgical guide determines a femoral component flexion.

In some embodiments, the virtual surgical guide corresponds to a physical anterior or posterior femoral surgical guide or cut block and the predetermined position of the virtual surgical guide determines a femoral component rotation.

In some embodiments, the virtual surgical guide corresponds to a physical chamfer femoral guide or cut block.

In some embodiments, the virtual surgical guide corresponds to a physical multi-cut femoral guide or cut block and the predetermined position of the virtual surgical guide determines one or more of an anterior cut, posterior cut, chamfer cuts and a femoral component rotation.

In some embodiments, the virtual surgical guide is used in a hip replacement and the predetermined position of the virtual surgical guide determines a leg length after implantation.

In some embodiments, the virtual surgical guide is a virtual plane for aligning the physical saw blade to guide the bone cut of the joint.

In some embodiments, the one or more intraoperative measurements include detecting one or more fiducial marker, sub-array, and/or array attached to a patient's joint, an operating room table, fixed structures in the operating room, one or more head mounted displays or combinations thereof. In some embodiments, one or more cameras or image capture or video capture systems and/or a 3D scanner included in the head mounted display can detect one or more fiducial marker, sub-array, and/or array including their coordinates (x, y, z) and at least one or more of a position, orientation, alignment, direction of movement or speed of movement of the one or more optical markers.

In some embodiments, registration of one or more of head mounted displays, surgical site, joint, spine, surgical instruments or implant components can be performed using spatial mapping techniques.

In some embodiments, registration of one or more of head mounted displays, surgical site, joint, spine, surgical instruments or implant components can be performed using depth sensors.

In some embodiments, the virtual surgical guide is configured to guide a bone cut of a distal tibia or a talus in an ankle joint replacement and the one or more head mounted display is configured to align the virtual surgical guide based on a predetermined tibial or talar implant component alignment, wherein the predetermined tibial or talar implant component alignment includes a coronal plane implant component alignment, a sagittal plane implant component alignment, an axial plane component alignment, an implant component rotation of an implant component or combinations thereof.

In some embodiments, the virtual surgical guide is configured to guide a bone cut of a proximal humerus in a shoulder joint replacement and wherein the one or more head mounted display is configured to align the virtual surgical guide based on a predetermined humeral implant component alignment, wherein the humeral implant component alignment includes a coronal plane implant component alignment, a sagittal plane implant component alignment, an axial plane component alignment, a humeral implant component rotation, or combinations thereof.

Aspects of the disclosure relate to a system comprising at least one head mounted display and a library of virtual implants, wherein the library of virtual implants comprises at least one virtual implant component, wherein the virtual implant component has at least one dimension that corresponds to a dimension of the implant component or has a dimension that is substantially identical to the dimension of the implant component, wherein the at least one head mounted display is configured to display the virtual implant component in substantial alignment with a tissue intended for placement of the implant component, wherein the placement of the virtual implant component is intended to achieve a predetermined implant component position and/or orientation. In some embodiments, the system further comprises at least one user interface.

Aspects of the disclosure relate to methods of selecting an implant or a prosthesis in three dimensions in a surgical site of a physical joint of a patient. In some embodiments, the method comprises registering, in a coordinate system, one or more head mounted displays worn by one or more users. In some embodiments, the head mounted display is a see-through head mounted display. In some embodiments, the method comprises obtaining one or more intra-operative measurements from the physical joint of the patient to determine one or more intra-operative coordinates. In some embodiments, the method comprises registering the one or more intra-operative coordinates from the physical joint of the patient in the coordinate system. In some embodiments, the method comprises displaying a three-dimensional graphical representation of a first implant or prosthesis projected over the physical joint using the one or more head mounted displays. In some embodiments, the three-dimensional graphical representation of the first implant or prosthesis is from a library of three-dimensional graphical representations of physical implants or prostheses. In some embodiments, the three-dimensional graphical representation corresponds to at least one portion of the physical implant or prosthesis. In some embodiments, the method comprises moving the three-dimensional graphical representation of the first implant or prosthesis to align with or to be near with or to intersect one or more of an internal or external margin, periphery, edge, perimeter, anteroposterior, mediolateral, oblique dimension, diameter, radius, curvature, geometry, shape or surface of one or more structures of the physical joint.

In some embodiments, the method comprises visually evaluating the fit or alignment between the three-dimensional graphical representation of the first implant or prosthesis and the one or more of an internal or external margin, periphery, edge, perimeter, anteroposterior, mediolateral, oblique dimension, diameter, radius, curvature, geometry, shape or surface, of the one or more structures of the physical joint. In some embodiments, the method comprises repeating the steps of displaying, optionally moving and visually evaluating the fit or alignment with one or more three-dimensional graphical representations of one or more additional physical implants or prostheses, wherein the one or more additional physical implants or prostheses have one or more of a different dimension, size, diameter, radius, curvature, geometry shape or surface than the first and subsequently evaluated implant or prosthesis. In some embodiments, the method comprises selecting a three-dimensional graphical representation of an implant or prosthesis with a satisfactory fit relative to the one or more structures of the physical joint from the library of three-dimensional graphical representations of physical implants or prostheses.

In some embodiments, the method comprises obtaining one or more intra-operative measurements from the physical joint of the patient to determine one or more intra-operative coordinates and registering the one or more intra-operative coordinates from the physical joint of the patient in a coordinate system.

In some embodiments, the step of visually evaluating the fit includes comparing one or more of a radius, curvature, geometry, shape or surface of the graphical representation of the first or subsequent prosthesis with one or more of an articular radius, curvature, shape or geometry of the joint. In some embodiments, the graphical representation of the first or subsequent implant or prosthesis is moved to improve the fit between the one or more of a radius, curvature, geometry, shape or surface of the graphical representation of the first or subsequent prosthesis and the one or more of an articular radius, curvature, shape or geometry of the joint. In some embodiments, the one or more of the size, location, position, and orientation of the selected graphical representation of the implant or prosthesis with its final coordinates is used to develop or modify a surgical plan for implantation of the implant or prosthesis. In some embodiments, the one or more of the location, position or orientation of the selected graphical representation is used to determine one or more bone resections for implantation of the implant or prosthesis. In some embodiments, the one or more of an internal or external margin, periphery, edge, perimeter, anteroposterior, mediolateral, oblique dimension, diameter, radius, curvature, geometry, shape or surface of one or more structures of the physical joint have not been surgically altered. In other embodiments, the one or more of an internal or external margin, periphery, edge, perimeter, anteroposterior, mediolateral, oblique dimension, diameter, radius, curvature, geometry, shape or surface of one or more structures of the physical joint have been surgically altered. For example, the surgically altering can include removal of bone or cartilage. In some embodiments, the bone removal can be a bone cut.

In some embodiments, the head mounted display is a see-through head mounted display. In some embodiments, the head mounted display is a virtual reality type head mounted display and the joint of the patient is imaged using one or more cameras and the images are displayed by the head mounted display.

In some embodiments, the satisfactory fit includes a fit within 1, 2, 3, 4 or 5 mm distance between the selected graphical representation of the prosthesis and at least portions of the one or more of an internal or external margin, periphery, edge, perimeter anteroposterior, mediolateral, oblique dimension, radius, curvature, geometry, shape or surface, of the one or more structures of the physical joint.

In some embodiments, the one or more structures of the physical joint include one or more anatomic landmarks. In some embodiments, the one or more anatomic landmarks define one or more anatomical or biomechanical axes.

In some embodiments, the steps of moving and visually evaluating the fit of the graphical representation of the prosthesis include evaluating the alignment of the graphical representation of the prosthesis relative to the one or more anatomic or biomechanical axis.

In some embodiments, the step of moving the three-dimensional graphical representation of the prosthesis is performed with one, two, three, four, five or six degrees of freedom. In some embodiments, the step of moving the three-dimensional graphical representation of the prosthesis includes one or more of translation or rotation of the three-dimensional graphical representation of the prosthesis.

In some embodiments, the step of visually evaluating the fit or alignment between the three-dimensional graphical representation of the first or subsequent prosthesis includes comparing one or more of an anteroposterior or mediolateral dimension of one or more of the prosthesis components with one or more with one or more of an anteroposterior or mediolateral dimension of the distal femur or the proximal tibia of the joint. In some embodiments, the step of visually evaluating the fit or alignment between the three-dimensional graphical representation of the first or subsequent prosthesis includes comparing one or more of a dimension, size, radius, curvature, geometry shape or surface of at least portions of the prosthesis with one or more of a dimension, size, radius, curvature, geometry shape or surface of at least portions of a medial condyle or a lateral condyle of the joint.

In some embodiments, the joint is a knee joint and the prosthesis includes one or more components of a knee replacement device. In some embodiments, the joint is a hip joint and the prosthesis includes one or more components of a hip replacement device. In some embodiments, the joint is a shoulder joint and the prosthesis includes one or more components of a shoulder replacement device. In some embodiments, the joint is an ankle and the prosthesis includes one or more components of an ankle replacement device.

In some embodiments, the library of three-dimensional graphical representations of physical implants or prostheses includes symmetrical and asymmetrical implant's or prosthesis' components. In some embodiments, the symmetrical or asymmetrical implant's or prosthesis' components include at least one of symmetrical and asymmetrical femoral components and symmetrical and asymmetrical tibial components.

Aspects of the disclosure relate to methods of selecting a medical device in three dimensions in a physical site of a patient selected for implantation. In some embodiments, the method comprises registering, in a coordinate system, one or more head mounted displays worn by a user. In some embodiments, the method comprises obtaining one or more measurements from the physical site of the patient to determine one or more coordinates. In some embodiments, the method comprises registering the one or more coordinates from the physical site of the patient in the coordinate system. In some embodiments, the method comprises displaying a three-dimensional graphical representation of a first medical device projected over the physical site using the one or more head mounted displays. In some embodiments, the three-dimensional graphical representation of the first medical device is from a library of three-dimensional graphical representations of physical medical devices and the three-dimensional graphical representation corresponds to at least one portion of the physical first medical device.

In some embodiments, the method comprises moving the three-dimensional graphical representation of the first medical device to align with or to be near with or to intersect one or more of an internal or external margin, periphery, edge, perimeter, anteroposterior, mediolateral, oblique dimension, diameter, radius, curvature, geometry, shape or surface of one or more structures at the physical site. In some embodiments, the method comprises visually evaluating the fit or alignment between the three-dimensional graphical representation of the first medical device and the one or more of an internal or external margin, periphery, edge, perimeter, anteroposterior, mediolateral, oblique dimension, diameter, radius, curvature, geometry, shape or surface, of the one or more structures at the physical site. In some embodiments, the method comprises repeating the steps of displaying, optionally moving and visually evaluating the fit or alignment with one or more three-dimensional graphical representations of one or more additional physical medical devices, wherein the one or more additional physical medical devices have one or more of a different dimension, size, diameter, radius, curvature, geometry shape or surface than the first and subsequently evaluated medical device. In some embodiments, the method comprises selecting a three-dimensional graphical representation of a medical device with a satisfactory fit relative to the one or more structures at the physical site from the library of three-dimensional graphical representations of physical medical devices.

In some embodiments, the one or more structures at the physical site include an anatomic or pathologic tissue intended for implantation. In some embodiments, the one or more structures at the physical site include an anatomic or pathologic tissue surrounding or adjacent or subjacent to the intended implantation site. In some embodiments, the one or more structures at the physical site include a pre-existing medical device near the implantation site or adjacent or subjacent or opposing or articulating with or to be connected with the medical device planned for implantation. In some embodiments, the one or more structures at the physical site include a one or more of a tissue, organ or vascular surface, diameter, dimension, radius, curvature, geometry, shape or volume.

In some embodiments, the one or more head mounted displays are registered with the physical surgical site, using, for example, one or more markers, e.g. attached to the surgical site or attached near the surgical site (for example by attaching the one or more markers to an anatomic structure), one or more of a pre- or intra-operative imaging study. The one or more HMDs can display live images of the physical surgical site, one or more of a pre- or intra-operative imaging study, 2D or 3D images of the patient, graphical representations of one or more medical devices, and/or CAD files of one or more medical devices. In some embodiments, the one or more HMDs are registered in relationship to at least one marker, e.g. attached to the patient, for example a bony structure in a spine, knee, hip, shoulder or ankle joint, or attached to the OR table or another structure in the operating room.

In some embodiments, the information from the one or more structures at the physical site and from the one or more of a pre- or intra-operative imaging study, 2D or 3D images of the patient, graphical representations of one or more medical devices, CAD files of one or more medical devices are used to select one or more of an anchor or attachment mechanism or fixation member.

In some embodiments, the information from the one or more structures at the physical site and from the one or more of a pre- or intra-operative imaging study, 2D or 3D images of the patient, graphical representations of one or more medical devices, CAD files of one or more medical devices are used to direct one or more of an anchor or attachment mechanism or fixation member.

In some embodiments, the medical device is one or more of an implant or a tool or an instrument. In some embodiments, the implant is an implant component. In some embodiments, the medical device can be, but not limited to, a joint replacement implant, a stent, a wire, a catheter, a screw, an otoplasty prosthesis, a dental implant, a dental implant component, a prosthetic disk, a catheter, a guide wire, a coil, an aneurysm clip.

Aspects of the disclosure relate to methods of aligning an implant or a prosthesis in a joint of a patient. In some embodiments, the method comprises registering, in a coordinate system, one or more head mounted displays worn by a user. In some embodiments, the method comprises obtaining one or more intra-operative measurements from the physical joint of the patient to determine one or more coordinates of the physical joint. In some embodiments, the method comprises registering the one or more coordinates of the physical joint of the patient in the coordinate system. In some embodiments, the method comprises displaying a three-dimensional graphical representation of an implant or implant component or a prosthesis or prosthesis component projected over the physical joint using the one or more head mounted displays, wherein the three-dimensional graphical representation corresponds to at least one portion of the physical prosthesis. In some embodiments, the method comprises moving the three-dimensional graphical representation of the prosthesis to align with or to be near with or to intersect one or more of an internal or external margin, periphery, edge, perimeter, anteroposterior, mediolateral, oblique dimension, diameter, radius, curvature, geometry, shape or surface of one or more structures of the physical joint.

In some embodiments, the method comprises registering one or more coordinates from the graphical representation of the prosthesis in the coordinate system after the moving and aligning.

In some embodiments, the moving of the three-dimensional graphical representation of the implant or prosthesis is performed using one or more of a computer interface (also referred to user interface), an acoustic interface, optionally including voice recognition, a virtual interface, optionally including gesture recognition. In some embodiments, the one or more coordinates from the graphical representation of the prosthesis in the coordinate system after the moving and aligning are used to derive or modify a surgical plan. In some embodiments, the one or more coordinates from the graphical representation of the implant or prosthesis in the coordinate system after the moving and aligning are used to determine one or more of a location, orientation, or alignment or coordinates of a bone removal for placing the implant or prosthesis. In some embodiments, the bone removal is one or more of a bone cut, a burring, a drilling, a pinning, a reaming, or an impacting. In some embodiments, the surgical plan is used to derive one or more of a location, position, orientation, alignment, trajectory, plane, start point, or end point for one or more surgical instruments. In some embodiments, the one or more of a location, orientation, or alignment or coordinates of bone removal are used to derive one or more of a location, position, orientation, alignment, trajectory, plane, start point, or end point for one or more surgical instruments. In some embodiments, the one or more head mounted displays visualize the one or more of a location, position, orientation, alignment, trajectory, plane, start point, or end point for one or more surgical instruments projected onto and registered with the physical joint. In some embodiments, the prosthesis is an acetabular cup of a hip replacement and wherein a graphical representation of the acetabular up is aligned with at least a portion of the physical acetabular rim of the patient. In some embodiments, the implant or prosthesis is a femoral component of a hip replacement and wherein a graphical representation of the femoral component is aligned with at least a portion of the physical endosteal bone or cortical bone of the patient. In some embodiments, the aligning means positioning the femoral component in substantially equidistant location between at least a portion of one or more of an anterior and a posterior endosteal or cortical bone or a medial and a lateral endosteal bone or cortical bone. In some embodiments, the femoral component includes a femoral neck. In some embodiments, the one or more coordinates from the femoral component in the coordinate system after the moving and aligning is used to determine at least one of a femoral component stem position, a femoral component stem orientation, a femoral component neck angle, a femoral component offset, and a femoral component neck anteversion. In some embodiments, the implant or prosthesis is a glenoid component of a shoulder replacement and wherein a graphical representation of the glenoid component is aligned with at least a portion of the physical glenoid rim of the patient. In some embodiments, the implant or prosthesis is a humeral component of a shoulder replacement and wherein a graphical representation of the humeral component is aligned with at least a portion of the physical endosteal bone or cortical bone of the patient. In some embodiments, the aligning means positioning the humeral component in substantially equidistant location between at least a portion of one or more of an anterior and a posterior endosteal or cortical bone or a medial and a lateral endosteal bone or cortical bone. In some embodiments, the humeral component includes a humeral neck. In some embodiments, the one or more coordinates from the humeral component in the coordinate system after the moving and aligning is used to determine at least one of a humeral component stem position, a humeral component stem orientation, a humeral component neck angle, a humeral component offset, and a humeral component neck anteversion. In some embodiments, the one or more of a margin, periphery, edge, perimeter, anteroposterior, mediolateral, oblique dimension, diameter, radius, curvature, geometry, shape or surface of one or more structures of the physical joint includes one or more of a cartilage, normal cartilage, damaged or diseased cartilage, subchondral bone or osteophyte. In some embodiments, the one or more of a margin, periphery, edge, perimeter, anteroposterior, mediolateral, oblique dimension, diameter, radius, curvature, geometry, shape or surface of one or more structures of the physical joint excludes one or more of a cartilage, normal cartilage, damaged or diseased cartilage, subchondral bone or osteophyte. In some embodiments, the one or more head mounted displays display registered with and superimposed onto the physical joint one or more of a pre- or intra-operative imaging study, 2D or 3D images of the patient, graphical representations of one or more medical devices, CAD files of one or more medical devices, wherein the display assists with the moving and aligning of the three-dimensional graphical representation of the graphical representation of the prosthesis. In some embodiments, the implant or prosthesis is a femoral component or a tibial component of a knee replacement system, wherein the one or more coordinates from the graphical representation of the implant or prosthesis in the coordinate system after the moving and aligning include a center of the graphical representation of the femoral component or a center of the graphical representation of the tibial component. In some embodiments, the moving or aligning includes aligning the femoral component on the distal femur. In some embodiments, the aligning includes aligning the femoral component substantially equidistant to a medial edge of the medial femoral condyle and the lateral edge of a lateral femoral condyle. In some embodiments, the aligning includes aligning the femoral component tangent with the articular surface of at least one of the medial condyle and the lateral condyle in at least one of a distal weight-bearing zone or a weight-bearing zone at 5, 10, 15, 20, 25, 30, 40 or 45 degrees of knee flexion. In some embodiments, the moving or aligning includes aligning the tibial component on the proximal tibia. In some embodiments, the aligning includes aligning the tibial component substantially equidistant to a medial edge of the medial tibial plateau and the lateral edge of a lateral tibial plateau and/or the anterior edge of the anterior tibial plateau and the posterior edge of the posterior tibial plateau or centered over the tibial spines. In some embodiments, the aligning includes aligning the tibial component tangent with at least portions of the articular surface of at least one of the medial tibial plateau and the lateral tibial plateau.

In some embodiments, the center of the graphical representation of the femoral component after the aligning and the center of the hip joint are used to determine a femoral mechanical axis. In some embodiments, the center of the graphical representation of the tibial component after aligning and the center of the ankle joint are used to determine a tibial mechanical axis. In some embodiments, the femoral and tibial mechanical axes are used to determine a desired leg axis correction relative to the mechanical axis of the leg. In some embodiments, the leg axis correction is one of a full correction to normal mechanical axis, partial correction to normal mechanical axis or no correction to normal mechanical axis. In some embodiments, the leg axis correction is used to determine the coordinates and/or alignment for the bone removal or bone cuts. In some embodiments, the bone removal or bone cuts for a full correction to normal mechanical axis or a partial correction to normal mechanical axis or no correction to normal mechanical axis are used to adjust the femoral and/or tibial prosthesis coordinates. In some embodiments, the bone removal or bone cuts are executed using at least one of a robot guidance, a surgical navigation system and visual guidance using the one or more of an head mounted displays. In some embodiments, the one or more head mounted display project a graphical representation of one or more of a cut block, a cut plane or a drill path registered with and superimposed onto the physical joint for aligning one or more of a physical cut guide, a saw blade or a drill.

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. The term live data of the patient, as used herein, includes the surgical site, anatomy, anatomic structures or tissues and/or pathology, pathologic structures or tissues of the patient as seen by the surgeon's or viewer's eyes without information from virtual data, stereoscopic views of virtual data, or imaging studies. The term live data of the patient does not include internal or subsurface tissues or structures or hidden tissues or structures that can only be seen with assistance of a computer monitor or HMD.

The terms real surgical instrument, actual surgical instrument, physical surgical instrument and surgical instrument are used interchangeably throughout the application; the terms real surgical instrument, actual surgical instrument, physical surgical instrument and surgical instrument do not include virtual surgical instruments. For example, the physical surgical instruments can be surgical instruments provided by manufacturers or vendors for spinal surgery, pedicle screw instrumentation, anterior spinal fusion, knee replacement, hip replacement, ankle replacement and/or shoulder replacement; physical surgical instruments can be, for example, cut blocks, pin guides, awls, reamers, impactors, broaches. Physical surgical instruments can be re-useable or disposable or combinations thereof. Physical surgical instruments can be patient specific. The term virtual surgical instrument does not include real surgical instrument, actual surgical instrument, physical surgical instrument and surgical instrument.

The terms real surgical tool, actual surgical tool, physical surgical tool and surgical tool are used interchangeably throughout the application; the terms real surgical tool, actual surgical tool, physical surgical tool and surgical tool do not include virtual surgical tools. The physical surgical tools can be surgical tools provided by manufacturers or vendors. For example, the physical surgical tools can be pins, drills, saw blades, retractors, frames for tissue distraction and other tools used for orthopedic, neurologic, urologic or cardiovascular surgery. The term virtual surgical tool does not include real surgical tool, actual surgical tool, physical surgical tool and surgical tool.

The terms real implant or implant component, actual implant or implant component, physical implant or implant component and implant or implant component are used interchangeably throughout the application; the terms real implant or implant component, actual implant or implant component, physical implant or implant component and implant or implant component do not include virtual implant or implant components. The physical implants or implant components can be implants or implant components provided by manufacturers or vendors. For example, the physical surgical implants can be a pedicle screw, a spinal rod, a spinal cage, a femoral or tibial component in a knee replacement, an acetabular cup or a femoral stem and head in hip replacement. The term virtual implant or implant component does not include real implant or implant component, actual implant or implant component, physical implant or implant component and implant or implant component.

The terms "image capture system", "video capture system", "image or video capture system", "image and/or video capture system, and/or optical imaging system" can be used interchangeably. In some embodiments, a single or more than one, e.g. two or three or more, image capture system, video capture system, image or video capture system, image and/or video capture system, and/or optical imaging system can be used in one or more locations (e.g. in one, two, three, or more locations), for example integrated into, attached to or separate from an HMD, attached to an OR table, attached to a fixed structure in the OR, integrated or attached to or separate from an instrument, integrated or attached to or separate from an arthroscope, integrated or attached to or separate from an endoscope, internal to the patient's skin, internal to a surgical site, internal to a target tissue, internal to an organ, internal to a cavity (e.g. an abdominal cavity or a bladder cavity or a cistern or a CSF space, or an internal to a vascular lumen), internal to a vascular bifurcation, internal to a bowel, internal to a small intestine, internal to a stomach, internal to a biliary structure, internal to a urethra and or urether, internal to a renal pelvis, external to the patient's skin, external to a surgical site, external to a target tissue, external to an organ, external to a cavity (e.g. an abdominal cavity or a bladder cavity or a cistern or a CSF space, or an external to a vascular lumen), external to a vascular bifurcation, external to a bowel, external to a small intestine, external to a stomach, external to a biliary structure, external to a urethra and or urether, and/or external to a renal pelvis. In some embodiments, the position and/or orientation and/or coordinates of the one or more image capture system, video capture system, image or video capture system, image and/or video capture system, and/or optical imaging system can be tracked using any of the registration and/or tracking methods described in the specification, e.g. direct tracking using optical imaging systems and/or a 3D scanner(s), in any of the foregoing locations and/or tissues and/or organs and any other location and/or tissue and/or organ described in the specification or known in the art. Tracking of the one or more image capture system, video capture system, image or video capture system, image and/or video capture system, and/or optical imaging system can, for example, be advantageous when the one or more 3D scanners are integrated into or attached to an instrument, an arthroscope, an endoscope, and/or when they are located internal to any structures, e.g. inside a joint or a cavity or a lumen.

In some embodiments, a single or more than one, e.g. two or three or more, 3D scanners can be present in one or more locations (e.g. in one, two, three, or more locations), for example integrated into, attached to or separate from an HMD, attached to an OR table, attached to a fixed structure in the OR, integrated or attached to or separate from an instrument, integrated or attached to or separate from an arthroscope, integrated or attached to or separate from an endoscope, internal to the patient's skin, internal to a surgical site, internal to a target tissue, internal to an organ, internal to a cavity (e.g. an abdominal cavity or a bladder cavity or a cistern or a CSF space, and/or internal to a vascular lumen), internal to a vascular bifurcation, internal to a bowel, internal to a small intestine, internal to a stomach, internal to a biliary structure, internal to a urethra and or urether, internal to a renal pelvis, external to the patient's skin, external to a surgical site, external to a target tissue, external to an organ, external to a cavity (e.g. an abdominal cavity or a bladder cavity or a cistern or a CSF space, and/or external to a vascular lumen), external to a vascular bifurcation, external to a bowel, external to a small intestine, external to a stomach, external to a biliary structure, external to a urethra and or urether, and/or external to a renal pelvis. In some embodiments, the position and/or orientation and/or coordinates of the one or more 3D scanners can be tracked using any of the registration and/or tracking methods described in the specification, e.g. direct tracking using optical imaging systems and/or a 3D scanner(s), in any of the foregoing locations and/or tissues and/or organs and any other location and/or tissue and/or organ mentioned in the specification or known in the art. Tracking of the one or more 3D scanners can, for example, be advantageous when the one or more 3D scanners are integrated into or attached to an instrument, an arthroscope, an endoscope, and/or when they are located internal to any structures, e.g. inside a joint or a cavity or a lumen.

In some embodiments, one or more image capture system, video capture system, image or video capture system, image and/or video capture system, and/or optical imaging system can be used in conjunction with one or more 3D scanners, e.g. in any of the foregoing locations and/or tissues and/or organs and any other location and/or tissue and/or organ described in the specification or known in the art.

With surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations of the first and the second virtual instruments are compared.

Aspects of the disclosure relates to devices, systems and methods for positioning a virtual path, virtual plane, virtual tool, virtual surgical instrument or virtual implant component in a mixed reality environment using a head mounted display device, optionally coupled to one or more processing units.

With guidance in mixed reality environment, a virtual surgical guide, tool, instrument or implant can be superimposed onto the physical joint, spine or surgical site. Further, the physical guide, tool, instrument or implant can be aligned with the virtual surgical guide, tool, instrument or implant displayed or projected by the HMD. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In some embodiments, the HMD can display one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration.

In some embodiments, the one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration can be displayed by the HMD at one or more predetermined coordinates, e.g. indicating a predetermined position predetermined orientation or combination thereof for superimposing and/or aligning a physical surgical tool, physical surgical instrument, physical implant, or a physical device.

In some embodiments, one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration displayed by the HMD can be a placement indicator for one or more of a physical surgical tool, physical surgical instrument, physical implant, or a physical device.

Any of a position, location, orientation, alignment, direction, speed of movement, force applied of a surgical instrument or tool, virtual and/or physical, can be predetermined using, for example, pre-operative imaging studies, pre-operative data, pre-operative measurements, intra-operative imaging studies, intra-operative data, and/or intra-operative measurements.

Any of a position, location, orientation, alignment, sagittal plane alignment, coronal plane alignment, axial plane alignment, rotation, slope of implantation, angle of implantation, flexion of implant component, offset, anteversion, retroversion, and position, location, orientation, alignment relative to one or more anatomic landmarks, position, location, orientation, alignment relative to one or more anatomic planes, position, location, orientation, alignment relative to one or more anatomic axes, position, location, orientation, alignment relative to one or more biomechanical axes, position, location, orientation, alignment relative to a mechanical axis of a trial implant, an implant component or implant, virtual and/or physical, can be predetermined using, for example, pre-operative imaging studies, pre-operative data, pre-operative measurements, intra-operative imaging studies, intra-operative data, and/or intra-operative measurements. Intra-operative measurements can include measurements for purposes of registration, e.g. of a joint, a spine, a surgical site, a bone, a cartilage, a HMD, a surgical tool or instrument, a trial implant, an implant component or an implant.

In some embodiments throughout the specification, measurements can include measurements of coordinate(s) or coordinate information. A coordinate can be a set of numbers used in specifying the location of a point on a line, on a surface, or in space, e.g. x, y, z. Coordinate can be predetermined, e.g. for a virtual surgical guide.

In some embodiments, multiple coordinate systems can be used instead of a common or shared coordinate system. In this case, coordinate transfers can be applied from one coordinate system to another coordinate system, for example for registering the HMD, live data of the patient including the surgical site, virtual instruments and/or virtual implants and physical instruments and physical implants.

Head Mounted Displays

In some embodiments, head mounted displays (HMDs) can be used. Head mounted displays can be of non-see through type (such as the Oculus VR HMD (Facebook, San Mateo, CA)), optionally with a video camera to image the live data of the patient as a video-see through head mounted display, or they can be of optical see through type as an optical see-through head mounted display or see-through optical head mounted display.

A head mounted display can include a first display unit for the left eye and a second display unit for the right eye. The first and second display units can be transparent, semi-transparent or non-transparent. The system, comprising, for example, the head mounted display, one or more computer processors and/or an optional marker attached to the patient, can be configured to generate a first view of virtual data, e.g. a virtual surgical guide, for the first display unit and a second view of virtual data, e.g. a virtual surgical guide, for the second display unit. The virtual data can be a placement indicator for a physical surgical tool, physical surgical instrument, physical implant or physical device. The virtual data, e.g. a virtual surgical guide, can be a three-dimensional digital representation at one or more predetermined coordinates indicating, for example, a predetermined position, predetermined orientation or combination thereof for superimposing and/or aligning a physical surgical tool, physical surgical instrument, physical implant or physical device.

The system can be configured to generate a first view displayed by a first display unit (e.g. for the left eye) and a second view displayed by a second display unit (e.g. for the right eye), wherein the first view and the second view create a 3D stereoscopic view of the virtual data, e.g. a virtual surgical guide, which can optionally be based on one or more predetermined coordinates. The system can be configured to display the 3D stereoscopic view by the head mounted display onto the patient.

In some embodiments, a pair of glasses is utilized. The glasses can include an optical head-mounted display. An optical see through head-mounted display (OHMD) can be a wearable display that has the capability of reflecting projected images as well as allowing the user to see through it. Various types of OHMDs known in the art can be used in order to practice embodiments of the present disclosure. These include curved mirror or curved combiner OHMDs as well as wave-guide or light-guide OHMDs. The OHMDs can optionally utilize diffraction optics, holographic optics, polarized optics, and reflective optics.

Traditional input devices that can be used with the HMDs include, but are not limited to touchpad or buttons, smartphone controllers, speech recognition, and gesture recognition. Advanced interfaces are possible, e.g. a brain-computer interface.

Optionally, a computer or server or a workstation can transmit data to the HMD. The data transmission can occur via cable, Bluetooth, WiFi, optical signals and any other method or mode of data transmission known in the art. The HMD can display virtual data, e.g. virtual data of the patient, in uncompressed form or in compressed form. Virtual data of a patient can optionally be reduced in resolution when transmitted to the HMD or when displayed by the HMD.

When virtual data are transmitted to the HMD, they can be in compressed form during the transmission. The HMD can then optionally decompress them so that uncompressed virtual data are being displayed by the HMD.

Alternatively, when virtual data are transmitted to the HMD, they can be of reduced resolution during the transmission, for example by increasing the slice thickness of image data prior to the transmission. The HMD can then optionally increase the resolution, for example by re-interpolating to the original slice thickness of the image data or even thinner slices so that virtual data with resolution equal to or greater than the original virtual data or at least greater in resolution than the transmitted data are being displayed by the HMD.

In some embodiments, the HMD can transmit data back to a computer, a server or a workstation. Such data can include, but are not limited to:

- Positional, orientational or directional information about the HMD or the operator or surgeon wearing the HMD
- Changes in position, orientation or direction of the HMD
- Data generated by one or more IMU's
- Data generated by markers (radiofrequency, optical, light, other) attached to, integrated with or coupled to the HMD
- Data generated by a surgical navigation system attached to, integrated with or coupled to the HMD, including position and/or orientation and/or coordinates of one or more fiducial marker, sub-array, and/or array, e.g. attached to the same HMD or a separate, e.g. second HMD
- Data generated by an image and/or video capture system attached to, integrated with or coupled to the HMD, including position and/or orientation and/or coordinates of one or more fiducial marker, sub-array, and/or array, e.g. attached to the same HMD or a separate, e.g. second HMD
- Parallax data, e.g. using two or more image and/or video capture systems attached to, integrated with or coupled to the HMD, for example one positioned over or under or near the left eye and a second positioned over or under or near the right eye
- Distance data, e.g. parallax data generated by two or more image and/or video capture systems evaluating changes in distance between the HMD and a surgical field or an object
- Motion parallax data
- Data related to calibration or registration phantoms (see other sections of this specification)
- Any type of live data of the patient captured by the HMD including image and/or video capture systems attached to, integrated with or coupled to the HMD
  - For example, alterations to a live surgical site
  - For example, use of certain surgical instruments detected by the image and/or video capture system
  - For example, use of certain medical devices or trial implants detected by the image and/or video capture system
- Any type of modification to a surgical plan
  - Portions or aspects of a live surgical plan
  - Portions or aspects of a virtual surgical plan Radiofrequency tags used throughout the embodiments can be of active or passive kind with or without a battery.

Exemplary optical see through head mounted displays include the ODG R-7, R-8 and R-8 smart glasses from ODG (Osterhout Group, San Francisco, CA), the NVIDIA 942

3-D vision wireless glasses (NVIDIA, Santa Clara, CA) the Microsoft Hololens and Hololens 2 (Microsoft, Redmond, WI), the Daqri Smart Glass (Daqri, Los Angeles, CA) the Meta2 (Meta Vision, San Mateo, CA), the Moverio BT-300 (Epson, Suwa, Japan), the Blade 3000 and the Blade M300 (Vuzix, West Henrietta, NY), Nreal Developer version or Nreal Light (Nreal, Beijing, China) and the Lenovo ThinkA6 (Lenovo, Beijing, China). The Microsoft Hololens is manufactured by Microsoft. It is a pair of augmented reality smart glasses. Hololens is a see through optical head mounted display (or optical see through head mounted display) 1125 (see FIG. 1). Hololens can use the Windows 10 operating system. The front portion of the Hololens includes, among others, sensors, related hardware, several cameras and processors. The visor includes a pair of transparent combiner lenses, in which the projected images are displayed. The Hololens can be adjusted for the interpupillary distance (IPD) using an integrated program that recognizes gestures. A pair of speakers is also integrated. The speakers do not exclude external sounds and allow the user to hear virtual sounds. A USB 2.0 micro-B receptacle is integrated. A 3.5 mm audio jack is also present. The Hololens has an inertial measurement unit (IMU) with an accelerometer, gyroscope, and a magnetometer, four environment mapping sensors/cameras (two on each side), a depth camera with a 120°×120° angle of view, a 2.4-megapixel photographic video camera, a four-microphone array, and an ambient light sensor. Hololens has an Intel Cherry Trail SoC containing the CPU and GPU. Hololens includes also a custom-made Microsoft Holographic Processing Unit (HPU). The SoC and the HPU each have 1 GB LPDDR3 and share 8 MB SRAM, with the SoC also controlling 64 GB eMMC and running the Windows 10 operating system. The HPU processes and integrates data from the sensors, as well as handling tasks such as spatial mapping, gesture recognition, and voice and speech recognition. Hololens includes a IEEE 802.11ac Wi-Fi and Bluetooth 4.1 Low Energy (LE) wireless connectivity. The headset uses Bluetooth LE and can connect to a clicker, a finger-operating input device that can be used for selecting menus and functions.

A number of applications are available for Microsoft Hololens, for example a catalogue of holograms, HoloStudio, a 3D modelling application by Microsoft with 3D print capability, Autodesk Maya 3D creation application, FreeForm, integrating Hololens with the Autodesk Fusion 360 cloud-based 3D development application, and others. Hololens utilizing the HPU can employ sensual and natural interface commands-voice, gesture, and gesture. Gaze commands, e.g. head-tracking, allows the user to bring application focus to whatever the user is perceiving. Any virtual application or button can be selected using an air tap method, similar to clicking a virtual computer mouse. The tap can be held for a drag simulation to move a display. Voice commands can also be utilized. The Hololens shell utilizes many components or concepts from the Windows desktop environment. A bloom gesture for opening the main menu is performed by opening one's hand, with the palm facing up and the fingers spread. Windows can be dragged to a particular position, locked and/or resized. Virtual windows or menus can be fixed at locations or physical objects. Virtual windows or menus can move with the user or can be fixed in relationship to the user. Or they can follow the user as he or she moves around. The Microsoft Hololens App for Windows 10 PC's and Windows 10 Mobile devices can be used by developers to run apps and to view live stream from the Hololens user's point of view, and to capture augmented reality photos and videos. Almost all Universal Windows Platform apps can run on Hololens. These apps can be projected in 2D. Select Windows 10 APIs are currently supported by Hololens. Hololens apps can also be developed on Windows 10 PC's. Holographic applications can use Windows Holographic APIs. Unity (Unity Technologies, San Francisco, CA) and Vuforia (PTC, Inc., Needham, MA) are some apps that can be utilized. Applications can also be developed using DirectX and Windows API's.

Many of the embodiments throughout the specification can be implemented also using non-see through head mounted displays, e.g. virtual reality head mounted displays. Non-see through head mounted displays can be used, for example, with one or more image or video capture systems (e.g. cameras) or 3D scanners to image the live data of the patient, e.g. a skin, a subcutaneous tissue, a surgical site, an anatomic landmark, an organ, or an altered tissue, e.g. a surgically altered tissue, as well as any physical surgical tools, instruments, devices and/or implants, or portions of the surgeon's body, e.g. his or her fingers, hands or arms. Non see through HMDs can be used, for example, for displaying virtual data, e.g. pre- or intra-operative imaging data of the patient, virtual surgical guides, virtual tools, virtual instruments, virtual implants and/or virtual implants, for example together with live data of the patient, e.g. from the surgical site, imaged through the one or more cameras or video or image capture systems or 3D scanners, for knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery. Exemplary non-see through head mounted displays, e.g. virtual reality head mounted displays, are, for example, the Oculus Rift (Google, Mountain View, CA), the HTC Vive (HTC, Taipei, Taiwan) and the Totem (Vrvana, Apple, Cupertino, CA).

Computer Graphics Viewing Pipeline

Figure 2:
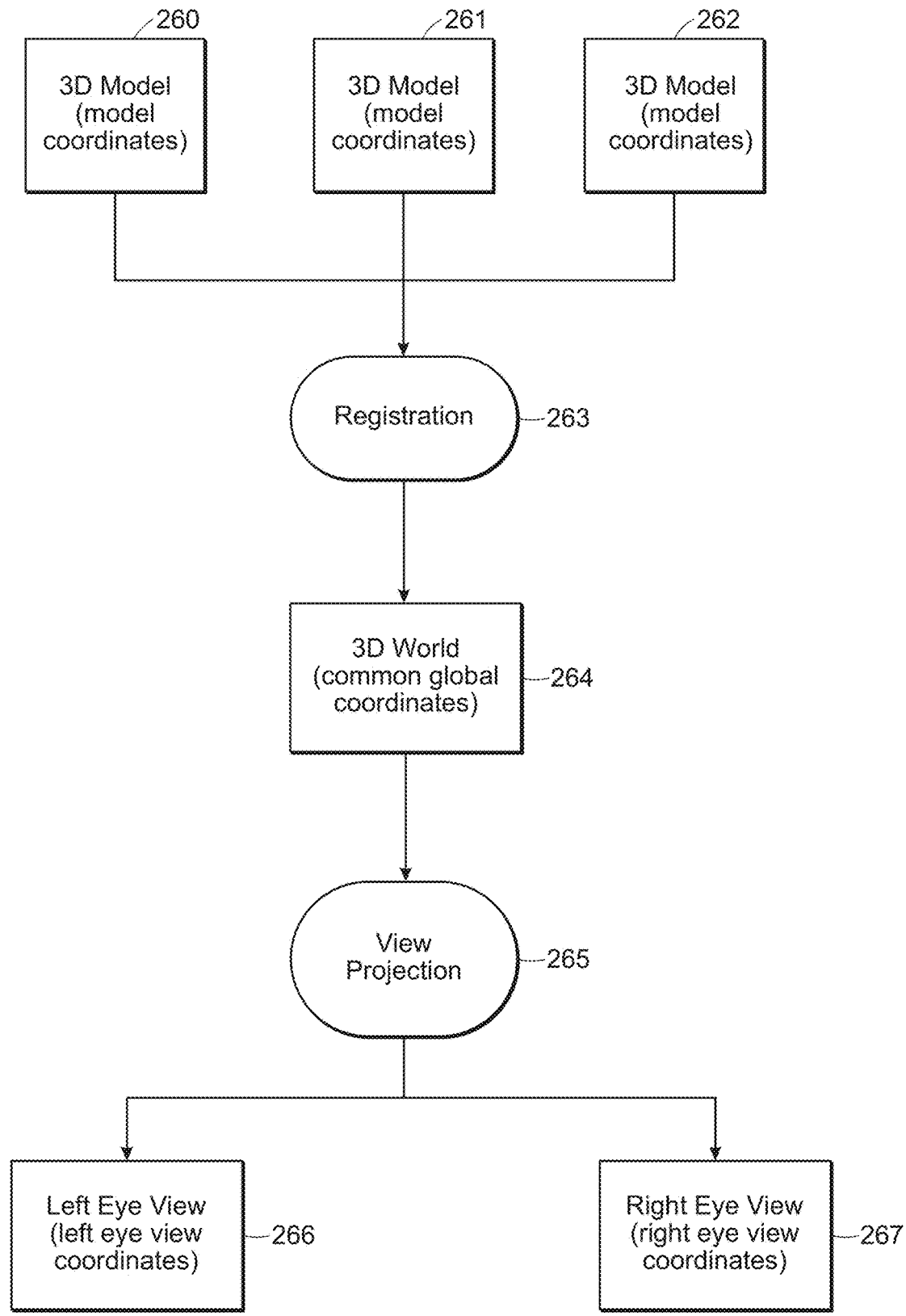
FIG. 2 is a flow chart summarizing model generation, registration and view projection for one or more head mounted displays (HMD), e.g. by a primary surgeon, second surgeon, surgical assistant nurse, or others according to some embodiments of the present disclosure.

In some embodiments, the head mounted display uses a computer graphics viewing pipeline that consists of the following steps to display 3D objects or 2D objects positioned in 3D space or other computer-generated objects and models FIG. 2:

1. Registration
2. View projection

Registration:

In some embodiments, the different objects to be displayed by the HMD computer graphics system (for instance virtual anatomical models, virtual models of instruments, geometric and surgical references and guides) are initially all defined in their own independent model coordinate system. During the registration process, spatial relationships between the different objects are defined, and each object is transformed from its own model coordinate system into a common global coordinate system. Different techniques that are described below can be applied for the registration process.

For augmented reality HMDs that superimpose computer-generated objects with live views of the physical environment, the global coordinate system is defined by the environment. A process called spatial mapping, described below, creates a computer representation of the environment that allows for merging and registration with the computer-generated objects, thus defining a spatial relationship between the computer-generated objects and the physical environment.

View Projection:

In some embodiments, once all objects to be displayed have been registered and transformed into the common global coordinate system, they are prepared for viewing on a display by transforming their coordinates from the global coordinate system into the view coordinate system and subsequently projecting them onto the display plane. This view projection step can use the viewpoint and view direction to define the transformations applied in this step. For stereoscopic displays, such as an HMD, two different view projections can be used, one for the left eye and the other one for the right eye. For see through HMDs (augmented reality HMDs) the position of the viewpoint and view direction relative to the physical environment can be known in order to correctly superimpose the computer-generated objects with the physical environment. As the viewpoint and view direction change, for example due to head movement, the view projections are updated so that the computer-generated display follows the new view.

Positional Tracking Systems

In some embodiments, the position and/or orientation of the HMDs can be tracked. For example, in order to calculate and update the view projection of the computer graphics view pipeline as described in the previous section and to display the computer-generated overlay images in the HMD, the view position and direction needs to be known.

Different methods to track the HMDs can be used. For example, the HMDs can be tracked using outside-in tracking. For outside-in tracking, one or more external sensors or cameras can be installed in a stationary location, e.g. on the ceiling, the wall or on a stand. In some embodiments, the location and/or orientation of the sensor or camera can be predetermined, e.g. in relationship to a patient, an anatomic structure, an OR table or a combination thereof. The sensors or camera capture the movement of the HMDs, for example through shape detection or markers attached to the HMDs or the user's head. The sensor data or camera image is typically processed on a central computer to which the one or more sensors or cameras are connected. The tracking information obtained on the central computer can then be used to compute the view projection for the HMD (including multiple HMDs). The view projection can be computed on the central computer or on the HMD. Outside-in tracking can be performed with use of surgical navigation system using, for example, infrared and/or RF markers, active and/or passive markers. One or more external infrared or RF emitters and receivers or cameras can be installed in a stationary location, e.g. on the ceiling, the wall or a stand or attached to the OR table. One or more infrared and/or RF markers, active and/or passive markers can be applied to the HMD for tracking the coordinates and/or the position and/or orientation of the HMD. One or more infrared and/or RF markers, active and/or passive markers can be applied to the anatomic structure or near the anatomic structure tracking the coordinates and/or the position and/or orientation of the anatomic structure. One or more infrared and/or RF markers, active and/or passive markers can be applied to a physical tool, physical instrument, physical implant or physical device tracking the coordinates and/or the position and/or orientation of the physical tool, physical instrument, physical implant or physical device. One or more infrared and/or RF markers, active and/or passive markers can be applied to the surgeon.

In some embodiments, outside-in tracking can be performed with use of an image capture or video capture system using, for example, optical markers, e.g. with geometric patterns. One or more external cameras can be installed in a stationary location, e.g. on the ceiling, the wall or a stand or attached to the OR table. One or more optical markers can be applied to the HMD for tracking the coordinates and/or the position and/or orientation of the HMD. One or more optical markers can be applied to the anatomic structure or near the anatomic structure tracking the coordinates and/or the position and/or orientation of the anatomic structure. One or more optical markers can be applied to a physical tool, physical instrument, physical implant or physical device tracking the coordinates and/or the position and/or orientation of the physical tool, physical instrument, physical implant or physical device. One or more optical markers can be applied to the surgeon.

In some embodiments, including for outside-in and inside-out tracking, a camera, image capture or video capture system can detect light from the spectrum visible to the human eye, e.g. from about 380 to 750 nanometers wavelength, or from about 400 to 720 nanometers wavelength, or from about 420 to 680 nanometers wavelength, or similar combinations. In embodiments throughout the specification, including for outside-in and inside-out tracking, a camera, image capture or video capture system can detect light from the spectrum not visible to the human eye, e.g. from the infrared spectrum, e.g. from 700 nm or above to, for example, 1 mm wavelength, 720 nm or above to, for example, 1 mm wavelength, 740 nm or above to, for example, 1 mm wavelength, or similar combinations. In embodiments throughout the specification, including for outside-in and inside-out tracking, a camera, image capture or video capture system can detect light from the spectrum visible and from the spectrum not visible to the human eye.

In some embodiments, including for outside-in and inside-out tracking, a marker, e.g. a marker with a geometric pattern and/or a marker used with a navigation system, can be configured to reflect or emit light from the spectrum visible to the human eye, e.g. from about 380 to 750 nanometers wavelength, or from about 400 to 720 nanometers wavelength, or from about 420 to 680 nanometers wavelength, or similar combinations. In embodiments throughout the specification, including for outside-in and inside-out tracking, a marker, e.g. a marker with a geometric pattern and/or a marker used with a navigation system, can be configured to reflect or emit light from the spectrum not visible to the human eye, e.g. from the infrared spectrum, e.g. from 700 nm or above to, for example, 1 mm wavelength, 720 nm or above to, for example, 1 mm wavelength, 740 nm or above to, for example, 1 mm wavelength, or similar combinations. In embodiments throughout the specification, including for outside-in and inside-out tracking, a marker, e.g. a marker with a geometric pattern and/or a marker used with a navigation system, can be configured to reflect or emit light from the spectrum visible and from the spectrum not visible to the human eye.

In some embodiments, outside-in tracking can be performed with use of a 3D scanner or a laser scanner. One or more external 3D scanners or laser scanners can be installed in a stationary location, e.g. on the ceiling, the wall or a stand or attached to the OR table. The 3D scanner or laser scanner can be used to track objects directly, e.g. the HMD, the anatomic structure, the physical tool, physical instrument, physical implant or physical device or the surgeon. Optionally, markers can be applied to one or more of the HMD, the anatomic structure, the physical tool, physical instrument, physical implant or physical device or the surgeon for tracking any of the foregoing using the 3D scanner or laser scanner.

In some embodiments, the inside-out tracking method can be employed. One or more sensors or cameras can be attached to the HMD or the user's head or integrated with the HMD. The sensors or cameras can be dedicated to the tracking functionality. The cameras attached or integrated into the HMD can include infrared cameras. Infrared LED's or emitters can also be included in the HMD. The sensors or cameras attached or integrated into the HMD can include an image capture system, a video capture system, a 3D scanner, a laser scanner, a surgical navigation system or a depth camera. In some embodiments, the data collected by the sensors or cameras is used for positional tracking as well as for other purposes, e.g. image recording or spatial mapping. Information gathered by the sensors and/or cameras is used to determine the HMD's position and orientation in 3D space. This can be done, for example, by detecting optical, infrared, RF or electromagnetic markers attached to the external environment. Changes in the position of the markers relative to the sensors or cameras are used to continuously determine the position and orientation of the HMD. Data processing of the sensor and camera information can be performed by a mobile processing unit attached to or integrated with the HMD, which can allow for increased mobility of the HMD user as compared to outside-in tracking. Alternatively, the data can be transmitted to and processed on the central computer.

Inside-out tracking can also utilize markerless techniques. For example, spatial mapping data acquired by the HMD sensors can be aligned with a virtual model of the environment, thus determining the position and orientation of the HMD in the 3D environment. Alternatively, or additionally, information from inertial measurement units can be used. Potential advantages of inside-out tracking include greater mobility for the HMD user, a greater field of view not limited by the viewing angle of stationary cameras and reduced or eliminated problems with marker occlusion.

Eye and Gaze Tracking Systems

Some aspects of the present disclosure provide for methods and devices of using the human eye including eye movements and lid movements as well as movements induced by the peri-orbital muscles for executing computer commands. Methods of executing computer commands by way of facial movements and movements of the head are provided.

Command execution induced by eye movements and lid movements as well as movements induced by the peri-orbital muscles, facial movements and head movements can be advantageous in environments where an operator does not have his hands available to type on a keyboard or to execute commands on a touchpad or other hand-computer interface. Such situations include, but are not limited, to industrial applications including automotive and airplane manufacturing, chip manufacturing, medical or surgical procedures and many other potential applications.

In some embodiments, the head mount display can include an eye tracking system. Different types of eye tracking systems can be utilized. The examples provided below are in no way thought to be limiting. Any eye tracking system known in the art now can be utilized.

Eye movement can be divided into fixations and saccades—when the eye gaze pauses in a certain position, and when it moves to another position, respectively. The resulting series of fixations and saccades can be defined as a scan path. The central one or two degrees of the visual angle provide most of the visual information; the input from the periphery is less informative. Thus, the locations of fixations along a scan path show what information locations were processed during an eye tracking session, for example during a surgical procedure.

Eye trackers can measure rotation or movement of the eye in several ways, for example via measurement of the movement of an object (for example, a form of contact lens) attached to the eye, optical tracking without direct contact to the eye, and measurement of electric potentials using electrodes placed around the eyes.

If an attachment to the eye is used, it can, for example, be a special contact lens with an embedded mirror or magnetic field sensor. The movement of the attachment can be measured with the assumption that it does not slip significantly as the eye rotates. Measurements with tight fitting contact lenses can provide very accurate measurements of eye movement. Additionally, magnetic search coils can be utilized which allow measurement of eye movement in horizontal, vertical and torsion direction.

Alternatively, non-contact, optical methods for measuring eye motion can be used. With this technology, light, optionally infrared, can be reflected from the eye and can be sensed by an optical sensor or a video camera. The information can then be measured to extract eye rotation and/or movement from changes in reflections. Optical sensor or video-based eye trackers can use the corneal reflection (the so-called first Purkinje image) and the center of the pupil as features to track, optionally over time. A more sensitive type of eye tracker, the dual-Purkinje eye tracker, uses reflections from the front of the cornea (first Purkinje image) and the back of the lens (fourth Purkinje image) as features to track. An even more sensitive method of tracking is to image features from inside the eye, such as the retinal blood vessels, and follow these features as the eye rotates and or moves. Optical methods, particularly those based on optical sensors or video recording, can be used for gaze tracking.

In some embodiments, optical or video-based eye trackers can be used. A camera focuses on one or both eyes and tracks their movement as the viewer performs a function such as a surgical procedure. The eye-tracker can use the center of the pupil for tracking. Infrared or near-infrared non-collimated light can be utilized to create corneal reflections. The vector between the pupil center and the corneal reflections can be used to compute the point of regard on a surface or the gaze direction. Optionally, a calibration procedure can be performed at the beginning of the eye tracking.

Bright-pupil and dark-pupil eye tracking can be employed. Their difference is based on the location of the illumination source with respect to the optics. If the illumination is co-axial relative to the optical path, then the eye acts is retroreflective as the light reflects off the retina creating a bright pupil effect similar to a red eye. If the illumination source is offset from the optical path, then the pupil appears dark because the retroreflection from the retina is directed away from the optical sensor or camera.

Bright-pupil tracking can have the benefit of greater iris/pupil contrast, allowing more robust eye tracking with all iris pigmentation. It can also reduce interference caused by eyelashes. It can allow for tracking in lighting conditions that include darkness and very bright lighting situations.

The optical tracking method can include tracking movement of the eye including the pupil as described above. The optical tracking method can also include tracking of the movement of the eye lids and also periorbital and facial muscles.

In some embodiments, the eye-tracking apparatus is integrated in an head mounted display.

In some embodiments, head motion can be simultaneously tracked, for example using a combination of accelerometers and gyroscopes forming an inertial measurement unit (see below).

In some embodiments, electric potentials can be measured with electrodes placed around the eyes. The eyes generate an electric potential field, which can also be detected if the eyes are closed. The electric potential field can be modelled to be generated by a dipole with the positive pole at the cornea and the negative pole at the retina. It can be measured by placing two electrodes on the skin around the eye. The electric potentials measured in this manner are called an electro-oculogram.

If the eyes move from the center position towards the periphery, the retina approaches one electrode while the cornea approaches the opposing one. This change in the orientation of the dipole and consequently the electric potential field results in a change in the measured electro-oculogram signal. By analyzing such changes eye movement can be assessed. Two separate movement directions, a horizontal and a vertical, can be identified. If a posterior skull electrode is used, a EOG component in radial direction can be measured. This is typically the average of the EOG channels referenced to the posterior skull electrode. The radial EOG channel can measure saccadic spike potentials originating from extra-ocular muscles at the onset of saccades.

EOG can be limited for measuring slow eye movement and detecting gaze direction. EOG is, however, well suited for measuring rapid or saccadic eye movement associated with gaze shifts and for detecting blinks. Unlike optical or video-based eye-trackers, EOG allows recording of eye movements even with eyes closed. The major disadvantage of EOG is its relatively poor gaze direction accuracy compared to an optical or video tracker. Optionally, both methods, optical or video tracking and EOG, can be combined in select embodiments. A sampling rate of 15, 20, 25, 30, 50, 60, 100, 120, 240, 250, 500, 1000 Hz or greater can be used. Any sampling frequency is possibly. In many embodiments, sampling rates greater than 30 Hz will be preferred.

Measuring Location, Orientation, Acceleration

The location, orientation, and acceleration of an HMD, a human head, portions of the human body, e.g. hands, arms, legs or feet, as well as portions of the patient's body, e.g. the patient's head or extremities, including the hip, knee, ankle, foot, shoulder, elbow, hand or wrist and any other body part, can, for example, be measured with a combination of gyroscopes and accelerometers. In select applications, magnetometers may also be used. Such measurement systems using any of these components can be defined as inertial measurement units (IMU). As used herein, the term IMU relates to an electronic device that can measure and transmit information on a body's specific force, angular rate, and, optionally, the magnetic field surrounding the body, using a combination of accelerometers and gyroscopes, and, optionally, magnetometers. An IMU or components thereof can be coupled with or registered with a navigation system or a robot, for example by registering a body or portions of a body within a shared coordinate system. Optionally, an IMU can be wireless, for example using WiFi networks or Bluetooth networks.

Pairs of accelerometers extended over a region of space can be used to detect differences (gradients) in the proper accelerations of frames of references associated with those points. Single- and multi-axis models of accelerometer are available to detect magnitude and direction of the acceleration, as a vector quantity, and can be used to sense orientation (because direction of weight changes), coordinate acceleration (so long as it produces g-force or a change in g-force), vibration, shock. Micromachined accelerometers can be utilized in some embodiments to detect the position of the device or the operator's head.

Piezoelectric, piezoresistive and capacitive devices can be used to convert the mechanical motion into an electrical signal. Piezoelectric accelerometers rely on piezoceramics or single crystals Piezoresistive accelerometers can also be utilized. Capacitive accelerometers typically use a silicon micro-machined sensing element.

Accelerometers used in some of the embodiments can include small micro electro-mechanical systems (MEMS), consisting, for example, of little more than a cantilever beam with a proof mass.

Optionally, the accelerometer can be integrated in the optical head mounted devices and both the outputs from the eye tracking system and the accelerometer(s) can be utilized for command execution.

With an IMU, the following exemplary information can be captured about the operator and the patient and respective body parts including a moving joint: Speed, velocity, acceleration, position in space, positional change, angular orientation, change in angular orientation, alignment, orientation, and/or direction of movement and or speed of movement (e.g. through sequential measurements). Operator and/or patient body parts about which such information can be transmitted by the IMU include, but are not limited to: head, chest, trunk, shoulder, elbow, wrist, hand, fingers, arm, hip, knee, ankle, foot, toes, leg, inner organs, e.g. brain, heart, lungs, liver, spleen, bowel, bladder, etc.

Any number of IMUs can be placed on the HMD, the operator and/or the patient and, optionally, these IMUs can be cross-referenced to each other within a single or multiple coordinate systems or, optionally, they can be cross-referenced in relationship to an HMD, a second and third or more HMDs, a navigation system or a robot and one or more coordinate systems used by such navigation system and/or robot. A navigation system can be used in conjunction with an HMD without the use of an IMU. For example, navigation markers including infrared markers, retroreflective markers, RF markers can be attached to an HMD and, optionally, portions or segments of the patient or the patient's anatomy. The HMD and the patient or the patient's anatomy can be cross-referenced in this manner or registered in one or more coordinate systems used by the navigation system and movements of the HMD or the operator wearing the HMD can be registered in relationship to the patient within these one or more coordinate systems. Once the virtual data and the live data of the patient and the HMD are registered in the same coordinate system, e.g. using IMUs, optical markers, navigation markers including infrared markers, retroreflective markers, RF markers, and any other registration method described in the specification or known in the art, any change in position of any of the HMD in relationship to the patient measured in this fashion can be used to move virtual data of the patient in relationship to live data of the patient, so that the visual image of the virtual data of the patient and the live data of the patient seen through the HMD are always aligned, irrespective of movement of the HMD and/or the operator's head and/or the operator wearing the HMD. Similarly, when multiple HMDs are used, e.g. one for the primary surgeon and additional ones, e.g. two, three, four or more, for other surgeons, assistants, residents, fellows, nurses and/or visitors, the HMDs worn by the other staff, not the primary surgeon, will also display the virtual representation(s) of the virtual data of the patient aligned with the corresponding live data of the patient seen through the HMD, wherein the perspective of the virtual data that is with the patient and/or the surgical site for the location, position, and/or orientation of the viewer's eyes for each of the HMDs used and each viewer. The foregoing embodiments can be achieved since the IMU's, optical markers, RF markers, infrared markers and/or navigation markers placed on the operator and/or the patient as well as any spatial anchors can be registered in the same coordinate system as the primary HMD and any additional HMDs. The position, orientation, alignment, and change in position, orientation and alignment in relationship to the patient and/or the surgical site of each additional HMD can be individually monitored thereby maintaining alignment and/or superimposition of corresponding structures in the live data of the patient and the virtual data of the patient for each additional HMD irrespective of their position, orientation, and/or alignment in relationship to the patient and/or the surgical site.

Figure 3:
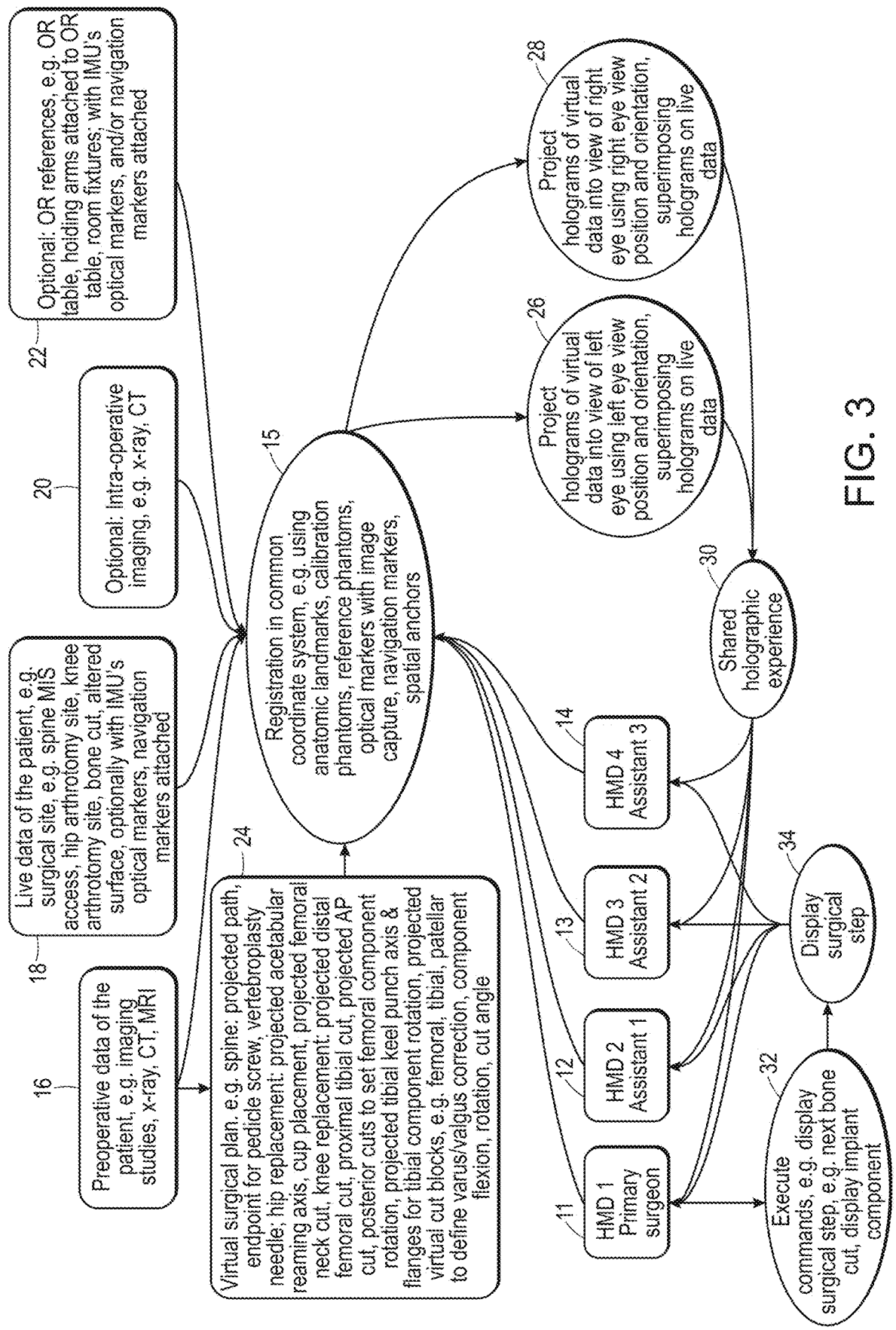
FIG. 3 shows the use of multiple HMDs for multiple viewers, e.g. a primary surgeon, second surgeon, surgical assistant(s) and/or nurses(s) according to some embodiments of the present disclosure.

Referring to FIG. 3, a system for using multiple HMDs (HMDs 11, 12, 13, 14) for multiple viewer's, e.g. a primary surgeon, second surgeon, surgical assistant(s) and/or nurses(s) is shown. The multiple HMDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMUs, optical markers, navigation markers, image or video capture systems and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMUs, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The HMDs 11, 12, 13, 14 can project digital holograms of the virtual data or virtual data into the view of the left eye using the view position and orientation of the left eye 26 and can project digital holograms of the virtual data or virtual data into the view of the right eye using the view position and orientation of the right eye 28 of each user, resulting in a shared digital holographic experience 30. Using a virtual or other interface, the surgeon wearing HMD 11 can execute commands 32, e.g. to display the next predetermined bone cut, e.g. from a virtual surgical plan or an imaging study or intra-operative measurements, which can trigger the HMDs 11, 12, 13, 14 to project digital holograms of the next surgical step 34 superimposed onto and aligned with the surgical site in a predetermined position and/or orientation.

Virtual data of the patient can be projected superimposed onto live data of the patient for each individual viewer by each individual HMD for their respective view angle or perspective by registering live data of the patient, e.g. the surgical field, and virtual data of the patient as well as each HMD in a common, shared coordinate system. Thus, virtual data of the patient including aspects of a virtual surgical plan can remain superimposed and/or aligned with live data of the patient irrespective of the view angle or perspective of the viewer and alignment and/or superimposition can be maintained as the viewer moves his or her head or body.

Fusing Physical World with Imaging and Other Data of a Patient

In some embodiments, an operator such as a surgeon may look through an HMD observing physical data or information on a patient, e.g. a surgical site or changes induced on a surgical site, while pre-existing data of the patient are superimposed onto the physical visual representation of the live patient. Systems, methods and techniques to improve the accuracy of the display of the virtual data superimposed onto the live data of the patient are described in International Patent Application No. PCT/US2018/012459, which is incorporated herein by reference in its entirety.

The pre-existing data of the patient can be an imaging test or imaging data or other types of data including metabolic information or functional information.

The pre-existing data of the patient including one or more imaging tests or other types of data including metabolic or functional information can be obtained at a time different from the time of the surgical procedure. For example, the pre-existing data of the patient can be obtained one, two, three or more days or weeks prior to the surgical procedure.

The pre-existing data of the patient including one or more imaging tests or other types of data including metabolic or functional information are typically obtained with the patient or the surgical site being located in a different location or a different object coordinate system in the pre-existing data when compared to the location or the object coordinate system of the live patient or the surgical site in the live patient. Thus, pre-existing data of the patient or the surgical site are typically located in a first object coordinate system and live data of the patient or the surgical site are typically located in a second object coordinate systems; the first and the second object coordinate system are typically different from each other. The first object coordinate system with the pre-existing data needs to be registered with the second object coordinate system with the live data of the patient including, for example, the live surgical site.

Scan Technology

The following is an exemplary list of scanning and imaging techniques that can be used or applied for various aspects of the present disclosure; this list is not exhaustive, but only exemplary. Anyone skilled in the art can identify other scanning or imaging techniques that can be used in practicing the present disclosure: X-ray imaging, 2D, 3D, supine, upright or in other body positions and poses, including analog and digital x-ray imaging; Digital tomosynthesis; Cone beam CT; Ultrasound; Doppler ultrasound; Elastography, e.g. using ultrasound or MRI; CT; MRI, including, for example, fMRI, diffusion imaging, stroke imaging, MRI with contrast media; Functional MRI (fMRI), e.g. for brain imaging and functional brain mapping; Magnetic resonance spectroscopy; PET; SPECT-CT; PET-CT; PET-MRI; Upright scanning, optionally in multiple planes or in 3D using any of the foregoing modalities, including x-ray imaging, ultrasound etc.; Contrast media (e.g. iodinated contrast agents for x-ray and CT scanning, or MRI contrast agents; contrast agents can include antigens or antibodies for cell or tissue specific targeting; other targeting techniques, e.g. using liposomes, can also be applied; molecular imaging, e.g. to highlight metabolic abnormalities in the brain and target surgical instruments towards area of metabolic abnormality; any contrast agent known in the art can be used in conjunction with the present disclosure); 3D optical imaging, including Laser scanning, Confocal imaging, e.g. including with use of fiberoptics, single bundle, multiple bundle, Confocal microscopy, e.g. including with use of fiberoptics, single bundle, multiple bundles, Optical coherence tomography, Photogrammetry, Stereovision (active or passive), Triangulation (active or passive), Interferometry, Phase shift imaging, Active wavefront sampling, Structured light imaging, Other optical techniques to acquire 3D surface information, Combination of imaging data, e.g. optical imaging, wavefront imaging, interferometry, optical coherence tomography and/or confocal laser imaging or scanning, Image fusion or co-display of different imaging modalities, e.g. in 2D or 3D, optionally registered, optionally more than two modalities combined, fused or co-displayed, e.g. optical imaging, e.g. direct visualization or through an arthroscope, and/or laser scan data, e.g. direct visualization or through an arthroscope, and/or virtual data, e.g. intra-articular, extra-articular, intra-osseous, hidden, not directly visible, and/or external to skin, and/or confocal imaging or microscopy images/data, e.g. direct visualization or through an arthroscope. For a detailed description of illustrative scanning and imaging techniques, see for example, Bushberg et al. The Essential Physics of Medical Imaging, 3rd edition, Wolters, Kluwer, Lippincott, 2012.

In embodiments, 3D scanning can be used for imaging of the patient and/or the surgical site and/or anatomic landmarks and/or pathologic structures and/or tissues (e.g. damaged or diseased cartilage or exposed subchondral bone) and/or the surgeon's hands and/or fingers and/or the OR table and/or reference areas or points and/or marker, e.g. optical markers, in the operating room and/or on the patient and/or on the surgical field. 3D scanning can be accomplished with multiple different modalities including combinations thereof, for example, optical imaging, e.g. using a video or image capture system integrated into, attached to, or separate from one or more HMDs, laser scanning, confocal imaging, optical coherence tomography, photogrammetry, active and passive stereovision and triangulation, interferometry and phase shift principles and/or imaging, wavefront sampling and/or imaging. One or more optical imaging systems or 3D scanners can, for example, be used to image and/or monitor, e.g. the coordinates, position, orientation, alignment, direction of movement, speed of movement of, Anatomic landmarks, patient surface(s), organ surface(s), tissue surface(s), pathologic tissues and/or surface(s), e.g. for purposes of registration, e.g. of the patient and/or the surgical site, e.g. one or more bones or cartilage, and/or one or more HMDs, e.g. in a common coordinate system One or more HMDs, optionally with one or more attached or integrated fiducial markers, subarrays or arrays The surgeon's hands and/or fingers, e.g. for
  Monitoring steps in a surgical procedure. Select hand and/or finger movements can be associated with corresponding surgical steps. When the 3D scanner system detects a particular hand and/or finger movement, it can trigger the display of the corresponding surgical step or the next surgical step, e.g. by displaying a predetermined virtual axis, e.g. a reaming, broaching or drilling axis, a virtual cut plane, a virtual instrument, a virtual implant component etc.
  Executing virtual commands, e.g. using gesture recognition or a virtual interface, e.g. a virtual touch pad One or more HMDs, e.g. registered in a common coordinate system, e.g. with the surgical site and/or the surgeon's hands and/or fingers The use of optical imaging systems and/or 3D scanners for registration, e.g. of the surgical site and/or one or more HMDs can be helpful when markerless registration is desired, e.g. without use of optical markers, e.g. with geometric patterns, and/or IMUs, and/or LEDs, and/or navigation markers. The use of optical imaging systems and/or 3D scanners for registration can also be combined with the use of one or more of optical markers, e.g. with geometric patterns, and/or IMUs, and/or LEDs, and/or navigation markers.

In embodiments, one or more 3D models and/or 3D surfaces generated by an optical imaging system and/or a 3D scanner can be registered with, superimposed with and/or aligned with one or more 3D models and/or 3D surfaces generated by another imaging test, e.g. a CT scan, MRI scan, PET scan, other scan, or combinations thereof, and/or a 3D model and/or 3D surfaces generated from or derived from an x-ray or multiple x-rays, e.g. using bone morphing technologies, as described in the specification or known in the art.

With optical imaging systems or 3D scanners, a virtual 3D model can be reconstructed by postprocessing single images, e.g. acquired from a single perspective. In this case, the reconstruction cannot be performed in real time with continuous data capture. Optical imaging systems or 3D scanners can also operate in real time generating true 3D data.

For example, with confocal microscopy using, for example, an active triangulation technique, a projector can project a changing pattern of light, e.g. blue light, onto the surgical field, e.g. an articular surface exposed by arthroscopy or a bone or a soft-tissue, e.g. using projection grids that can have a transmittance random distribution and which can be formed by sub regions containing transparent and opaque structures. By using elements for varying the length of the optical path, it can possible, for each acquired profile, to state a specific relationship between the characteristic of the light and the optical distance of the image plane from the imaging optics. A light source can produce an illumination beam that can be focused onto the surface of the surgical field, e.g. the articular surface. An image sensor can receive the observation beam reflected by the surface of the target object. A focusing system can focus the observation beam onto the image sensor. The light source can split into a plurality of regions that can be independently regulated in terms of light intensity. Thus, the intensity of light detected by each sensor element can be a direct measure of the distance between the scan head and a corresponding point on the target object.

Parallel confocal imaging can be performed, e.g. by shining an array of incident laser light beams, e.g. passing through focusing optics and a probing face, on the surgical field, e.g. an articular surface, a bone or a soft-tissue. The focusing optics can define one or more focal planes forward to the probe face in one or more positions which can be changed, e.g. by a motor or other mechanism. The laser light beams can generate illuminated spots or patterns on the surgical field and the intensity of returning light rays can be measured at various positions of the focal plane determining spot-specific positions yielding a maximum intensity of the reflected light beams. Data can be generated which can represent the topology of the three-dimensional structure of the surgical field, e.g. an articular surface, e.g. exposed and/or visible and/or accessible during arthroscopy, a bone or a soft-tissue. By determining surface topologies of adjacent portions or tissues, e.g. an adjacent articular surface or bone or soft-tissue, from two or more different angular locations and then combining such surface topologies, a complete three-dimensional representation of the entire surgical field can be obtained. Optionally, a color wheel can be included in the acquisition unit itself. In this example, a two-dimensional (2D) color image of the 3D structure of the surgical field, e.g. an articular surface, a bone or a soft-tissue, can also be taken at the same angle and orientation with respect to the structure. Thus, each point with its unique coordinates on the 2D image can correspond to a similar point on the 3D scan having the same x and y coordinates. The imaging process can be based on illuminating the target surface with three differently-colored illumination beams (e.g. red, green or blue light) combinable to provide white light, thus, for example, capturing a monochromatic image of the target portion of the surgical field, e.g. an articular surface, a bone, a cartilage or a soft-tissue, corresponding to each illuminating radiation. The monochromatic images can optionally be combined to create a full color image. Three differently-colored illumination beams can be provided by means of one white light source optically coupled with color filters.

With optical coherence tomography (OCT), using, for example, a confocal sensor, a laser digitizer can include a laser source, e.g. coupled to a fiber optic cable, a coupler and a detector. The coupler can split the light from the light source into two paths. The first path can lead to the imaging optics, which can focus the beam onto a scanner mirror, which can steer the light to the surface of the surgical field, e.g. an articular surface, e.g. as seen or accessible during arthroscopy, a cartilage, a bone and/or a soft-tissue. A second path of light from the light source can be coupled via the coupler to the optical delay line and to the reflector. The second path of light, e.g. the reference path, can be of a controlled and known path length, as configured by the parameters of the optical delay line. Light can be reflected from the surface of the surgical field, e.g. an articular surface, a cartilage, a bone and/or a soft-tissue, returned via the scanner mirror and combined by the coupler with the reference path light from the optical delay line. The combined light can be coupled to an imaging system and imaging optics via a fiber optic cable. By utilizing a low coherence light source and varying the reference path by a known variation, the laser digitizer can provide an optical coherence tomography (OCT) sensor or a low coherence reflectometry sensor. The focusing optics can be placed on a positioning device in order to alter the focusing position of the laser beam and to operate as a confocal sensor. A series of imaged laser segments on the object from a single sample/tissue position can be interlaced between two or multiple 3D maps of the sample/tissue from essentially the same sample/tissue position. The motion of the operator between each subframe can be tracked mathematically through reference points. Operator motion can optionally be removed.

Active wavefront sampling and/or imaging can be performed using structured light projection. The scanning system can include an active three-dimensional imaging system that can include an off-axis rotating aperture element, e.g. placed in the illumination path or in the imaging path. Out-of-plane coordinates of object points can be measured by sampling the optical wavefront, e.g. with an off-axis rotating aperture element, and measuring the defocus blur diameter. The system can include a lens, a rotating aperture element and an image plane.

The single aperture can help avoid overlapping of images from different object regions and can help increase spatial resolution. The rotating aperture can allow taking images at several aperture positions. The aperture movement can make it possible to record on a CCD element a single exposed image at different aperture locations. To process the image, localized cross correlation can be applied to reveal image disparity between image frames.

In another embodiment, a scanner can use a polarizing multiplexer. The scanner can project laser sheet onto the surgical cite, e.g. an articular surface, e.g. as exposed or accessible during arthroscopy, a cartilage, damaged, diseased or normal, a subchondral bone, a cortical bone etc., and can then utilize the polarizing multiplexer to optically combine multiple views of the profile illuminated by the sheet of laser light. The scanner head can use a laser diode to create a laser beam that can pass through a collimating lens which can be followed by a sheet generator lens that can convert the beam of laser light into a sheet of laser light. The sheet of laser light can be reflected by a folding mirror and can illuminate the surface of the surgical field. A system like this can optionally combine the light from two perspectives onto a single camera using passive or active triangulation. A system like this system can be configured to achieve the independence of lateral resolution and depth of field. In order to achieve this independence, the imaging system, can be physically oriented so as to satisfy the Scheimpflug principle. The Scheimpflug principle is a geometric rule that describes the orientation of the plane of focus of an optical system wherein the lens plane is not parallel to the image plane. This enables sheet of light based triangulation systems to maintain the high lateral resolution required for applications requiring high accuracy, e.g. accuracy of registration, while providing a large depth of focus.

A 3D scanner probe can sweep a sheet of light across one or more tissue surfaces, where the sheet of light projector and imaging aperture within the scanner probe can rapidly move back and forth along all or part of the full scan path, and can display, for example near real-time, a live 3D preview of the digital 3D model of the scanned tissue surface(s). A 3D preview display can provide feedback on how the probe is positioned and oriented with respect to the target tissue surface.

In other embodiments, the principle of active stereophotogrammetry with structured light projection can be employed. The surgical field can be illuminated by a 2D array of structured illumination points. 3D models can be obtained from the single image by triangulation with a stored image of the structured illumination onto a reference surface such as a plane. A single or multiple camera can be used. To obtain information in z-direction, the surgical site can be illuminated by a 2D image of structured illumination projected from a first angle with respect to the surgical site. Then the camera can be positioned at a second angle with respect to the surgical site, to produce a normal image containing two-dimensional information in x and y direction as seen at that second angle. The structured illumination projected from a photographic slide can superimpose a 2D array of patterns over the surgical site and can appear in the captured image. The information in z-direction is then recovered from the camera image of the surgical site under the structured illumination by performing a triangulation of each of the patterns in the array on the image with reference to an image of the structured illumination projected on a reference plane, which can also be illuminated from the first angle. In order to unambiguously match corresponding points in the image of the surgical site and in the stored image, the points of the structured illumination can be spatially-modulated with two-dimensional random patterns which can be generated and saved in a projectable medium. Random patterns are reproducible, so that the patterns projected onto the surgical site to be imaged are the same as the corresponding patterns in the saved image.

Accordion fringe interferometry (AFI) can employ light from two-point sources to illuminate an object with an interference fringe pattern. A high precision digital camera can be used to record the curvature of the fringes. The degree of apparent fringe curvature coupled with the known geometry between the camera and laser source enable the AFI algorithms to digitize the surface of the object being scanned. AFI can offer advantages over other scanners as lower sensitivity to ambient light variations and noise, high accuracy, large projector depth of field, enhanced ability to scan shiny and translucent surfaces, e.g. cartilage, and the ability to scan without targets and photogrammetric systems. A grating and lens can be used. Alternatively, coherent point source of electromagnetic radiation can also be generated without a grating and lens. For example, electromagnetic radiation can be emitted from a pair or pairs of optical fibers which can be used to illuminate target objects with interferometric fringes. Consequently, movement of a macroscopic grating which requires several milliseconds or more to effect a phase shift can be avoided. A fiber-based phase shifter can be used to change the relative phase of the electromagnetic radiation emitted from the exit ends of two optical fibers in a few microseconds or less. Optical radiation scattered from surfaces and subsurface regions of illuminated objects can be received by a detector array. Electrical signals can be generated by a detector array in response to the received electromagnetic radiation. A processor receives the electrical signals and calculates three-dimensional position information of tissue surfaces based on changes in the relative phase of the emitted optical radiation and the received optical radiation scattered by the surfaces. Sources of optical radiation with a wavelength between about 350 nm and 500 nm can be used; other wavelengths are possible.

Other optical imaging systems and/or 3D scanners can use the principle of human stereoscopic vision and the principle of linear projection: if straight lines are projected onto an object the lines will be curved around the object. This distortion of the lines allows conclusions to be drawn about the surface contour.

When optical imaging and/or 3D scanning is performed in the context of an arthroscopy procedure, the optical imaging and/or 3D scanning apparatus can be integrated into the endoscope, including by sharing the same fiberoptic(s) or with use of separate fiberoptic(s), e.g. in the same housing or a separate housing. An arthroscopic optical imaging and/or 3D scanning probe can be inserted through the same portal as the one used for the arthroscope, including when integrated into the arthroscope or in a common housing with the arthroscope, or it can be inserted through a second, separate portal. An optical imaging and/or 3D scanning probe used with an arthroscopic procedure can optionally be tracked by tracking the position, location, orientation, alignment and/or direction of movement using optical markers, e.g. with one or more geometric patterns, e.g. in 2D or 3D, or LED's using one or more camera or video systems integrated into, attached to, or separate from one or more HMDs. The camera or video systems can be arranged at discrete, defined angles thereby utilizing angular information including parallax information for tracking distances, angles, orientation or alignment of optical markers attached to the probe, e.g. the arthroscope and/or optical imaging and/or 3D scanning probe. An optical imaging and/or 3D scanning probe and/or an arthroscope used with an arthroscopic procedure can optionally be tracked by tracking the position, location, orientation, alignment and/or direction of movement using navigation markers, e.g. infrared or RF markers, and a surgical navigation system. An optical imaging and/or 3D scanning probe and/or an arthroscope used with an arthroscopic procedure can optionally be tracked by tracking the position, location, orientation, alignment and/or direction of movement directly with one or more camera or video systems integrated into, attached to or separate from one or more HMDs, wherein a computer system and software processing the information can use image processing and pattern recognition to recognize the known geometry of the one or more probes and their location within a coordinate system, e.g. in relationship to the patient, the surgical site and/or the OR table.

With any of the optical imaging and/or 3D scanner techniques, if there are holes in the acquisition and/or scan and/or 3D surface, repeat scanning can be performed to fill the holes. The scanned surface can also be compared against a 3D surface or 3D model of the surgical site, e.g. an articular surface, a cartilage, damaged or diseased or normal, a subchondral bone, a bone and/or a soft-tissue, obtained from an imaging study, e.g. an ultrasound, a CT or MRI scan, or obtained via bone morphing from x-rays as described in other parts of the specification. Discrepancies in surface geometry between the 3D model or 3D surface generated with the optical imaging system and/or the 3D scanner and the 3D surface or 3D model obtained from an imaging study or bone morphing from x-rays, can be determined; similarly, it can be determined if the surfaces or 3D models display sufficient commonality to allow for registration of the intra-operative 3D surface or 3D model obtained with the optical imaging system and/or 3D scanner and the 3D surface or 3D model obtained from the pre-operative imaging study or bone morphing from x-rays. If there is not sufficient commonality, additional scanning can be performed using the optical imaging and/or 3D scanner technique, for example in order to increase the spatial resolution of the scanned data, the accuracy of the scanned data and/or to fill any holes in the model or surface. Any surface matching algorithm known in the art can be utilized to register overlapping surface areas and thereby transform all surface portions into the same coordinate space, for example the Iterative Closest Point method described in Besl et al., *A Method for Registration of 3-D Shapes;* 1992; *IEEE Trans PAMI* 14(2): 239-255.

Optionally, with any of the foregoing embodiments, the optical imaging system or 3D scanner can have a form of boot or stabilization advice attached to it, which can, for example, be rested against and moved over the target tissue, e.g. an articular surface, a bone or a soft-tissue. The boot or stabilization device can help maintain a constant distance between the scanner and the target tissue. The boot or stabilization device can also help maintain a constant angle between the scanner and the target tissue. For example, a boot or stabilization device can be used with an optical imaging system or scanner used during arthroscopy, maintaining, for example, a constant distance to the articular surface or intra-articular ligament, cartilage, bone or other structures, e.g. a femoral notch or a tibial spine or a tri-radiate cartilage region or fovea capitis in a hip.

Registering Virtual Data with Live Data Seen Through Head Mounted Display

In some embodiments, virtual data of a patient can be superimposed onto live data seen through the head mounted display. The virtual data can be raw data in unprocessed form, e.g. preoperative images of a patient, or they can be processed data, e.g. filtered data or segmented data.

Data Segmentation

Figure 4:
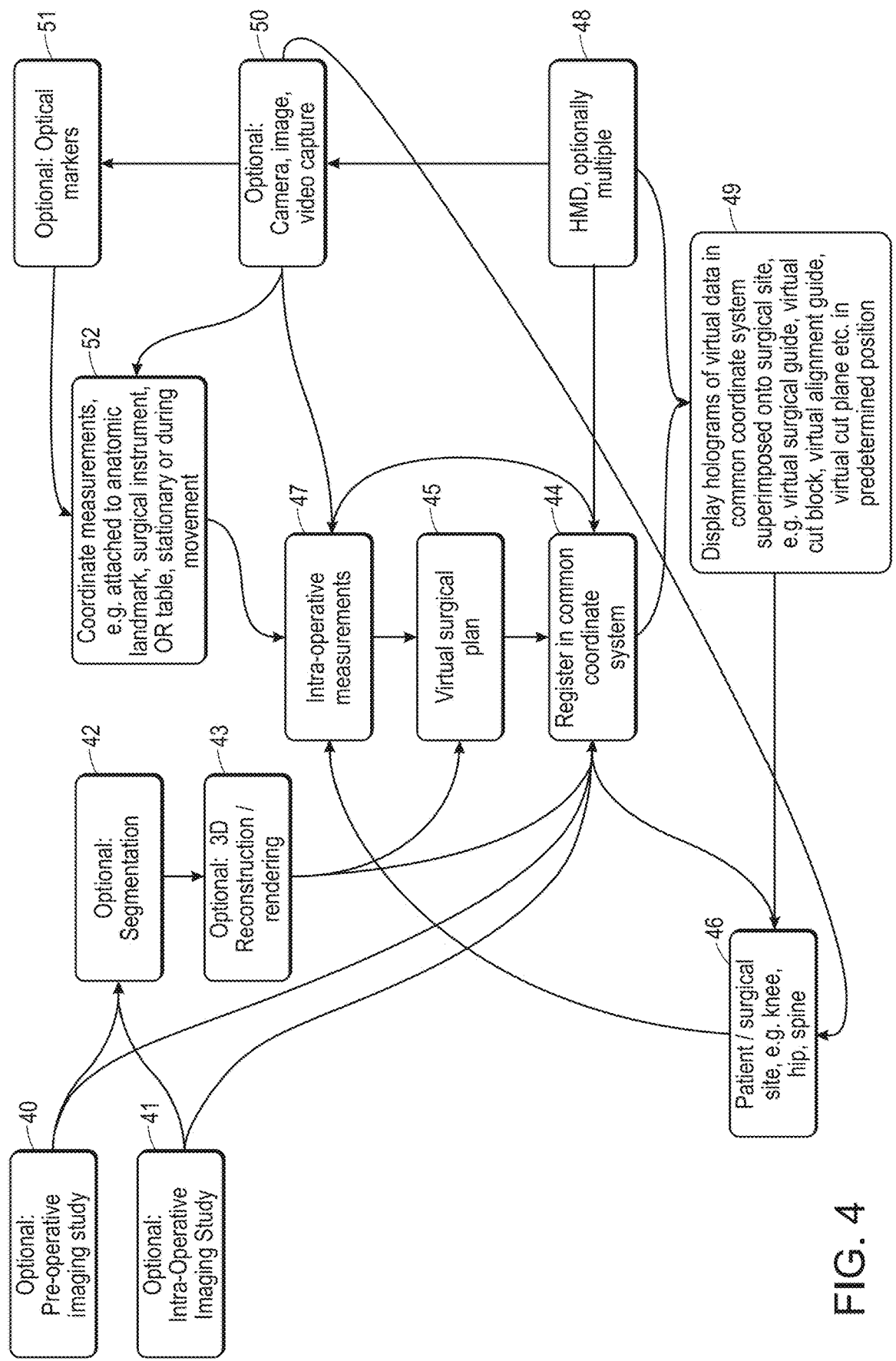
FIG. 4 shows a representative, non-limiting flow chart describing the steps of registering intra-operative measurements, an optional virtual surgical plan and optional pre- or intra-operative imaging studies in a coordinate system, along with other optional process steps such as segmented, or 3D surface rendering, for display by one or more HMDs.

When images of the patient are superimposed onto live data seen through the head mounted display, in many embodiments image segmentation can be desirable. Any known algorithm in the art can be used for this purpose, for example thresholding, seed point techniques, live wire, deformable models, statistical models, active shape models, level set methods, marching cubes algorithms, artificial neural networks, deep learning techniques, or combinations thereof and the like. Many of these algorithms are available is part of open-source or commercial libraries, for instance the Insight Segmentation and Registration Toolkit (ITK), the Open Source Computer Vision Library OpenCV, G'MIC (GREYC's Magic for Image Computing), Caffe, or MATLAB (MathWorks, Natick, Mass.). A non-limiting representative workflow for optional segmentation and subsequent registration is provided in FIG. 4. An optional pre-operative imaging study 40 can be obtained. An optional intra-operative imaging study 41 can be obtained. The pre-operative 40 or intra-operative 41 imaging study can be segmented 42, extracting, for example, surfaces, volumes or key features. An optional 3D reconstruction or 3D rendering 43 can be generated. The pre-operative 40 or intra-operative 41 imaging study and any 3D reconstruction or 3D rendering 43 can be registered in a common coordinate system 44. The pre-operative 40 or intra-operative 41 imaging study and any 3D reconstruction or 3D rendering 43 can be used for generating a virtual surgical plan 45. The virtual surgical plan 45 can be registered in the common coordinate system 44. The surgical site 46 can be registered in the common coordinate system 44. Intra-operative measurements 47 can be obtained and can be used for generating a virtual surgical plan 45. An head mounted display 48 can project or display digital holograms of virtual data or virtual data 49 superimposed onto and aligned with the surgical site. The HMD 48 is configured to use a built-in camera or image capture or video capture system 50 to optionally detect and/or measure the position and/or orientation and/or alignment of one or more optical markers 51, which can be used for the coordinate measurements 52, which can be part of the intra-operative measurements 47.

Software and Algorithms for Registration

Registration of virtual data with live data can be performed using a variety of techniques know in the art. These include, but are not limited to, surface registration algorithms such as the Iterative Closest Point algorithm, statistical models, Active Shape Models, mutual information-based or other volume registration algorithms, object recognition, pattern recognition or computer vision techniques, deep learning or other artificial intelligence methods. The processed data can, for example, consist of mesh data, parametric surface data, point cloud data, volume data or a combination thereof. These methods are known in the art and have been implemented in publicly and/or commercially available code libraries and application programming interfaces (API's), such as the Insight Segmentation and Registration Toolkit (ITK), the open-source computer vision library OpenCV, Elastix, Plastimatch, or the Medical Image Registration Toolkit (MIRTK).

Superimposition of Virtual Data and Live Data by the HMD

In some embodiments, segmented data or raw data can be superimposed on the patient's live data seen through the head mounted display. This superimposition can occur in unregistered form, i.e. the patient's virtual data may not be aligned with the live data seen through the head mounted display. In this case, the operator who is wearing the HMD may move his/her head in a direction of orientation that will superimpose corresponding features of virtual data and live patient data. The surgeon or operator can also move and re-orient the virtual data using other means, e.g. a trackball or a virtual display interface displayed in the HMD, unrelated to the surgeon/operator head movement. The operator can adjust the magnification of the live data so that the size, shape, length, thickness of certain features of the virtual data matches that of the live data for a given distance to the object/patient.

For example, during brain surgery, the surgeon may visually in live data look at the exposed gyri and sulci of the patient's brain. The HMD can display a virtual 3D model of the gyri and sulci of the patient. The surgeon can optionally adjust the magnification of the 3D model so that the model will match the size or width or the length of the corresponding gyri and sulci in the live data. The surgeon can optionally adjust the transparency or opacity of the virtual data displayed in the HMD. The ratio of virtual vs. live data transmitted through the HMD can be 1:10, 1:9, 1:8, 1:5, 1:2, 1:1, 2:1, 3:1, 5:1, 8:1, 10:1, as well as fractions or multiples thereof. Any combination of transparency or opacity of virtual data and live data is possible. The surgeon can move his/her head in a direction or orientation that will superimpose virtual features, e.g. the patient's gyri and sulci, with the live patient data.

Once the data have been superimposed, the surgeon can optionally register the virtual data with the live data. This registration can be as simple as described here, e.g. a visual confirmation from the surgeon that virtual and live data are substantially matching or substantially superimposed. At this time, the surgeon can optionally reference the virtual data and/or the coordinate system of the virtual data in 2, 3 or more dimensions with the live data and/or the coordinate system of the live data. Once the data are registered, the surgeon can move his/her head into any desired position or orientation, for example for viewing the patient's brain or a lesion and adjacent, e.g. sensitive, anatomy from different view angles. The IMU of the HMD will register the head movement, the direction of the head movement, the new head position and head orientation. The change in location and orientation of the surgeon's head can be simultaneously or, if desired, non-simultaneously applied to the virtual data which can now be superimposed with the resultant new position and orientation in relationship to the live data. In addition, when the surgeon moves his/her head or body further away from the target anatomy, the change in position and the increase in distance from the target anatomy can be measured by the IMU. Depending on the distance from the IMU, a magnification or minification factor can be applied to the virtual data so that the size, shape and dimensions of the virtual data will, in some embodiments, be close to or match the size, shape and dimensions of the live data, irrespective of the distance, location and orientation of the surgeon's head.

For purposes of registration of virtual data and live data, the HMD can be optionally placed in a fixed position, e.g. mounted on a stand or on a tripod. While the HMD is placed in the fixed position, live data can be viewed by the surgeon and they can be, optionally recorded with a camera and/or displayed on a monitor. Virtual data can then be superimposed and the matching and registration of virtual data and live data can be performed. At this point, the surgeon or an operator can remove HMD from the fixed position and the surgeon can wear the HMD during the surgical procedure.

The virtual data can optionally be displayed using a different color, e.g. red, green, yellow etc. Optionally, only the outline of select features of the virtual data may be displayed. For example, these features can be the sulci of the patient's brain (e.g. with a black line or black or lines with other colors), with no visualization of the gyri that these sulci border. Or, for example, only a lesion, e.g. a tumor such as, in the example of the brain, glioblastoma, can be displayed. Or combinations of virtual data of normal tissue and pathologic tissue can be displayed.

The virtual data can be registered with the live data seen through the head mounted display. The registration can occur using any method known in the art for registering or cross-referencing virtual and live data, in 2, 3, or more dimensions.

In some embodiments, the registration of the virtual data and the live data will be maintained through the surgical procedure. In some embodiments, the registration of the virtual data and the live data will be maintained during select portions of the surgical procedure or the surgical plan, which can be or can include a virtual, e.g. a preoperatively generated, surgical plan.

In some embodiments, the superimposition of the virtual data and the live data by the HMD occurs simultaneously. In some embodiments, the superimposition of the virtual data and the live data by the HMD is not simultaneous. For example, the virtual data can be superimposed intermittently.

Virtual data can be transparent, translucent or opaque. If virtual data are opaque, they may be displayed intermittently so that the operator or surgeon can see how they project in relationship to the live data of the patient.

If combinations of virtual data are displayed simultaneously with the live data, the different types of virtual data can be displayed with different colors. Representative combinations of virtual and live data are provided below. The following is only illustrative in nature and by no means meant to be limiting:

Live data: the patient's brain; surgically exposed gyri and sulci.

Live data: surgical instrument, e.g. biopsy needle or cutting tool

Virtual data: the patient's brain with gyri and sulci derived and optionally segmented from an imaging modality, e.g. a CT scan or an MRI scan Virtual data: a brain tumor, deep seated inside the brain Virtual data: the same surgical instrument currently used by the surgeon, in a virtual representation of the instrument, the virtual data indicating the desired orientation, location or direction of the surgical instrument.

Any of the foregoing virtual data can be displayed in two dimensions or three dimensions. Multi-dimensional displays as outlined in other sections of the specification are possible. For example, the patient's normal tissue, e.g. normal brain tissue, can optionally be displayed in two dimensions, e.g. using grey level images, while the patient's abnormal tissue, e.g. a stroke, a hemorrhage or a tumor, can be displayed in three dimensions. Any combination of 2D, 3D, and multi-dimensional images is possible for display by the HMD; any combination of 2D, 3D, and multi-dimensional images can be superimposed on live patient data by the HMD. The virtual 2D, 3D, and multi-dimensional data can be generated or acquired by different data acquisition technologies, e.g. different imaging tests etc.

Locking or Moving of Virtual Data

In some embodiments, virtual data can be locked in relationship to the surgeon or operator or in relationship to the patient or a certain target anatomy within a patient. This means even if the surgeon moves his or her head or the body or parts of the patient's anatomy are being moved, the virtual data will not move in the HMD display. For example, once registration has occurred, the HMD can display a virtual image of a target tissue or adjacent tissue. The virtual image of the target tissue or adjacent tissue can be, for example, an image through a tumor or other type of pathologic tissue. As the surgeon or operator moves his or her head or body during the surgical procedure, the virtual data will not move, but are being displayed within the same location.

In some embodiments, virtual data can move in relationship to the surgeon or operator or in relationship to the patient or a certain target anatomy within a patient. This means if the surgeon moves his or her head, and with that the HMD, or the body or parts of the patient's anatomy are being moved, the virtual data can move in the HMD display. This can include an adjustment of the focal plane or focal point or a selection of a different focal plane or focal point for the virtual display of the virtual data by the one or more HMDs. For example, once registration has occurred, the HMD can display a virtual image of a target tissue or adjacent tissue. The virtual image of the target tissue or adjacent tissue can be, for example, an image through a tumor or other type of pathologic tissue. As the surgeon or operator moves his or her head or body during the surgical procedure, A computer processor can be configured to move and change the location and orientation of the virtual data and can adjust or change focal plane or focal point to the extent and reflecting how the surgeon moves his/her head or body, typically reflecting the change in perspective or view angle that the surgeon obtained by moving his or her head or body.

Optionally the moving of the virtual data can be at greater virtual distance or greater angle or lesser virtual distance or lesser angle than the movement of the surgeon's head or body.

Improving the Accuracy of Moving or Re-Orienting Virtual Data

Once registration between virtual data and physical data has occurred, the moving or re-orienting of virtual data to follow, for example, the surgeon's head movements or body movements or operating arm or hand movements, or the movements of the patient or certain body parts of the patient can be accomplished, for example, by monitoring the movement and change in location and/or orientation of the surgeon's head using the IMU of the HMD.

In some embodiments, optical or RF tracker's or other tracking devices known in the art can be applied to the HMD and/or the patient including select body parts or target tissues of the patient, e.g. the patient's knee. Using standard surgical navigation techniques known in the art, the spatial location of the optical or RF trackers can be recorded, for example for a starting pose or position or location. Movement of the trackers, e.g. induced by movement of the surgeon's head or body or by movement of at least a part of the patient, can then be tracked using the navigation system. The information on positional change, orientational change or movement direction of the surgeon's head or the patient or both can then be used to update the virtual data, or the display of the virtual data in the HMD, or both correspondingly. In this manner, the virtual data and the live data can be superimposed by the HMD, typically in an accurate manner.

Optionally, positional, orientational, directional data and the like generated by the IMU can be used in conjunction with such data generated by a surgical navigation system. A combination of data can be beneficial for more accurate measurement of changes in position or orientation of the surgeon's head, body, operating arm, hand, or the patient.

The head mounted display can be of optical see-through type, with the anatomic structures directly visible to the user's eye through the transparent or partially transparent HMD. The head mounted display can be of video see through type, with the anatomic structure imaged using one or more video cameras, optionally stereoscopic, attached to the head mounted display, with the anatomic structures imaged with the video cameras and then displayed by the head mounted display, but typically not directly visible to the user's eye. In some embodiments, hybrid applications of both can be used, for example with a partially transparent HMD that receives also feed from one or more video cameras for display by the HMD.

The following embodiments describe in detail how tracking information acquired during surgery can be used to determine head mounted display parameters for convergence, focal plane, focal point and/or scale for the overlay display or superimposition of virtual data on live surgery data or live images including anatomic data or structures of the patient. The focal plane, focal point, scale/magnification, or convergence of virtual data, e.g. a virtual surgical guide, displayed by a first display unit for the left eye and a second display unit for the right eye of the HMD, e.g. an optical see through head mounted display or a video see through head mounted display, can be adjusted continuously or intermittently based on a distance determined between a target anatomic site or structure, a target surgical site (e.g. with one or more anatomic structures, a marker attached to the patient (e.g. attached to an anatomic structure, e.g. at or near a surgical site) and the HMD, e.g. the first display unit for the left eye and the second display unit for the right eye; the refresh rate or the frequency of such adjustments can be, for example, a frequency of 0.01 Hz, 0.05 Hz, 0.1 Hz, 0.5 Hz, 1.0 Hz, 3.0 Hz, 5.0 Hz, 8.0 Hz, 10 Hz, 15 Hz or 20 Hz, or at the refresh rate of the HMD or at a refresh rate of a navigation system or inside out tracking system or any combinations thereof.

The adjusting of a focal plane, focal point, scale/magnification, or convergence of virtual data, e.g. a virtual surgical guide, displayed by a first display unit for the left eye and a second display unit for the right eye of the HMD can be effected, for example, by moving the virtual data displayed by the first display unit for the left eye and the virtual data displayed by the second display unit for the right eye by 0.01 mm, 0.05 mm, 0.1 mm, 0.5 mm, 1.0 mm, 3.0 mm, 5.0 mm, or any other number including fractional number. The moving of the virtual data, e.g. the virtual surgical guide, can be effected with a deformable lens or deformable mirror. The moving can be a translation, rotation and/or pivoting.

The adjusting of a focal plane, focal point, scale/magnification, or convergence of virtual data, e.g. a virtual surgical guide, displayed by a first display unit for the left eye and a second display unit for the right eye of the HMD can be effected, for example, by moving the first display unit for the left eye and the second display unit for the right eye by 0.01 mm, 0.05 mm, 0.1 mm, 0.5 mm, 1.0 mm, 3.0 mm, 5.0 mm, or any other number including fractional number. The moving can be a translation, rotation and/or pivoting. The moving of the first and second display units can be effected with mechanical, electrical, electromagnetic and/or piezo-electric adjustment effectors, means, mechanism, or systems including active optical elements known in the art. The moving of the first and second display units can be effected with a deformable lens or deformable mirror.

In some embodiments, the system, e.g. comprising a head mounted display, one or more computer processors, optionally one or more cameras, optionally one or more markers, e.g. attached to a patient, can be configured so that one or more processors are configured to determine the distance between one or more predetermined coordinates of virtual data, e.g. a virtual surgical guide, and a head mounted display during movement of a marker (e.g. attached to a patient (for example a surgical site or anatomic structure), movement of the head mounted display, or movement of the marker and the head mounted display, wherein the one or more processors can be configured to adjust the focal plane, focal point, convergence or combination thereof based on the change in the determined distance.

In some embodiments, the distance between the virtual data projected onto, superimposed onto, aligned with or projected inside an anatomic structure and the view point of the user/operator can be used to adjust convergence, focal plane, focal point and/or scale display parameters. Virtual data can, for example, consist of pre- or intra-operative imaging data of the patient, virtual surgical guides (e.g. virtual planes, virtual axes, virtual cut guides), virtual tools, virtual instruments, virtual implants, and virtual devices. The virtual data is commonly registered into a common coordinate system with the live surgery data, e.g. with a corresponding anatomical structure, physical tool, physical instrument, physical implant or physical device using a suitable registration method, for example using the methods and system disclosed throughout the specification. After this registration of the virtual data in a common coordinate system with the live surgical data, e.g. the anatomic structures, the position and pose of the virtual data relative to the live surgical data, e.g. the anatomic structures, is known, and therefore tracking information about the live surgical data can be used to determine the distance between virtual data and the HMD and/or the viewpoint of the user/operator and the virtual data and any physical instruments, physical tools, physical implants, or physical devices. The following embodiments therefore include a description of different methods to track live surgical data, e.g. anatomic structures (including, for example anatomic and or biomechanical axes), and how they relate to determining convergence, focal plane, focal point and/or scale parameters for display of the virtual data in the HMD. Any of the registration and tracking techniques described in the specification or known in the art can be used.

Convergence

In some embodiments, a video see through or an optical see through head mounted display can be configured to account for convergence and/or accommodation of the user's eye(s). Convergence can be the convergent rotation of the eyes where the visual axes of the two eyes are being brought into intersection at a 3D location in space. The head mounted display can, for example, be configured to account for convergence by measuring the inter-pupillary or inter-ocular distance. The inter-pupillary or inter-ocular distance can be measured using a ruler or an inter-ocular measurement device, for example, or any other technique known in the art. The head mounted display can, for example, be configured to account for convergence by measuring the amount of convergence using eye tracking, e.g. using systems or methods described in the specification for eye tracking or gaze tracking or known in the art, and by moving, e.g. rotating the left and right eye display unit of the head mounted display so that the display unit of each eye is substantially vertical to the visual axis of the left eye and the right eye, and/or by adjusting or moving the virtual data displayed by the HMD for the left eye and the right eye.

The head mounted display can, for example, be configured to account for convergence by measuring, with a computer system, the distance between an head mounted display and an anatomic structure, for example using an image capture, a video capture, a 3D scanner, a laser scanner, a navigation system, and/or using any of the techniques described in the specification or known in the art.

Outside-In Tracking

Figure 5A:
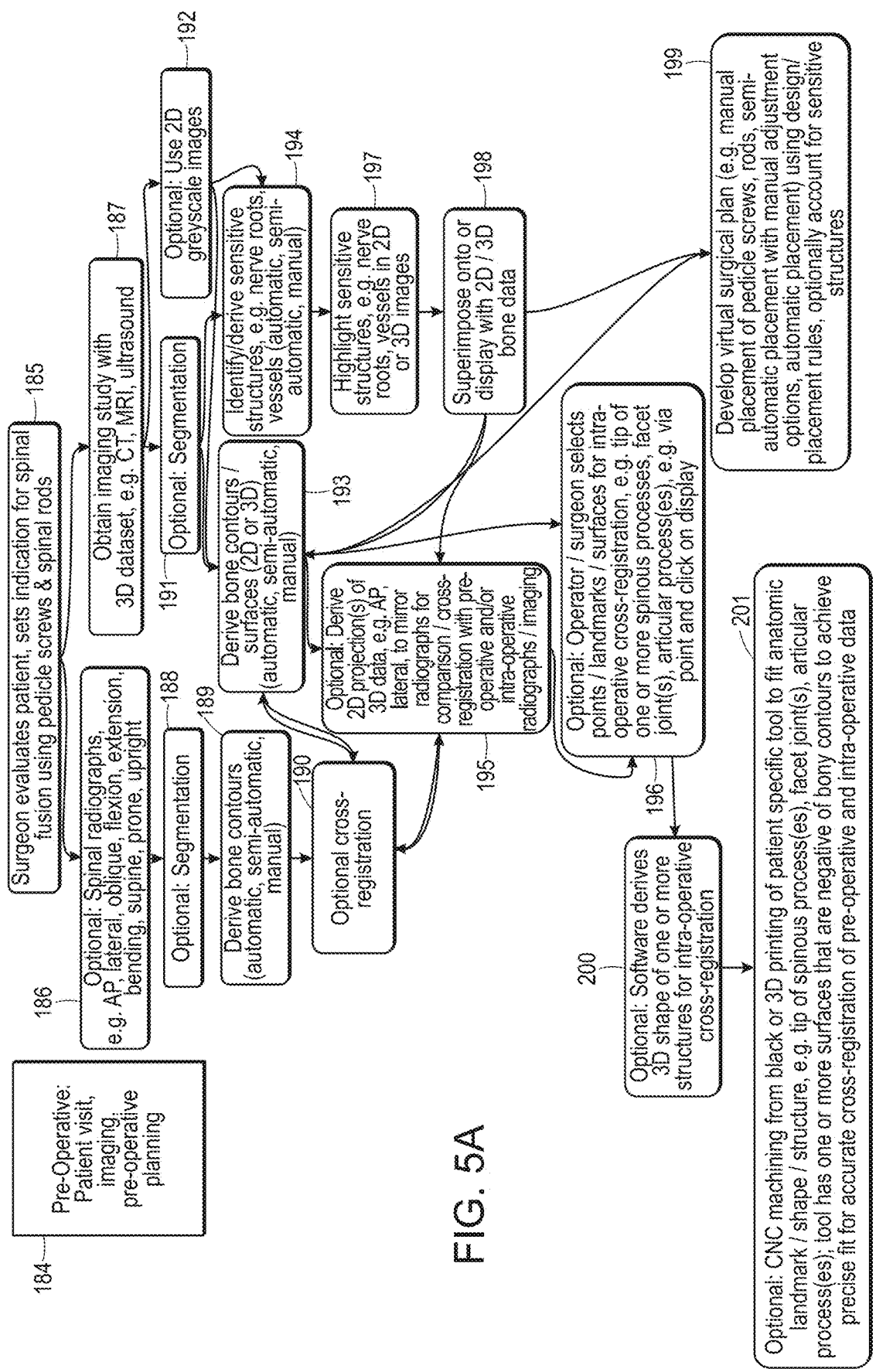
FIGS. 5A, 5B, 5C and 5D are illustrative flow charts of select options and approaches for performing spine surgery in a mixed reality environment according to some embodiments of the present disclosure.
Figure 5B:
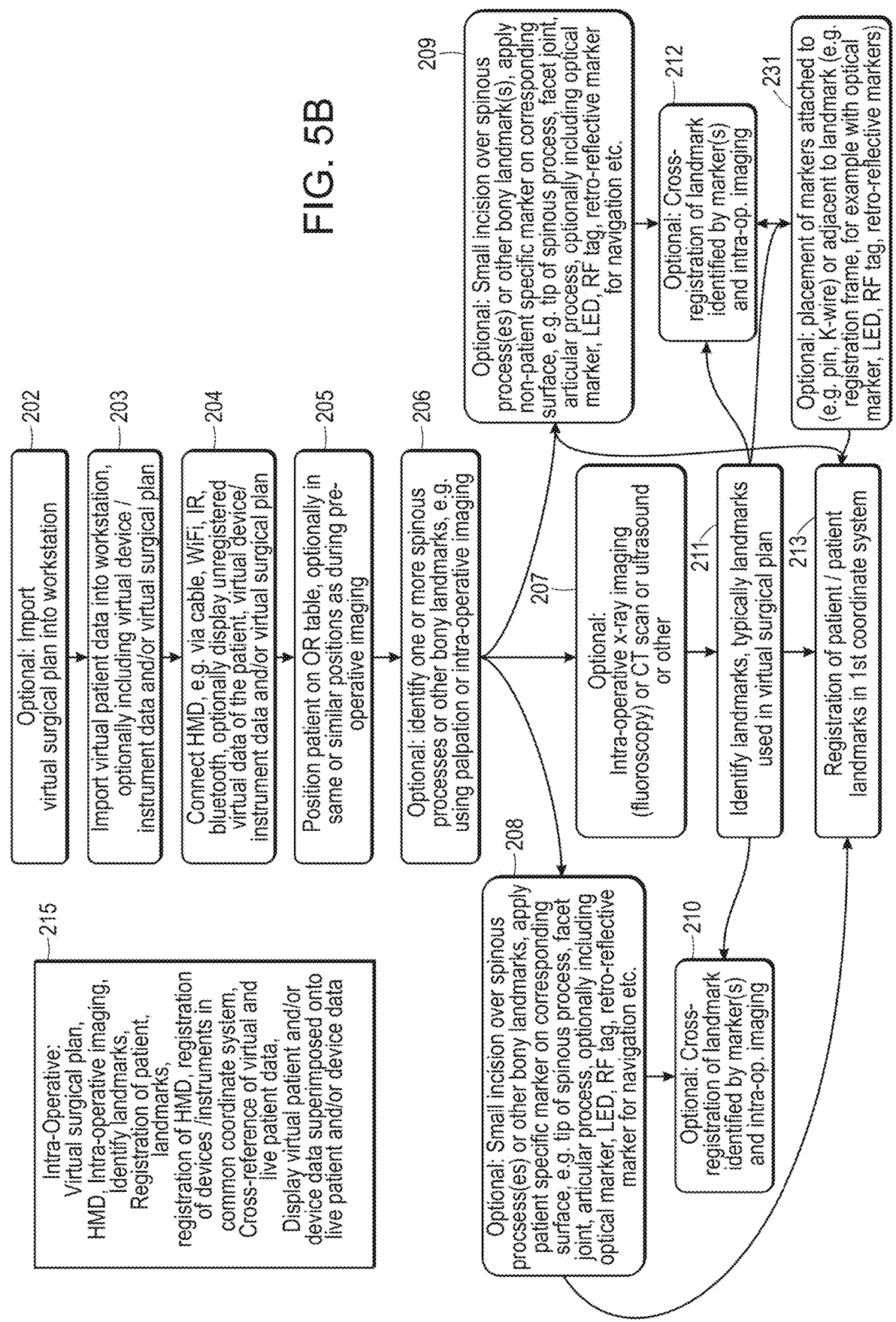
Figure 5C:
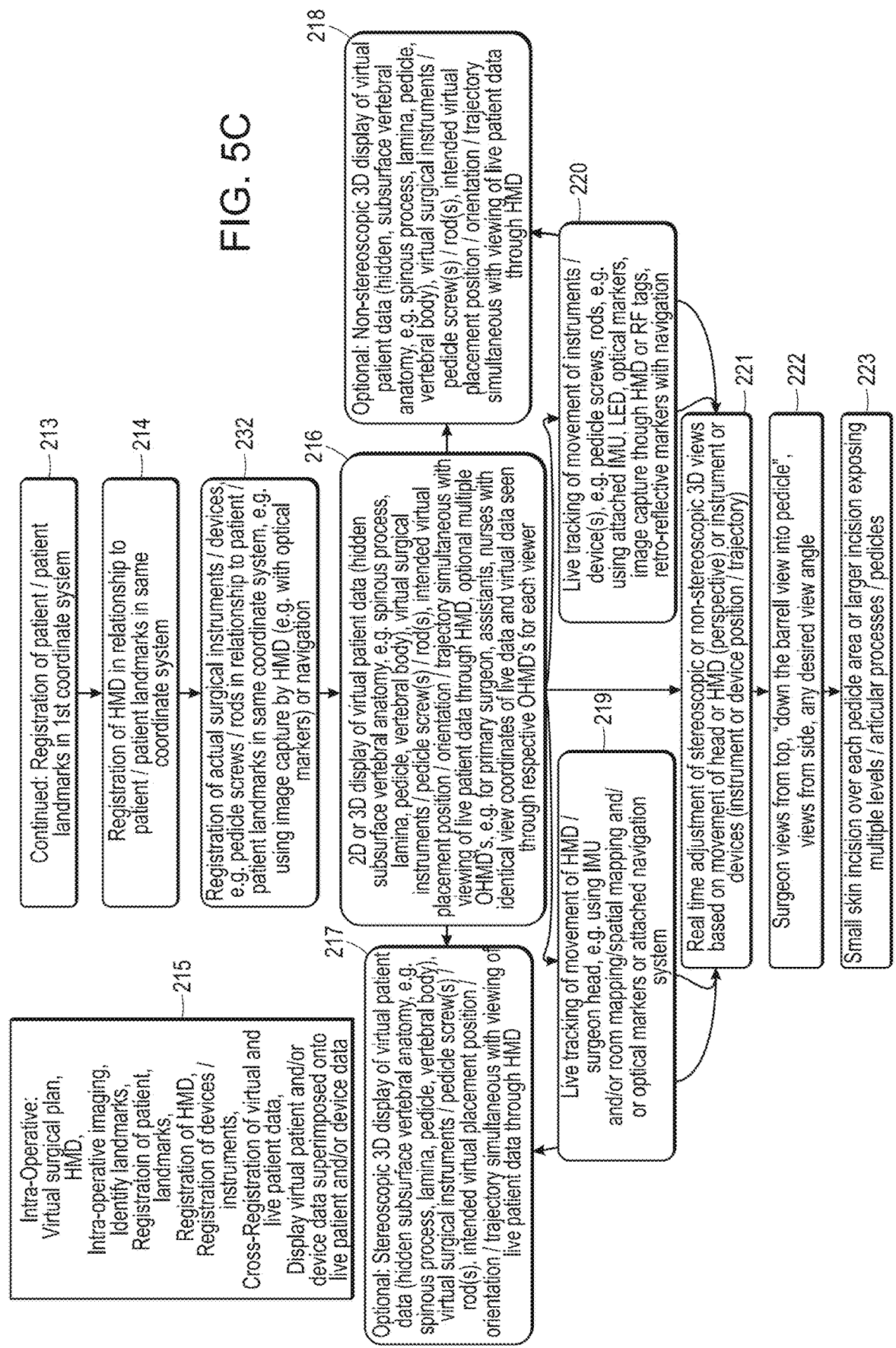
Figure 5D:
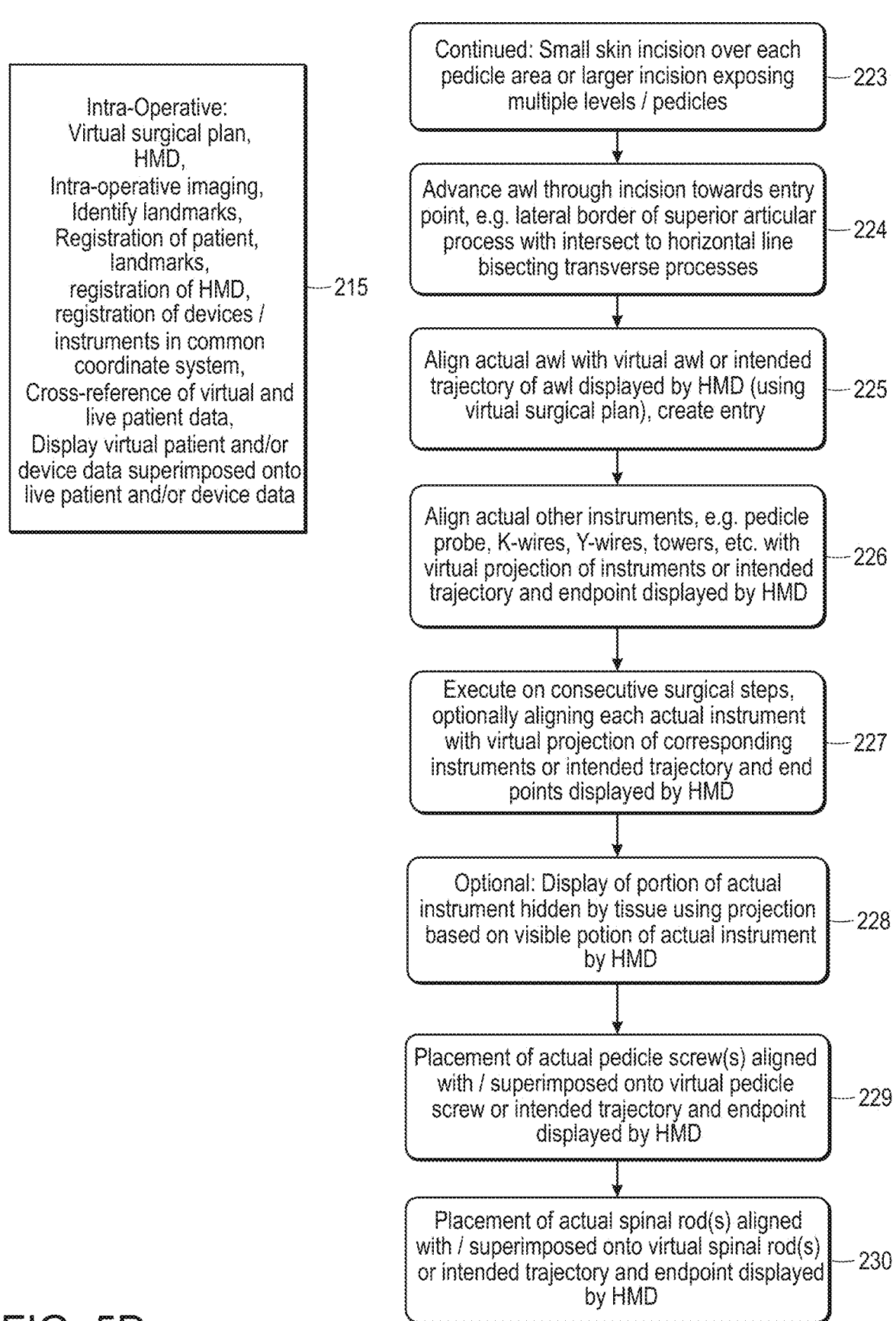

With outside-in tracking an image capture or video capture system 1100 using, for example, optical markers 1120, e.g. with geometric patterns, calibration phantoms or reference phantoms 1120 can be used for coordinate determination in the common coordinate system 1110 and distance measurements, as shown in exemplary fashion in FIG. 5B. One or more external cameras can be installed in a stationary location, e.g. on the ceiling, the wall or a stand or attached to the OR table. One or more optical markers 1120 can be applied to the HMD 1125 for tracking the coordinates and/or the position and/or orientation of the HMD 1125. One or more optical markers 1120 can be applied to the surgeon 1130 for tracking the coordinates and/or the position and/or orientation of the surgeon 1130. One or more optical markers 1120 can be applied to the anatomic structure 1140 or near the anatomic structure 1140 tracking the coordinates and/or the position and/or orientation of the anatomic structure. One or more optical markers 1120 can be applied to a physical tool, physical instrument 1150, physical implant or physical device 1160 tracking the coordinates and/or the position and/or orientation of the physical tool, physical instrument 1150, physical implant or physical device 1160.

Figure 6:
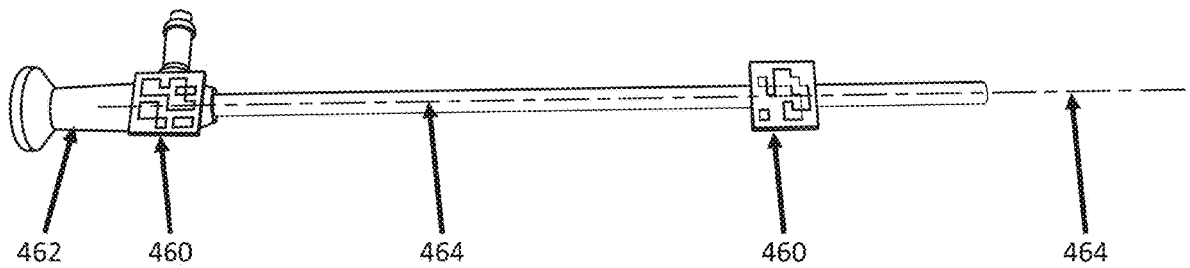
FIG. 6 shows an illustrative, non-limiting example of a surgical instrument with multiple optical markers attached for tracking the surgical instrument.
Figure 7:
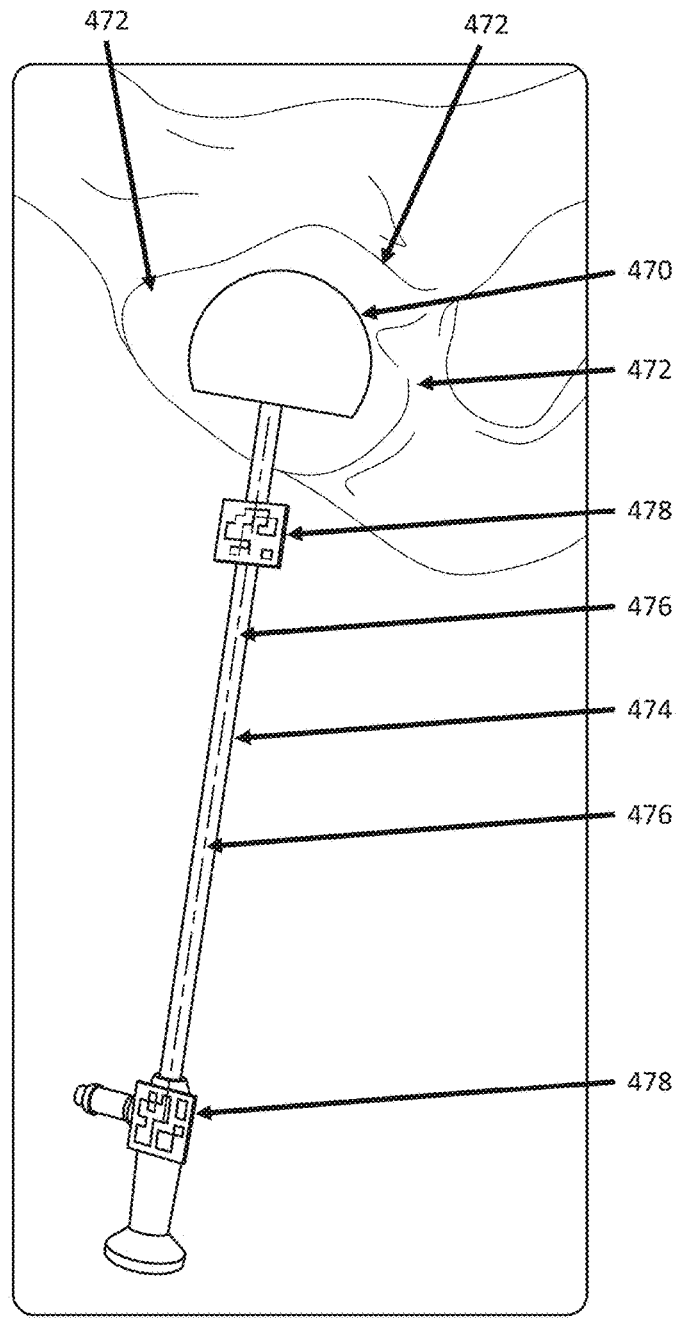
FIG. 7 shows an illustrative, non-limiting example of an acetabular placement instrument or tool with attached fiducial markers, in this example optical markers.

Multiple different technical approaches are possible to track the surgical instruments in the surgeon's live view of the patient through the HMD and to project the invisible parts of an instrument hidden by the tissue and its direction with the MHD. None of these approaches are meant to be limiting, but are only exemplary in nature. Someone skilled in the art can recognize other approaches for tracking surgical instruments using embodiments of the present disclosure. Multiple optical markers 460 can be attached to a surgical instrument 462 as shown in FIG. 6. For example, the markers can be fixed at defined positions on the instrument. With the geometry of the instrument known, the position and orientation of the instrument can be calculated, e.g. for an instrument like an awl with a tip for which its rotary orientation is aligned with the pointing axis only two markers 460 are needed as shown in FIG. 6. More markers can be used, e.g. in different geometric locations on the instrument with overlapping or separate, distinct x, y, and z coordinates (FIG. 7). The markers' 3D coordinates are recognized by the OMHD using the methods described in the preceding sections. Using the coordinates of a first and second marker, a vector 464, line in FIG. 6 pointing in the direction of the tip is calculated and displayed by the HMD to indicate the direction of the hidden portions of the instrument superimposed onto the surgical site, enabling the surgeon to align the physical awl or pedicle screw including its hidden portions with the intended path defined using the standard or virtual planning interface and also projected by the HMD. Rather than using two or more markers, a single marker can be used, for example with sufficient geometric information, e.g. along the long axis or other axis of the instrument, for accurate coordinate determination, e.g. 2, 3, 4, 5, 6, 7, 8, 9 or 10 cm long and, for example, 1, 2, 3, 4, 5, 6, or 7 or other cm wide, depending also on the spatial resolution of the camera system. In general, the greater the spatial resolution of the camera or video system, the smaller the marker size that can be used for accurate coordinate and/or vector determination. In addition, smaller marker sizes can be possible when markers are stationary, e.g. rigidly attached to a non-moving anatomic part of the patient or the OR table. Larger marker sizes can be used, for example, when markers are attached to a moveable anatomic landmark, e.g. a distal femoral condyle or a proximal tibial plateau, or a humerus, or a humeral tuberosity, or when they are attached to the HMD and are thus, for example, subject to movement as the surgeon moves his or her head.

Another approach uses pivoting, a mathematical technique for determining the position of the tip. With pivoting, the instruments tip is fixed in one position on the tissue while the whole instrument is moved. The attached optical markers move on a spherical surface. This leads, for example, to an accurate registration of an entry point.

In some embodiments, the computer processor can be configured to maintain the 2D imaging slice or imaging cross-section projected by the HMD superimposed and/or aligned with the physical tissue of the patient always in a constant or the same position relative to the physical tool, physical instrument, physical implant, e.g. intersecting with the tip or located at the tip, while maintaining a fixed anatomic orientation, e.g. sagittal, coronal, axial, oblique sagittal, oblique coronal, oblique axial, curved sagittal, curved coronal, curved axial. This can be advantageous, for example, when a biopsy needle or a tissue harvester is moved or advanced through soft-tissue or hard tissue, e.g. during a brain, heart, lung, thyroid, parathyroid, liver, spleen, kidney, adrenal, prostate, ovary, bone, cartilage or any other biopsy. This can also be advantageous, for example, for any surgical procedure where a physical surgical tool, physical surgical instrument, physical implant or any other physical surgical device is moved or advanced through soft-tissue or hard tissue, e.g. through a brain, heart, lung, thyroid, parathyroid, liver, spleen, kidney, adrenal, prostate, ovary, bone, cartilage or any other tissue. For example, as a surgeon moves and advances a physical needle, physical awl, physical screw through a vertebra or a portion of a vertebra, e.g. a pedicle [for example for a spinal fusion], the computer processor can be configured to move and/or advance 2D imaging slices through the vertebra, portion of the vertebra, e.g. the pedicle, and the imaging slices can always be located at the tip of the tracked physical needle, physical awl or physical screw and can always be in a fixed anatomic orientation, e.g. in a sagittal, coronal, axial, oblique sagittal, oblique coronal, oblique axial, curved sagittal, curved coronal, or curved axial plane. Thus, as the surgeon moves the physical needle, physical awl or physical screw from a first position with a first set of coordinates to a second position with a second set of coordinates, the HMD can display a first 2D imaging slice through the pedicle at the first position, with the 2D imaging slices intersecting with or located at the tip of the physical needle, physical awl or physical screw and, for example, oriented in a coronal plane or a sagittal plane or an axial plane at the first position or first coordinates and the HMD can then display a second 2D imaging slice through the pedicle at the second position, with the 2D imaging slices intersecting with or located at the tip of the physical needle, physical awl or physical screw and, for example, oriented in a coronal plane or a sagittal plane or an axial plane at the second position or second coordinates. In this manner, the surgeon can always monitor the location of the physical needle, physical awl or physical screw inside the physical tissue of the patient and relative to the 2D images obtained pre- or intra-operatively from the patient. This can be beneficial, for example, when complex 3D structures, e.g. a spine reconstructed in 3D from a CT scan or MRI scan, can potentially obscure fine anatomic detail inside the patient due to superimposition of multiple structures. This can also be beneficial during spinal fusion surgery with pedicle screws since the cortex of the pedicle and the inner pedicle wall or endosteum can be difficult to see on a superimposed and/or aligned 3D display of the spine, e.g. reconstructed from a CT scan, while it can be readily visible on the superimposed and/or aligned 2D imaging, e.g. a CT slice superimposed and/or aligned with the corresponding physical tissue/pedicle slice of the patient. In some embodiments, the 2D image(s) displayed by the HMD can be maintained by the computer processor in a fixed location, e.g. the center of a pedicle, while the physical tool, physical instrument, physical implant or physical device is moved, e.g. inside the pedicle.

In some embodiments, more than one 2D slice can be displayed by the HMD, for example at least two or more of a sagittal, coronal, axial, oblique sagittal, oblique coronal, oblique axial, curved sagittal, curved coronal, or curved axial slices or images. The two or more 2D slices can be moved through the tissue, e.g. anterior, posterior, medial, lateral, superior, inferior, by the computer processor of the HMD display following the movement of a tracked physical tool, physical instrument, physical implant or physical device so that the two or more 2D slices displayed by the computer processor of the HMD display are always superimposed onto and/or aligned with a corresponding slice of the patient's physical tissue in the coordinate system while the physical tool, physical instrument, physical implant or physical device is moved in the patient's tissue and in the coordinate system and their position and/or orientation relative to the physical tool, physical instrument, physical implant or physical device can be maintained during the movement. The two or more 2D slices or cross-sections can intersect in the display of the HMD. The intersection can be, for example, centered around an anatomic structure or maintained [e.g. during movement of the patient, the surgical site, the HMD, the physical tool, physical instrument, physical implant or physical device] at or over an anatomic structure or site, e.g. the center of a pedicle or a line through the pedicle. The intersection can be centered around or maintained at or around a physical surgical tool, physical surgical instrument, physical implant or any other physical surgical device, e.g. around a long axis or other portion of the physical surgical tool, physical surgical instrument, physical implant or any other physical surgical device. The maintaining of the intersection of the two or more imaging planes over a portion of the physical surgical tool, physical surgical instrument, physical implant or any other physical surgical device can be performed by the computer processor while the tracked physical surgical tool, physical surgical instrument, physical implant or any other physical surgical device are moved inside the physical tissue of the patient, e.g. while an awl is advanced inside a pedicle.

Use of Virtual Data in 3 or More Dimensions

In some embodiments, the HMD can display a 3D virtual image of the patient. A 3D representation of the patient can include a 3D display of different types of anatomy, for example in an area of intended surgery or a surgical site.

A 3D reconstruction of image data or other data of the patient can be generated preoperatively, intraoperatively and/or postoperatively. A virtual 3D representation can include an entire anatomic area or select tissues or select tissues of an anatomic area. Different tissues can be virtually displayed by the HMD in 3D using, for example, different colors. Normal tissue(s) and pathologic tissue(s) can be displayed in this manner.

Normal tissue can, for example, include brain tissue, heart tissue, lung tissue, liver tissue, vascular structures, bone, cartilage, spinal tissue, intervertebral disks, nerve roots. Any tissue can be visualized virtually by the HMD.

Registration of Virtual Data and Live Data of a Patient, for Example Over a Surgical Site In some embodiments, virtual data of a patient displayed by an HMD and live data of a patient seen through an HMD are spatially registered in relationship to each other, for example in a common coordinate system, for example with one or more optical HMDs in the same common coordinate system. Virtual and physical surgical instruments and implant components can also be registered in the common coordinate system. Spatial co-registration can have the benefit that the simultaneous display of virtual and live data of the patient is not affected or less affected when the surgeon moves his or her head or body, when the HMD moves or when the patient moves. Thus, the view perspective of the live data of the patient seen by the surgeon's eyes through the HMD, e.g. the live surgical field, can stay the same as the view perspective of the virtual data of the patient seen by the surgeon's eyes through the display of the HMD unit, e.g. the virtual surgical field, virtual surgical plane, virtual paths, virtual cut paths or planes, projected into the surgeon's eyes, even as the surgeon moves his or her head or body. In this manner, the surgeon does not need to re-think or adjust his hand eye coordination since live data of the patient seen through the surgeon's eye and virtual data of the patient seen through the HMD display are superimposed, which is fundamentally different from other approaches such as surgical navigation which employ a separate computer monitor in the OR with a view angle for the surgeon that is different than his or her view angle for the live data of the patient and the surgical field. Also, with surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations the first and the second virtual instruments are compared.

With guidance in mixed reality environment, e.g. with stereoscopic display like an electronic holographic environment, a virtual surgical guide, tool, instrument or implant can be superimposed onto the joint, spine or surgical site. Further, the physical guide, tool, instrument or implant can be aligned with the 2D or 3D representation of the virtual surgical guide, tool, instrument or implant. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In some embodiments, virtual data can move in relationship to the surgeon or operator or in relationship to the patient or a certain target anatomy within a patient. This means if the surgeon moves his or her head or the body or parts of the patient's anatomy are being moved, the virtual data will move in the HMD display. For example, once registration of the HMD, the virtual data of the patient and the live data of the patient in a common coordinate system has occurred, the HMD can display a virtual image of a target tissue or adjacent tissue. The virtual image of the target tissue or adjacent tissue can be, for example, an image of or through a tumor or other type of pathologic tissue or a spine or a spinal pedicle. As the surgeon or operator moves his or her head or body during the surgical procedure, the virtual data will move and change location and orientation the same way how the surgeon moves his/her head or body, typically reflecting the change in perspective or view angle that the surgeon obtained by moving his or her head or body. The virtual data can include a 3D representation of a surgical tool or instrument such as a needle for kyphoplasty or vertebroplasty, where the virtual representation of the needle shows its intended location, orientation or path in relationship to the spine and/or a pedicle. The virtual data can also include a medical device, such as a pedicle screw, wherein the virtual data of the pedicle screw shows its intended location, orientation or path in relationship to the spine, and/or a pedicle, and/or a vertebral body.

In some embodiments, registration is performed with at least three or more points that can be superimposed or fused into a common object coordinate system for virtual data and live data. Registration can also be performed using a surface or a 3D shape of an anatomic structure present in both virtual data and live data of the patient. In this case the virtual surface can be moved until it substantially matches the live surface of the patient or the virtual shape can be moved until it substantially matches the live shape of the patient.

Registration of virtual data of a patient and live data of a patient can be achieved using different means. The following is by no means meant to by limiting, but is only exemplary in nature.

Registration of Virtual Patient Data and Live Patient Data Using Directly or Indirectly Connected Object Coordinate Systems Registration of virtual and live data of the patient can be performed if the virtual data, e.g. imaging data of the patient, are acquired with the patient located in a first object coordinate system and the live data, e.g. during surgery, are observed or acquired with the patient located in a second object coordinate system, wherein the first and the second object coordinate system can be connected by direct, e.g. physical, or indirect, e.g. non-physical, means. A direct connection of the first and second object coordinate system can be, for example, a physical connection between the first and second object coordinate system. For example, the patient can be moved from the first to the second object coordinate system along the length of a tape measure. Or the patient can be scanned inside a scanner, e.g. a CT scanner or MRI scanner, and the scanner table can be subsequently moved out of the scanner for performing a surgical procedure with the patient still located on the scanner table. In this case, the scanner table can be a form of physical connection between the first and the second object coordinate system and the length of the table movement between the scan position and the outside the scanner position (for the live data, e.g. the surgical procedure) can define the coordinate transformation from the first to the second object coordinate system.

An indirect connection between the first (virtual data) and second (live data) object can be established if the patient is moved between the acquiring the virtual data, e.g. using an imaging test, and the live data, e.g. while performing a surgical procedure, along a defined path, wherein the direction(s) and angle(s) of the path are known so that the first and the second object coordinate system can be cross-referenced and an object coordinate transfer can be applied using the known information of the defined path and virtual data of the patient, live data of the patient and the HMD can be registered in a common coordinate system. Virtual and physical surgical instruments and implant components can also be registered in the common coordinate system.

Registration of virtual patient data and live patient data is also possible without directly or indirectly connected object coordinate systems using other means and methods as will be explained in the following paragraphs and columns, for example when the patient performed one or more movements of unknown direction, length or magnitude. Combinations of all different registration methods described in the specification are possible, e.g. for switching registration methods during a procedure or for simultaneously using multiple registration methods, e.g. for enhancing the accuracy of the registration.

Registration Using Spatial Mapping

Live data, e.g. live data of the patient, the position and/or orientation of a physical instrument, the position and/or orientation of an implant component, the position and/or orientation of one or more HMDs, can be acquired or registered, for example, using a spatial mapping process. This process creates a three-dimensional mesh describing the surfaces of one or more objects or environmental structures using, for example and without limitation, a depth sensor, laser scanner, structured light sensor, time of flight sensor, infrared sensor, or tracked probe. These devices can generate 3D surface data by collecting, for example, 3D coordinate information or information on the distance from the sensor of one or more surface points on the one or more objects or environmental structures. The 3D surface points can then be connected to 3D surface meshes, resulting in a three-dimensional surface representation of the live data. The surface mesh can then be merged with the virtual data using any of the registration techniques described in the specification.

The live data can be static, or preferably, it can be intermittently, continuously, or in real time updated with additional information to incorporate changes in the position or surface of the one or more objects or environmental structures. The additional information can, for example be acquired by a depth sensor, laser scanner, structured light sensor, time of flight sensor, infrared sensor, or tracked probe.

For initial spatial mapping and updating of mapping data, commonly available software code libraries can be used. For example, this functionality can be provided by the Microsoft HoloToolkit or the Google Project Tango platform. Various techniques have been described for spatial mapping and tracking including those described in U.S. Pat. No. 9,582,717, which is expressly incorporated by reference herein in its entirety.

Registration of Virtual Patient Data and Live Patient Data Using Visual Anatomic Features a) Visual registration of virtual patient data in relationship to live patient data by the surgeon or operator In some embodiments, a surgeon or operator can visually align or match virtual patient data with live patient data. Such visually aligning or matching of virtual patient data and live patient data can, for example, be performed by moving the HMD, for example via movement of the head of the operator who is wearing the HMD. In this example, the virtual patient data can be displayed in a fixed manner, not changing perspective as the operator moves the HMD. The operator will move the HMD until the live patient data are aligned or superimposed onto the fixed projection of the virtual patient data. Once satisfactory alignment, matching or superimposition of the live patient data with the virtual patient data has been achieved, the surgeon can execute a registration command, for example via a voice command or a keyboard command or using a user interface. The virtual patient data and the live patient data are now registered. At this point, upon completion of the registration, the virtual patient data will move corresponding to the movement of the HMD, for example as measured via the movement of an integrated IMU, image and field of view tracking, e.g. using anchor points in an image or field of view using an image and/or video capture system, and/or an attached navigation system with optical or RF or other trackers, which can be attached to the patient, the surgical site, a bone or any other tissue of the patient, the surgeon, the surgeon's arm, the surgeon's head or an HMD worn by the surgeon.

Thus, once a satisfactory alignment or match has been achieved the surgeon can execute a command indicating successful registration. The registration can include changes in at least one of position, orientation, and magnification of the virtual data and the live data in order to achieve the alignment or match. Magnification applied to the virtual data can be an indication of the distance from the HMD or the surgeon's head to the matched tissue. As a means of maximizing the accuracy of the registration, the estimated distance between the HMD and the target tissue or the skin surface or other reference tissue can be confirmed with an optional physical measurement of the distance, in particular if the HMD is, for example, in a fixed position, e.g. on a stand or tripod, which may be used optionally during the initial registration. Upon successful alignment or matching, the surgeon command can register, for example, the virtual patient data and the live patient data or images and the HMD in the same common coordinate system. Virtual and physical surgical instruments and implant components can also be registered in the common coordinate system.

In some embodiments, the visual anatomic data can be, for example, gyri of the brain or osteophytes or bone spurs or pathologic bone deformations or tumor nodes or nodules, e.g. on the surface of a liver or a brain.

Figure 8:
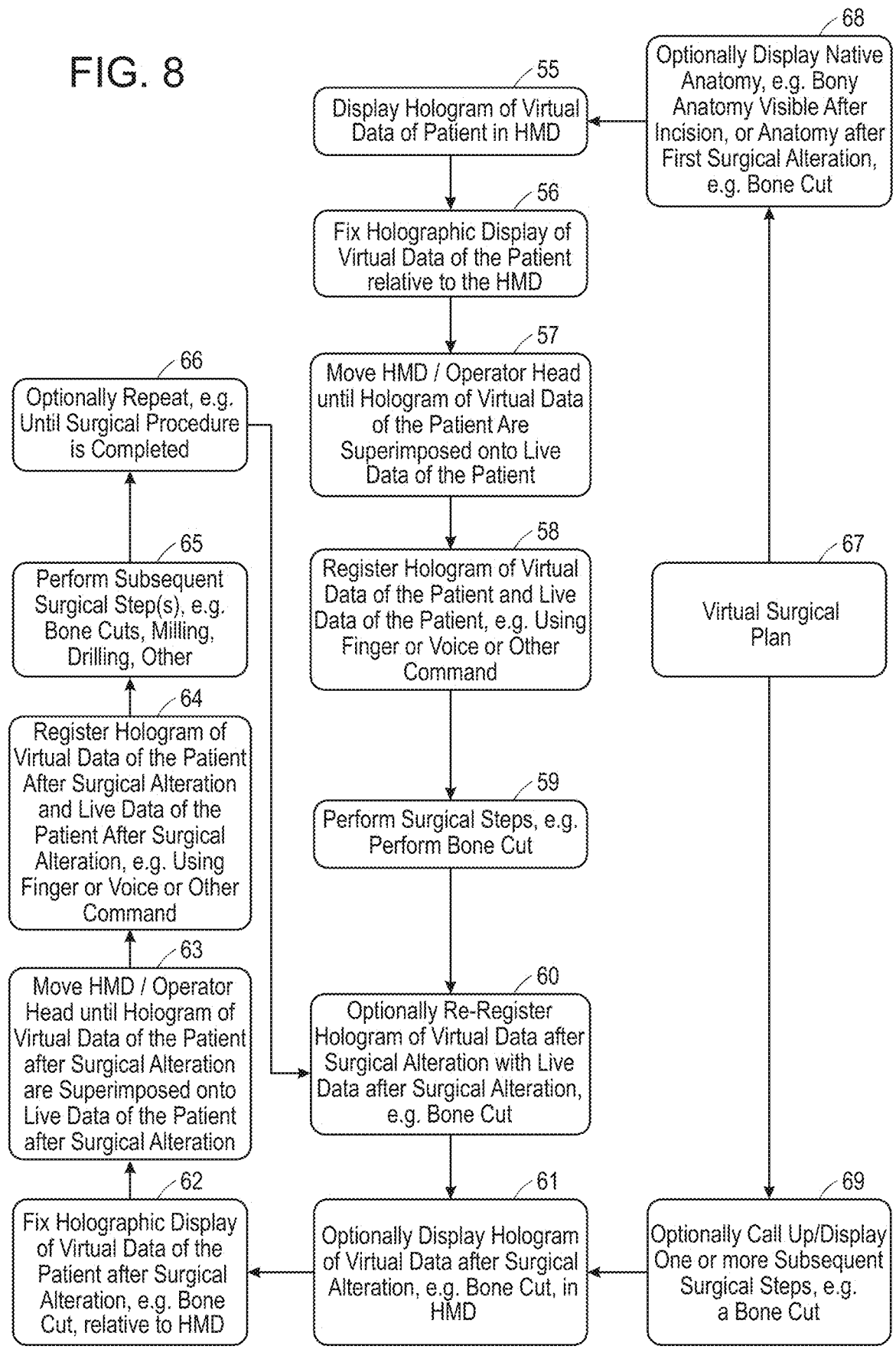
FIG. 8 illustrates an example of registering a digital hologram for an initial surgical step, performing the surgical step and re-registering one or more digital holograms for subsequent surgical steps according to some embodiments of the present disclosure.

In some embodiments, the registration of virtual patient data and live patient data using the methods described herein can be repeated after one or more surgical steps have been performed. In this case, the surgically altered tissue or tissue surface or tissue contour or shape, e.g. shape of a bone after milling or reaming, or tissue perimeter, e.g. perimeter of a bone cut, or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, with substantially identical view angle of the virtual data of the patient seen by the surgeon's eyes through the display of the HMD unit and the live data of the patient seen by the surgeon's eyes through the HMD unit. The matching, superimposing and/or registering of the live data of the patient and the virtual data of the patient after the surgical tissue alteration can be performed using the same methods described in the foregoing or any of the other registration methods described in the specification or any other registration method known in the art. Referring to FIG. 8 illustrates an example of registering a digital hologram or virtual data for an initial surgical step, performing the surgical step and re-registering one or more holograms for subsequent surgical steps. An head mounted display can project or display a digital hologram of virtual data or virtual data of the patient 55. The digital hologram can optionally be fixed to the HMD so that it will move with the movement of the HMD 56. The operator can move the HMD until digital hologram of the virtual data or virtual data of the patient is superimposed and aligned with the live data of the patient, e.g. the surgical site 57. The digital hologram of the virtual data or virtual data can then be registered using the same or similar coordinates as those of the live data with which the digital hologram is superimposed 58. The surgeon can then perform one or more predetermined surgical steps, e.g. bone cuts 59. A digital hologram of the virtual data or virtual data can optionally be registered or re-registered after the surgical alteration with the live data 60. The digital hologram of the virtual data or virtual data after the surgical alteration can optionally be displayed by the HMD 61. The digital hologram of the virtual data or virtual data after the surgical alteration can optionally be fixed relative to the HMD so that it will move with the movement of the HMD 62. The operator can move the HMD until digital hologram of the virtual data or virtual data of the patient after the surgical alteration is superimposed and aligned with the live data of the patient after the surgical alteration 63. The digital hologram of the virtual data or virtual data can then be registered using the same or similar coordinates as those of the live data after the surgical alteration with which the digital hologram is superimposed 64. The surgeon can then perform one or more predetermined subsequent surgical steps, e.g. bone cuts, milling or drilling 65. The preceding steps can optionally be repeated until the surgical procedures are completed 66. A virtual surgical plan 67 can be utilized. Optionally, the native anatomy of the patient including after a first surgical alteration can be displayed by the HMD 68. The HMD can optionally display digital holograms of subsequent surgical steps 69.

b) Automatic or semi-automatic registration of virtual patient data in relationship to live patient data using image processing and/or pattern recognition and matching techniques c) In some embodiments, image processing techniques, pattern recognition techniques or deep learning/artificial neural-network based techniques can be used to match virtual patient data and live patient data. Optionally, image processing and/or pattern recognition algorithms can be used to identify certain features, e.g. gyri or sulci on the brain surface of virtual data of a patient. An ear including its unique shape can also be used for the purpose of matching virtual patient data and live patient data.

For example, with brain surgery, the patient can be placed on the operating table. Optionally, cleaning or sterilization fluid can be applied to the shaved skull, for example using betadine. The HMD can be placed over the patient, either on a tripod or worn by the operator, for example with the head of the patient turned sideways over the live patient's ear and lateral skull. The HMD will be placed over an area of the live patient that includes the virtual data of the patient to be displayed.

Virtual data of the patient can be displayed in the HMD. The virtual data of the patient can include, for example, a visualization of the patient's skin or other data, e.g. the patient's ear or nose, for example derived from preoperative MRI data. The virtual data of the patient's skin or other structures, e.g. the patient's ear or nose, can be displayed simultaneous with the live patient data. The virtual data of the patient can then be moved, re-oriented, re-aligned and, optionally, magnified or minified until a satisfactory alignment, match or superimposition has been achieved. Optionally, the HMD can be moved also during this process, e.g. to achieve a satisfactory size match between virtual data and live data of the patient, optionally without magnification or minification of the virtual data of the patient.

Once a satisfactory alignment, match or superimposition has been achieved between virtual data and live data of the patient, the operator can execute a command indicating successful registration. Changes in position, orientation, or direction of the HMD, for example as measured via an integrated IMU, image and field of view tracking, e.g. using anchor points in an image or field of view using an image and/or video capture system, and/or a navigation system attached to the HMD, can be used to move the virtual patient data with the view of the live patient data through the HMD, with substantially identical object coordinates of the virtual data of the patient and the live data of the patient, thereby maintaining registration during the course of the surgery irrespective of any movements of the HMD, e.g. head movement by the operator wearing the HMD, and ensuring that the virtual data of the patient is correctly superimposed with the live data of the patient when projected into the surgeon's view.

After successful registration of the virtual patient data to the patient's skin or other structures, e.g. an ear or a nose, the operator or an assistant can apply a marker or calibration or registration phantom or device on the patient, for example close to the intended site of a craniotomy. The marker or calibration or registration phantom or device will not be covered by any drapes or surgical covers that will be placed subsequently. A secondary registration of the virtual patient data to the live patient data can then occur, by registering the virtual patient data to the live patient data, using the live marker or calibration or registration phantom or device placed on the patient and by cross-referencing these to the live data of the patient's skin or other structures, e.g. an ear or a nose. This can be achieved, for example, by registering the patient's skin or other structures, e.g. an ear or a nose, in the same coordinate system as the marker or calibration or registration phantom or device placed on the patient, e.g. by co-registering the virtual patient data of the patient's skin or other structures, e.g. an ear or a nose or an osteophyte or bone spur or other bony anatomy or deformity, with the live data of the marker or calibration or registration phantom or device. The distance, offset, angular offset or overall difference in coordinates between the patient's skin or other structures, e.g. an ear or nose or an osteophyte or bone spur or other bony anatomy or deformity, to the marker or calibration or registration phantom or device attached to the patient can be measured and can be used to switch the registration of the virtual patient data to the live patient data from the live data of the patient's skin or other structures, e.g. an ear or a nose, to the live data of the marker or calibration or registration phantom or device. Optionally, registration can be maintained to both the live data of the patient's skin or other structures, e.g. an ear or a nose, and the live data of the marker or calibration or registration phantom or device. Optionally, the system can evaluate if registration to the live data of the patient's skin or other structures, e.g. an ear or a nose, or to the live data of the marker or calibration or registration phantom or device is more accurate and the system can switch back and forth between either. For example, if the distance increases or decreases from the HMD to the patient's skin or other structure, e.g. an ear or a nose, beyond a certain level, e.g. a threshold, which can be optionally predefined, or if some of them is partially covered by a drape, the system can switch the registration to the live data of the marker or calibration or registration phantom or device. The reverse is possible. Or, if the angle from the HMD increases or decreases beyond a certain level, e.g. a threshold, which can be optionally predefined, to the patient's skin or other structure, e.g. an ear or a nose or an osteophyte or bone spur or other bony anatomy or deformity, the system can switch the registration to the live data of the marker or calibration or registration phantom or device. The reverse is possible.

The operator or the assistants can then place sterile drapes or surgical covers over the site, however preferably not covering the marker or calibration or registration phantom or device. Registration can be maintained via the live data of the marker or calibration or registration phantom or device attached to the patient, e.g. adjacent to or inside a craniotomy site.

Image processing and/or pattern recognition of the live data of the patient can then be performed through the HMD, e.g. using a built-in image capture apparatus and/or a 3D scanner for capturing the live data of the patient or image and/or video capture systems and/or a 3D scanner attached to, integrated with or coupled to the HMD.

Virtual and live data features or patterns can then be matched. The matching can include a moving and/or reorienting and/or magnification and/or minification of virtual data for successful registration with the live data of the patient and superimposition of both. Virtual and live data can include an osteophyte or bone spur or other bony anatomy or deformity. Combination of (a) and (b), e.g. automatic registration with manual adjustment option, e.g. by moving the virtual image data in relation to the live image data after image processing software and/or pattern recognition software and/or matching software have identified a potential match or performed an initial matching, which can then be followed by manual/operator based adjustments. Alternatively, manual/operator based matching and registration can be performed first, followed then by fine-tuning via software or algorithm (image processing, pattern recognition, etc.) based matching and registration. Virtual and live data can include an osteophyte or bone spur or other bony anatomy or deformity.

In some embodiments, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art.

Registration of Virtual Patient Data and Live Patient Data Using Anatomic Landmarks In some embodiments, a surgeon can identify select anatomic landmarks on virtual data of the patient, e.g. on an electronic preoperative plan of the patient, and on live data of the patient. For example, the surgeon can identify a landmark by placing a cursor or a marker on it on an electronic image of the virtual data of the patient and by clicking on the landmark once the cursor or marker is in the desired location. In a spine, such a landmark can be, for example, the posterior tip of a spinous process, a spinal lamina, an inferior facet on the patient's left side, a superior facet on the patient's left side, an inferior facet on the patient's right side, a superior facet on the patient's right side, a tip of a facet joint, a bone spur, an osteophyte etc. In a hip, such landmarks can be the most anterior point of the acetabulum, an osteophyte, e.g. on the acetabular rim, in the acetabulum, adjacent to the acetabulum, on the femoral head, on the femoral neck or the neck shaft junction, the center of the femoral head in a 2D or 3D image, the most anterior point of the femoral head, an anterosuperior iliac spine, an anteroinferior iliac spine, a symphysis pubis, a greater trochanter, a lesser trochanter etc. In a knee, such landmarks can be a femoral condyle, a femoral notch, an intercondylar space, a medial or lateral epicondyle, a femoral axis, an epicondylar axis, a trochlear axis, a mechanical axis, a trochlear groove, a femoral osteophyte, a marginal femoral osteophyte, a central femoral osteophyte, a dome of the patella, a superior, medial, lateral, inferior edge of the patella or the femur or femoral articular surface, a patellar osteophyte, an anterior tibia, a tibial spine, a medial, lateral, anterior, posterior edge of the tibia, a tibial osteophyte, a marginal tibial osteophyte, a central tibial osteophyte. The surgeon can then identify the same landmarks live in the patient. For example, as the surgeon looks through the HMD, the surgeon can point with the finger or with a pointing device at the corresponding anatomic landmark in the live data. The tip of the pointer or the tip of the finger can, optionally, include a tracker which locates the tip of the pointer or the finger in space. Such locating can also be done visually using image and/or video capture and/or a 3D scanner, e.g. in a stereoscopic manner through the HMD for more accurate determination of the distance and location of the pointer or finger in relationship to the HMD. An image and/or video capture system and/or a 3D scanner can also be attached to, integrated with or coupled to the HMD. Virtual and live data can include an osteophyte or bone spur or other bony anatomy or deformity.

Representative anatomic landmarks that can be used for registration of virtual and live data of the patient can include (but are not limited to):

In Spine: A portion or an entire spinous process; A portion or an entire spinal lamina; A portion or an entire spinal articular process; A portion of or an entire facet joint; A portion of or an entire transverse process; A portion of or an entire pedicle; A portion of or an entire vertebral body; A portion of or an entire intervertebral disk; A portion of or an entire spinal osteophyte; A portion of or an entire spinal bone spur; A portion of or an entire spinal fracture; A portion of or an entire vertebral body fracture or Combinations of any of the foregoing Hip: A portion of or an entire acetabulum; A portion of or an entire edge of an acetabulum; Multiple portions of an edge of an acetabulum; A portion of an iliac wall; A portion of a pubic bone; A portion of an ischial bone; An anterior superior iliac spine; An anterior inferior iliac spine; A symphysis pubis; A portion of or an entire greater trochanter; A portion of or an entire lesser trochanter; A portion of or an entire femoral shaft; A portion of or an entire femoral neck; A portion of or an entire femoral head; A fovea capitis; A transverse acetabular ligament; A pulvinar; A ligamentum teres; A labrum; One or more osteophytes, femoral and/or acetabular or Combinations of any of the foregoing Knee: A portion or an entire medial femoral condyle; A portion or an entire lateral femoral condyle; A portion or an entire femoral notch; A portion or an entire trochlea; A portion of an anterior cortex of the femur; A portion of an anterior cortex of the femur with adjacent portions of the trochlea; A portion of an anterior cortex of the femur with adjacent portions of the trochlea and osteophytes when present; One or more osteophytes femoral and/or tibial; One or more bone spurs femoral and/or tibial; An epicondylar eminence; A portion or an entire medial tibial plateau; A portion or an entire lateral tibial plateau; A portion or an entire medial tibial spine; A portion or an entire lateral tibial spine; A portion of an anterior cortex of the tibia; A portion of an anterior cortex of the tibia and a portion of a tibial plateau, medially or laterally or both; A portion of an anterior cortex of the tibia and a portion of a tibial plateau, medially or laterally or both and osteophytes when present; A portion or an entire patella; A medial edge of a patella; A lateral edge of a patella; A superior pole of a patella; An inferior pole of a patella; A patellar osteophyte; An anterior cruciate ligament; A posterior cruciate ligament; A medial collateral ligament; A lateral collateral ligament; A portion or an entire medial meniscus; A portion or an entire lateral meniscus or Combinations of any of the foregoing Shoulder: A portion or an entire glenoid; A portion or an entire coracoid process; A portion or an entire acromion; A portion of a clavicle; A portion or an entire humeral head; A portion or an entire humeral neck; A portion of a humeral shaft; One or more humeral osteophytes; One or more glenoid osteophytes; A portion or an entire glenoid labrum; A portion or an entire shoulder ligament, e.g. a coracoacromial ligament, a superior, middle, or inferior glenohumeral ligament; A portion of a shoulder capsule or Combinations of any of the foregoing Skull and brain: A portion of a calvarium; A portion of an occiput; A portion of a temporal bone; A portion of a occipital bone; A portion of a parietal bone; A portion of a frontal bone; A portion of a facial bone; A portion of a facial structure; A portion or an entire bony structure inside the skull; Portions or all of select gyri; Portions or all of select sulci; A portion of a sinus; A portion of a venous sinus; A portion of a vessel; A portion of an ear; A portion of an outer auditory canal or combinations of any of the foregoing.

Organs: A portion of an organ, e.g. a superior pole or inferior pole of a kidney; An edge or a margin of a liver, a spleen, a lung; A portion of a hepatic lobe; A portion of a vessel; A portion of a hiatus, e.g. in the liver or spleen; A portion of a uterus.

Someone skilled in the art can identify other anatomic landmarks of hard tissues, soft-tissues and or organs including brain that can be used for registration of virtual data (including optionally including virtual surgical plans) and live data of the patient and the HMD in a common coordinate system. Virtual and physical surgical instruments and implant components can also be registered in the common coordinate system.

In some embodiments, the HMD can display an arbitrary virtual plane over the surgical field. The arbitrary virtual plane can be moveable using a virtual or other interface. For example, the arbitrary virtual plane can include a "touch area", wherein gesture recognition software, for example the one provided by Microsoft with the Microsoft Hololens including, for example, the integrated virtual "drag function" for holograms can be used to move the arbitrary virtual plane. For example, one or more cameras integrated or attached to the HMD can capture the movement of the surgeon's finger(s) in relationship to the touch area; using gesture tracking software, the virtual plane can then be moved by advancing the finger towards the touch area in a desired direction.

The HMD can display the arbitrary virtual plane in any location initially, e.g. projected onto or outside the surgical field, e.g. a hip joint, knee joint, shoulder joint, ankle joint, or a spine. The HMD can optionally display the arbitrary virtual plane at a defined angle, e.g. orthogonal or parallel, relative to a fixed structure in the operating room, which can, for example, be recognized using one or more cameras, image capture or video capture systems and/or a 3D scanner integrated into the HMD and spatial recognition software such as the one provided by Microsoft with the Microsoft Hololens or which can be recognized using one or more attached optical markers or navigation markers including infrared or RF markers. For example, one or more optical markers can be attached to an extension of the operating table. The HMD can detect these one or more optical markers and determine their coordinates and, with that, the horizontal plane of the operating room table. The arbitrary virtual plane can then be displayed perpendicular or at another angle relative to the operating room table.

For example, in a hip replacement, the HMD can display a virtual arbitrary plane over the surgical site. The virtual arbitrary plane can be perpendicular to the operating table or at another predefined or predetermined angle relative to the OR table. Using a virtual interface, e.g. a touch area on the virtual surgical plane and gesture tracking, the HMD can detect how the surgeon is moving the virtual arbitrary plane. Optionally, the virtual arbitrary plane can maintain its perpendicular (or of desired other angle) orientation relative to the OR table while the surgeon is moving and/or re-orienting the plane; a perpendicular orientation can be desirable when the surgeon intends to make a perpendicular femoral neck cut. A different angle can be desirable, when the surgeon intends to make the femoral neck cut with another orientation.

Using the touch area or other virtual interface, the surgeon can then move the arbitrary virtual plane into a desired position, orientation and/or alignment. The moving of the arbitrary virtual plane can include translation and rotation or combinations thereof in any desired direction using any desired angle or vector. The surgeon can move the arbitrary virtual plane to intersect with select anatomic landmarks or to intersect with select anatomic or biomechanical axes. The surgeon can move the arbitrary virtual plane to be tangent with select anatomic landmarks or select anatomic or biomechanical axes.

Figure 9A:
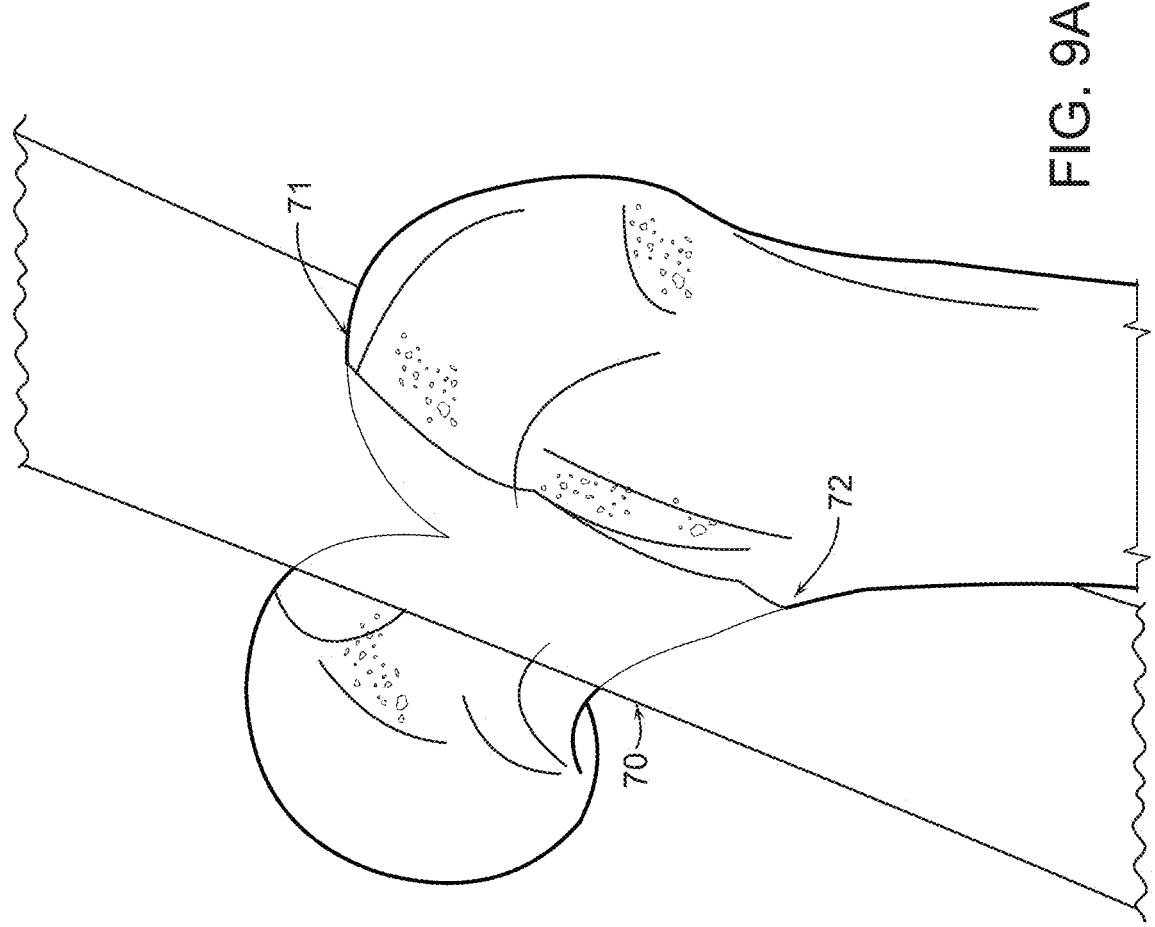

For example, in a hip replacement, the surgeon can move the arbitrary virtual plane to be tangent with the most superior aspect of the greater trochanter and the most superior aspect of the lesser trochanter. FIG. 9A shows an illustrative example of a virtual plane 70 that a primary surgeon has moved and aligned to be tangent with the most superior aspect of the greater trochanter 71 and the most superior aspect of the lesser trochanter 72. FIG. 9B shows an illustrative example of the same virtual plane 70 that was moved and aligned to be tangent with the most superior aspect of the greater trochanter 71 and the most superior aspect of the lesser trochanter 72, now with the view from the head mounted display of a second surgeon or surgical assistant, e.g. on the other side of the OR table.

Optionally, for example with a pointer with an attached optical marker or an attached navigation marker, or with his finger detected using an image or video capture system integrated into the HMD and gesture recognition software such as the one provided by Microsoft with the Hololens, or with his finger with an attached optical marker or navigation marker, the surgeon can point at and identify the sulcus point, e.g. the lowest point between the greater trochanter and the femoral neck, which can be an additional reference. The line connecting the most superior aspect of the greater trochanter and the most superior aspect of the lesser trochanter can then be determined on a pre-operative or intra-operative AP radiograph of the hip; optionally, the sulcus point can also be detected on the AP radiograph. The AP radiograph can include a template used by the surgeon for selecting and sizing, for example, the femoral and acetabular component, as well as the liner and/or femoral heads. The radiographic template can include an indication for the femoral neck cut. The angle between the line connecting the most superior aspect of the greater trochanter and the most superior aspect of the lesser trochanter and the indication for the femoral neck cut can be determined. FIG. 9C is an illustrative example that shows that a second virtual plane 73, the virtual femoral neck cut plane 73, can then be projected or displayed by the HMD, also perpendicular to the OR table like the arbitrary virtual plane 70, the latter tangent with the most superior aspect of the greater trochanter 71 and the most superior aspect of the lesser trochanter 72, and the femoral neck cut plane 73 at the same angle and/or distance to the arbitrary virtual plane as the angle and distance between the line connecting the most superior aspect of the greater trochanter and the most superior aspect of the lesser trochanter and the indication for the femoral neck cut on the radiograph. In this manner, the femoral neck cut plane can be defined using a second virtual plane prescribed or predetermined based on the intra-operatively placed arbitrary virtual plane, moved by the operator to be tangent with the most superior aspect of the greater trochanter and the most superior aspect of the lesser trochanter. The virtual femoral neck cut plane prescribed and projected or displayed in this manner can also be a virtual guide, e.g. a virtual cut block that projects, for example, a virtual slot for guiding a physical saw. The virtual guide or virtual cut block can have one or more dimensions identical to a physical guide or cut block, so that the physical guide or cut block can be aligned with the virtual guide or cut block. The virtual guide or cut block can be an outline, 2D or 3D, partial or complete, of the physical guide or cut block, with one or more identical dimensions, so that the surgeon can align the physical guide or cut block with the virtual guide or cut block. The virtual guide or cut block can include placement indicia for the physical guide or cut block.

If radiographic magnification is a concern for prescribing a second virtual plane, e.g. a virtual cut plane, based on a first virtual plane, e.g. a plane tangent with or intersecting one or more anatomic landmarks or one or more anatomic or biomechanical axes, at an angle incorporated from or derived from a pre-operative radiograph, optionally, distance measurements can be incorporated and magnification correction can be applied. For example, the distance between one or more landmarks, e.g. the ones with which the virtual plane is tangent with or that the virtual plane intersects, can be measured in the live data of the patient and can be measured on the radiograph. If the radiographic distance is larger or smaller than the distance in the live patient, a magnification correction can be applied and, for example, the distance between the first virtual plane, e.g. a plane tangent with or intersecting one or more anatomic landmarks or one or more anatomic or biomechanical axes, and the second virtual plane, e.g. a virtual cut plane, can be corrected based on the radiographic magnification factor.

In addition to virtual planes, the surgeon can place one or more virtual points, e.g. with a pointer with an attached optical marker or an attached navigation marker, or with his or her finger detected using an image or video capture system integrated into the HMD and gesture recognition software such as the one provided by Microsoft with the Hololens, or with his or her finger with an attached optical marker or navigation marker. The surgeon can point at and identify an anatomic landmark, e.g. a medial epicondyle of a knee or a sulcus point in a proximal femur or a medial malleolus, using any of the foregoing methods and/or devices. Optionally, the surgeon can then fixate optical markers to the virtual point and the underlying or corresponding anatomic landmark, for example using a screw or pin. By identifying two or more virtual points the surgeon can define a virtual axis or vector.

In embodiments, the HMD display of virtual data, e.g. of one or more of virtual surgical tool, virtual surgical instrument including a virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration, can be superimposed onto and/or aligned with the corresponding anatomic structure, e.g. a target tissue or an exposed joint surface, e.g. an exposed articular surface, seen directly through the see-through head mounted display (as they would be seen by the surgeon without wearing an HMD). The surgeon can then, for example, move a physical instrument, surgical guide, surgical tool, implant, implant component, device to align with the virtual projection.

Orienting, Aligning, Projecting and/or Superimposing Virtual Data Relative to Anatomic Structures and/or Surfaces In embodiments, the HMD display of virtual data, e.g. of one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration, can be projected onto and/or superimposed onto and/or aligned with and/or oriented with the surface of an anatomic structure seen directly through the see-through head mounted display (as they would be seen by the surgeon without wearing an HMD). The one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration can be projected onto and/or superimposed onto and/or aligned with and/or oriented with so that at least portions of them are tangent with, intersecting with, orthogonal to, at a defined angle to, and/or offset with, e.g. at a predetermined distance or angle, with the surface of the anatomic structure.

The surface of the anatomic structure can be at least a portion of one or more of a cartilage, a damaged or diseased cartilage, a subchondral bone, a cortical bone, any combination of a cartilage, a damaged or diseased cartilage, a subchondral bone, or a cortical bone, an articular surface, a weight-bearing zone of an articular surface, a non-weight bearing zone of an articular surface, a periosteum, a soft-tissue, a fascia, a muscle, a tendon, a ligament, a meniscus, a labrum, an intervertebral disk, a skin, a subcutaneous tissue (e.g. in an incision), a subcutaneous fat (e.g. in an incision), a mucosa or mucosal surface (e.g. of an oral cavity, a sinus, a nose, a nasopharyngeal area, a pharynx, a larynx, a gut, a small or large bowel, a colon, a rectum an intestine, a stomach, an esophagus, a bile duct, a pancreatic duct, a gallbladder, a gallbladder duct, or a bladder), a mucosal fold, a gingiva, a gingival fold, a marginal gum, an attached gum, an interdental gum, an enamel, a tooth, an epithelium or epithelial surface (e.g. in a lumen), a synovial membrane (e.g. in an exposed joint), a peritoneum or peritoneal surface (e.g. in an abdominal cavity or a pelvis, e.g. lining a mesentery or internal organs or a liver surface or a spleen), a capsule (e.g. a Glisson capsule of a liver or a renal capsule, an adrenal capsule, a thyroid capsule or a parathyroid capsule), a diaphragm, a pleura, a pericardium, a meninx (e.g. a dura mater, arachnoid mater, pia mater), a sinus (e.g. a cavernous sinus or a sigmoid or other sinus), a calvarium, a facial structure (e.g. a nose, an ear, an earlobe), a surface of an eye (e.g. a cornea, a lens, a sclera), an eyelid.

In some embodiments, one or more physical surgical tools or physical surgical instruments can be configured to effect a tissue removal in a patient. The tissue removal can be, for example, a removal of bone or a removal of cartilage or combinations thereof, e.g. using an awl, a drill, a tap, a screw, a pin, a mill, a reamer, a burr, an impactor, a broach, a saw, a saw blade.

The surface(s) of these one or more anatomic structures can be exposed during surgery, e.g. using an incision or tissue removal, and the one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, and/or one or more of a virtual predetermined tissue change or alteration can be projected, aligned and/or superimposed by one or more HMDs onto the surface(s) of the one or more anatomic structures so that at least portions of the virtual data and/or virtual display(s) are tangent with, intersecting with, orthogonal to, at a defined angle to, and/or offset with, e.g. at a predetermined distance or angle, with the surface(s) of the one or more anatomic structures. Once the anatomic surface(s) is (are) exposed, the one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration can be projected, aligned and/or superimposed by one or more HMDs onto the surface(s) of the one or more anatomic structures and the surgeon or a robot can then, for example, move and/or align and/or superimpose a physical tool, a physical instrument, a physical surgical guide, physical implant component, a physical implant and/or a physical device to align and/or superimpose it with the virtual projection(s).

Using Light Sources for Referencing Live Anatomic Landmarks

The tracker or pointing device can also be a light source, which can, for example, create a red point or green point created by a laser on the patient's tissue highlighting the anatomic landmark intended to be used for registration. A light source can be chosen that has an intensity and/or a color that will readily distinguish it from the live tissue of the patient.

The laser or other light source can optionally be integrated into or attached to the HMD. For example, the laser or the light source can be integrated into or attached to a bridge connecting the frame pieces between the left and the right eye portion of the HMD, for example over the nasal region.

Image and/or video capture and/or a 3D scanner, for example integrated into or attached to or coupled to the HMD, can be used to identify the location of the light on the patient's tissue or the patient's anatomic landmark. Once the light has been directed to the desired location on the live data of the patient, specifically, the live landmark of the patient, registration can be performed by executing a registration command, registering the live data of the patient with the virtual data of the patient, e.g. the live landmark with the laser or other light being reflected of it and the corresponding virtual landmark of the patient. This process can be repeated for different anatomic landmarks, e.g. by pointing the light source at the next live anatomic landmark of the patient, confirming accurate placement or pointing, the light, e.g. a red or green laser point being reflected from the live patient landmark can be captured via the image and/or video capture device and/or 3D scanner, and the next anatomic live landmark can be registered with the corresponding virtual anatomic landmark of the patient. Virtual and live data can include an osteophyte or bone spur or other bony anatomy or deformity. In this manner, the HMD, live data of the patient and virtual data of the patient can be registered in a common coordinate system. Virtual and physical surgical instruments and implant components can also be registered in the common coordinate system.

In some embodiments, more than one live and virtual anatomic landmark of the patient will be used, e.g. two, three or more.

Optionally, a live anatomic surface can be used for registration purposes. In this embodiment, the live anatomic surface can be derived, for example, using a light scanning, infrared scanning or ultrasound technique, or ultrasonic scanning technique during the surgery. The live surfaces of the patient that are detected and generated in this manner can be matched or aligned with virtual surfaces of the patient, for example obtained preoperatively using an imaging test such as x-ray imaging, ultrasound, CT or MRI or any other technique known in the art. Virtual and live data and anatomic surfaces can include an osteophyte or bone spur or other bony anatomy or deformity.

In some embodiments, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art.

Registration of Virtual Patient Data and Live Patient Data Using Implantable or Attachable Fiducial Markers or Calibration or Registration Phantoms or Devices Including Optical Markers In some embodiments, a surgeon is optionally using implantable or attachable fidcucial markers, sub-arrays, or arrays to register virtual data of the patient with live data of the patient. A sub-array can comprise one or more fiducial markers. An array can comprise one or more sub-arrays and/or fiducial markers. This embodiment can, for example, be useful if the surgery is very extensive and results in the removal of tissue in the surgical site, as can be the case during brain surgery, e.g. removal of a brain tumor, liver surgery, e.g. removal of a liver tumor, joint replacement surgery and many other types of surgery. Virtual and live data can include an osteophyte or bone spur or other bony anatomy or deformity.

The terms markers, fiducial markers, implantable markers, attachable markers, skin markers, soft-tissue markers, calibration or registration phantoms or devices, and image capture markers as used throughout the application can include optical markers, e.g. optical markers with different geometric shapes or patterns, with QR codes, with bar codes, with alphanumeric codes. Fiducial markers can comprise active markers or passive markers, infrared markers, optical markers, RF markers, and/or LEDs. Different fiducial markers can be combined. An array or sub-array can comprise different types of fiducial markers, e.g. active markers or passive markers, infrared markers, optical markers, RF markers, and/or LEDs. Implantable or attachable markers or calibration or registration phantoms or devices can be implanted prior to the actual surgery and can be included in pre-, intra- and/or postoperative imaging. Implantable or attachable markers or calibration or registration phantoms or devices can be implanted on or attached to osteophytes or bone spurs or other bony anatomy or deformity.

If the implantable or attachable markers or calibration or registration phantoms or devices are present in the virtual image data, the surgeon can optionally identify the implantable or attachable markers or calibration or registration phantoms or devices after an incision as he or she gains access to the target tissue and the implantable markers placed next to the target tissue or inside the target tissue. Such implantable or attachable markers or calibration or registration phantoms or devices can, for example, include radiation beets or metallic beets, for example also used for stereographic imaging or registration.

Alternatively, implantable or attachable markers or calibration or registration phantoms or devices can be placed during the surgery and, for example using a camera, an image and/or video capture system and/or 3D scanner attached to, integrated with or coupled to the HMD, the location of the implantable or attachable markers or calibration or registration phantoms or devices can be determined and/or the markers can be tracked using the a camera, an image and/or video capture system and/or 3D scanner. The location of the implantable or attachable markers or calibration or registration phantoms or devices on the patient in the live data of the patient can then be matched with the location of the anatomic structure to which the implantable or attachable markers or calibration or registration phantoms or devices is attached in the virtual data of the patient. For example, the anatomic structure in the virtual and live data can include an osteophyte or bone spur or other bony anatomy or deformity. In some embodiments, a pointer or pointing device can optionally include implantable or attachable markers or calibration or registration phantoms or device or optical markers followed by image capture through the HMD or other image and/or video capture device and/or 3D scanner attached to, integrated with or coupled to the HMD and registration of the tip of the pointer. In this manner, the HMD, the implantable or attachable markers or calibration or registration phantoms or devices including optical markers and, through the use of the implantable or attachable markers or calibration or registration phantoms or devices including optical markers, the anatomic structures, pathologic structures, instruments, implant components and any other objects to which one or more implantable or attachable markers or calibration or registration phantoms or devices including optical markers can be attached, as well as the virtual data of the patient can be registered in a common coordinate system. Virtual and physical surgical instruments and implant components can also be registered in the common coordinate system.

Implantable or attachable markers or calibration or registration phantoms or devices can include rigid or fixed registration markers. Such rigid or fixed registration markers can be used to maintain registration as surgical field is being altered. A rigid or fixed registration marker can, for example, be a screw or a pin. Virtual and live data can include an osteophyte or bone spur or other bony anatomy or deformity. The rigid or fixed registration marker can be attached to the osteophyte or bone spur or other bony anatomy or deformity. In some embodiments, the medical device that is being implanted or a component thereof that has been, for example, already temporarily or permanently attached to the patient's tissue, e.g. an osteophyte or bone spur or bony anatomy or deformity, or the anatomic site or the surgical site can be used as an implantable or attachable marker or calibration or registration phantom or device during the surgery, for example while subsequent steps of the surgery are being completed. Such subsequent steps can, for example, include the implantation of additional components of the medical device. For example, in spinal fusion surgery, a first pedicle screw can be implanted. Live data and virtual data of the first pedicle screw can be registered. Subsequent pedicle screws or other components can be virtually displayed in the HMD including their intended path, position, location or orientation, by maintaining registration between live and virtual data using the registered first pedicle screw. Any other rigid or fixed registration marker or implantable device can be used in this manner for different types of surgeries of the human body.

The one or more implantable or attachable markers or calibration or registration phantoms or devices can be attached to bone, cartilage, soft-tissues, organs or pathologic tissues such as osteophytes or bone spur or other bony anatomy or deformity, etc.

The one or more implantable or attachable markers or calibration or registration phantoms or devices can optionally include optical markers, retroreflective markers, infrared markers, or RF markers or any other marker device described in the art.

Optical markers can be markers that can emit or reflect light within the visible spectrum, i.e. the portion of the electromagnetic spectrum that is visible to the human eye, with wavelengths from about 390 to 700 nm or a frequency band from about 430-770 THz. Optical markers can also emit or reflect light that includes a mix of different wavelengths within the visible spectrum. The light reflected by the optical markers can be detected by an image and/or video capture system integrated into, attached to or separate from the HMD. Optical markers can be detected with regard to their location, position, orientation, alignment and/or direction of movement and/or speed of movement with use of an image and/or video capture system integrated into, attached to or separate from the HMD with associated image processing and, optionally, pattern recognition software and systems. Optical markers can include markers with select geometric patterns and/or geometric shapes that an image and/or video capture system, for example integrated into, attached to or separate from the HMD, can recognize, for example using image processing and/or pattern recognition techniques. Optical markers can include markers with select alphabetic codes or patterns and/or numeric codes or patterns and/or alphanumeric codes or patterns or other codes or patterns, e.g. bar codes or QR codes, that an image and/or video capture system, for example integrated into, attached to or separate from the HMD, can recognize, for example using image processing and/or pattern recognition techniques. QR codes or quick response codes include any current or future generation matrix code including barcode. Barcodes and QR codes are machine readable optical labels that can include information, for example, about the patient including patient identifiers, patient condition, type of surgery, about the surgical site, the spinal level operated if spine surgery is contemplated, the patient's side operated, one or more surgical instruments, one or more trial implants, one or more implant components, including type of implant used and/or implant size, type of polyethylene, type of acetabular liner (e.g. standard, lipped, offset, other) if hip replacement is contemplated. A QR code can use different standardized encoding modes, e.g. numeric, alphanumeric, byte/binary, and/or kanji to store data. Other encoding modes can be used. Any current and/or future version of QR codes can be used. QR codes using single or multi-color encoding can be used. Other graphical markers, such as the ones supported by the Vuforia (PTC, Needham, Mass.) augmented reality platform, can be used as well.

A bar code, QR code or other graphical marker can be the optical marker. A bar code, QR code or other graphical marker can be part of an optical marker or can be integrated into an optical marker. The same QR code or bar code or other graphical marker can contain
  information related to the patient and/or the surgical site, e.g. patient identifiers, age, sex, BMI, medical history, risk factors, allergies, site and side (left, right), spinal level to be operated
  information related to inventory management, e.g. of surgical instruments and/or implants or implant components, e.g. left vs. right component, selected component size (match against virtual surgical plan and/or templating and/or sizing)
and can be used to obtain information about the location, position, orientation, alignment and/or direction of movement, and/or speed of movement, if applicable, of the surgical site, surgically altered tissue, one or more surgical instruments and one or more trial implants and/or implant components.

Geometric patterns, geometric shapes, alphabetic, numeric, alphanumeric, and other codes or patterns including bar codes and QR codes included in or part of one or more optical markers can be predefined and, optionally, stored in database accessible by an image and/or video capture system and associated image processing software and pattern recognition software. Geometric patterns, geometric shapes, alphabetic, numeric, alphanumeric, and other codes or patterns including bar codes and QR codes included in or part of one or more optical markers can be in 2D and some of it in 3D. For example, one or more planar or 2D patterns can be used in select embodiments. Alternatively, select 3D geometric shapes can be used, e.g. cubes, cuboids, prisms, cones, cylinders, spheres. Any 3D shape can be used including irregular shapes and/or asymmetric shapes. The 3D geometric shape can include 2D geometric patterns and/or alphabetic, numeric, alphanumeric, and other codes or patterns including bar codes and QR codes on one or more surfaces. For example, if a cuboid or other 3D shape is used for an optical marker, the same or different geometric patterns and/or alphabetic, numeric, alphanumeric, and other codes or patterns including bar codes and QR codes can be included in, affixed to or integrated into one or more of its surfaces or faces, e.g. two opposing surfaces or two adjacent surfaces oriented, for example, perpendicularly. 2D geometric patterns and/or alphabetic, numeric, alphanumeric, and other codes or patterns including bar codes and QR codes included in, affixed to or integrated into one or more surfaces or faces of a 3D geometric shape can be used to determine the orientation of select surfaces or faces of the geometric shape including the optical marker and, with that, the orientation and/or alignment of the surface or face and with that the geometric shape, for example in relationship to a surgical site, a surgical alteration, e.g. a cut bone surface or a reamed bone surface, a surgical instrument and/or one or more implant components including trial implants. In this manner, movement of a limb or surgical site can be tracked in embodiments. For example, an optical marker with a 3D shape can be attached to a trochlea or an anterior tibia. The optical marker can have a first surface with a first geometric pattern. The optical marker can have a second surface with a second geometric pattern. The first surface with the first geometric pattern can, for example, be anteriorly facing. The second surface with the second geometric pattern can, for example, be medially or laterally facing.

When the operator looks through the HMD, optionally with one or more video systems integrated into, attached to or separate from the HMD, at the optical marker and the video system, in this example, detects predominantly the first surface, the information can be used to indicate that the knee is in a frontal, e.g. non-rotated position; if the video system detects a different ratio of first vs. second surface visible or detectable, e.g. with a larger portion of the second surface visible or detectable, the information can be used to indicate that the knee is in a somewhat or more rotated position. Similarly, a third surface with a third geometric pattern can be superior or inferior facing. If the video detects that a greater portion of the third surface is visible or detectable, the information can indicate that the knee is in a more flexed position. Any combination is possible.

A 3D optical marker can, optionally, not have distinct surfaces with distinct geometric patterns, but can include a continuum of the same or, optionally changing, geometric patterns along its 3D surface or 3D surfaces. The location and/or or position and/or orientation and/or coordinates of the changing, different portions of the geometric pattern along the 3D surface(s) can be known, e.g. prior to tracking a surgical site, a surgical instrument, an implant, a medical device or a limb or bone, e.g. during movement. A video system integrated into, attached to or separate from the HMD can detect the location and/or position and/or orientation and/or coordinates of one or more of the different portions of the geometric patterns and can use the information to track a surgical site, a surgical instrument, an implant, a medical device or a limb or bone, e.g. during movement.

The detection of one or more surfaces with geometric patterns or one or more portions of geometric patterns, e.g. on a 2D optical marker or a 3D optical marker, can be used to trigger one or more computer demands. Similarly, the disappearance of one or more surfaces with geometric patterns or one or more portions of geometric patterns or an entire geometric pattern can be used to trigger one or more computer demands. Such computer commands can, for example, include activating a motion tracking mode, de-activating a motion tracking mode, activating an HMD display, de-activating an HMD display, displaying a surgical step, e.g. a next surgical step or a prior surgical step, displaying a proposed correction for a surgical step, initiating an alarm, terminating an alarm, displaying a surgical instrument, tracking a surgical instrument, displaying a next surgical instrument, displaying an implant component, displaying a medical device, tracking any of the foregoing, terminating any of the foregoing commands. Someone skilled in the art can recognize other commands that can be initiated or executed in this manner. Such commands can also be used, for example, to initiate action by a robot, e.g. activating a bone saw, guiding a robot or executing a bone cut or bone removal with a robot. The robot can be configured for use with a robotic arm. The robot can be handheld. An actuator, e.g. a drill or a saw, can be handheld and can be simultaneously attached to a robotic arm.

In another embodiment, one or more video systems or cameras integrated into, attached to or separate from an HMD can detect a change in angular orientation of a 2D or 3D optical marker and/or geometric pattern and/or portions of one or more of the foregoing; the change in angular orientation detected in this manner can also be used to trigger or execute one or more commands.

Geometric patterns and/or geometric shapes, alphabetic, numeric, alphanumeric, and other codes or patterns including bar codes and QR codes can be in color or black and white. Geometric patterns and/or geometric shapes and/or alphabetic, numeric, alphanumeric, and other codes or patterns including bar codes and QR codes can include portions that include color and black and white sections, portions that include only color and portions that are only black and white. Geometric shapes can include faces or surfaces that include color and black and white, faces or surfaces that include only black and white, and faces or surfaces that include only color. Different colors and different color codes can be used for different faces or surfaces of a geometric shape part of an optical marker. Different colors and different color codes can be used for different geometric patterns and/or geometric shapes and/or alphabetic, numeric, alphanumeric, and other codes or patterns including bar codes and QR codes. Different colors and different color codes can be used for different optical markers. Different colors, e.g. red, blue, green, orange, cyan etc., can be used for different geometric patterns and/or geometric shapes and/or alphabetic, numeric, alphanumeric, and other codes or patterns including bar codes and QR codes. Different colors, e.g. red, blue, green, orange, yellow, pink, cyan can be used for different optical markers. Different optical markers can optionally be associated with different surgical steps and/or different surgical instruments and/or different implant components; the use of a particular marker can be recognized by an image and/or video capture system integrated into, attached to or separate from the HMD using standard image processing and/or pattern recognition software, including, optionally a database of patterns, e.g. with their associations with a particular surgical step and/or surgical instruments. As the image and/or video capture system recognizes a particular optical marker in the field of view, for example based on a particular geometric patterns and/or geometric shape and/or alphabetic, numeric, alphanumeric, and other codes or patterns including bar codes and QR codes used, it can then optionally display the corresponding surgical step and/or surgical instrument and/or implant component associated with that optical marker.

2D geometric patterns, alphabetic, numeric, alphanumeric, and other codes or patterns including bar codes and QR codes or combinations thereof, optionally with color and/or black and white coding, included in, affixed to or integrated into one or more surfaces or faces of a 3D geometric shape can be used to determine the orientation and/or alignment of select surfaces or faces of the geometric shape and, with that, the orientation and/or alignment of the geometric shape and/or the optical marker, for example in relationship to an anatomic landmark, a surgical site, a surgical alternation, e.g. a cut bone surface or a reamed bone surface, a surgical instrument and/or one or more implant components including trial implants. One or more 2D geometric patterns, alphabetic, numeric, alphanumeric, and other codes or patterns including bar codes and QR codes, optionally with color and/or black and white coding, included in, affixed to or integrated into an optical marker can be used to determine the orientation and/or alignment of the optical marker, which can, for example, be affixed to or integrated into an anatomic landmark, a surgical site, a surgical alternation, e.g. a cut bone surface or a reamed bone surface, a surgical instrument and/or one or more implant components including trial implants. Optical markers can be affixed to an anatomic landmark, a surgical site, a surgical alteration, e.g. a cut bone surface or a reamed bone surface, or a drill hole of the patient and the corresponding anatomic landmark, surgical site, or surgical alternation can be identified in the virtual data of patient thereby enabling registration of the virtual data and the live data of the patient in the same coordinate system. Fiducial markers, e.g. integrated or attached to HMDs: Fiducial markers, sub-arrays, and/or arrays can also be attached to an HMD including multiple HMDs if multiple HMDs are used during a surgery.

A fiducial marker can comprise a retroreflective marker (e.g. a marker ball or a disc), an infrared marker, an RF marker, an active marker, a passive marker, a marker, e.g. an optical marker, comprising one or more geometric patterns (e.g. an ArUco marker [for example generated with OpenCV or Python], a QR code, a bar code, or other geometric patterns), a marker with a unique shape (e.g. rhomboid, cone, cube shaped, optionally with different x, y, z dimensions, regular and/or irregular shapes), an LED, or a combination thereof.

Two or more fiducial marker can be arranged in a defined, predetermined spatial relationship or orientation to form an array, which can be detected by a camera or a 3D scanner.

An array can comprise two or more sub-arrays. A sub-array can comprise two or more fiducial markers. A sub-array can be a facet or face in a multi-faceted or multi-face array, e.g. using spheres or discs.

The system can be configured to detect a first dimension, shape, geometry, or geometric pattern or combination thereof of a first fiducial marker, sub-array or array and track it as part of the first fiducial marker, sub-array or array. The system can be configured to detect a second dimension, shape, geometry, or geometric pattern or combination thereof of a second fiducial marker, sub-array or array and track it as part of the second fiducial marker, sub-array or array. The system can be configured to detect a third dimension, shape, geometry, or geometric pattern or combination thereof of a third fiducial marker, sub-array or array and track it as part of the third fiducial marker, sub-array or array. The system can be configured to detect a fourth dimension, shape, geometry, or geometric pattern or combination thereof of a fourth fiducial marker, sub-array or array and track it as part of the fourth fiducial marker, sub-array or array. The system can be configured to detect an nth dimension, shape, geometry, or geometric pattern or combination thereof of an nth fiducial marker, sub-array or array and track it as part of the nth fiducial marker, sub-array or array. The first, second, third fourth, . . . nth dimension, shape, geometry, or geometric pattern or combination thereof of the first, second, third, fourth, . . . nth fiducial marker, sub-array or array can be different.

An HMD can comprise a first fiducial marker, a first sub-array of fiducial markers or a first array of fiducial markers having a first location, first orientation, or first location and orientation, wherein the first fiducial marker, first sub-array of fiducial markers or first array of fiducial markers is attached to or integrated into the head mounted display; the HMD can comprise a second fiducial marker, a second sub-array of fiducial markers or a second array of fiducial markers having a second location, orientation, or location and orientation, wherein the second fiducial marker, second sub-array of fiducial markers or second array of fiducial markers is attached to or integrated into the head mounted display, wherein the first and the second location, the first and the second orientation, or the first and the second location and orientation are different. The system can be configured to track the first fiducial marker, first sub-array or first array over a first movement range of the head mounted display detectable by the at least one camera. The system can be configured to track the second fiducial marker, second sub-array or second array over a second movement range of the head mounted display detectable by to the at least one camera. The first movement range and the second movement range can be different.

The system can be configured to detect a first dimension, shape, geometry, or geometric pattern or combination thereof and track it as part of a first fiducial marker, sub-array or array integrated or attached to the HMD; the system can be configured to detect a second dimension, shape, geometry, or geometric pattern or combination thereof and track it as part of a second fiducial marker, sub-array or array integrated or attached to the HMD. The system can be configured to detect a third dimension, shape, geometry, or geometric pattern or combination thereof and track it as part of a third fiducial marker, sub-array or array integrated or attached to the HMD.

The movement range can be the range of movement of an HMD visible to a camera and/or detectable by a camera, with at least one fiducial marker, sub-array or array visible or detectable and trackable by the camera. The movement range can be the range of movement of the viewing direction of an HMD, in which one or more attached fiducial markers, sub-arrays or arrays are visible to a camera and/or detectable by a camera, with at least one fiducial marker, sub-array or array trackable by the camera.

A first movement range of an HMD can be detectable or visible and trackable by a camera for a first fiducial marker, sub-array or array; a second movement range of an HMD can be detectable or visible and trackable by a camera for a second fiducial marker, sub-array or array; a third movement range of an HMD can be detectable or visible and trackable by a camera for a third fiducial marker, sub-array or array; a fourth movement range of an HMD can be detectable or visible and trackable by a camera for a fourth fiducial marker, sub-array or array; and so forth. The first, second, third, fourth etc. movement range can be different. The first, second, third, fourth etc. movement range can be non-overlapping. The first, second, third, fourth etc. movement range can be overlapping. The first movement range can be non-overlapping with the second movement range; the second movement range can be overlapping with a third movement range. When more than two fiducial markers, sub-arrays or arrays are used for tracking an HMD, any combination of overlapping or non-overlapping movement ranges of a first, second, third, fourth, etc. fiducial marker, sub-array or array can be supported by the system.

The system can be configured to generate a composite movement range of a head mounted display formed by the combination of a first movement range and a second movement range detectable by at least one camera and/or visible by the at least one camera and tracked by the system, wherein the composite movement range can be greater than the first movement range or the second movement range. The combination can be formed as the sum of the area or volume of the first movement range and the non-overlapping portion of the second movement range. The combination can be formed as the sum of the area or volume of the second movement range and the non-overlapping portion of the first movement range. The combination can be formed as the sum of the area or volume of the first movement range and the non-overlapping portions of a second movement range, third movement range, fourth movement range etc., when more than first fiducial marker, sub-array or array and a second fiducial marker, sub-array and array are used, e.g. a third, fourth, fifth fiducial marker, sub-array or array.

A composite movement range can be greater than a first movement range or a second movement range. For example, a first and a second movement range detectable or visible and trackable by a camera for a first fiducial marker, sub-array or array and a second fiducial marker, sub-array or array can be in relationship to a camera position and/or orientation (optionally fixed and/or predetermined) starting from a neutral head neck position:

$1^{st}$ movement range: up +80°, down −10°; left +90°, right −15°.

$2^{nd}$ movement range: up +10°, down −80°; left +15°, right −90°.

Composite movement range: up +80°, down −80°; left +90°, right −90°.

In the foregoing example, the first and second movement range overlap in up-down orientation by 20° and in left-right orientation by 30°.

A first and a second movement range detectable or visible and trackable by a camera for a first fiducial marker, sub-array or array and a second fiducial marker, sub-array or array can be in relationship to an initial viewing direction of an HMD:

$1^{st}$ movement range: up +70°, down −0°; left +100°, right −0°.

$2^{nd}$ movement range: up +0°, down −60°; left +25°, right −100°.

Composite movement range: up +70°, down −60°; left +100°, right −100°.

In the foregoing example, the first and second movement range overlap in up-down orientation by 0° (no overlap) and in left-right orientation by 25°.

A first and a second movement range detectable or visible and trackable by a camera for a first fiducial marker, sub-array or array and a second fiducial marker, sub-array or array can be in relationship to a predetermined viewing direction of an HMD:

1$^{st}$ movement range: up +50°, down −10°; left +85°, right −5°.

2$^{nd}$ movement range: up +10°, down −50°; left +5°, right −85°.

Composite movement range: up +50°, down −50°; left +85°, right −85°.

In the foregoing example, the first and second movement range overlap in up-down orientation by 20° and in left-right orientation by 10°.

A movement range can be defined or predetermined in relationship to an initial viewing direction of an HMD and/or user wearing an HMD, e.g. a first, second, third, fourth HMD, a predetermined viewing direction of an HMD and/or user wearing an HMD a camera, two or more cameras, a 3D scanner, two or more 3D scanners, a patient, an anatomic structure of the patient, a fiducial marker attached to the patient, a sub-array of fiducial markers attached to the patient, an array of fiducial makers attached to the patient, a surgeon, a starting, mid, or end position and/or orientation of a surgeon's head or neck an HMD, a neutral position of the surgeon's head or neck, a predetermined position of the surgeon's head or neck, two or more HMDs, an OR table, a fixed structure in the operating room, or a combination thereof. For example, a movement range can be defined or predetermined in relationship to a camera position and/or orientation and a surgeon's head/neck position and/or orientation, e.g. an anatomic neutral position and/or orientation or a predetermined starting, mid or end position and/or orientation of the surgeon's head/neck during a surgical procedure. A movement range can be defined or predetermined in relationship to an initial viewing direction or a predetermined viewing direction of an HMD and/or user wearing an HMD.

A composite movement range detectable or visible and trackable by a camera for a first fiducial marker, sub-array or array and a second fiducial marker, sub-array or array can be the total range of viewing directions of an HMD trackable by the system, comprising a computer processor and a camera.

The movement of a head mounted display can comprise a movement in x direction, y direction, z direction, a rotation, a flexion, an extension or a combination thereof. A first movement range of a first fiducial marker, first sub-array or first array can be different from a second movement range of a second fiducial marker, second sub-array or second array in at least a x direction, a y direction, z direction, a rotation, or a combination thereof. The system can be configured so that the first movement range comprises a range of −10 to +10 degrees, −20 to +20 degrees, −30 to +30 degrees, −40 to +40 degrees, −50 to +50 degrees, −60 to +60 degrees, −70 to +70 degrees, −80 to +80 degrees, −90 to +90 degrees, −100 to +100 degrees, −110 to +110 degrees, or value or range therebetween in up or down, left or right, forward or backward movement, rotation, or a combination thereof of the head mounted display in relationship to an initial or a predetermined viewing direction of the head mounted display or in relationship to a neutral position of the surgeon's head or neck, a predetermined position of the surgeon's head or neck, an anatomic structure of the patient, a fiducial marker attached to the patient, a sub-array of fiducial markers attached to the patient, an array of fiducial makers attached to the patient, an OR table, a fixed structure in the operating room, the camera, or a combination thereof, or wherein the first movement range comprises a range of −10 to +10 mm, −20 to +20 m, −30 to +30 mm, −40 to +40 m, −50 to +50 mm, −60 to +60 mm, −70 to +70 mm, −80 to +80 mm, −90 to +90 mm, −100 to +100 mm, −120 to +120 mm, −130 to +130 mm, −150 to +150 mm, −200 to +200 mm, −300 to +300 mm, −400 to +400 mm, −500 to +500 mm, −600 to +600 mm, or value or range therebetween in up or down, left or right, forward or backward movement, rotation, or a combination thereof of the head mounted display in relationship to an initial or a predetermined viewing direction of the head mounted display or in relationship to a neutral position of the surgeon's head or neck, a predetermined position of the surgeon's head or neck, an anatomic structure of the patient, a fiducial marker attached to the patient, a sub-array of fiducial markers attached to the patient, an array of fiducial makers attached to the patient, an OR table, a fixed structure in the operating room, the camera, or a combination thereof; wherein the second movement range comprises a range of −10 to +10 degrees, −20 to +20 degrees, −30 to +30 degrees, −40 to +40 degrees, −50 to +50 degrees, −60 to +60 degrees, −70 to +70 degrees, −80 to +80 degrees, −90 to +90 degrees, −100 to +100 degrees, −110 to +110 degrees, or value or range therebetween in up or down, left or right, forward or backward movement, rotation, or a combination thereof of the head mounted display in relationship to an initial or a predetermined viewing direction of the head mounted display or in relationship to a neutral position of the surgeon's head or neck, a predetermined position of the surgeon's head or neck, an anatomic structure of the patient, a fiducial marker attached to the patient, a sub-array of fiducial markers attached to the patient, an array of fiducial makers attached to the patient, an OR table, a fixed structure in the operating room, the camera, or a combination thereof, or wherein the second movement range comprises a range of −10 to +10 mm, −20 to +20 m, −30 to +30 mm, −40 to +40 m, −50 to +50 mm, −60 to +60 mm, −70 to +70 mm, −80 to +80 mm, −90 to +90 mm, −100 to +100 mm, −120 to +120 mm, −130 to +130 mm, −150 to +150 mm, −200 to +200 mm, −300 to +300 mm, −400 to +400 mm, −500 to +500 mm, −600 to +600 mm, or value or range therebetween in up or down, left or right, forward or backward movement, rotation, or a combination thereof of the head mounted display in relationship to an initial or a predetermined viewing direction of the head mounted display or in relationship to a neutral position of the surgeon's head or neck, a predetermined position of the surgeon's head or neck, an anatomic structure of the patient, a fiducial marker attached to the patient, a sub-array of fiducial markers attached to the patient, an array of fiducial makers attached to the patient, an OR table, a fixed structure in the operating room, the camera, or a combination thereof.

Discs can have a more limited visible range or movement range (detectable and trackable by a camera) compared to spheres in relationship to the camera, e.g. a camera integrated or attached to an HMD or a camera separate for an HMD or combinations thereof. For example, for disks a visible range or range trackable by the camera in superior-inferior and/or left-right and/or anterior-posterior can be 70°, 80°, 90°, 100°, or 110° or similar ranges, for example measured in relationship to the camera or a fiducial marker, sub-array or array on a patient or in relationship to an initial or predetermined viewing direction of an HMD. For spheres, a visible range or movement range trackable by the camera in superior-inferior and/or left-right and/or anterior-posterior direction can be 120°, 130°, 140°, 150°, 160°, 170°, 180°, 190°, 200°, 210°, 220°, 230°, 240°, 250°, 260°, 270°, 280°, 290°, or more degrees), for example measured in relationship to the camera or a fiducial marker, sub-array or array on a patient or in relationship to an initial or predetermined viewing direction of an HMD.

In some embodiments, fiducial markers and/or sub-arrays and/or arrays with different dimensions, shapes, geometry, and/or geometric pattern can be used to differentiate a first from a second, third, fourth and/or more HMDs:

A 1st HMD can comprise a 1st fiducial marker and/or subarray and/or array with a 1st unique identifier, e.g. a 1st unique ID, dimension, shape and/or geometry and/or geometric pattern.

A 2nd HMD can comprise a 2nd fiducial marker and/or subarray and/or array with a 2nd unique identifier, e.g. a 2nd unique ID, dimension, shape and/or geometry and/or geometric pattern.

A 3rd HMD can comprise a 3rd fiducial marker and/or subarray and/or array with a 3rd unique identifier, e.g. a 3rd unique ID, dimension, shape and/or geometry and/or geometric pattern.

A 4th HMD can comprise a 4th fiducial marker and/or subarray and/or array with a 4th unique identifier, e.g. a 4th unique ID, dimension, shape and/or geometry and/or geometric pattern.

A camera can be integrated or attached to an HMD or separate from an HMD. A camera can be integrated or attached to or be part of a surgical navigation system or a surgical robot. A camera can be integrated or attached to an OR light or other fixed or movable structure in the OR.

At least one camera integrated or attached to a first head mounted display can be configured to track a first fiducial marker, sub-array or array and a second, third, fourth etc. fiducial marker, sub-array, or array integrated into or attached to one or more different head mounted displays.

At least one camera can be integrated or attached to a first head mounted display. The at least one camera integrated or attached to the first head mounted display can be configured to track a first fiducial marker, first sub-array or first array integrated into or attached to a second head mounted display. The at least one camera integrated or attached to the first head mounted display can be configured to track a second fiducial marker, second sub-array or second array integrated into or attached to the second head mounted display. The at least one camera integrated or attached to the first head mounted display can be configured to track a first fiducial marker, first sub-array or first array integrated into or attached to a second head mounted display and a second fiducial marker, second sub-array or second array integrated into or attached to the second head mounted display.

At least one camera can be integrated or attached to a second head mounted display. The at least one camera integrated or attached to the second head mounted display can be configured to track a first fiducial marker, first sub-array or first array integrated into or attached to a first head mounted display. The at least one camera integrated or attached to the second head mounted display can be configured to track a second fiducial marker, second sub-array or second array integrated into or attached to the first head mounted display. The at least one camera integrated or attached to a second head mounted display can be configured to track a first fiducial marker, first sub-array or first array integrated into or attached to a first head mounted display and a second fiducial marker, second sub-array or second array integrated into or attached to the first head mounted display.

In some embodiments, a first sub-array, a second sub-array, or a first sub-array and a second sub-array can comprise at least one fiducial marker.

In some embodiments, a first array or a second array can comprise at least one fiducial marker, or the first array or the second array or the first and the second array can comprise at least one sub-array, or the first array and/or the second array can comprise at least one fiducial marker and at least one subarray.

In some embodiments, the system can comprise a third fiducial marker, sub-array or array integrated into or attached to a head mounted display at a third location, orientation, or location and orientation different from a first and/or second location, orientation, or location and orientation of a first and/or second fiducial marker, sub-array or array, and the system can be configured to track the third fiducial marker, sub-array or array over a third movement range of the head mounted display detectable and trackable by the at least one camera, wherein the third movement range can be at least in part different from a first trackable movement range of the first fiducial marker, sub-array or array and a second trackable movement range of a second fiducial marker, sub-array or array.

One or more fiducial markers and/or sub-arrays and/or arrays can optionally be attached to the operating room table and they can be registered in a coordinate system, for example the same coordinate system in which the one or more HMDs, the patient, and portions of the surgical site can be registered. One or more fiducial markers and/or sub-arrays and/or arrays can optionally be attached to other structures in the operating room including fixed structures, e.g. walls, and movable structures, e.g. OR lights, and they can be registered in a coordinate system, for example the same coordinate system in which the one or more HMDs, the patient, and portions of the surgical site can be registered. In this example, fiducial markers and/or sub-arrays and/or arrays can also be mounted to fixed structures on holding arms or extenders, optionally moveable and, for example, of known dimensions, orientations, lengths and angles.

Fiducial markers and/or sub-arrays and/or arrays attached to fixed structures such as OR walls can be used to enhance the accuracy of room recognition and spatial mapping, in particular when the coordinates and/or the angles and/or distances between different optical markers are known. Fiducial markers attached to fixed structures such as OR walls can also be used to enhance the determination of the location and pose and change in location or pose or the coordinates and change in coordinates of one or more head mounted displays, which can assist with increasing the accuracy of the display of virtual data and their superimposition on corresponding live data.

Fiducial markers and/or sub-arrays and/or arrays attached to movable structures can be used to track their location in the operating room. Fiducial markers attached to OR lights can be used to estimate the direction of light and the orientation and/or trajectory of shadows in the OR or a room. If the orientation and/or trajectory of shadows in the OR or the room is known, virtual shadowing or shading with the same or similar orientation or trajectory can be applied to virtual data display by the HMD.

Different coordinate systems can be used. For example, a global coordinate system, can include one or more of a femoral coordinate system, tibial coordinate system, ankle coordinate system, hip coordinate system, acetabular coordinate system, humeral coordinate system, glenoid coordinate system, vertebral coordinate system etc. A coordinate system can be the coordinate system of a first, second, third or fourth head mounted display or a combination thereof. A coordinate system can be a coordinate system of a patient.

A coordinate system can be a coordinate system of an anatomic structure. A coordinate system can be the coordinate system of an OR table. A coordinate system can be the coordinate system of a camera, e.g. integrated or attached to an HMD or separate from an HMD. A coordinate system can be the coordinate system of a fiducial marker and/or sub-array and/or array, e.g. attached to a patient, an HMD, an OR table, an OR fixture, a camera, or a combination thereof.

In some embodiments, one or more fiducial markers, e.g. optical markers, sub-arrays or arrays can be used in conjunction with a spinal surgery, e.g. a vertebroplasty, a kyphoplasty, a posterior spinal fusion, an anterior spinal fusion, a lateral spinal fusion and/or a disk replacement. For example one or more optical markers can be included in, integrated into, or attached to a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps and the like. The foregoing list is only exemplary and not to be construed limiting. The one or more fiducial markers, sub-arrays or arrays can be used to designate the patient's left side and the patient's right side and/or they can be used to designate the patient's spinal level, using, for example, one or more geometric shapes (e.g. marker ball configurations or arrangements on an array), geometric patterns, alphabetic, numeric, alphanumeric, and other codes or patterns that can be detected with an image and/or video capture system integrated into, attached to or separate from the HMD and that can be recognized using image processing and/or pattern recognition.

One or more fiducial markers, sub-arrays or arrays can be used to determine the position, location, orientation, alignment and/or direction of a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component with use of an image and/or video capture system integrated into, attached to or separate from the HMD. For example, after the initial registration or any subsequent registration of the patient, the surgical site, the HMD, optionally an image and/or video capture system integrated into, attached to or separate from the HMD, the virtual data and/or the live data of the patient have been performed, the image and/or video capture system can detect an optical marker included in, integrated into, and/or attached to the surgical instrument. Since the location, position, alignment and/or orientation of the optical marker on the surgical instrument are known and the dimensions, e.g. at least one of them, or geometry of the surgical instrument are known, the image and/or video capture system can track the optical marker and the surgical instrument with regard to its location, position, orientation, alignment and/or direction of movement.

In another example, two or more fiducial markers, sub-arrays, or arrays can be integrated into or attached to different, optionally defined locations along the long axis of a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component, for example instruments or trial implants or implant components in knee replacement or hip replacement. An image and/or video capture system can detect the two or more optical markers and their respective location can be determined. With the location of the two or more optical markers captured and defined by the image and/or video capture system, the long axis of the needle, pin, awl, probe, tap, mill, saw, reamer, broach, impactor, and/or other surgical instrument and/or trial implant and/or implant component can be determined; other axes can be determined in addition to the long axis or instead of the long axis. With the location of the optical markers on the needle, pin, awl, probe, tap, mill, saw, reamer, broach, impactor, and/or other surgical instrument and/or trial implant and/or implant component known, the long axis or other axis of the needle, pin, awl, probe, tap, mill, saw, reamer, broach, impactor, and/or other surgical instrument and/or trial implant and/or implant component known and the dimensions of the needle, pin, awl, probe, tap, mill, saw, reamer, broach, impactor, and/or other surgical instrument and/or trial implant and/or implant component known, any portions of the needle, pin, awl, probe, tap, mill, saw, reamer, broach, impactor, and/or other surgical instrument and/or trial implant and/or implant component hidden by the tissue, e.g. below the skin and/or inside or within muscle or the cartilage or the bone, can be estimated and can optionally be displayed by the HMD in addition to the virtual or intended path or projected path or any other aspects of a virtual surgical plan. Rather than using two or more optical markers in the foregoing embodiment, an optical marker long enough or wide enough or deep enough to define one or more axes of a needle, pin, awl, probe, tap, mill, saw, reamer, broach, impactor, and/or other surgical instrument and/or trial implant and/or implant component can also be used.

Optionally, when two or more fiducial markers, sub-arrays or arrays are used included in, integrated into or attached to a surgical instrument, the optical markers, can be arranged at the same angles, e.g. parallel or on the same axis, or at different angles, e.g. orthogonal angles or non-orthogonal angles. Similarly, in determining an axis of a joint, e.g. an epicondylar axis, optical markers, e.g. optical markers attached to a medial or a lateral femoral epicondyle, can be arranged at the same angles, e.g. parallel or on the same axis, or at different angles, e.g. orthogonal angles or non-orthogonal angles. This can be particularly useful, when the optical markers include one or more of a geometric shape, geometric pattern, alphabetic, numeric, alphanumeric, and other codes or patterns including bar codes and QR codes or combinations thereof. By arranging the optical markers and any associated geometric shapes, geometric patterns, alphabetic, numeric, alphanumeric, and other codes or patterns including bar codes and QR codes or combinations thereof in this manner, the angular orientation of the surgical instrument or an axis can be determined in a more accurate manner. For example, at certain view angles from an image and/or video capture system integrated into or attached to an HMD select geometric shapes, geometric patterns, alphabetic, numeric, alphanumeric, and other codes or patterns including bar codes and QR codes or combinations thereof of a first optical marker on a surgical instrument or an anatomic landmark may be only partially visualized or not visualized at all due to the angular orientation; when a second optical marker is oriented at a different angle, location and/or orientation on the same surgical instrument or an anatomic landmark, the view angle from the image and/or video capture system integrated into or attached to the HMD to the second optical marker can allow for a complete or a more complete visualization of the one or more geometric shapes, geometric patterns, alphabetic, numeric, alphanumeric, and other codes or patterns including bar codes and QR codes or combinations thereof, thereby allowing a more accurate determination of the angular orientation of the second optical marker and, with that, the surgical instrument. In addition, the respective projections of the first optical marker and/or the second optical marker measured by the image and/or video capture system, optionally paired with any parallax information when two or more cameras are used, e.g. one positioned near the left eye and another positioned near the right eye, can be used to more accurately determine their relative position and the position of the surgical instrument.

An image and/or video capture system integrated into or attached to or separate from an HMD can detect a fiducial marker, sub-array or array included in, integrated into or attached to a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach an impactor, a cutting or drilling block, and/or other surgical instrument and/or trial implant and/or implant component as it enters the surgeon's field of view triggering a command to display the predetermined path or plane or a virtual display of the a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component or other display mode or type of the virtual surgical plan, for example with the intended position, location and/or alignment and/or direction for the intended surgical step; as the optical marker with the surgical instrument exits the surgeon's field of view, the image and/or video capture system can detect it triggering a command to stop the display of the predetermined path or the virtual display of the surgical instrument or other aspects of the virtual surgical plan, optionally switching to the next surgical step and corresponding virtual display. In a spinal procedure as well as select other procedures, the next surgical step can involve the same side of the patient or the opposite side of the patient at the same spinal level, where the corresponding virtual display for the next surgical step for a given level and side can be initiated by the HMD display. The next surgical step can involve the same side of the patient or the opposite side of the patient at an adjoining or different spinal level, where the corresponding virtual display for the next surgical step for a given level and side can be initiated by the HMD display.

Optical markers can include one or more QR codes. QR codes can be part of or can be embedded in a geometric pattern or geometric shape included in an optical marker. Optical markers can be a QR code.

If a fiducial marker, sub-array or array is attached to a surgical instrument, the attachment can occur in a defined location and/or position and/or alignment, for example at an end of the surgical instrument. The attachment can include, for example, an opening with a stop thereby defining the location and/or position and/or alignment of the optical marker on the surgical instrument. For example, the fiducial marker, sub-array or array can have an opening with a stop that is large enough to accommodate the surgeon facing end of a pin or drill, for example inserted into a spinous process or a facet joint or a portion of a pedicle. With this type of attachment and other attachments that secure the fiducial marker, sub-array or array in a defined location, position and/or orientation on the surgical instrument, an image and/or video capture system can detect the fiducial marker, sub-array or array and its location, position and/or orientation can be used to determine the location, position, and/or orientation of the surgical instrument, e.g. a pin, including its tip or frontal portion inside the patient due to their defined spatial relationship and due to the known geometry of the surgical instrument.

In some embodiments, an fiducial marker, sub-array or array can be used to determine or identify the position, location, orientation, alignment, dimensions, axis or axes, plane or planes of a surgical alteration. For example, if a bone cut has been performed in a surgical step, one or more optical markers can be attached to the cut bone to determine one or more of its position, location, orientation, alignment, dimensions, shape, geometry, axis or axes, plane or planes. For example, one, two or more fiducial marker, sub-array or array can be placed near or attached to the periphery or the edge of the cut bone or surgical alteration; an image and/or video capture system integrated into, attached to or separate from the HMD can detect the location, position, and/or orientation of the optical markers and software can be used, for example, to analyze the location, position, and/or orientation information of the fiducial marker, sub-array or array to derive information on the periphery and/or edge and/or shape of the cut bone or surgical alteration. One, two or more optical markers can be placed near or attached to the cut bone or surgical alteration; an image and/or video capture system integrated into, attached to or separate from the HMD can detect the location, position, and/or orientation of the fiducial marker, sub-array or array and software can be used, for example, to analyze the location, position, and/or orientation information of the fiducial marker, sub-array or array to derive information on the shape or geometry of the cut bone or surgical alteration. If the bone cut is planar, one or more fiducial marker, sub-array or array with a planar bone facing surface or one or more optical markers attached to a carrier or instrument, e.g. a plastic piece, with a planar bone facing surface can be held against, affixed to or attached to the cut bone surface; an image and/or video capture system integrated into, attached to or separate from an HMD can then be used to detect the one or more fiducial marker, sub-array or array and software can be used, for example, to analyze the location, position and/or orientation information of the one or more optical markers to derive information on the location and/or position and/or orientation and/or alignment of the plane of the bone cut, including for example in relationship to other anatomic landmarks and/or other optical markers. The carrier or instrument for the fiducial marker, sub-array or array can be transparent or semi-transparent so that the surgeon can check or confirm that the carrier or instrument and the attached optical marker(s) are flush against the bone cut prior to determining or confirming, for example, the plane of the bone cut. Once the plane of the bone cut has been determined or confirmed in this manner, the fiducial marker, sub-array or array attached to the cut bone and/or the determined plane of the bone cut can be used to plan the next surgical alteration, e.g. the next bone cut or surgical alteration, e.g. an anterior or posterior femoral cut after the distal femoral cut in knee replacement, or a chamfer cut after the anterior and posterior femoral cuts in knee replacement, or a cut on an opposing articular surface. By determining, confirming and/or referencing a preceding surgical alteration, e.g. a bone cut, in this manner, the accuracy of subsequent surgical steps can be improved thereby ultimately improving the overall accuracy of the surgical procedure. Fiducial marker, sub-array or array on fixed structures in the OR: In some embodiments, one or more fiducial marker, sub-array or array can be attached to an operating room (OR) table. If the fiducial marker, sub-array or array is parallel to the OR table, a single marker can be sufficient to determine the principal plane of the OR table, e.g. the horizontal plane, which can be the plane on which the patient is resting, for example in supine, prone, lateral or oblique or other positions known in the art. This can be aided by using fiducial marker, sub-array or array and/or LEDs that include a surface or plane that is parallel or perpendicular or at a defined angle to the OR table and that is large enough to be detected by the camera, image or video capture system integrated into, attached to or separate from the HMD. For example, such a plane of the fiducial marker, sub-array or array can measure 1×1 cm, 2×2 cm, 2×3 cm, 4×4 cm, 4×6 cm and so forth. Alternatively, multiple, e.g. two, three or more, fiducial marker, sub-array or array and/or LEDs can be used to determine a plane through the markers corresponding to the principal plane of the OR table or a plane parallel to the principal plane of the OR table or, for example, a plane vertical to the OR table or, for example, a plane at a defined angle to the OR table. If the OR table is hidden by surgical drapes, one or more magnetic or otherwise attachable bases can be attached to the OR table prior to placing the drapes. After the drapes have been placed, one or more magnetic or otherwise attachable fiducial marker, sub-array or array and/or LEDs can be affixed to the magnetic bases or attachment mechanisms with the interposed surgical drapes. The magnetic base can be radiopaque which can help identify the location, orientation and/or coordinates of the fiducial marker, sub-array or array(s) in radiographic images or other images using ionizing radiation.

Alternatively, one or more holding arms or extenders of known geometry can be attached to the OR table and one or more fiducial marker, sub-array or array and/or LEDs can be attached to or can be integrated into the holding arms or extenders. An image and/or video capture system integrated into, attached to or separate from the HMD can then identify the location, position, orientation and/or alignment of the one or more fiducial marker, sub-array or array and/or LEDs. The resultant information can be used to determine the principal plane of the OR table on which the patient is lying. One or more HMDs can be referenced using, for example, an image and/or video capture system integrated into or attached to the HMD relative to the OR table and/or the attached fiducial marker, sub-array or array and/or LEDs. Once the principal plane of the OR table is determined in the system, virtual surgical steps can be planned in the virtual surgical plan of the patient in relationship to the principal plane of the OR table. For example, one or more bone cuts can be planned and/or performed perpendicular to the principal plane of the OR table, for example with the patient in supine or prone position or any other desired position. One or more bone cuts can be planned and/or performed at defined angles other than 90 degrees relative to the horizontal plane of the OR table, for example with the patient in supine or prone position or any other desired position.

One or more bone cuts can be planned and/or performed at a non-orthogonal plane or orientation relative to the principal plane or horizontal plane of the OR table, for example with the patient in supine or prone position or any other desired position, optionally referencing a plane vertical to the OR table, displayed by the HMD. The principal plane of the OR table can be used as a reference in this manner including for comparing or referencing virtual data of the patient and live data of the patient and including for comparing or referencing a virtual surgical plan. Such bone cuts at orthogonal angles or non-orthogonal angles, e.g. relative to the OR table or relative to anatomy, anatomic landmarks, anatomic or biomechanical axes of the patient, can be executed using one or more virtual surgical guides or cut blocks and/or one or more physical surgical guides or cut blocks. Virtual surgical guides or cut blocks can include one or more dimensions corresponding to physical surgical guides or cut blocks. One or more anatomic axes or biomechanical axes or combinations thereof can also be referenced to the OR table in this manner, e.g. the principal plane of the OR table, a plane parallel to the OR table, a plane perpendicular to the OR table, a plane oblique to the OR table or combinations thereof.

One or more fiducial marker, sub-array or array and/or LEDs attached to or referencing the OR table can also serve as a fixed reference for the one or more HMDs during a surgical procedure. This can be useful, for example, when the patient and/or the extremity and/or the surgical site moves during the procedure. A fixed reference to the OR table can aid in maintaining registration of the one or more HMDs and the virtual surgical plan and the live data of the patient and/or OR.

In some embodiments, one or more fiducial marker, sub-array or array and/or LEDs can be placed on or attached to the patient in the area of the surgical field and/or in an area away from the surgical field. An image and/or video capture system integrated into, attached to or separate from the HMD can be used to identify the one or more fiducial marker, sub-array or array and/or LEDs and to determine their location, position, orientation and/or alignment. The image and/or video capture system can also, optionally, determine the location, position, orientation and/or alignment of one or more fiducial marker, sub-array or array and/or LEDs attached to or referencing the OR table. The system can reference the coordinates and/or the spatial relationship of the one or more fiducial marker, sub-array or array and/or LEDs attached to the patient in the area of the surgical field and/or in an area away from the surgical field and the one or more fiducial marker, sub-array or array and/or LEDs attached to or referencing the OR table. In this manner, if the patient's body moves during the procedure, e.g. during a broaching of a proximal femur or an acetabular reaming during hip replacement, or a femoral or tibial component impacting during knee replacement, or during a pinning or cutting of a bone, or during a placement of a spinal device, e.g. a cage or a pedicle screw, the movement between the one or more fiducial marker, sub-array or array and/or LEDs attached to the patient in the area of the surgical field and/or in an area away from the surgical field and the one or more fiducial marker, sub-array or array and/or LEDs attached to or referencing the OR table and the change in coordinates of the one or more fiducial marker, sub-array or array and/or LEDs attached to the patient in the area of the surgical field and/or in an area away from the surgical field can be detected and the amount of movement, direction of movement and magnitude of movement can be determined; the resultant information can, for example, be used to update or adjust or modify a virtual surgical plan or to update or adjust or modify the display of the virtual surgical plan or virtual surgical steps or virtual displays for the movement of the patient, including for example by updating, moving or adjusting one or more aspects or components of the virtual surgical plan including one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the new patient coordinates or the new coordinates of the surgical field.

Radiopaque fiducial marker, sub-array or array: In some embodiments, portions of the fiducial marker, sub-array or array or the entire fiducial marker, sub-array or array can be radiopaque, so that the fiducial marker, sub-array or array can also be visible on a radiograph or other imaging studies that utilize ionizing radiation including, for example, fluoroscopy, digital tomosynthesis, cone beam CT, and/or computed tomography. Different levels or degrees of radiopacity can be present in different portions or areas of the fiducial marker, sub-array or array. Different levels or degrees of radiopacity can be utilized to encode information. For example, different levels of radiopacity can be used to encode information also contained, for example, in an optically readable alphanumeric code, bar code or QR or other code. The different levels of radiopacity can optionally be arranged in a bar like thickness distribution, which can optionally mirror portions or all of the information contained in a bar code. The different levels of radiopacity can optionally be arranged in a point or square like thickness distribution, which can optionally mirror portions of the information contained in a QR code. Different radiopacity can be obtained by varying the thickness of the metal, e.g. lead. Radiopaque fiducial marker, sub-array or array and/or LED's with information encoded in such manner can, for example, be manufactured using 3D metal printers. They can also be CNC machined, e.g. from bar stock or cast blanks. Fiducial marker, sub-array or array s can include portions that are radiopaque and portions that are not radiopaque. Radiopaque portions can include radiopaque elements, e.g. radiopaque struts, disks, sphere and/or other shapes. Any shape known in the art can be used. The fiducial marker, sub-array or array can be attached to the radiopaque elements and/or radiopaque portions. The fiducial marker, sub-array or array can be integrated into the radiopaque elements and/or radiopaque portions. The fiducial marker, sub-array or array can be separate from the radiopaque elements and/or radiopaque portions, e.g. at a defined or known distance, defined or known angle and/or defined or known geometric and/or spatial arrangement.

The radiopaque portions of the fiducial marker, sub-array or array can include information on laterality, e.g. L for left and R for right, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the HMD. The radiopaque portions of the fiducial marker, sub-array or array can include information on anatomical site, e.g. L5 or L4, T1 or T2, C3 or C7, knee, hip, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the HMD. Image processing techniques and/or software can be applied to the radiographic information including the fiducial marker, sub-array or array and radiographically encoded information such as laterality and/or site and the information included in the radiograph can be compared against the information included on the optical scan. If any discrepancies are detected, an alert can be triggered, which can, for example, be displayed in the HMD.

Multiple partially or completely radiopaque fiducial markers, sub-arrays or arrays can be used. The radiopaque fiducial markers, sub-arrays or arrays can be applied at different locations and in different planes around the surgical site. In spinal surgery, for example, one, two, three or more radiopaque fiducial markers, sub-arrays or arrays can be applied to the skin around the spinal levels for the intended surgery; one, two, three or more radiopaque fiducial markers, sub-arrays or arrays can be attached to a pin, drill or screw inserted into a spinous process and/or a pedicle or other spinal element; one, two, three or more radiopaque fiducial markers, sub-arrays or arrays can be applied to the patient's flank or abdomen. In hip replacement surgery, one, two, three or more radiopaque fiducial markers, sub-arrays or arrays can be applied to the anterior superior iliac spine on the patient's intended surgical side, e.g. with an adhesive to the skin or attached to a pin or drill to the bone; one, two, three or more radiopaque fiducial markers, sub-arrays or arrays can be applied to the anterior superior iliac spine on the patient's contralateral side, e.g. with an adhesive to the skin or attached to a pin or drill to the bone; one, two, three or more radiopaque fiducial markers, sub-arrays or arrays can be applied to the symphysis pubis, e.g. with an adhesive to the skin or attached to a pin or drill to the bone; one, two, three or more radiopaque fiducial markers, sub-arrays or arrays can be applied to the acetabulum on the patient's intended surgical side, e.g. attached to a pin or drill to the bone; one, two, three or more radiopaque fiducial markers, sub-arrays or arrays can be applied to the greater trochanter on the patient's intended surgical side, e.g. attached to a pin or drill to the bone. By using multiple radiopaque fiducial markers, sub-arrays or arrays in multiple different locations and in different planes around the surgical site, the accuracy of any three-dimensional spatial registration and cross-reference of the fiducial markers, sub-arrays or arrays in different modalities, e.g. radiographs, image capture, can be increased, for example by obtaining multiple x-rays at different angles, e.g. AP, lateral and/or oblique, and/or by imaging the radiopaque fiducial markers, sub-arrays or arrays from multiple view angles using an image and/or video capture system integrated into, attached to or separate from the HMD or by imaging the radiopaque fiducial markers, sub-arrays or arrays from multiple view angles using multiple image and/or video capture system integrated into, attached to or separate from the HMD leveraging information from multiple view angles or leveraging parallax information. By using multiple fiducial markers, sub-arrays or arrays in multiple different locations and in different planes around the surgical site, the accuracy of any three-dimensional spatial registration of the fiducial markers, sub-arrays or arrays can be increased, for example by imaging the fiducial markers, sub-arrays or arrays from multiple view angles using an image and/or video capture system integrated into, attached to or separate from the HMD. In addition, the accuracy of the registration can be better maintained as the view angle or radiographic angle changes, for example during the course of the surgical procedure or due to patient movement.

Representative, non-limiting examples of patient surfaces to which a fiducial marker, sub-array or array can be attached include:

Spine:
A portion or an entire spinous process
A portion or an entire spinal lamina
A portion or an entire spinal articular process
A portion of or an entire facet joint
A portion of or an entire transverse process
A portion of or an entire pedicle
A portion of or an entire vertebral body
A portion of or an entire intervertebral disk
A portion of or an entire spinal osteophyte
A portion of or an entire spinal bone spur
A portion of or an entire spinal fracture
A portion of or an entire vertebral body fracture
Combinations of any of the foregoing
Hip:
A portion of or an entire acetabulum
A portion of or an entire edge of an acetabulum
Multiple portions of an edge of an acetabulum
A portion of an iliac wall
A portion of a pubic bone
A portion of an ischial bone
A portion of or an entire greater trochanter
A portion of or an entire lesser trochanter
A portion of or an entire femoral shaft
A portion of or an entire femoral neck
A portion of or an entire femoral head
A fovea capitis
A transverse acetabular ligament
A pulvinar
A ligamentum *teres*
A labrum
One or more osteophytes, femoral and/or acetabular
Combinations of any of the foregoing
Knee:
A portion or an entire medial femoral condyle
A portion or an entire lateral femoral condyle
A portion or an entire femoral notch
A portion or an entire trochlea
A portion of an anterior cortex of the femur
A portion of an anterior cortex of the femur with adjacent portions of the trochlea
A portion of an anterior cortex of the femur with adjacent portions of the trochlea and osteophytes when present
One or more osteophytes femoral and/or tibial
One or more bone spurs femoral and/or tibial
An epicondylar eminence
A portion or an entire medial tibial plateau
A portion or an entire lateral tibial plateau
A portion or an entire medial tibial spine
A portion or an entire lateral tibial spine
A portion of an anterior cortex of the tibia
A portion of an anterior cortex of the tibia and a portion of a tibial plateau, medially or laterally or both
A portion of an anterior cortex of the tibia and a portion of a tibial plateau, medially or laterally or both and osteophytes when present
A portion or an entire patella
A medial edge of a patella
A lateral edge of a patella
A superior pole of a patella
An inferior pole of a patella
A patellar osteophyte
An anterior cruciate ligament
A posterior cruciate ligament
A medial collateral ligament
A lateral collateral ligament
A portion or an entire medial meniscus
A portion or an entire lateral meniscus
Combinations of any of the foregoing
Shoulder:
A portion or an entire glenoid
A portion or an entire coracoid process
A portion or an entire acromion
A portion of a clavicle
A portion or an entire humeral head
A portion or an entire humeral neck
A portion of a humeral shaft
One or more humeral osteophytes
One or more glenoid osteophytes
A portion or an entire glenoid labrum
A portion or an entire shoulder ligament, e.g. a coracoacromial ligament, a superior, middle, or inferior glenohumeral ligament
A portion of a shoulder capsule
Combinations of any of the foregoing
Skull and brain:
A portion of a calvarium
A portion of an occiput
A portion of a temporal bone
A portion of an occipital bone
A portion of a parietal bone
A portion of a frontal bone
A portion of a facial bone
A portion or an entire bony structure inside the skull
Portions or all of select gyri
Portions or all of select sulci
A portion of a sinus
A portion of a venous sinus
A portion of a vessel
Organs:
A portion of an organ, e.g. a superior pole or inferior pole of a kidney
An edge or a margin of a liver, a spleen, a lung
A portion of a hepatic lobe
A portion of a vessel
A portion of a hiatus, e.g. in the liver or spleen
A portion of a uterus Registration of Virtual Patient Data and Live Patient Data Using Intraoperative Imaging In some embodiments, intraoperative imaging, for example using x-ray imaging or CT imaging and/or ultrasound imaging, can be performed. Virtual patient data obtained intraoperatively using intraoperative imaging can be used to register virtual patient data obtained preoperatively, for example using preoperative x-ray, ultrasound, CT or MRI imaging. The registration of preoperative and intraoperative virtual data of the patient and live data of the patient in a common coordinate system with one or more HMDs can be performed, for example, by identifying and, optionally, marking corresponding landmarks, surfaces, object shapes, e.g. of a surgical site or target tissue, in the preoperative virtual data of the patient, the intraoperative virtual data of the patient, e.g. on electronic 2D or 3D images of one or more of the foregoing, and the live data of the patient. Virtual preoperative, virtual intraoperative and live data can include an osteophyte or bone spur or other bony anatomy or deformity. Virtual and physical surgical instruments and implant components can also be registered in the common coordinate system.

This embodiment can be advantageous when the amount of information obtained with intraoperative imaging is, for example, anatomically or in other ways more limited than the amount of information available with preoperative imaging or vice versa.

For example, intraoperative imaging may be performed using x-ray imaging, which is commonly only two-dimensional in nature. X-ray imaging can be augmented through image acquisition in more than one plane, e.g. orthogonal planes or one or more planes separated by a defined angle. Intraoperative x-ray images can be used to identify certain landmarks or shapes that can then be registered to preoperative imaging and/or live data of the patient during surgery. Preoperative imaging can, optionally, include 3D image data, for example obtained with CT or MRI. Acquisition of intraoperative images in multiple planes can be helpful to more accurately define the location of certain landmarks, contours or shapes intended for use in a registration of preoperative virtual data, intraoperative virtual data and live data of the patient. For purposes of clarification, intraoperative virtual data of the patient can be intraoperative images of the patient in 2D or 3D.

For example, in a spinal procedure such as vertebroplasty, kyphoplasty, pedicle screw placement, or placement of anterior spinal device including artificial disks or cages, intraoperative x-ray imaging can be used to identify, for example, the spinal level targeted for the surgery, in an AP projection certain landmarks or contours, e.g. the tip of a spinous process, a facet joint, the superior or inferior tip of a facet joint, the cortical edge of a lamina, a superior or inferior endplate or an osteophyte or bone spur or other bony anatomy or deformity. Optionally, the distance of the x-ray tube from the patient resulting in x-ray magnification can be factored into any registration in order to improve the accuracy of the registration of virtual preoperative data of the patient and virtual intraoperative data of the patient or live data of the patient. The intraoperative x-ray images can then be registered and, optionally, superimposed onto the preoperative data of the patient or the live data of the patient in the projection by the HMD. The intraoperative virtual data of the patient, e.g. the tip of a spinous process, a facet joint, the superior or inferior tip of a facet joint, the cortical edge of a lamina, a superior or inferior endplate, can be registered to the live data of the patient, for example by touching the corresponding anatomic landmarks with a pointing device or a needle or a pin inserted through the skin and by cross-referencing the location of the tip of the live data pointing device with the intraoperative virtual data of the patient. In this manner, any one of preoperative virtual data of the patient, intraoperative virtual data of the patient, and live data of the patient and combinations thereof can be co-registered. Two or three of these data sets, preoperative virtual data of the patient, intraoperative virtual data of the patient, and live data of the patient, can optionally be seen in the HMD. However, in many embodiments, intraoperative imaging may only be used for enhancing the accuracy of the registration of preoperative virtual data of the patient and live data of the patient and, for example, preoperative virtual data of the patient and/or a medical device intended for placement in a surgical site will be displayed by the HMD together with the view of the live data of the patient or the surgical site.

In some embodiments, the registration of virtual patient data and live patient data using the techniques described herein can be repeated after one or more surgical steps have been performed and, optionally, intraoperative imaging can be repeated. In this case, the surgically altered tissue or tissue surface or tissue contour or tissue perimeter or tissue volume or other tissue features in the live patient or in the intraoperative repeat imaging data of the patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Skin Markers or Soft-Tissue Markers In some embodiments, fiducial marker, sub-array or array, e.g. including skin markers and soft-tissue markers, calibration or registration phantoms or devices can be used for registering preoperative virtual data, optionally intraoperative virtual data such as data obtained from intraoperative x-ray imaging, and live data seen through the HMD in a common coordinate system with one or more HMDs. Virtual and physical surgical instruments and implant components can also be registered in the common coordinate system. For example, an initial registration between preoperative virtual data and live data of the patient can happen at the beginning of the procedure. The initial registration can, for example, be performed using corresponding anatomic landmarks, surfaces or shapes, or using intraoperative imaging resulting in intraoperative virtual data or any of the other embodiments described in the present disclosure. The registration can be used, for example, to place the virtual data and the live data and the head mounted display into a common coordinate system. Fiducial markers, sub-arrays or arrays including skin markers, calibration or registration phantoms or devices can then be applied. Virtual and physical surgical instruments and implant components can also be registered in the common coordinate system. Alternatively, or in addition, soft-tissue markers, calibration or registration phantoms or devices can be applied. Typically, more than one, such as two, three, four or more fiducial markers, sub-arrays or arrays including skin markers and soft-tissue markers, calibration or registration phantoms or devices will be applied. For clarity, the terms fiducial marker, sub-array, array, implantable markers, attachable markers, skin markers, soft-tissue markers, calibration or registration phantoms or devices as used through the application can include optical markers (e.g. optical markers with different geometric shapes or patterns, with QR codes, with bar codes, with alphanumeric codes), infrared markers, RF markers, active markers, passive markers, LEDs or combinations thereof. Fiducial markers, sub-arrays or arrays, e.g. skin markers and soft-tissue markers, calibration or registration phantoms or devices can, for example, be applied to the skin or the soft-tissue using a form of tissue compatible adhesive, including fibrin glue and the like. In some embodiments, one, two, three, four or more fiducial markers, sub-arrays or arrays, e.g. skin markers and soft-tissue markers, calibration or registration phantoms or devices, can be included in a surgical drape or dressing or a transparent film applied to the skin prior to the procedure. The fiducial markers, sub-arrays or arrays, e.g. skin markers and soft-tissue markers, calibration or registration phantoms or devices can then be registered in the live data and cross-referenced to virtual data. The fiducial markers, sub-arrays or arrays, e.g. skin markers and soft-tissue markers, calibration or registration phantoms or devices can subsequently be used, for example, when the surgical site is altered and the landmarks, surface or shape that was used for the initial registration of virtual and live data have been altered or removed and cannot be used or cannot be used reliably for maintaining registration between virtual data and live data. Virtual preoperative, virtual intra-operative and live data can include an osteophyte or bone spur or other bony anatomy or deformity.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The same fiducial markers, sub-arrays or arrays, e.g. skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new fiducial markers, sub-arrays or arrays, e.g. skin markers or soft-tissue markers or calibration phantoms or registration phantoms can be applied and cross-referenced to the re-registered live and virtual data after the surgical step or alteration. The fiducial markers, sub-arrays or arrays, e.g. skin markers or soft-tissue markers or calibration phantoms or registration phantoms can then be used for subsequent matching, superimposition, movement and registration of live patient data and virtual patient data.

Registration of Virtual Patient Data and Live Patient Data Using Calibration or Registration Phantoms with Defined Dimensions or Shapes In some embodiments, calibration or registration phantoms with defined dimensions or shapes can be used to perform the registration of virtual data of the patient and live data of the patient. The calibration or registration phantoms can be of primarily two-dimensional or three-dimensional nature. For example, a calibration or registration phantom can be arranged or located primarily in a single plane. Other calibration phantoms can be located in multiple planes, thereby creating the opportunity for registration using more than one planes. For clarity, the terms calibration or registration phantoms, implantable markers, attachable markers, skin markers, soft-tissue markers, or devices as used through the application can include fiducial markers, sub-arrays or arrays. Fiducial markers can include optical markers, e.g. optical markers with different geometric shapes or patterns, with QR codes, with bar codes, with alphanumeric codes.

A fiducial marker, sub-array or array can be, for example, attached to the patient's skin. The fiducial marker, sub-array or array can be integrated or attached to a surgical drape. The fiducial marker, sub-array or array can be attached to the patient's tissue. The fiducial marker, sub-array or array can be part of or a component of a medical device. The part or component of the medical device will typically have known dimensions. By using fiducial marker, sub-array or array s, as well as other markers, the live data of a patient and the virtual data of the patient can be registered in a common coordinate system, for example with one or more HMDs. Virtual and physical surgical instruments and implant components can also be registered in the common coordinate system.

In some embodiments, the fiducial marker, sub-array or array includes known dimensions, angles or geometric 2D or 3D shapes. For example, the fiducial marker, sub-array or array can include structures such as circles, ovoids, ellipses, squares, rectangles, complex 2D geometries, 2D geometries with one or more defined distances, 2D geometries with one or more defined angles spheres, egg shaped structures, cylinders, cubes, cuboids, complex 3D geometries or shapes, 3D geometries with one or more defined distances, 3D geometries with one or more defined angles, 3D geometries with one or more defined surfaces Optionally, the fiducial marker, sub-array or array can be radiopaque if pre-operative or intra-operative imaging is performed using an imaging modality with ionizing radiation, e.g. x-ray imaging, fluoroscopy in 2D or 3D, CT, cone beam CT etc.

In some embodiments, the fiducial marker, sub-array or array can be MRI visible or nuclear scintigraphy or SPECT visible or PET visible, for example by including portions or containers in the phantom containing Gadolinium-DTPA doped or radionuclide doped or PET isotope emitting water. Any contrast agent or MRI or nuclear scintigraphy or SPECT or PET visible agent known in the art can be used in this fashion.

In some embodiments, the fiducial marker, sub-array or array includes retroreflective markers or features which facilitate detection by an image and/or video capture system. The fiducial marker, sub-array or array can also be highlighted against the patient's tissue(s) including blood as well as surgical drapes through a choice of select colors, e.g. a bright green, bright blue, bright yellow, bright pink etc. Color combinations are possible. Any color or color combination known in the art can be used.

The fiducial marker, sub-array or array can optionally include LEDs, optionally battery powered. More than one LED can be used. The LEDs can emit a light of a known color, hue and intensity, preferably selected to be readily identifiable by the image and/or video capture system and any segmentation techniques or algorithms used for detecting the location, position and/or orientation of the LEDs.

The LEDs can be arranged in a spatially defined way, with two or more LEDs arranged at a defined distance or distances, at a defined angle or angles, in substantially the same plane or different planes. If LEDs are arranged in different planes, the spatial orientation of the planes is for example known and defined.

When two or more LEDs are used, the two or more LEDs can emit light utilizing different wavelengths, colors, intensity and, optionally also, blinking frequency. In this manner, an image and/or video capture system integrated into, attached to or separate from the HMD can recognize each different LED based on one or more of their different wavelength, color, intensity and/or blinking frequency. When the LEDs are arrange in a spatially defined and known manner, e.g. using known distances or angles within the same plane or different planes, the identification of each individual LED and the change in distances and angles measured by the image and/or video capture system can be used to determine the position, location and/or orientation of the HMD and/or the operator's head (e.g. if the image and/or video capture system is integrated into the HMD or attached to the HMD) or, in some applications, the movement of the patient or body part to which the fiducial marker, sub-array or array and LEDs are attached.

LEDs used throughout the specification can be re-useable. LEDs used throughout the specification can also be disposable, optionally with integrated, disposable battery cells/batteries. LEDs can be operated utilizing wires, e.g. connected to a power supply and/or connected to a wired user interface or control unit. LEDs can be wireless, e.g. without attached power supply (e.g. battery operated) and/or connected to a wireless (e.g. WiFi, Bluetooth) control unit.

LEDs can be connected and/or organized in LIF networks. One or more LIF networks can be used, for example, to transmit or receive data or information back and forth from the one or more HMDs to a control unit or computer, optionally with a user interface. In this example, LEDs participating or connected in the one or more LIF networks can be integrated into or attached to the HMD. LEDs participating or connected in the one or more LIF networks can be attached to or, when applicable, integrated into any location or site on the surgeon, the OR staff, the patient, the surgical site, one or more HMDs, one or more navigation systems, one or more navigation markers, e.g. retroreflective markers, infrared markers, RF markers; one or more fiducial marker, sub-array or array, e.g. optical markers, calibration or registration phantoms.

An LIF network can also be used to transmit or receive data or information about the spatial position, orientation, direction of movement, speed of movement etc. of individual LEDs. The same LEDs whose relative position, orientation, direction of movement, speed of movement, e.g. in relationship to the surgeon or the patient or the surgical site, is being measured, e.g. using an image and/or video capture system, can be used to transmit or receive information in the LIF network, optionally using different wavelengths, color, frequency, blinking patterns depending on the type of data being transmitted. The information can be about the position, orientation, direction of movement, speed of movement of individual LEDs. The information can also be data that are being transmitted or received by the HMD. The information can be the information or data that are being displayed by the HMD. The information can be information generated or received by navigation markers, RF markers. The information can be information captured by one or more image and/or video capture systems or cameras. 1, 2, 3, 4 or more LEDs can be connected to or attached to the patient, the target anatomy, the surgical site, the surgical site after a first, second or more surgical alterations, for example executed using a virtual surgical plan, the HMD, a second, third and/or additional HMDs, for example worn by a second surgeon, a scrub nurse, other OR personnel, the hand, forearm, upper arm and or other body parts of the surgeon/operator.

The relative position, orientation, movement, direction of movement, velocity of movement of each LED can be determined, for example using one or more image and/or video capture systems, e.g. integrated into, attached to or separate from the one or more HMDs, e.g. when the one or more LED's emit light utilizing different wavelengths, colors, intensity and, optionally also, blinking frequency.

A calibration or registration phantom can optionally include one or more lasers, optionally battery powered. More than one laser can be used. The laser can emit a light of a known color, hue and intensity, for example selected to be readily identifiable by the image and/or video capture system and any segmentation techniques or algorithms used for detecting the location, position and/or orientation of the laser.

The laser can be arranged in a spatially defined way, with two or more lasers arranged at a defined distance or distances, at a defined angle or angles, in substantially the same plane or different planes. If lasers are arranged in different planes, the spatial orientation of the planes can be known and defined.

A fiducial marker, sub-array or array can optionally include radiofrequency (RF) transmitters, optionally battery powered. More than one RF transmitter can be used. The RF transmitters can transmit a signal or signals selected to be readily identifiable by an RF receiver system used for detecting the location, position and/or orientation of the RF transmitters. One or more RF transmitters can transmit signals with different frequency and intensity, thereby permitting differentiation of the different RF transmitters by the RF receiver system.

The RF transmitters can be arranged in a spatially defined way, with two or more RF transmitters arranged at a defined distance or distances, at a defined angle or angles, in substantially the same plane or different planes. If RF transmitters are arranged in different planes, the spatial orientation of the planes is can be known and defined.

A fiducial marker, sub-array or array can optionally include ultrasound (US) transmitters, optionally battery powered. More than one US transmitter can be used. The US transmitters can transmit a signal or signals selected to be readily identifiable by an US receiver or transducer system used for detecting the location, position and/or orientation of the US transmitters. One or more US transmitters can transmit signal with different frequency and intensity, thereby permitting differentiation of the different US transmitters by the US receiver or transducer system.

The US transmitters can be arranged in a spatially defined way, with two or more US transmitters arranged at a defined distance or distances, at a defined angle or angles, in substantially the same plane or different planes. If US transmitters are arranged in different planes, the spatial orientation of the planes is can be known and defined.

Calibration phantoms or registration phantoms can be used for pre-operative imaging and/or for intraoperative imaging and/or image capture of live data, for example using an image and/or video capture system attached to or integrated into the HMD or coupled to the HMD or separate from the HMD. Virtual preoperative, virtual intraoperative and live data can include an osteophyte or bone spur or other bony anatomy or deformity.

If the same fiducial marker, sub-array or array is used for pre-operative imaging and for intra-operative imaging, optionally, the imaging can be performed using the same imaging modality, e.g. x-ray imaging, and, for example, using the same orientation of the patient in relationship to the x-ray source and the detector system and, for example using the same distance of the patient in relationship to the x-ray source and the detector system. Using this approach, the anatomic structures visualized on the pre-operative imaging and intra-operative imaging can be superimposed and registered, optionally in the same coordinate system.

In the event, the fiducial marker, sub-array or array has been positioned differently on the patient for the pre-operative imaging and for the intraoperative imaging data acquisition, the difference in location or position or coordinates can be determined using the co-registration of the anatomic data visualized on the pre-operative imaging and intra-operative imaging. An adjustment for the difference in phantom location from the pre-operative to the intraoperative data can be performed; this adjustment can optionally be defined as a phantom offset between pre-operative and intra-operative data. Virtual preoperative, virtual intraoperative and live data can include an osteophyte or bone spur or other bony anatomy or deformity.

As an alternative to the anatomic registration from the anatomic structures visualized on the pre-operative imaging and intra-operative imaging, the registration between pre-operative imaging data and intra-operative live data visualized through the HMD or an attached, integrated or separate image and/or video capture system can be performed alternatively now using a fiducial marker, sub-array or array as visualized or as identified optically during the surgery, for example using the phantom offset between pre-operative and intra-operative data.

In general, the initial registration of virtual data and live data is possible using any of the techniques described herein, e.g. using anatomic features, anatomic landmarks, intraoperative imaging etc. Then co-registration of a fiducial marker, sub-array or array, e.g. in the same coordinate system, can be performed. If initial registration fails during the surgical procedure, registration can be maintained using the fiducial marker, sub-array or array. For this purpose, the position, location, orientation and/or alignment of the fiducial marker, sub-array or array will be continuously or intermittently monitored using an image and/or video capture system, which can be integrated into or attached to the HMD or coupled to the HMD or separate from the HMD.

In some embodiments, the preoperative imaging can entail a cross-sectional imaging modality, e.g. computed tomography, which can optionally generate 3D data of the patient, e.g. in the form of a spiral or a helical CT scan and, optionally, a 3D reconstruction. The 3D data of the patient, e.g. the spiral or helical CT scan or 3D reconstruction, can be re-projected into a 2D image, creating an x-ray like transmission image of the patient, e.g. of the bony structures of the patient including, but not limited to an osteophyte or bone spur or other bony anatomy or deformity. Optionally, this 2D re-projection of the 3D data, e.g. CT data, can be performed using the same plane or projection or view angle and, for example, the same or similar magnification as can be used subsequently during surgery with an intraoperative x-ray imaging test. The film-focus and, optionally, object distance of the x-ray system used for the intraoperative imaging part can be known at the time of the re-projection of the preoperative 3D data, so that the magnification of the patient or anatomic data resulting for a given intraoperative film-focus and optionally object distance will be matched or reflected in the re-projected pre-operative data. If the film-focus and, optionally, object distance of the x-ray system used for the intraoperative imaging part is not known at the time of the re-projection of the preoperative 3D data, the magnification of the re-projected data can be adjusted when they are visualized with and optionally superimposed onto the 2D intraoperative imaging data of the patient or anatomic data resulting for a given intraoperative film-focus and optionally object distance so that the magnification of both re-projected and intraoperative imaging data will be matched or substantially similar. Such matching in magnification can be achieved, for example, by aligning certain features or anatomic landmarks or pathologic tissues including an osteophyte or bone spur or other bony anatomy or deformity in the pre-operative re-projected data with the intraoperative data and adjusting the magnification until the feature or landmarks are substantially superimposed or substantially matching. With this approach, pre-operative imaging data can use the benefit of 3D data including, for example, more accurate three-dimensional placement of an implant component such as a spinal component or a component for joint replacement or fracture repair. Similarly, certain anatomic landmarks or features can be detected and utilized for surgical planning in the 3D data set. When the 3D data are then re-projected into a 2D re-projection or view, anatomic landmarks, features or data or pathologic data can be readily matched up or aligned with corresponding anatomic landmarks, features or data or pathologic data in the corresponding portions of the intraoperative 2D imaging study, e.g. intraoperative x-rays. Thus, while different 3D preoperative and 2D intraoperative imaging modalities can be used, 2D re-projection allows for cross-referencing and, optionally, co-registration of the 2D and 3D data sets. Any 2D and 3D imaging modality known in the art can be used in this manner.

In additional embodiments, a fiducial marker, sub-arrays or array, including a combination thereof or pluralities thereof can be used 1.) To estimate distance, position, orientation, coordinates of HMD relative to the patient, for primary or back-up registration, for example used in conjunction with an image and/or video capture system integrated into, attached to or coupled to or separate from the HMD 2.) To estimate distance, position, orientation, coordinates of target tissue or surgical site underneath the patient's skin, e.g. after cross-registration with pre-operative and/or intra-operative imaging data 3.) To estimate the path, coordinates of a surgical instrument or to estimate the location, orientation, coordinates of a desired implantation site for a medical device or implant or transplant 4.) To update a surgical plan A fiducial marker, sub-arrays or array, including a combination thereof or pluralities thereof can be used in physical time mode, using physical time registration, for example using an image and/or video capture system integrated into, attached to, coupled to, or separate from the HMD, which can optionally operate in physical time mode. Physical time mode can, for example, mean that image capture is performed with more than 5 frames/second, 10 frames/second, 15 frames/second, 20 frames/second, 30 frames/second etc.

A fiducial marker, sub-arrays or array, including a combination thereof or pluralities thereof can be used in real time mode, e.g. with greater than 30, 35, 40, 50, 60 etc. frames per second.

A fiducial marker, sub-arrays or array, including a combination thereof or pluralities thereof can be used in non-physical time mode, e.g. an intermittent mode, for example using an image and/or video capture system integrated into, attached to, coupled to, or separate from the HMD, which can optionally operate in intermittent mode. Intermittent mode use of the calibration or registration phantom can be performed, for example, by using a timer or timing device, wherein image capture and registration is performed every 10 seconds, 8 seconds, 5 seconds, 3 seconds, 2 seconds, 1 second etc.

In some embodiments, real-time and intermittent registration using the calibration or registration phantom will be selected or designed so that the data generated will for example not exceed the temporal resolution of the image and/or video capture system and/or the temporal resolution of the segmentation or image processing or pattern recognition used for the registration.

In any of the foregoing embodiments, the accuracy of registration can optionally be improved by using multiple fiducial markers, sub-arrays or arrays, registration points, patterns, planes or surfaces. In general, the accuracy of registration will improve with an increasing number of fiducial markers, sub-arrays or arrays, registration points, patterns, planes or surfaces. These may, in some embodiments, not exceed the spatial resolution of the image and/or video capture system. In some embodiments, these may exceed the spatial resolution of the image and/or video capture system. In that situation, optionally, down-sampling of data can be performed, e.g. by reducing the effective spatial resolution in one, two or three planes or by reducing the spatial resolution in select areas of the field of view seen through the HMD or visualized in the virtual data. Virtual preoperative, virtual intraoperative and live data can include an osteophyte or bone spur or other bony anatomy or deformity.

To Estimate Distance, Position, Orientation of HMD from the Patient

If registration of virtual patient data and live patient data has occurred using any of the techniques or techniques described in this specification and if a fiducial marker, sub-array or array, is also registered in relationship to the live patient data, the fiducial marker, sub-array or array or any other registration technique described in the specification or known in the art can be used to maintain registration, for example on an intermittent or a real-time basis, including while the surgeon or operator moves his or her head or body. The fiducial marker, sub-array or array can, for example, not be moved during the surgery. If the fiducial marker, sub-array or array needs to be moved, it may optionally be re-registered in relationship to any live patient data, virtual patient data, pre-operative data and intra-operative data.

In this and related embodiments, the fiducial marker, sub-array or array can be identified with regard to its location, position, orientation, alignment, surfaces or shape using an image and/or video capture system and, optionally, segmentation, image processing or pattern recognition and any other techniques known in the art for identifying an object in image data. The image and/or video capture system can be integrated into or attached to the HMD. The image and/or video capture system can be coupled to or separate from the HMD. The image and/or video capture system can be used to determine the location, position, orientation, alignment, surfaces or shape of the fiducial marker, sub-array or array in relationship to the patient, the operator and/or the HMD.

Any other techniques known in the art, including as described in this specification, that can be used to determine the location, position, orientation, alignment, surfaces or shape of the fiducial marker, sub-array or array in relationship to the patient, the operator and/or the HMD, can be used, including, but not limited to surgical navigation including optical or RF tracking, laser based distance measurements and the like.

The fiducial marker, sub-array or array can be used for primary or back-up registration. Optionally, synchronized registration can be used, wherein, for example, more than one technique of registration is used simultaneously to maintain registration between virtual patient data and live patient data, for example by simultaneously maintaining registration between virtual patient data and live patient data using one or more fiducial marker, sub-array or array s in conjunction with maintaining registration using corresponding anatomic landmarks or surfaces between virtual patient data and live patient data. If synchronized registration is used, optionally, rules can be applied to resolve potential conflicts between a first and a second registration technique for registering virtual and live patient data.

For example, with an image and/or video capture system integrated into or attached to the HMD or coupled to the HMD, any change in the position, location or orientation of the surgeon's or operator's head or body will result in a change in the perspective view and visualized size and/or shape of the fiducial marker, sub-array or array. The change in perspective view and visualized size and/or shape of the fiducial marker, sub-array or array can be measured and can be used to determine the change in position, location or orientation of the surgeon's or operator's head or body, which can then be used to maintain registration between the virtual patient data and the live patient data, by moving the virtual patient data into a position, location, orientation and/or alignment that ensures that even with the new position location or orientation of the surgeon's or operator's head or body the registration is maintained and the virtual and the live patient data are, for example, substantially superimposed or matched where desired. Similarly, when more than one HMD is used, e.g. one for the primary surgeon, a second HMD for an assistant, a third HMD for a resident, a fourth HMD for a scrub nurse and a fifth HMD for a visitor, with an image and/or video capture system integrated into or attached to each of the different HMDs or coupled to each of the different HMDs, any change in the position, location or orientation of the user's or viewer's head or body will result in a change in the perspective view and visualized size and/or shape and/or geometry of the calibration or registration phantom. The change in perspective view and visualized size and/or shape and/or geometry of the fiducial marker, sub-array or array can be measured and can be used to determine the change in position, location or orientation of the user's or viewer's head or body, which can then be used to maintain registration between the virtual patient data and the live patient data, by moving the virtual patient data into a position, location, orientation and/or alignment that ensures that even with the new position location or orientation of the user's or viewer's head or body the registration is maintained and the virtual and the live patient data are, for example, substantially superimposed or aligned or matched where desired, with substantially identical view angle of the virtual data of the patient seen by the viewer's left eye through the display of the HMD unit and the live data of the patient seen by the viewer's left eye through the HMD unit and substantially identical view angle of the virtual data of the patient seen by the viewer's right eye through the display of the HMD unit and the live data of the patient seen by the viewer's right eye through the HMD unit for each of the HMDs used.

In some embodiments, the fiducial marker, sub-array or array can be used to check the accuracy of an integrated or attached or coupled or separate image and/or video capture system.

In a further embodiment, the fiducial marker, sub-array or array can be used to calibrate an integrated or attached or coupled or separate image and/or video capture system.

In some embodiments, the fiducial marker, sub-array or array can be used to calibrate the IMU, e.g. for distance measurements, movement, distance to object, since fiducial marker, sub-array or array includes known geometries, e.g. known distances or angles.

Registration of Virtual Patient Data and Live Patient Data Accounting for Tissue Deformation In some embodiments, tissue deformation, a shape change or removal of tissue caused by the surgery or surgical instruments can be simulated in the virtual data. The resultant simulated virtual data can then be registered related to the live patient data, either before and/or after deformation, alteration of shape or removal of tissue of the live patient. The tissue deformation, shape change or removal of tissue caused by the surgery or surgical instruments can include the shape alteration or removal of one or more osteophytes or bone spurs or other bony anatomy or deformity. The virtual data of the patient and the live data of the patient can be registered in a common coordinate system, for example with one or more HMDs. Virtual and physical surgical instruments and implant components can also be registered in the common coordinate system.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. Re-registration of live patient data and virtual patient data can be particularly helpful if the surgical alteration or surgical step has led to some tissue deformation. For example, the re-registration can be performed by matching, superimposing, and/or registering tissues that have not been performed by the surgical step or surgical alteration. Alternatively, the re-registration can be performed by matching, superimposing and/or registering deformed live patient data, e.g. from surgically deformed tissue, with virtual patient data that simulate the same tissue deformation after the virtual surgical step, e.g. an osteophyte or tissue removal.

Registration of Virtual Patient Data and Live Patient Data Using CAD Files or Data or 3D Files or Data, e.g. of a Medical Device In some embodiments, a CAD file or CAD data of a medical device can be displayed by the HMD and superimposed on live data of the patient. The CAD file or CAD data can be a medical device intended for use or implantation during the surgical procedure. Any type of CAD file or CAD data or any type of 3D file or 3D data of a medical device, a surgical instrument or an implantable device can be superimposed and registered in relationship to the live data of the patient including normal anatomy or pathologic tissue, e.g. one or more osteophytes or bone spurs or other bony anatomy or deformity or soft-tissue or neoplastic tissue or abnormality in a common coordinate system, for example with one or more HMDs. Physical surgical instruments and implant components can also be registered in the common coordinate system.

Medical Devices can Include Non-Biologic as Well as Biologic Devices, e.g. Tissue Scaffolds, Cells, Cell Matrices Etc. That can be Implanted in a Human Body.

In some embodiments, multiple CAD files and/or 3D files of virtual data can be superimposed onto the live data of the patient. For example, CAD files can be CAD files of a medical device available in different sizes or shapes. Virtual 2D or 3D data of the patient, for example obtained from a preoperative imaging test, can be superimposed onto live data of the patient, e.g. a surgical site. The surgeon can then optionally introduce a 3D CAD file of a medical device into the display by the HMD. The surgeon can check the size or shape of the medical device in relationship to the virtual 2D or 3D data of the patient and/or the live data of the patient. If the surgeon is not satisfied with the projected size or shape of the medical device in relationship to the virtual 2D or 3D data of the patient and/or the live data of the patient, the surgeon can select a different CAD file of a medical device with a different size and/or shape, project the CAD file optionally onto the virtual 2D or 3D data of the patient and the live data of the patient in the HMD display and repeat the process as many times as needed until the surgeon is satisfied with the resultant size or shape of the selected medical device in relationship to the virtual 2D or 3D data of the patient and/or the live data of the patient. The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. For example, CAD files simulating the virtual surgical step or surgical alteration in the virtual patient data can be matched, superimposed or registered with live patient data after the physical surgical step or surgical alteration in the live patient. In this manner, live and virtual data can be re-registered after the surgical step or surgical alteration.

Registration of Virtual Patient Data and Live Patient Data Using Non-Anatomic Data Registration of virtual data of the patient and live data of the patient can be performed using data other than anatomic or pathologic structures. Registration can be performed, for example, based on motion data, kinematic data (for example to determine the center of rotation of a joint in the live data which can then be registered to an estimate or simulated center of rotation in the virtual data of the patient). Registration can be performed using metabolic data, for example using an area of high 18 FDG-PET uptake in a PET scan or PET-MRI or PET CT, which can be, for example matched to an area of increased body temperature in a target surgical site. Registration can be performed using functional data, e.g. using functional MRI studies. Virtual data and live data of the patient can be registered in a common coordinate system, for example with one or more HMDs. Virtual and physical surgical instruments and implant components can also be registered in the common coordinate system.

Optionally, different types of data, e.g. anatomic, motion, kinematic, metabolic, functional, temperature and/or vascular flow data can be used alone or in combination for registered virtual and live data of the patient.

The registration of virtual patient data and live patient data using the techniques described herein can be repeated after one or more surgical steps have been performed using non-anatomic data. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, optionally using non-anatomic data. The matching, superimposing and/or registering of the live data of the patient and the virtual data of the patient after the surgical tissue alteration can be performed using the same techniques described in the foregoing or any of the other registration techniques described in the specification or any other registration technique known in the art.

Virtual Surgical Plans

Virtual and physical surgical instruments and implant components can be registered in a common coordinate system, for example with one or more HMDs and live data of the patient. When pre-operative imaging studies, intra-operative imaging studies or intra-operative measurements are registered in a common coordinate system with one or more HMDs using, for example, anatomic features, anatomic landmarks, implantable and attachable markers, calibration and registration phantoms including optical markers, LEDs with image capture, navigation markers, infrared markers, RF markers, IMUs, or spatial anchors and spatial recognition, one or more of an instrument or implant position, orientation, alignment can be predetermined using the information from the pre- and intra-operative imaging studies and/or the intra-operative measurements.

In some embodiments, a surgeon or an operator can develop a virtual surgical plan. The virtual surgical plan can include the virtual removal of select tissues, e.g. bone or cartilage or soft-tissue, e.g. for installing or implanting a medical device. The virtual surgical plan can include removal of a tumor or other tissues. The virtual surgical plan can include placing a graft or a transplant. Any surgical procedure known in the art can be simulated in a virtual surgical plan, for example spinal fusion including anterior and posterior, spinal disk replacement using motion preservation approaches, hip replacement, knee replacement, ankle replacement, shoulder replacement, ACL repair or reconstruction, ligament reconstruction.

A virtual surgical plan can be developed using intra-operative data or measurements, including measurements obtained using one or more optical markers which can, for example, be detected using one or more cameras, an image capture system, a video capture system and/or 3D scanner integrated into, attached to or separate from an HMD. The one or more cameras, an image capture system, a video capture system and/or 3D scanner integrated into, attached to or separate from an HMD can, for example, detect the coordinates of one or more optical markers attached to the surgical site, e.g. a bone or cartilage, an altered surgical site, e.g. a bone cut, the operating room table, an extension of the operating room table, and/or fixture structures in the operating room, e.g. walls. The one or more cameras, an image capture system, a video capture system and/or 3D scanner integrated into, attached to or separate from an HMD can detect the one or more optical markers in static positions and/or dynamic, moving positions. The coordinates (x, y, z) of the optical markers can be measured in static and dynamic conditions.

Any other sensor described in the specification, e.g. IMUs, navigation markers, e.g. infrared markers and/or RF markers, LED's, can be used for obtaining intraoperative measurements and can be combined, for example with optical marker measurements, for deriving intra-operative measurements and for generating and/or developing a virtual surgical plan.

Intra-operative measurements using one or more cameras, an image capture system, a video capture system and/or 3D scanner integrated into or attached to an HMD can be beneficial when measurements are desired to be obtained from the view angle of the surgeon or, when multiple HMDs are used, from the view angle of a surgical assistant or second surgeon. Intra-operative measurements using one or more cameras, an image capture system, a video capture and/or 3D scanner separate from an HMD can be advantageous when measurements are desired to be obtained from a view angle other than the surgeon or, when multiple HMDs are used, from a view angle other than of a surgical assistant or second surgeon.

Pre-operative data, e.g. pre-operative imaging studies or kinematic studies of a patient, e.g. with the joint or the spine measured or imaged in motion, can also be incorporated into a virtual surgical plan. Pre-operative data alone can be used to develop a virtual surgical plan. The virtual surgical plan can be developed with use of a computer or computer workstation as well as a local or remote computer or computer network. The computer or computer workstation can include one or more displays, keyboard, mouse, trackball, mousepad, joystick, human input devices, processor, graphics processors, memory chips, storage media, disks, and software, for example for 3D reconstruction, surface displays, volume displays or CAD design and display, as well as optional CAM output. The software can include one or more interfaces for CAD design, for displaying the patient's anatomy, for displaying virtual surgical instruments and for displaying virtual implants, implant components, medical devices and/or medical device components.

Figure 10:
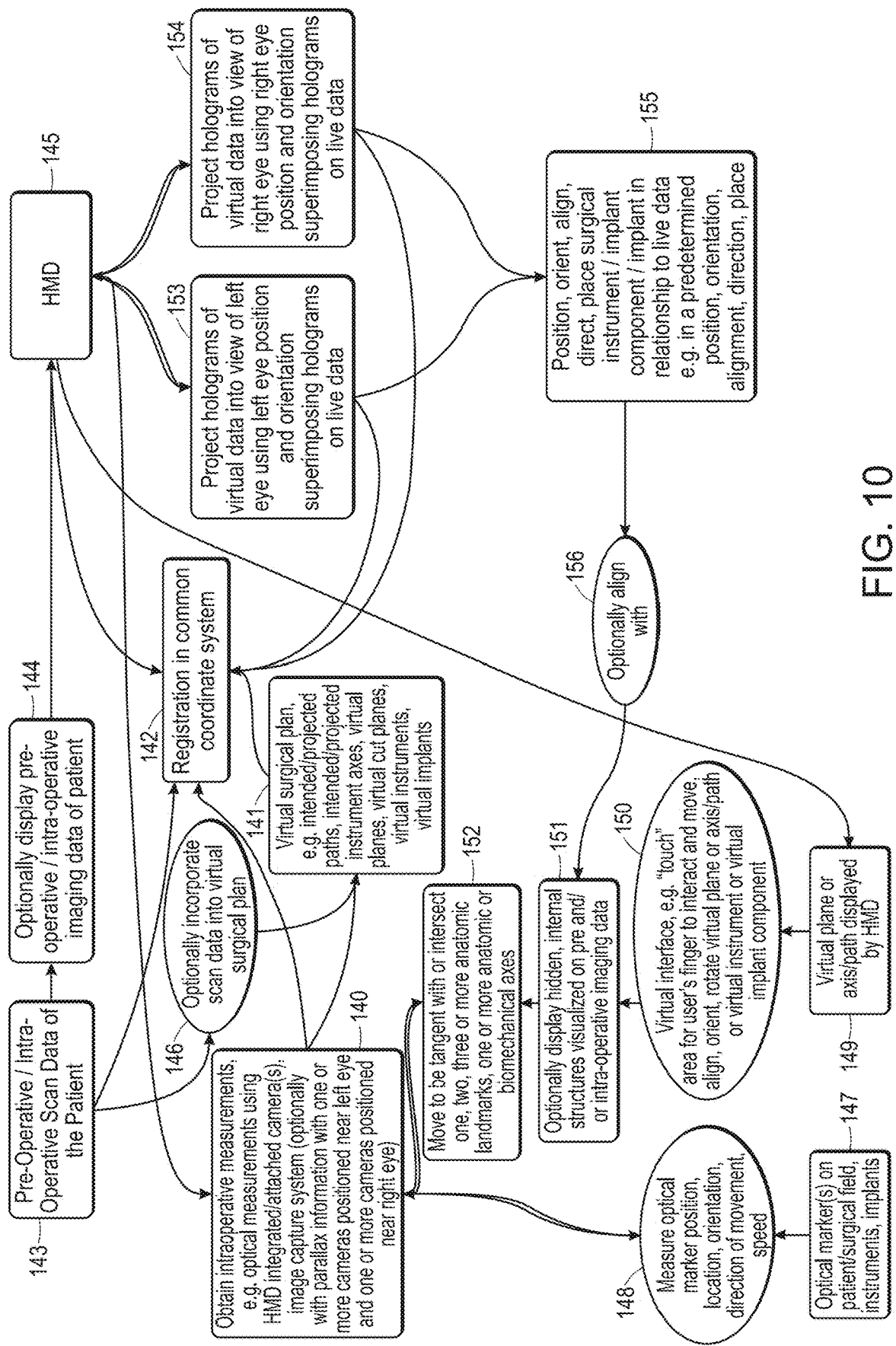
FIG. 10 is an illustrative example how a virtual surgical plan can be generated using intraoperative data, e.g. intraoperative measurements, for example measurements obtained with one or more cameras, an image capture system or a video capture system and/or a 3D scanner integrated into, attached to or separate from an head mount display according to some embodiments of the present disclosure.

The different anatomic and pathologic structures as well as the different virtual instruments, e.g. virtual surgical guides including drill guides or cut blocks, virtual implants, implant components, medical devices and/or medical device components can optionally be displayed simultaneously on the same screen or screen section or non-simultaneously, e.g. on different screens, on the same screen at different times, or no different screen sections. The different anatomic and pathologic structures including hidden and/or obscured or partially hidden and/or obscured anatomic and pathologic structures as well as the different virtual instruments, e.g. virtual surgical guides including drill guides or cut blocks, virtual implants, implant components, medical devices and/or medical device components can optionally be displayed using different colors or different shading. Some of the different anatomic and pathologic structures as well as the different virtual instruments, e.g. virtual surgical guides including drill guides or cut blocks, virtual implants, implant components, medical devices and/or medical device components can optionally be displayed in a form of outline mode or pattern mode, where only the outline or select features or patterns of the anatomic and pathologic structures as well as the virtual instruments, e.g. virtual surgical guides including drill guides or cut blocks, different virtual implants, implant components, medical devices and/or medical device components are being displayed, for example with solid, dotted or stippled lines or geometric patterns. FIG. 10 shows an example how a virtual surgical plan 157 can be modified using intraoperative data, e.g. intraoperative measurements 140. The virtual surgical plan 157 can be developed using pre-operative and intra-operative imaging data of the patient 143. The virtual surgical plan 157 can be registered in a common coordinate system 142. Preoperative and/or intraoperative scan data 143 can be generated and can be optionally displayed 144 in two or three dimensions in an HMD 145. Preoperative and/or intraoperative scan data 143 can be used to develop the virtual surgical plan 157 which can be optionally displayed 158 by the HMD 145. Fiducial markers, e.g. optical markers, 147 can be present on the patient, the surgical field, surgical instruments or implants and can be measured with regard to their position, location, orientation, direction of movement and/or speed 148. A virtual plane or path or axis 149 can be displayed by the HMD 145 and, using a virtual interface 150, the plane or path or axis, as well as optionally virtual implants or instruments, can be moved by the surgeon. Optionally, the HMD 145 can display hidden or internal structures 151, e.g. visualized on preoperative or intraoperative imaging studies or combinations of both, and the surgeon can align the planes, axis or path, as well as optionally virtual implants or instruments, relative to the hidden or internal structures 149. The plane, axis or path or virtual surgical instruments or virtual implants can be moved to be tangent with or intersect anatomic landmarks, and/or anatomical axes and/or biomechanical axes 152, for example for alignment purposes or to achieve a predetermined position and/or orientation of an instrument or an implant. The HMD can project stereoscopic views for the left eye and right eye by displaying virtual data superimposing the virtual data using the left eye position and orientation on the live data for the left eye 153 and superimposing the virtual data using the right eye position and orientation on the live data for the right eye 154. The projected virtual data in 153 and 154 can be used to position, orient, align, direct or place one or more of a surgical instrument, an implant component and an implant in relationship to the live data of the patient, e.g. in a predetermined position, orientation, alignment direction or place 155. The position, orientation, alignment direction or place of the one or more of a surgical instrument, an implant component and an implant can optionally be aligned with hidden anatomy or internal structures 151, optionally using a virtual interface 150. Intraoperative measurements 140 can be utilized to generate or modify a virtual surgical plan 157. The virtual surgical plan 157 and/or a modified virtual surgical plan 162 can optionally be superimposed on pre-operative and intraoperative imaging data of the patient 159. The virtual surgical plan 157 and/or a modified virtual surgical plan 162 can optionally be superimposed on pre-operative and intraoperative imaging data of the patient 159. The modified virtual surgical plan 162 can be further modified based on visual or optical feedback or input 161 and it can be used to position, orient, align, direct, place one or more virtual or physical instruments, implant components and/or implants in a predetermined position 155.

Someone skilled in the art can recognize that multiple coordinate systems can be used instead of a common coordinate system. In this case, coordinate transfers can be applied from one coordinate system to another coordinate system, for example for registering the HMD, live data of the patient including the surgical site, virtual instruments and/or virtual implants and physical instruments and physical implants.

In some embodiments, one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be moved, re-oriented and/or re-aligned by the surgeon using a virtual or other interface. For example, the virtual representation of the one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can include a "touch area", wherein an image or video capture system and/or 3D scanner and gesture recognition software, for example the one provided by Microsoft with the Microsoft Hololens including, for example, the integrated virtual "drag function" for holograms can be used to move the virtual data. For example, one or more cameras integrated or attached to the HMD can capture the movement of the surgeon's finger(s) in relationship to the touch area; using gesture tracking software, the hologram(s) can then be moved by advancing the finger towards the touch area in a desired direction. A surgeon can, for example, also "hold" the hologram(s) by closing two fingers, e.g. thumb and index finger, over the touch area and then moving the fingers in the desired direction.

FIG. 3 shows an illustrative example how multiple HMDs can be used during a surgery, for example by a first surgeon, a second surgeon, a surgical assistant and/or one or more nurses and how a surgical plan can be modified and displayed during the procedure by multiple HMDs while preserving the correct perspective view of virtual data and corresponding live data for each individual operator. A system 10 for using multiple HMDs 11, 12, 13, 14 for multiple viewer's, e.g. a primary surgeon, second surgeon, surgical assistant(s) and/or nurses(s) is shown. The multiple HMDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMUs, optical markers, navigation markers, image or video capture systems and/or 3D scanner and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMUs, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The HMDs 11, 12, 13, 14 can maintain alignment and superimposition of virtual data of the patient and live data of the patient for each HMD 11, 12, 13, 14 for each viewer's perspective view and position and head position and orientation 27. Using a virtual or other interface, the surgeon wearing HMD 1 11 can execute commands 32, e.g. to display the next predetermined bone cut, e.g. from a virtual surgical plan or an imaging study or intra-operative measurements, which can trigger the HMDs 11, 12, 13, 14 to project virtual data of the next surgical step 34 superimposed onto and aligned with the surgical site in a predetermined position and/or orientation. Any of the HMDs 11, 12, 13, 14 can acquire one or more optical measurements or measurement inputs, e.g. of anatomic landmarks, axes from cameras, anatomic axes, biomechanical axes, a mechanical axis of a leg 17, using for example an integrated or attached camera, image capture or video system. By using multiple HMDs 11, 12, 13, 14 from different view angles with multiple cameras, image capture or video systems, the accuracy of the measurements can optionally be improved. Optionally, parallax measurements can be performed using the multiple HMDs 11, 12, 13, 14 from different view angles with multiple cameras, image capture or video systems. The one or more optical measurements can be used to modify the virtual surgical plan 19, optionally using the information from multiple HMDs 11, 12, 13, 14. Someone skilled in the art can recognize that multiple coordinate systems can be used instead of a common coordinate system. In this case, coordinate transfers can be applied from one coordinate system to another coordinate system, for example for registering the HMD, live data of the patient including the surgical site, virtual instruments and/or virtual implants and physical instruments and physical implants.

Virtual Data and Live Data Seen Through One or More HMDs

A virtual surgical plan using, for example, virtual data of the patient, can be used to develop or determine any of the following for placing or directing a surgical tool, a surgical instrument, a trial implant component, a trial implant, an implant component, an implant, a device including any type of biological treatment or implant or matrix known in the art:

Predetermined start point
Predetermined start position
Predetermined start orientation/alignment
Predetermined intermediate point(s)
Predetermined intermediate position(s)
Predetermined intermediate orientation/alignment
Predetermined end point
Predetermined end position
Predetermined intermediate orientation/alignment
Predetermined path
Predetermined plane (e.g. for placing or orienting a surgical instrument or an implant component)
Predetermined cut plane (e.g. for directing a saw or other surgical instruments (e.g. drills, pins, cutters, reamers, rasps, impactors, osteotomes) and/or for placing or orienting an implant component or a trial implant component)
Projected contour/outline/cross-section/surface features/shape/projection
Predetermined depth marker or depth gauge, predetermined stop, optionally corresponding to a physical depth marker or depth gauge on the physical surgical tool, surgical instrument, trial implant, implant component, implant or device
Predetermined angle/orientation/rotation marker, optionally corresponding to a physical angle/orientation/rotation marker on the physical surgical tool, surgical instrument, trial implant, implant component, implant or device
Predetermined axis, e.g. rotation axis, flexion axis, extension axis
Predetermined axis of the physical surgical tool, surgical instrument, trial implant, implant component, implant or device, e.g. a long axis, a horizontal axis, an orthogonal axis, a drilling axis, a pinning axis, a cutting axis
Estimated/projected non-visualized portions of device/implant/implant component/surgical instrument/surgical tool, e.g. using image capture or markers attached to device/implant/implant component/surgical instrument/surgical tool with known geometry
Predetermined virtual tissue change/alteration.

Any of the foregoing, e.g. a cut plane or an outline, e.g. an outline of an implant or a surgical instrument, can be displayed in 2D and/or in 3D, optionally alternatingly. For example, a 2D visualization, e.g. a line, of a cut plane can be used when a surgeon looks substantially on end on a bone, e.g. a distal femur, for orienting and/or directing a cutting instrument, e.g. a saw or a saw blade. When the surgeon looks from the side, e.g. at an angle, the visualization can optionally switch to a 3D display to show the desired angular orientation of the cut and/or the blade in relationship to the bone. The display can also remain in 2D mode. The switching between 2D and 3D display can be manual, e.g. through a voice command or a command on a virtually projected keyboard or a virtually projected user interface, or automatic, e.g. based on the position and/or orientation of the operator's head and/or the HMD in relationship to the surgical site (e.g. operator head/HMD in frontal orientation relative to surgical site, or close to including 90 degree side (near orthogonal) orientation, or angular, non-90 degree side orientation, e.g. 30, 40, 50, 60, 70 degree angles). A 2D or 3D display of a cut plane can help determine/display the desired angular orientation of the intended cut. The angular orientation can, for example, be a reflection of a planned/intended mechanical axis correction in a knee replacement, a planned/intended femoral component flexion or extension in a knee replacement, a planned/intended tibial slope in a knee replacement or a planned/intended femoral neck resection for a planned/intended leg length in a hip replacement.

In some embodiments, the HMD unit of the surgeon can capture the live data of the patient using one or more image and/or video capture systems and/or 3D scanners integrated into or attached to the HMD. The captured live data of the patient can then be transmitted in electronic, digital form as live stream to slave HMD units, optionally together with the virtual data of the patient, e.g. superimposed onto or co-displayed with the virtual data of the patient. Alternatively, the slave units in this example can be non-see through virtual reality (VR) systems such as the Google Daydream system or the Zeiss VR One system and others known in the art.

Two-Dimensional and Three-Dimensional Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the HMD in two dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the HMD in three dimensions.

Stereoscopic and Non-Stereoscopic Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the HMD in a non-stereoscopic manner in three dimensions, with similar view angle of the virtual data of the patient seen by the surgeon's eyes through the display of the HMD unit and the live data of the patient seen by the surgeon's eyes through the HMD unit.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the HMD in a stereoscopic manner in three dimensions.

When stereoscopic projection is used by the HMD, the display for the left eye and the right eye can be adjusted for the surgeon's or operator's inter-ocular distance, including, for example, the inter-pupillary distance. For example, the distance between the left pupil and the right pupil can be measured prior to operating the HMD. Such measurements can be performed using an image and/or video capture system and/or 3D scanner integrated into, attached to or separate from the HMD. Such measurements can also be performed using any other technique known in the art, including, for example, mechanical rulers, optical measurement tools and standard tools used by optometrists.

Any of the foregoing stereoscopic or non-stereoscopic displays for the display of virtual data by one or more HMDs can be performed using adjustment or selection of the focal plane or focal point for the display of the virtual data, for example based on coordinates of the HMD and/or the coordinates of the surgical site or anatomic structure(s) on which surgery is contemplated to be performed or is being performed on and/or the coordinates of one or more physical surgical tools, instruments, implants or devices.

Adjusting the HMD Unit Including the Display

In some embodiments, once the inter-ocular, e.g. the inter-pupillary distance, of the surgeon or operator is known, it can be entered into the display system interface and/or software and the 3D projection of the left and the right eye can be adjusted for the user. For example, with a narrow inter-ocular or inter-pupillary distance, the projection for the left eye and the right eye can be moved closer to the nose so that the center of the left and the right projections will be aligned with the center of the left eye/pupil and the right eye/pupil. With a wide inter-ocular or inter-pupillary distance, the projection for the left eye and the right eye can be moved further away from the nose so that the center of the left and the right projections will be aligned with the center of the left eye/pupil and the right eye/pupil. Different user settings can be stored in the system, e.g. by username. In this manner, when a different user is placing the HMD on his or her head, the user or the system can call up their preferred user settings, including their respective inter-ocular or inter-pupillary distance. User settings can be called up, for example, using a visual or optical keyboard interface, projected by the HMD, where the operator can select virtual buttons. User settings can also be called up using voice commands, keyboards and any other known technique or technique for executing user commands.

Stereoscopic and Non-Stereoscopic 3D Display of Virtual Data of the Patient with Superimposition on Live Data of the Patient In some embodiments, the HMD can display a virtual 2D or 3D image of the patient's normal or diseased tissue or an organ or a surgical site or target tissue with a view angle or a perspective or projection that is different for the display for the left eye compared to the display for the right eye resulting in a stereoscopic projection of the anatomy or the pathologic tissue. The virtual data of the patient is thus superimposed on the live data of the patient, e.g. the surgical site, for the left and right eye of the surgeon, respectively, using both the left and the right view angle for the surgeon. This means that two separate views are rendered from the virtual 2D or 3D data sets, one for the left eye and one for the right eye. Multidimensional views exceeding three dimensions generated for the left eye and the right eye are possible. For example, in addition to the virtual anatomy of the patient vascular flow or joint motion can be displayed separately for the left eye and the right eye. The difference in perspective between the left eye and the right eye projection of virtual data or parallax can be selected or programmed so that it will change, for example, with the distance of the HMD, the surgeon's head or the surgeon's eye in relationship to the target site, surgical site or target tissue. The distance between the surgeon's or operator's eyes can also be taken into account.

In some embodiments, the difference in perspective or parallax will be selected or programmed so that a 3D effect is generated in a stereoscopic 3D manner or effect. The difference in perspective or parallax can change depending on any changes in the distance of the HMD, the surgeon's or operator's head or the surgeon's or operator's eye in relationship to the target site, surgical site or target tissue. For example, as the surgeon or operator moves away from the target site, surgical site or target tissue, the difference in perspective or parallax can decrease. As the surgeon or operator moves towards the target site, surgical site or target tissue, the difference in perspective or parallax can increase. The decrease or increase can be linear, non-linear, exponential or algorithmic. Any other mathematical function is possible. In some embodiments, the difference in perspective or parallax will change similar to the change experienced by the human eye as the surgeon or operator moves towards or away from a target.

The distance of the HMD (e.g. tracked with use of a camera and one or more fiducial marker, sub-array or array attached or integrated into the HMD), the surgeon's or operator's head or the surgeon's or operator's eye in relationship to the target site, surgical site or target tissue can be measured via image capture, anatomic landmark embodiments, image capture used in conjunction with fiducial markers, sub-arrays or arrays, surgical navigation or any of the other embodiments described in this specification and or spatial mapping. The distance and any changes in distance of the HMD, the surgeon's or operator's head or the surgeon's or operator's eye in relationship to the target site, surgical site or target tissue can be used to change the difference in perspective views or parallax in views for the left eye and the right eye.

Figure 11A:
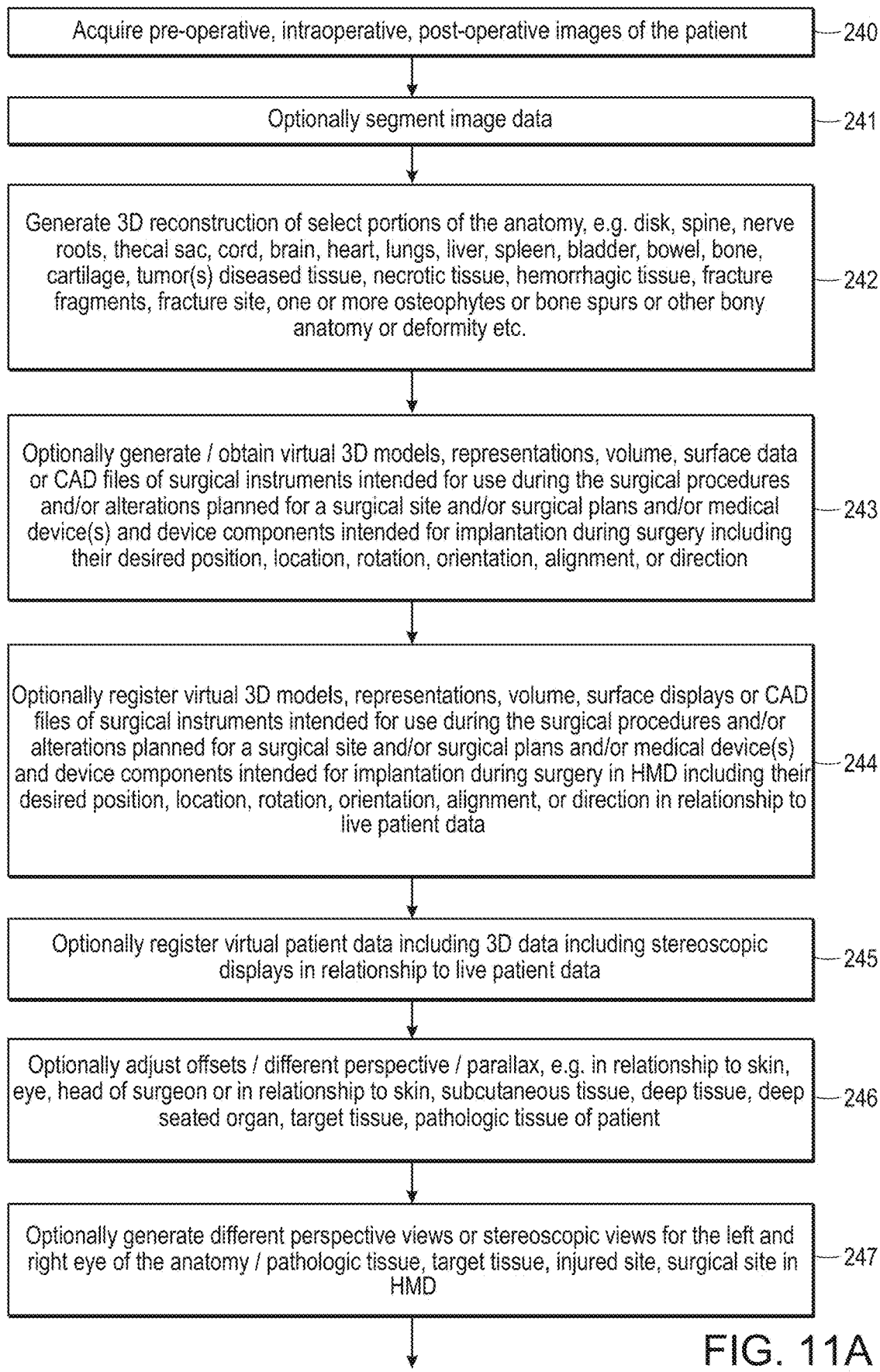
FIGS. 11A and 11B are flow charts summarizing model generation, registration and view projection for one or more HMDs, e.g. by a primary surgeon, second surgeon, surgical assistant nurse, or others according to some embodiments of the present disclosure.
Figure 11B:
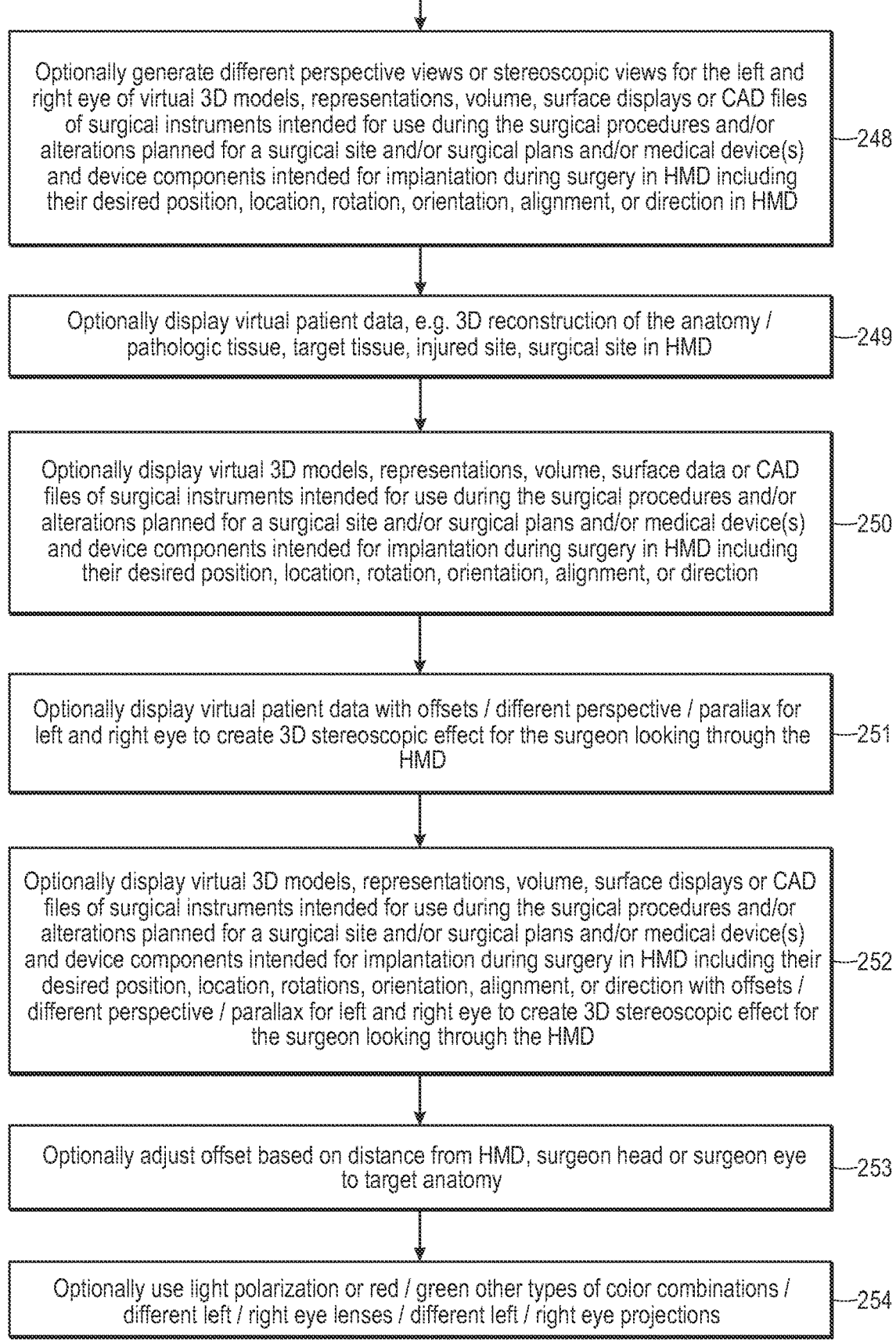

FIGS. 11A-11B are flow charts summarizing model generation, registration and view projection for one or more HMDs, e.g. by a primary surgeon, second surgeon, surgical assistant nurse, or others. Pre-operative, intra-operative or post-operative images of the patient can be acquired 240. The image data can optionally be segmented 241. 3D reconstructions of the patient's anatomy or pathology including multiple different tissues, e.g. using different colors or shading, can be generated 242. Virtual 3D models of surgical instruments and devices components can be generated which can include their predetermined position, location, rotation, orientation, alignment and/or direction 243. The virtual 3D models can be registered, for example in relationship to the HMD and the patient 244. The virtual 3D models can be registered relative to the live patient data 245. Optionally, adjustments can be made for different view perspectives, parallax, skin, skin movement and other tissue specific issues 246. Different perspective views can be generated for the user's left eye and right eye to facilitate a stereoscopic viewing experience, e.g. like an electronic hologram, of the virtual models of subsurface or hidden anatomic or pathologic tissues 247 and the virtual 3D models of tools, instruments, implants and devices 248.

Virtual patient data 249 and virtual 3D models of tools, instruments, implants and devices 250 can be displayed in the HMD, optionally with different view perspectives adjusted for the left and the right eye of the user 251 and 252. Left eye and right eye offsets or parallax can optionally be adjusted based on the distance from the HMD, surgeon head or surgeon eyes to the surgical site using, for example, depth sensors or spatial mapping or other registration techniques and also based on inter-ocular distance 253. Polarization or color techniques for stereoscopic views 254 can be combined with electronic holograms such as those provided by the Microsoft Hololens. In an alternative description in FIG. 2, multiple 3D models 260, 261, 262 can be generated, e.g. one for subsurface anatomic or pathologic structures of the patient, one for virtual surgical tools or instruments and one for virtual surgical implant components. These can be registered, e.g. in a common coordinate system or multiple coordinate systems using coordinate transfers, also with the HMD 263. Using shared coordinates for the different virtual 3D models 260, 261, 262 multiple viewers using multiple HMDs can share a 3D World 264 with projection or display of one or more of the models onto the live data of the patient 265. The display can be generated separately for the left eye of each user using the user's left eye coordinates 266 and the right eye of each user using the user's right eye coordinates 267. Stereoscopic views or different perspective views or views with a parallax for the left eye and the right eye can be generated for multiple virtual data sets or data volumes of the patient. Any virtual structures, tissues or data mentioned in the application can be displayed separately for the left eye and the right eye using stereoscopic views or different perspective views or views with a parallax, simultaneously, non-simultaneously, or sequentially. In addition, any of the virtual data can be displayed using stereoscopic views or different perspective views or views with a parallax for the left eye and the right eye. Multiple different virtual data can be displayed simultaneously, non-simultaneously or sequentially, for example also with the live data or images of the patient seen through the HMD, stereoscopically or non-stereoscopically.

Optical head mounted displays (HMD), for example of optical see through head mounted display type or video see through head mounted display type, can be used for displaying virtual surgical guides, e.g. virtual planes, virtual axes, virtual points, virtual guides, virtual cut blocks, virtual tools, virtual instruments, virtual implants, virtual devices, and/or 2D or 3D imaging data directly onto a surgical site, such as a joint, a spine, an abdomen, an organ, e.g. a heart, lung, liver, spleen, kidney, a portion of the gastrointestinal tract, a neural structure, e.g. a brain or spinal cord, during a surgical procedure. A computer processor can be configured to generate the virtual surgical guides, devices, and/or implants for display by the HMD so that a physical tool, instrument, device, and/or implant can be superimposed and/or aligned with the virtual surgical guide and/or virtual devices and/or a virtual implant displayed by one or more HMDs, as described, for example, in U.S. Pat. Nos. 10,154, 239, 9,861,446 and Patent application publication No. WO2019/148154A1, which are hereby incorporated by reference in their entirety.

As the operator is moving his or her head around the surgical site, the computer processor can be configured to update the display in real time adjusting the 3D stereoscopic view(s) for the position of the HMD, e.g. in relationship to a coordinate system and/or the surgical site, as described, for example, in U.S. Pat. Nos. 10,154,239, 9,861,446 and patent application publication No. WO2019/148154A1, which are hereby incorporated by reference in their entirety. Both the left and the right eye display can be adjusted in real-time.

The display can also be adjusted in real-time for movement of a surgical site, an anatomic structure, or a patient. The display can be adjusted for head movement with movement of the HMD and/or movement of the surgical site, anatomic structure, or patient.

The HMD can optionally be tracked, for example using a video or image capture system or a surgical navigation system, e.g. using one or more infrared cameras, as described, for example, in U.S. Pat. Nos. 10,154,239, 9,861, 446 and Patent application publication No. WO2019/148154A1, which are hereby incorporated by reference in their entirety. If a video or image capture system is used for tracking, optical markers, e.g. with geometric patterns and/or different geometric shapes can be attached or affixed to the HMD. If a surgical navigation system is used for tracking, navigation markers, e.g. reflective balls or disks, LED's, active markers or passive markers can be used for tracking, e.g. of one or more HMDs, the surgical site, the patient, a bone, the surgeon, one or more instruments or tool and/or one or more implants or devices.

In tracking one or more HMDs, an important consideration can be to have a wide movement range of the HMD within which the HMD is visible, detected and/or tracked using the video or image capture system and/or the surgical navigation system. The trackable or detectable movement range of the HMD can also determine the movement range of the head of the user or the user. A movement range can be from 0 to 20 degrees, 0 to 30 degrees, 0 to 40 degrees, 0 to 50 degrees, 0 to 60 degrees, 0 to 70 degrees, 0 to 80 degrees, 0 to 90 degrees, 0 to 100 degrees, 0 to 110 degrees, 0 to 120 degrees, 0 to 130 degrees, 0 to 140 degrees, 0 to 150 degrees, 0 to 160 degrees, 0 to 170 degrees, 0 to 180 degrees, 0 to 190 degrees, 0 to 200 degrees, 0 to 210 degrees, 0 to 220 degrees, 0 to 230 degrees, 0 to 240 degrees, 0 to 250 degrees, 0 to 260 degrees, 0 to 270 degrees, 0 to 280 degrees, 0 to 290 degrees, or any other value or range.

A movement range can be from −10 to +10 degrees, −20 to +20 degrees, −30 to +30 degrees, −40 to +40 degrees, −50 to +50 degrees, −60 to +60 degrees, −70 to +70 degrees, −80 to +80 degrees, −90 to +90 degrees, −100 to +100 degrees, −110 to +110 degrees, or any other value or range, for example to the left or right of the surgical site or up and down relative to the surgical site (e.g. if looking straight at the surgical site without neck flexion is selected as representing 0 degrees).

The movement range can, for example, be defined so that at a 0 degree position the user's visual field and/or frontal facial plane and/or frontal plane intersecting the two eyes is substantially perpendicular and/or parallel (or any other predetermined or predefined angle) to the principal plane or axis of the surgical field, e.g. the long axis of a spine or a sagittal plane of the spine, and/or at a 0 degree position the user's visual field and/or frontal facial plane and/or frontal plane intersecting the two eyes can be substantially perpendicular and/or parallel (or any other predetermined or predefined angle) to the long axis or side edge of an OR table. The movement range can, for example, be defined so that at a 0 degree position the user's visual field and/or frontal facial plane and/or frontal plane intersecting the two eyes is substantially perpendicular and/or parallel (or any other predetermined or predefined angle) to the principal plane or axis of a video or image capture system or a surgical navigation system, e.g. the axis or plane connecting to infrared cameras integrated into the surgical navigation system.

A fiducial marker can be, for example, an optical marker, e.g. with a geometric pattern, a bar code, a QR code, a navigation markers, e.g. a marker ball, a marker disk, a retroreflective marker ball, a retroreflective marker disk, a retroreflective marker cube (or other shapes), an active marker or a passive marker, an RF marker or an infrared marker. Video cameras, image capture systems, and/or surgical navigation system cameras used throughout the specification can use visible light or light from portions of the spectrum that are not visible, e.g. infrared.

In some embodiments, an HMD can be tracked using a single array attached to or integrated into the HMD, with the array, for example, comprised of one, two, three, four or more optical markers and/or one, two, three, four or more navigation markers, e.g. marker balls, marker disks, retroreflective marker balls, retroreflective marker disks, retroreflective marker cubes or other shapes, active markers or passive markers, or combinations thereof. When a single array is used, it can comprise sub-arrays, with each sub-array, for example, comprising one or more different configurations of one, two, three, four or more optical markers and/or one, two, three, four or more navigation markers, e.g. marker balls, marker disks, retroreflective marker balls, retroreflective marker disks, retroreflective marker cubes or other shapes, active markers or passive markers, or combinations thereof.

In some embodiments, an HMD can be tracked using multiple arrays and/or subarrays attached to or integrated into the HMD, with each array and/or subarray, for example, comprised of one, two, three, four or more optical markers and/or one, two, three, four or more navigation markers, e.g. marker balls, marker disks, retroreflective marker balls, retroreflective marker disks, retroreflective marker cubes or other shapes, active markers or passive markers, or combinations thereof.

Figure 12B:
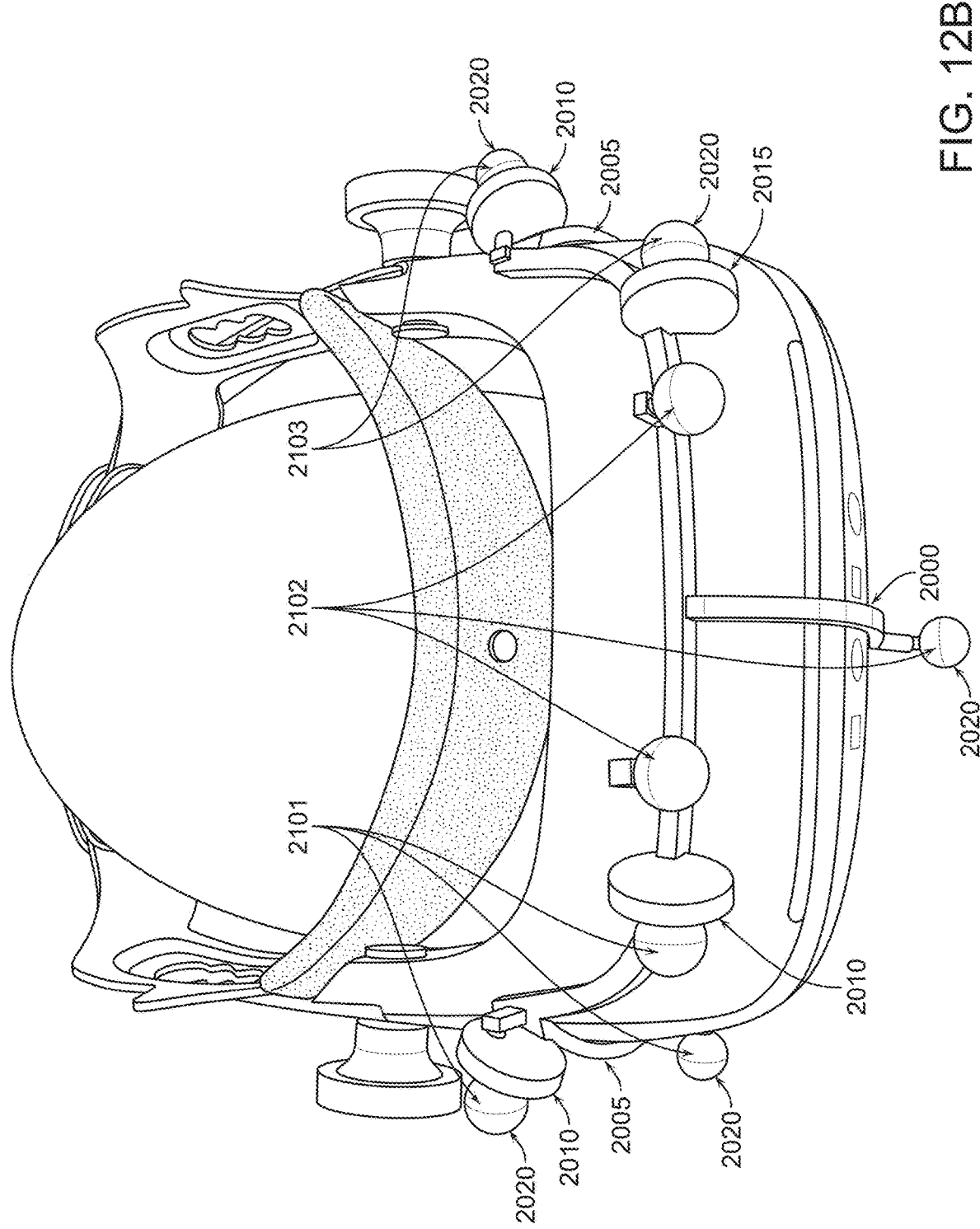
Figure 12C:
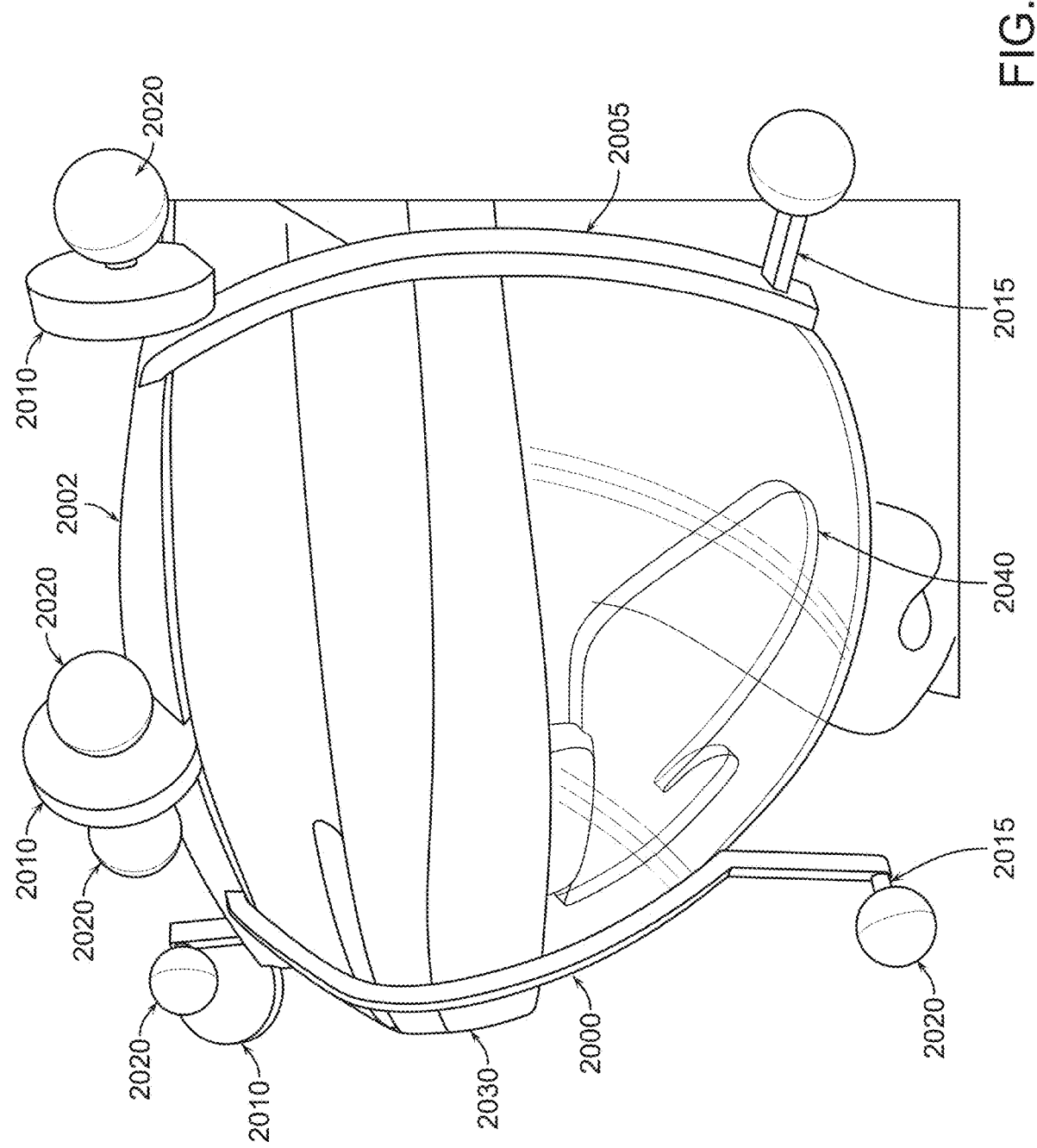

In some embodiments, one or more fiducial markers, sub-arrays, or arrays can be attached or integrated into the HMD, e.g. the HMD housing. FIGS. 12A-G are non-limiting examples of a holding or attachment apparatus configured to attach to an HMD, including various disk, shields, or barriers, and fiducial marker, sub-array or array configurations trackable through a range of viewing directions of an HMD. In some embodiments, fiducial markers, sub-arrays, or arrays can be attached directly to an HMD, e.g. using adhesive and/or mechanical fixation means or mechanical fixation apparatus. FIG. 12A is a Computer Assisted Design (CAD) drawing of an exemplary holding or attachment apparatus. In some embodiments, one or more members of a holding or attachment apparatus can have a radius of curvature or inner dimension that is slightly smaller than a radius of curvature or inner dimension of a corresponding, mating surface of the HMD 2030 as shown in FIG. 12C; in this manner, the holding or attachment apparatus can be snapped on, e.g. in a snap on design. In some embodiments, the holding or attachment apparatus can be glued to the HMD 2030, e.g. attached to the HMD 2030 using an adhesive. In some embodiments, the holding or attachment apparatus can be attached to the HMD 2030 using one or more magnets or hold and loop fasteners, e.g. Velcro, or a mechanical attachment apparatus or any other known attachment mechanism known in the art. The holding or attachment apparatus can be an integral part of the HMD 2030 housing. The holding or attachment apparatus can have one or more members or elements, e.g. vertical members or elements 2000 2005, frontal members or elements 2000, lateral or side members or elements 2005, and/or top members or elements 2002 (FIG. 12A—FIG. 12D). The HMD 2030 can comprise one or more waveguides, combiners, mirrors 2040 etc.

Figure 12D:
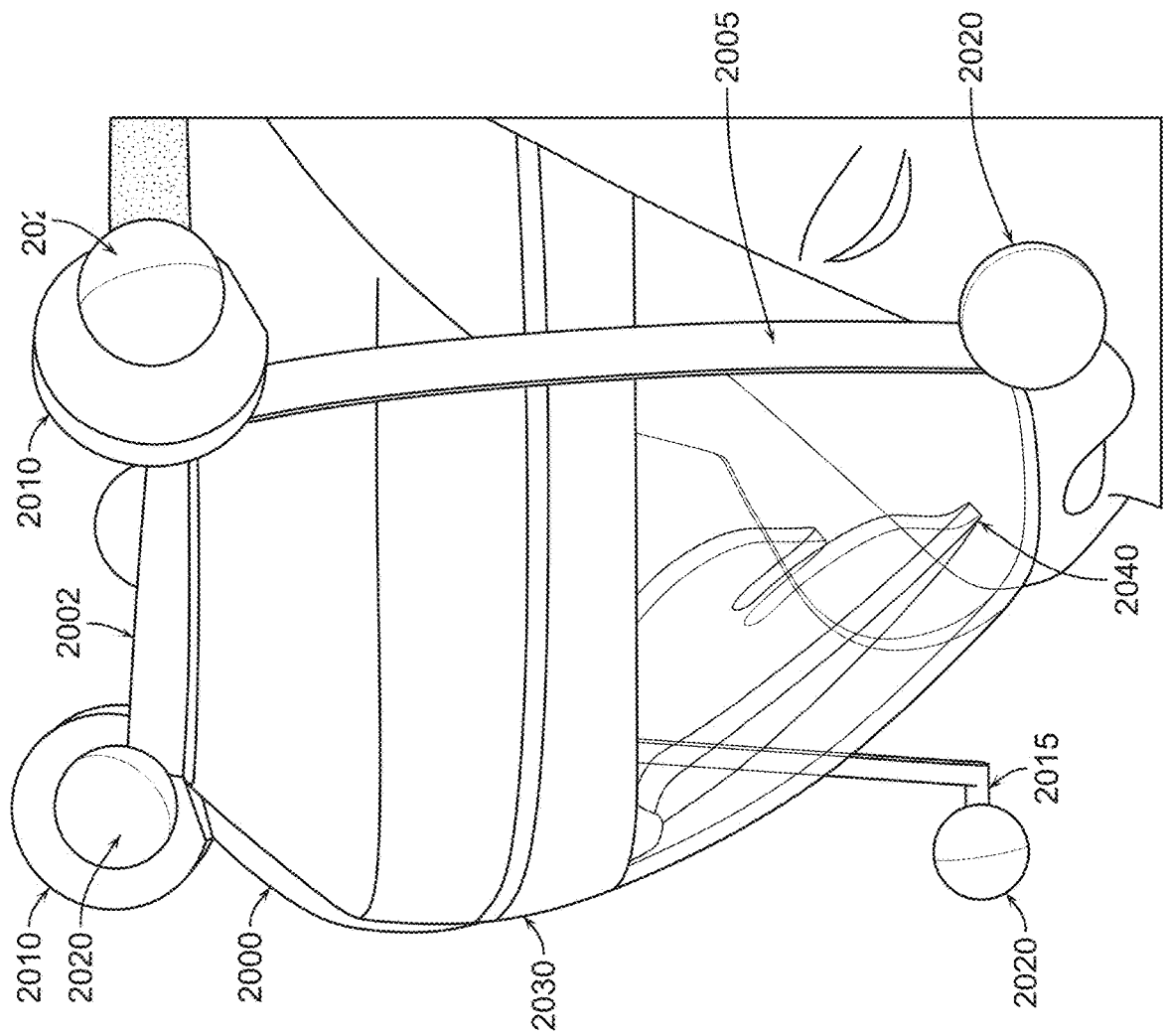

The holding or attachment apparatus can comprise one or more struts, extenders, attachment or holding members 2015 for attaching or securing one or more fiducial markers 2020, for example, an optical marker, e.g. with a geometric pattern, a bar code, a QR code, a navigation marker, e.g. a marker ball, a marker disk, a retroreflective marker ball, a retroreflective marker disk, a retroreflective marker cube (or other shapes), an active marker or a passive marker, an RF marker or an infrared marker. FIG. 12B—FIG. 12D are non-limiting examples of fiducial markers (in this non-limiting example marker balls) 2020 attached via a holding member, extender or strut 2015 to the holding or attachment apparatus 2000 2002 2005 for the one or more fiducial arrays or fiducial sub-arrays.

The system can be configured so that the HMD position and/or orientation can be captured or tracked by the one or more computer processors using the video, image capture, and/or surgical navigation system (e.g. integrated or attached to the HMD or separate from the HMD) with use of more than one array and/or sub-array 2101 2102 2103 (see, for example, FIGS. 12B-12G) attached to the HMD 2030. For example, a first array or sub-array 2102 can be placed or located in the central portion of the HMD 2030, e.g. in proximity to the left and right eye of the user. In some embodiments, a second array 2101 or sub-array 2101 can be attached to the HMD 2030, for example on a right side of the HMD. In some embodiments, a third array 2103 or sub-array 2103 can be attached to the HMD 2030, for example on a left side of the HMD. In some embodiments, a fourth array or sub-array can be attached to the HMD 2030, for example on a posterior head band holding the HMD on the user's head. Any number of arrays or sub-arrays can be used, for example depending on the application or the desired movement range (e.g. up to 360 degree movement range).

Each array or subarray can comprise 1, 2, 3, 4 or more fiducial markers, for example 1, 2 3, 4 or more optical markers (e.g. with a geometric pattern, a bar code, a QR code), 1, 2 3, 4 or more navigation markers (e.g. a marker ball, a marker disk, a retroreflective marker ball, a retroreflective marker disk, a retroreflective marker cube (or other shapes)), 1, 2 3, 4 or more active marker or passive marker or a combination thereof, 1, 2 3, 4 or more RF markers or infrared markers, or a combination thereof.

As the surgeon moves his or her head during the procedure, two or more fiducial markers from different arrays or subarrays attached to or integrated into the HMD can potentially overlap in the line of sight of the video camera, image capture system, and/or surgical navigation system camera. As the surgeon moves his or her head during the procedure, two or more fiducial arrays and/or sub-arrays attached to or integrated into the HMD can potentially overlap in the line of sight of the video camera, image capture system, and/or surgical navigation system camera. An overlap of different arrays or sub-arrays or fiducial markers from different arrays or sub-arrays in the line of sight can, at times, result in mis-registration of an array or sub-array or non-recognition or detection of an array or sub-array, with the potential to lose tracking of the HMD or to have inaccurate tracking and resultant display of the HMD, for example intermittently or for an extended period of time. Mis-registration or loss of tracking can adversely affect the accuracy of the virtual display superimposed onto the physical surgical site, e.g. a bone, a spine, a joint, an organ, a brain, etc.

In some embodiments of the disclosure, a disk, shield or barrier 2010 can be positioned behind and/or adjacent a fiducial marker and/or an array and/or a sub-array to avoid overlap of the projection of different fiducial markers, sub-arrays, and/or arrays in the line of sight of the video camera system, image capture system, and/or surgical navigation system. The disk, shield or barrier 2010 can be positioned and/or placed to avoid overlap of a first fiducial marker and/or array and/or sub-array with a second fiducial marker and/or array and/or subarray, for example for particular view angles or lines of sight, e.g. a frontal view angle and/or line of sight, a lateral view angle and/or line of sight (e.g. left or right), and/or a posterior view angle and/or line of sight. For example, a disk, shield or barrier 2010 can be placed behind a first fiducial marker and/or an array and/or a sub-array relative to the line of sight or view angle to avoid overlap with a second fiducial marker, sub-array, and/or array in the line of sight or view angle of the video camera system, image capture system, and/or surgical navigation system.

A disk, shield or barrier can be an integral part of an HMD, e.g. part of a housing. A disk, shield or barrier can be attached or affixed to an HMD, e.g. attached or affixed to part of a housing. A disk, shield or barrier can be an integral part of a mechanical fixation means or a mechanical fixation apparatus, which in turn can be attached or affixed to an HMD. A disk, shield or barrier can be attached or affixed to a mechanical fixation means or a mechanical fixation apparatus, which in turn can be attached or affixed to an HMD. A disk, shield or barrier can be part of or can be formed by a headlight, e.g. attached or integrated into an HMD. A disk, shield or barrier can be part of or can be formed by a loupe, e.g. attached or integrated into an HMD. At least a portion of a first fiducial marker, first sub-array or first array can be separated from at least a portion of a second fiducial marker, second sub-array or second array by a disk, shield or barrier. The disk, shield or barrier can be configured to avoid overlap of the at least a portion of the first fiducial marker, first sub-array or array with the at least a portion of the second fiducial marker, second sub-array or second array in the line of sight of the at least one camera.

A disk, shield or barrier can be positioned between at least a portion of a first fiducial marker, first sub-array or first array and at least a portion of a second fiducial marker, second sub-array or second array. The disk, shield or barrier can be configured to avoid overlap of the at least a portion of the first fiducial marker, first sub-array or first array with the at least a portion of the second fiducial marker, second sub-array or second array in the line of sight of the at least one camera.

Figure 12E:
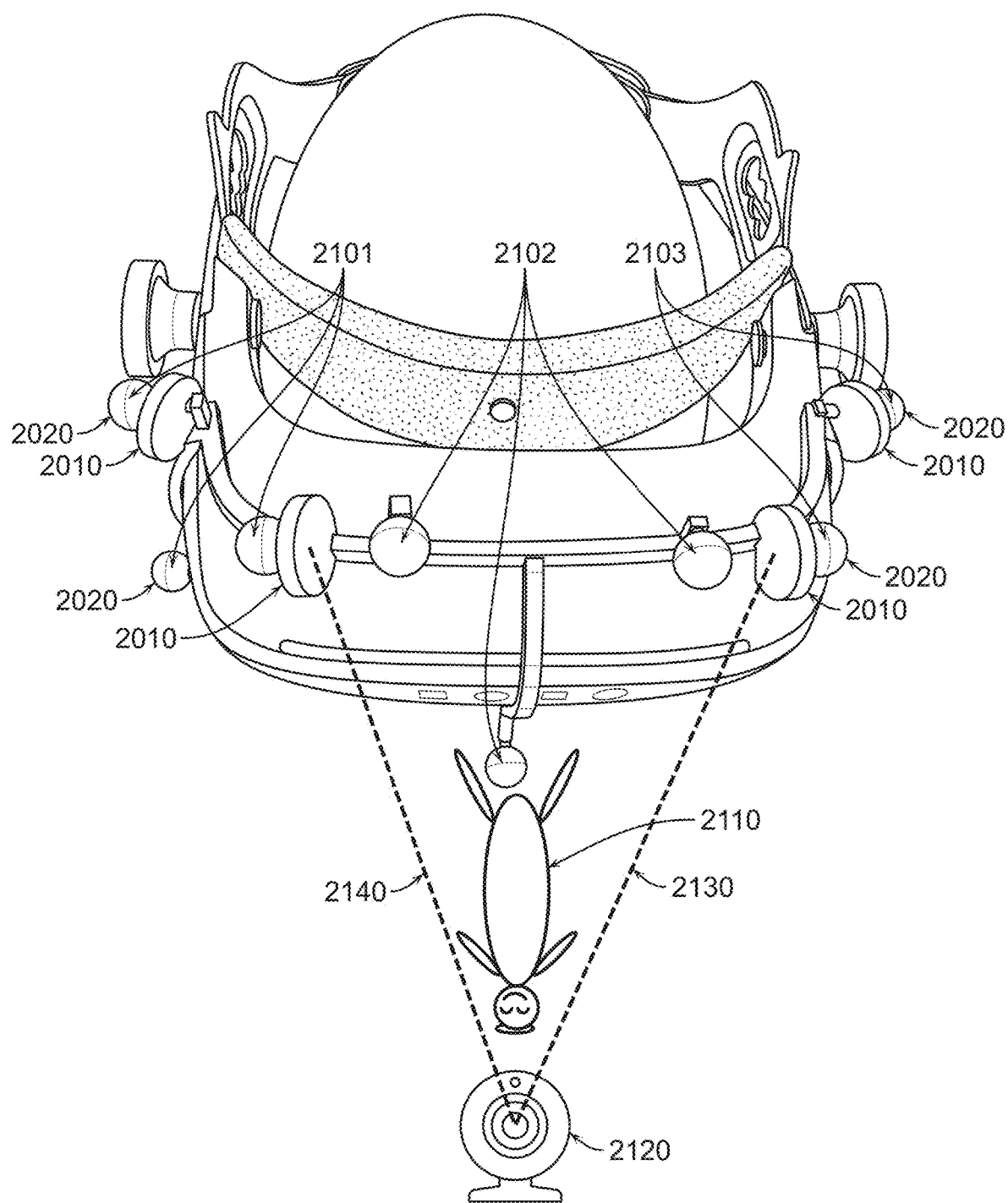
Figure 12F:
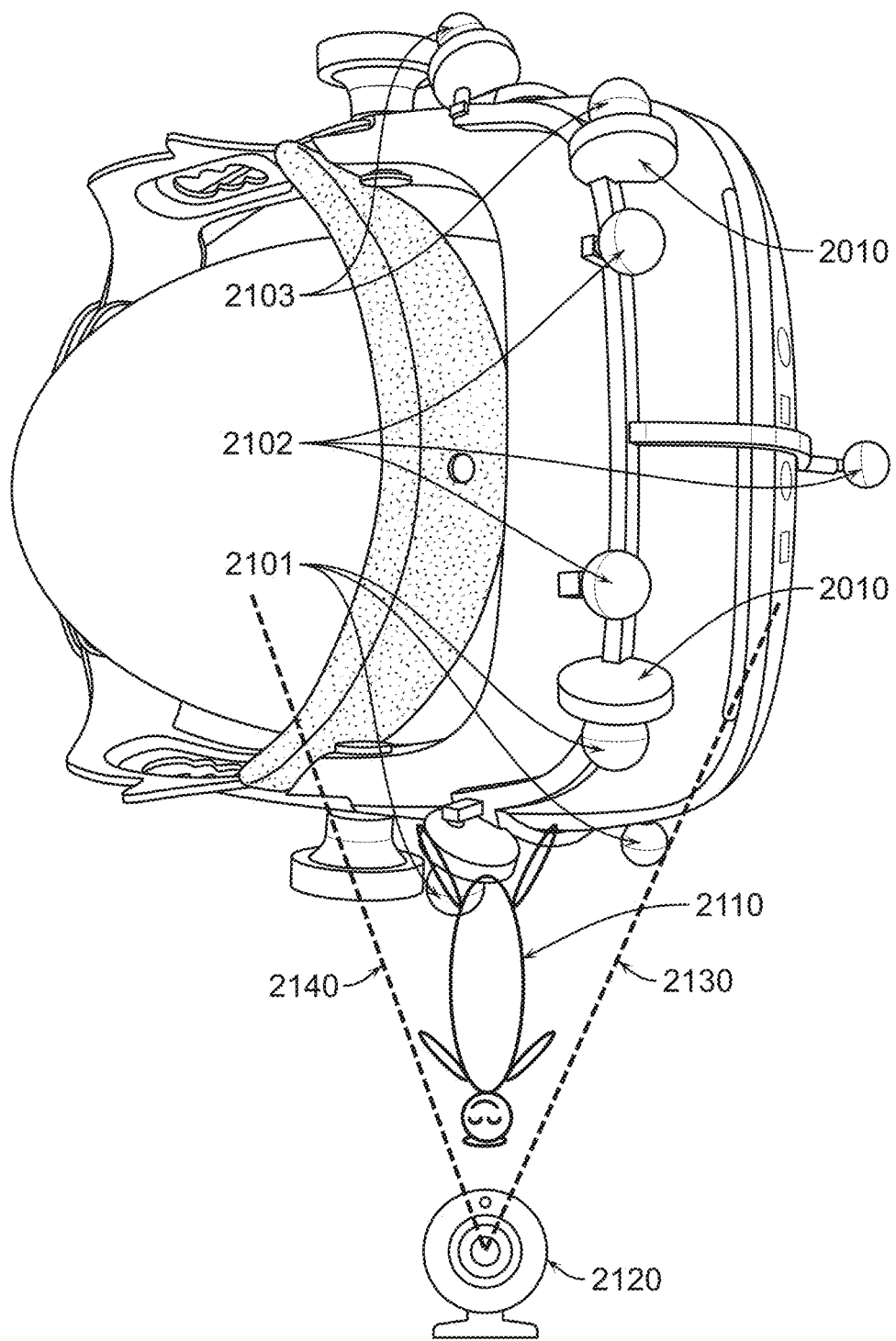
Figure 12G:
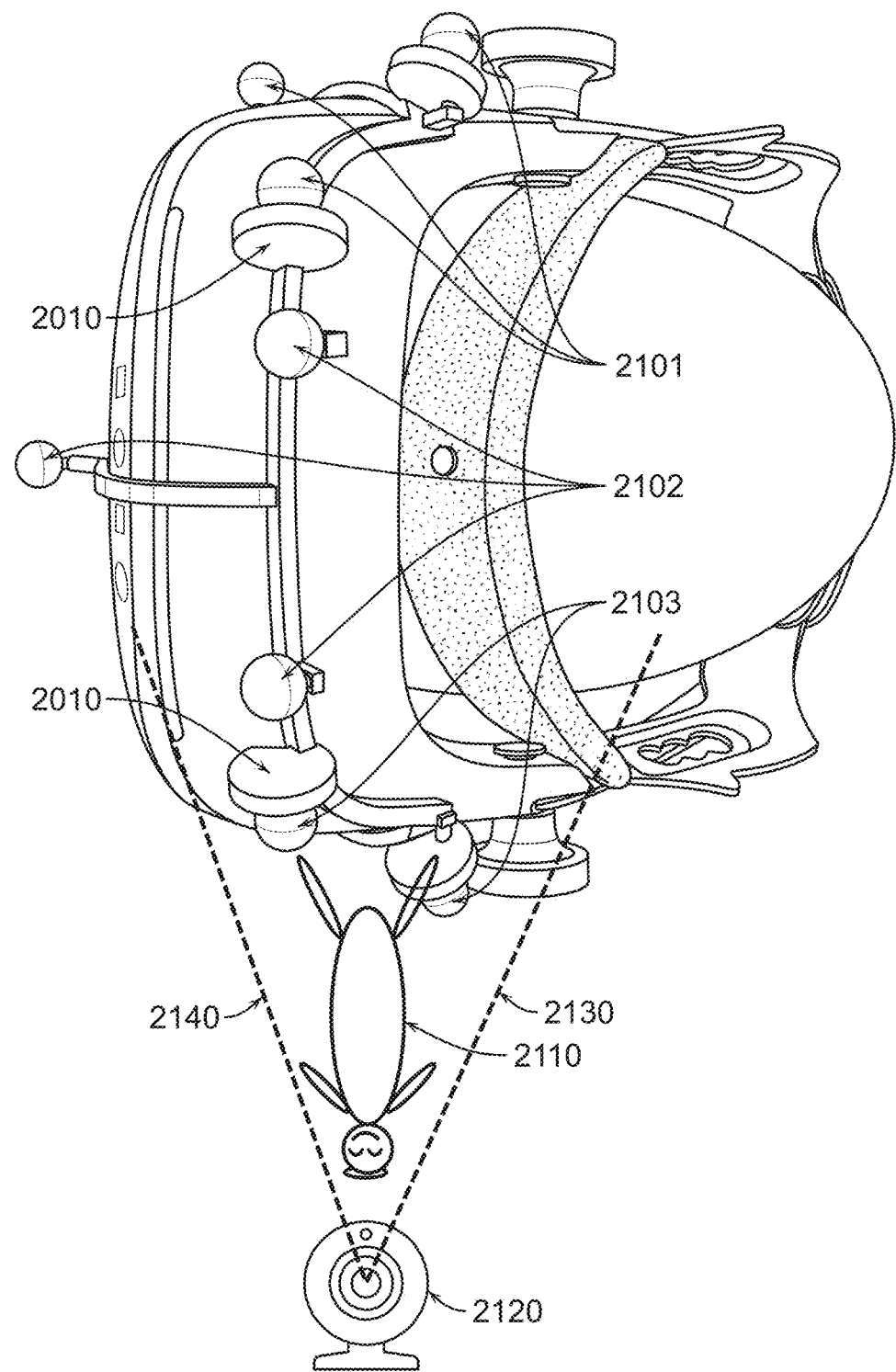

FIGS. 12E-12G are non-limiting examples of a camera 2120 for tracking a patient 2110 and/or one or more anatomic structures of a patient 2110 and a head mounted display 2030. In FIG. 12E, the viewing direction of the HMD 2030 is in frontal direction relative to the patient 2110 and the camera 2120. Array 2102 or sub-array 2102 is tracked by the camera 2120 within the viewable or trackable boundaries 2130 (right relative to camera) and 2140 (left relative to camera). (Note, H M D 2030 is intentionally oversized to show various features including discs, shields or barriers 2010 and fiducial markers 2020.)

In FIG. 12F, the viewing direction of the HMD 2030 is in right lateral direction relative to the patient 2110 and the camera 2120. Array 2101 or sub-array 2101 is tracked by the camera 2120 within the viewable or trackable boundaries 2130 (right relative to camera) and 2140 (left relative to camera). (Note, H M D 2030 is intentionally oversized to show various features including discs, shields or barriers 2010 and fiducial markers 2020.)

In FIG. 12G, the viewing direction of the HMD 2030 is in left lateral direction relative to the patient 2110 and the camera 2120. Array 2103 or sub-array 2103 is tracked by the camera 2120 within the viewable or trackable boundaries 2130 (right relative to camera) and 2140 (left relative to camera). (Note, H M D 2030 is intentionally oversized to show various features including discs, shields or barriers 2010 and fiducial markers 2020.)

A composite movement range detectable or visible and trackable by a camera for a first fiducial marker, sub-array 2102 or array 2102, a second fiducial marker, sub-array 2101 or array 2101, a third fiducial marker, sub-array 2103 or array 2103 etc. can be the total, composite or maximum range of viewing directions of an HMD trackable by the system. The composite movement range can be influenced, set or determined by the position, orientation, or position and orientation of one or more fiducial marker, sub-array, or array, the dimensions, shape, geometry and/or geometric pattern(s) of one or more fiducial marker, sub-array, or array, the field of view of the HMD, the field of view of the camera, the relative distance between camera, patient, HMD, and/or one or more fiducial markers, sub-arrays and/or arrays, and the respective geometric arrangement of the different components and/or the patient.

In any of the embodiments, two or more arrays or sub-arrays can share at least one or more fiducial marker, with other, different one or more fiducial markers not being shared by the two or more arrays or sub-arrays.

The geometric arrangement (e.g. position and/or orientation) of one or more fiducial marker, sub-array or array can be configured so that the one or more one or more fiducial marker, sub-array or array is only detectable and/or trackable by a camera (within its field of view) within a predetermined range of head positions and/or orientations, HMD positions and/or orientations, and/or HMD view directions.

The geometric arrangement (e.g. position and/or orientation) of one or more fiducial marker, sub-array or array can be configured so that the one or more one or more fiducial marker, sub-array or array is/are hidden from a camera within a predetermined range of head positions and/or orientations, HMD positions and/or orientations, and/or HMD view directions. The geometric arrangement (e.g. position and/or orientation) of the one or more fiducial marker, sub-array or array can be configured so that components of the HMD and/or holding or attachment apparatus and/or a disc, shield or barrier and/or facial features of the user facilitate the hiding of the one or more one or more fiducial marker, sub-array or array from the camera.

The system can be configured so that the system automatically detects and/or tracks, for example, a second fiducial marker, sub-array or array when a first fiducial marker, sub-array or array is not visible to or detected or tracked by the camera.

The system can be configured to perform a $1^{st}$ calibration for a $1^{st}$ fiducial marker, sub-array and/or array for a first view direction or range of view directions of an HMD. The calibration can use a priori knowledge about one or more dimensions, shape, geometry, geometric pattern or a combination thereof of the $1^{st}$ fiducial marker, sub-array and/or array, for example a shape and/or edge length of a $1^{st}$ array, or x, y, and z-coordinates of a $1^{st}$, $2^{nd}$, $3^{rd}$ and/or $4^{th}$ marker ball or disk of an array or sub-array. The calibration can be stored by the system, e.g. using retrievable computer media.

The system can be configured to perform a $2^{nd}$ calibration for a $2^{nd}$ fiducial marker, sub-array and/or array for a $2^{nd}$ view direction or range of view directions of an HMD. The calibration can use a priori knowledge about one or more dimensions, shape, geometry, geometric pattern or a combination thereof of the $2^{nd}$ fiducial marker, sub-array and/or array, for example a shape and/or edge length of a $1^{st}$ array, or x, y, and z-coordinates of a $1^{st}$, $2^{nd}$, $3^{rd}$ and/or $4^{th}$ marker ball or disk of an array or sub-array. The calibration can be stored by the system, e.g. using retrievable computer media.

The system can be configured to perform a $3^{rd}$ calibration for a $3^{rd}$ fiducial marker, sub-array and/or array for a $3^{rd}$ view direction or range of view directions of an HMD. The calibration can use a priori knowledge about one or more dimensions, shape, geometry, geometric pattern or a combination thereof of the $3^{rd}$ fiducial marker, sub-array and/or array, for example a shape and/or edge length of a $1^{st}$ array, or x, y, and z-coordinates of a $1^{st}$, $2^{nd}$, $3^{rd}$ and/or $4^{th}$ marker ball or disk of an array or sub-array. The calibration can be stored by the system, e.g. using retrievable computer media.

The system can be configured to perform a $4^{th}$ calibration for a $4^{th}$ fiducial marker, sub-array and/or array for a $4^{th}$ view direction or range of view directions of an HMD. The calibration can use a priori knowledge about one or more dimensions, shape, geometry, geometric pattern or a combination thereof of the $4^{th}$ fiducial marker, sub-array and/or array, for example a shape and/or edge length of a $1^{st}$ array, or x, y, and z-coordinates of a $1^{st}$, $2^{nd}$, $3^{rd}$ and/or $4^{th}$ marker ball or disk of an array or sub-array. The calibration can be stored by the system, e.g. using retrievable computer media.

The system can be configured to perform an nth calibration for an nth fiducial marker, sub-array and/or array for an nth view direction or range of view directions of an HMD. The calibration can use a prior knowledge about one or more dimensions, shape, geometry, geometric pattern or a combination thereof of the nth fiducial marker, sub-array and/or array. The calibration can be stored by the system, e.g. using retrievable computer media.

A $1^{st}$, $2^{nd}$, $3^{rd}$, $4^{th}$ or more fiducial marker, sub-array, or array can be configured to expose or hide one or more fiducial markers, sub-arrays or arrays to/from a camera for predetermined HMD positions and/or orientations and/or HMD view directions, e.g. in relationship to a patient, an anatomic structure of a patient, a surgical site, the camera, and/or an OR table.

A $1^{st}$, $2^{nd}$, $3^{rd}$, $4^{th}$ or more disc, shield or barrier can be configured to hide one or more fiducial markers, sub-arrays or arrays from a camera for predetermined HMD positions and/or orientations and/or HMD view directions, e.g. in relationship to a patient, an anatomic structure of a patient, a surgical site, the camera, and/or an OR table.

In some embodiments, the disk, shield or barrier 2010 can be composed of a plastic, a metal, and/or a metal alloy, or any other suitable material known in the art. Metals or metal alloys can comprise aluminum or titanium, which can be beneficial in view of their low weight. Plastic can also have a low weight. Plastic can be made with 3D printing or other processes known in the art, including, for example, injection molding. The material, e.g. a metal, can be selected to, optionally, block RF signal, for example using mesh like structures surrounding at least a portion of the perimeter or periphery of a fiducial marker and/or an array and/or a sub-array.

In some embodiments, the disk, shield or barrier 2010 can comprise one or more non-reflective surfaces and/or one or more reflection-reducing surfaces, or be composed of one or more non-reflective material and/or one or more reflection reducing materials. In this manner, potential mirror images of the fiducial marker(s) can be reduced and potential mis-registration of marker and, with that, HMD coordinates can be reduced or avoided. Non-reflective or reflection reducing surfaces can, for example, be black or can have different grey shades. Non-reflective or reflection reducing surfaces can be matte. In some embodiments, the disk, shield or barrier 2010 can have one or more anti-reflective coatings, including, for example, textured coatings. Any anti-reflective coating or anti-reflective material known in the art can be used.

In some embodiments, the disk, shield or barrier 2010 can be 0.01, 0.1, 0.2, 0.3, 0.4, 0.5, 0.6, 0.7, 0.8, 0.9, 1.0, 1.1, 1.2, 1.3, 1.4, 1.5, 1.6, 1.8, 2.0, 2.5, 3.0, 3.5, 4.0, 5.0, 6.0, 7.0, 8.0, 9.0, 10.0, 15.0, 20.0 mm or any other value distant from the fiducial marker, sub-array or array.

In some embodiments, a surface or principal plane or principal axis of the disk, shield or barrier 2010 can be substantially perpendicular or parallel relative to a surface or principal plane or axis of a fiducial marker, a sub-array, and/or an array. In some embodiments, a surface or principal plane or principal axis of the disk, shield or barrier 2010 can be at an angle not substantially perpendicular or parallel relative to a surface or principal plane or axis of a fiducial marker, a sub-array, and/or an array. In some embodiments, a surface or principal plane or principal axis of the disk, shield or barrier 2010 can be at an angle relative to a surface or principal plane or principal axis of a fiducial marker, a sub-array, and/or an array; the angle can be 0, 1, 3, 5, 7, 10, 15, 20, 25, 30, 40, 50, 60, 70, 80, 90, 100, 110, 120, 130, 140, 150, 160, 170, 180 degrees, or any other value.

More than one disk, shield or barrier 2010 can be used with a fiducial marker, sub-array or array. A disk, shield or barrier can comprise one or more planar, one or more convex, one or more concave, one or more multi-radius, one or more irregular surfaces and/or shapes.

In some embodiments, the holding or attachment apparatus for the fiducial arrays, including one or more of its components 2000 2002 2005, can be composed of a plastic, a metal, and/or a metal alloy, or any other suitable material known in the art. Metals or metal alloys can comprise aluminum or titanium, which can be beneficial in view of their low weight. Plastic can also have a low weight. Plastic can be made with 3D printing or other processes known in the art, including, for example, injection molding.

In some embodiments, the holding or attachment apparatus for the fiducial arrays, including one or more of its components 2000 2002 2005, can comprise one or more non-reflective and/or reflection reducing surfaces or be composed of a non-reflective and/or reflection reducing material. In this manner, potential mirror images of the fiducial marker(s) can be reduced and potential mis-registration of marker and, with that, HMD coordinates can be reduced or avoided. Non-reflective and/or reflection reducing surfaces can, for example, be black or can have different grey shades. Non-reflective surfaces and/or reflection reducing can be matte. In some embodiments, the holding or attachment apparatus for the fiducial arrays or sub-arrays can have one or more anti-reflective and/or reflection reducing coatings, including, for example, textured coatings. Any anti-reflective and/or reflection reducing coating or anti-reflective material known in the art can be used. The following examples show representative applications of various embodiments of the disclosure. The examples are not meant to be limiting. Someone skilled in the art will recognize other applications or modifications of the methods, techniques, devices and systems described. Any embodiment described for one joint or anatomic region, e.g. a spine or pedicle, can be applied to other joints or other regions, e.g. a hip, hip replacement, knee, knee replacement, vascular imaging study, angiography etc.

In some embodiments, when a physical guide, tool, instrument or implant is aligned with or superimposed onto a virtual surgical guide, tool, instrument or implant displayed or projected by the HMD, the aligning or superimposing can be performed with a location accuracy of about 10 mm, about 9 mm, about 8 mm, about 7 mm, about 6 mm, about 5 mm, about 4 mm, about 3 mm, about 2 mm, about 1 mm, about 0.5 mm, about 0.25 mm, or less, 0.25 mm to 0.5 mm, 0.25 mm to 1 mm, 0.25 mm to 2 mm, 0.25 mm to 3 mm, 0.25 mm to 4 mm, 0.25 mm to 5 mm, 0.25 mm to 6 mm, 0.25 mm to 7 mm, 1 mm to 2 mm, 1 mm to 3 mm, 1 mm to 4 mm, 1 mm to 5 mm, 1 mm to 6 mm, 1 mm to 7 mm, 2 mm to 3 mm, 2 mm to 4 mm, 2 mm to 5 mm, 2 mm to 6 mm, 2 mm to 7 mm, 3 mm to 4 mm, 3 mm to 5 mm, 3 mm to 6 mm, 3 mm to 7 mm, 4 mm to 5 mm, 4 mm to 6 mm, 4 mm to 7 mm, 5 mm to 6 mm, 5 mm to 7 mm, 6 mm to 7 mm or as needed depending on the clinical application, in one, two or three directions, x, y, z. When the physical guide, tool, instrument or implant is aligned with or superimposed onto the virtual surgical guide, tool, instrument or implant displayed or projected by the OHMD, the aligning or superimposing can be performed with an orientation or angle accuracy of about 10°, about 9°, about 8°, about 7°, about 6°, about 5°, about 4°, about 3°, about 2°, about 1°, about 0.5°, about 0.25° or less, 0.25-10°, 0.25 to 9°, 0.25-8°, 0.25-7°, 0.25-6°, 0.25-5°, 0.25-4°, 0.25-3°, 0.25-2°, 0.25-1°, 0.25-0.5°, 0.5 to 9°, 0.5-8°, 0.5-7°, 0.5-6°, 0.5-5°, 0.5-4°, 0.5-3°, 0.5-2°, 0.5-1°, 1 to 9°, 1-8°, 1-7°, 1-6°, 1-5°, 1-4°, 1-3°, 1-2°, 2-9°, 2-8°, 2-7°, 2-6°, 2-5°, 2-4°, 2-3°, 3-9°, 3-8°, 3-7°, 3-6°, 3-5°, 3-4°, 4-9°, 4-8°, 4-7°, 4-6°, 4-5°, 5-9°, 5-8°, 5-7°, 5-6°, 6-9°, 6-8°, 6-7°, 7-9°, 7-8°, 8-9° or as needed depending on the clinical application, in one, two or three directions, x, y, z.

In some embodiments, when a virtual display, e.g. a virtual model, virtual surgical guide, tool, instrument or implant displayed or projected by the HMD is superimposed and/or aligned with a physical anatomic structure of a patient, the superimposing and/or aligning can be performed with a location accuracy of about 10 mm, about 9 mm, about 8 mm, about 7 mm, about 6 mm, about 5 mm, about 4 mm, about 3 mm, about 2 mm, about 1 mm, about 0.5 mm, about 0.25 mm, or less, 0.25 mm to 0.5 mm, 0.25 mm to 1 mm, 0.25 mm to 2 mm, 0.25 mm to 3 mm, 0.25 mm to 4 mm, 0.25 mm to 5 mm, 0.25 mm to 6 mm, 0.25 mm to 7 mm, 1 mm to 2 mm, 1 mm to 3 mm, 1 mm to 4 mm, 1 mm to 5 mm, 1 mm to 6 mm, 1 mm to 7 mm, 2 mm to 3 mm, 2 mm to 4 mm, 2 mm to 5 mm, 2 mm to 6 mm, 2 mm to 7 mm, 3 mm to 4 mm, 3 mm to 5 mm, 3 mm to 6 mm, 3 mm to 7 mm, 4 mm to 5 mm, 4 mm to 6 mm, 4 mm to 7 mm, 5 mm to 6 mm, 5 mm to 7 mm, 6 mm to 7 mm or as needed depending on the clinical application, in one, two or three directions, e.g. x, y, z. In some embodiments, when a virtual display, e.g. a virtual model, virtual surgical guide, tool, instrument or implant displayed or projected by the OHMD is superimposed and/or aligned with a physical anatomic structure of a patient, the superimposing and/or aligning can be performed with an orientation or angle accuracy of about 10°, about 9°, about 8°, about 7°, about 6°, about 5°, about 4°, about 3°, about 2°, about 1°, about 0.5°, about 0.25° or less, 0.25-10°, 0.25 to 9°, 0.25-8°, 0.25-7°, 0.25-6°, 0.25-5°, 0.25-4°, 0.25-3°, 0.25-2°, 0.25-1°, 0.25-0.5°, 0.5 to 9°, 0.5-8°, 0.5-7°, 0.5-6°, 0.5-5°, 0.5-4°, 0.5-3°, 0.5-2°, 0.5-1°, 1 to 9°, 1-8°, 1-7°, 1-6°, 1-5°, 1-4°, 1-3°, 1-2°, 2-9°, 2-8°, 2-7°, 2-6°, 2-5°, 2-4°, 2-3°, 3-9°, 3-8°, 3-7°, 3-6°, 3-5°, 3-4°, 4-9°, 4-8°, 4-7°, 4-6°, 4-5°, 5-9°, 5-8°, 5-7°, 5-6°, 6-9°, 6-8°, 6-7°, 7-9°, 7-8°, 8-9° or as needed depending on the clinical application, in one, two or three directions, x, y, z.

Aspects of the disclosure relate to methods for tracking a head mounted display for generating a virtual display superimposed onto a patient during a surgical procedure, the method comprising: (a) tracking a first fiducial marker, first sub-array of fiducial markers or first array of fiducial markers over a first movement range of a head mounted display by at least one camera, wherein the first fiducial marker, first sub-array or first array has a first location, first orientation, or first location and orientation, wherein the first fiducial marker, first sub-array or first array is attached to or integrated into the head mounted display; (b) tracking the second fiducial marker, second sub-array of fiducial markers or second array of fiducial markers over a second movement range of the head mounted display by to the at least one camera, wherein the second fiducial marker, second sub-array or second array has a second location, orientation, or location and orientation, wherein the second fiducial marker, second sub-array or second array is attached to or integrated into the head mounted display, wherein the first and the second location, the first and the second orientation, or the first and the second location and orientation are different, wherein the first movement range and the second movement range are different, and (c) generating the virtual display superimposed onto the patient within the first movement range and the second movement range. In some embodiments, methods are provided for superimposing the virtual display superimposed onto the patient over an HMD movement range that is greater than the first movement range for the first fiducial marker, first sub-array of fiducial markers or first array of fiducial markers or greater than the second movement range of the second fiducial marker, second sub-array of fiducial markers or second array of fiducial markers. Without being bound by the theory, if only one fiducial marker, sub-array of fiducial markers, or array of fiducial markers were used, the resultant trackable movement range of the HMD would only be the same or less than the first movement range or the second movement range or the same or less than a maximum movement range possible for a single fiducial marker, sub-array of fiducial markers, or array of fiducial markers.

Aspects of the disclosure relate to systems for guiding a physical surgical tool, instrument, implant or device in a surgical procedure of a patient, the system comprising: (a) a head mounted display, (b) at least one computer processor, (c) at least one camera, (c) a first fiducial marker, a first sub-array of fiducial markers or a first array of fiducial markers having a first location, first orientation, or first location and orientation, wherein the first fiducial marker, first sub-array of fiducial markers or first array of fiducial markers is attached to or integrated into the head mounted display, and (d) a second fiducial marker, a second sub-array of fiducial markers or a second array of fiducial markers having a second location, orientation, or location and orientation, wherein the second fiducial marker, second sub-array of fiducial markers or second array of fiducial markers is attached to or integrated into the head mounted display, wherein the first and the second location, the first and the second orientation, or the first and the second location and orientation are different, wherein the system is configured to track the first fiducial marker, first sub-array or first array over a first movement range of the head mounted display with the at least one camera, wherein the system is configured to track the second fiducial marker, second sub-array or second array over a second movement range of the head mounted display with the at least one camera, and wherein the first movement range and the second movement range are different.

Aspects of the disclosure relate to systems for guiding a physical surgical tool, instrument, implant or device in a surgical procedure of a patient, the system comprising: (a) a head mounted display, (b) at least one computer processor, (c) at least one camera, (c) a first fiducial marker, a first sub-array of fiducial markers or a first array of fiducial markers having a first location, first orientation, or first location and orientation, wherein the first fiducial marker, first sub-array of fiducial markers or first array of fiducial markers is attached to or integrated into the head mounted display, and (d) a second fiducial marker, a second sub-array of fiducial markers or a second array of fiducial markers having a second location, orientation, or location and orientation, wherein the second fiducial marker, second sub-array of fiducial markers or second array of fiducial markers is attached to or integrated into the head mounted display, wherein the first and the second location, the first and the second orientation, or the first and the second location and orientation are different, wherein the system is configured to track the first fiducial marker, first sub-array or first array over a first movement range of the head mounted display with the at least one camera, wherein the system is configured to track the second fiducial marker, second sub-array or second array over a second movement range of the head mounted display with the at least one camera, and wherein the first movement range and the second movement range are different, wherein the system is configured to superimpose, by the head mounted display, a virtual display onto at least a portion of the patient, wherein the system is configured to maintain the virtual display superimposed onto the at least portion of the patient over a composite movement range that is greater than the first movement range or the second movement range.

EXAMPLES

Example 1: AR Display System for Surgical Guidance with Extended Tracked Viewing Range Movement of the surgeon's head and of the patient, e.g. a spine, a knee, a hip, or any other anatomic structure, during surgery can, for example, result in line of sight issues and failure of the system to respond. An AR compatible tracking system needs to support a wide range of head movement, for example 50%, 60%, 70%, 80%, 90%, 100%, 110%, 120% of normal, anatomically supported and/or feasible head movement. In many human beings, normal, anatomically feasible head movement is near approximately 160° up-down or superior-inferior movement (e.g. an anatomic movement range in superior-inferior orientation and/or direction of +80° to −80° [e.g. +80° (superior) to 0° (neutral) and 0° (neutral) to −80° inferior], e.g. relative to a neutral head/neck position), 180° left-right (e.g. an anatomic movement range in left-right orientation and/or direction of +90° to −90° [e.g. +90° (left) to 0° (neutral) and 0° (neutral) to −90° right], e.g. relative to a neutral head/neck position). Head movement can, for example, be greater when a surgeon moves, shifts, turns, and/or rotates his or her body or moves his or her feet.

Movement of a patient's knee joint, can comprise, for example, a flexion of the knee of 160°, for example with a similar range of up down/superior-inferior (or reverse) movement of tracked instruments. Based on internal/external rotation of the hip, left-right movement of the knee can be, for example, plus or minus 40°, 50°, 60°, 70°, 80° in one (left) or the other (right) direction. Thus, considering for anatomically feasible movement of the surgeon's head, movement of the patient, for example the anatomic site or structure being operated on, and movement of the instruments, tools or implants used by a surgeon, a wide tracking range of HMDs, instruments, and the patient are desirable. Movement ranges can also be defined in relationship to a predetermined or current camera position, e.g. integrated or attached to an HMD or separate from an HMD, an anatomic structure of a patient, an anatomic structure of a surgeon, a structure in the operating room, e.g. an OR light, an OR table, or a combination thereof.

With some navigation cameras, the number of arrays that can be simultaneously tracked can be limited. For example, the Polaris NDI (NDI International, Waterloo, ON, Canada) or the Atracsys system (Atracsys LLC, Puidoux, Switzerland) can only track up to 15 or 16 arrays, respectively. In order to overcome this limitation, a new type of multiple-facet array is one non-limiting, exemplary embodiment of the disclosure.

Ball type reflective fiducial markers can have a wide visibility range, but can be contaminated by blood or body fluids, which can result in registration errors or loss of registration. Disc type reflective fiducial markers have been used with navigation systems for the knee and hip; external cup-like extenders or rims can protect them from being contaminated to some extent.

Discs can have a more limited visible range or movement range (detectable by a camera) compared to spheres in relationship to the camera, e.g. a camera integrated or attached to an HMD or a camera separate for an HMD or combinations thereof. For example, for disks a visible range or range detectable by the camera in superior-inferior and/or left-right and/or anterior-posterior can be 70°, 80°, 90°, 100°, or 110° or similar ranges, for example measured in relationship to the camera or a fiducial marker, sub-array or array on a patient. For spheres, a visible range or movement range detectable by the camera in superior-inferior and/or left-right and/or anterior-posterior can be 120°, 130°, 140°, 150°, 160°, 170°, 180°, 190°, 200°, 210°, 220°, 230°, 240°, 250°, 260°, 270°, 280°, 290°, or more degrees), for example measured in relationship to the camera or a fiducial marker, sub-array or array on a patient.

It may be necessary in some applications to attach multiple sets of reflective discs to an instrument or an HMD, which can point in different directions in order to increase the detectable or visible range by the camera. If each set has a different geometry definition and is thus recognized as a different array, it is possible that the total number of arrays and/or sub-arrays required can exceed the maximum supported by the navigation camera, in particular when multiple HMDs are used.

Instead of different arrays, multiple sets of discs with the same geometry definition, which can be recognized as the same array, can be attached to an instrument and/or the patient and/or an HMD. With each set of discs facing, for example, in a different direction, the array can be configured so that at least one set of discs is visible from the camera when an instrument, HMD or the patient move during surgery. However, if multiple sets of discs share the same geometry definition, in select configurations, the camera cannot differentiate them on the basis of their ID. In some embodiments of the present disclosure, the system (e.g. the camera and a computer processor) can use the fiducial marker's, e.g. a disc, coordinate system relative to the camera rather than the ID to differentiate the different sets of fiducial markers, e.g. discs.

Figure 13:
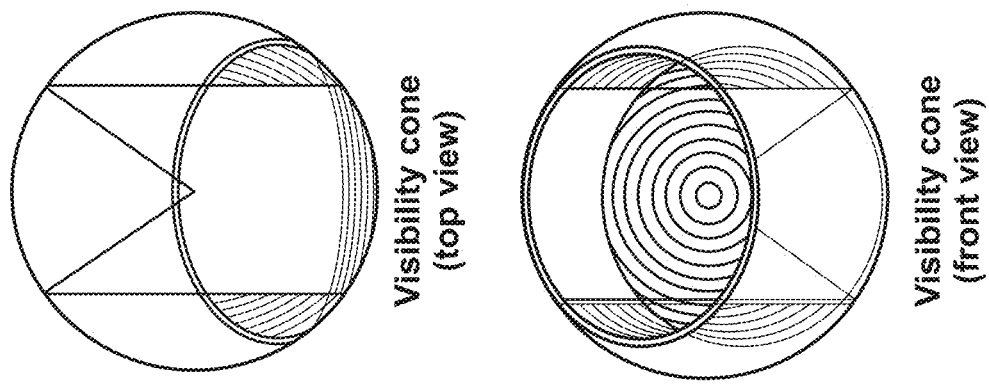
FIG. 13 is a non-limiting example of an HMD array with 4 sets of facets, and a resultant exemplary visibility cone.
Figure 13:
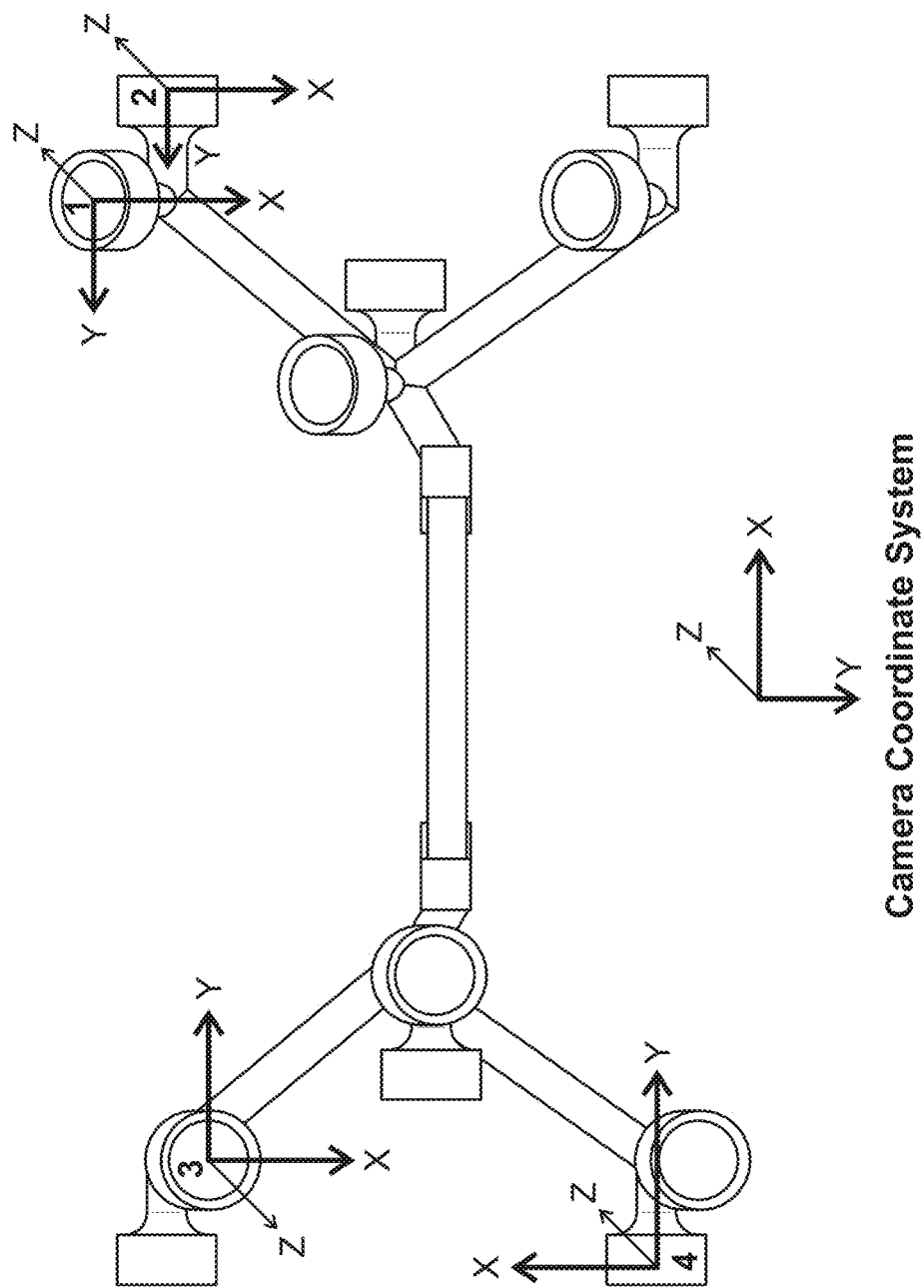

FIG. 13 illustrates 4 sets of discs/facets in an array and their associated coordinate systems (CS): facing left, facing forward, facing right, and facing backward. The visibility cone (right) shows the range of visibility for each set and their overlap. Using the visibility cone and the orientation of the coordinate system, aspects of the present invention allow to uniquely identify different sets of discs/facets for the arrays we have constructed: 1.) Number of sets detected with the same ID 2.) Orientation of z-axis relative to camera 3.) Orientation of camera viewing direction relative to visibility cone 4.) Distance between CS origins if multiple sets returned 5.) Vector between CS origins if multiple sets returned. These multiple sets of facets or discs can provide a much wider viewing angle than is possible with a single set of facets or discs. These concepts were applied to tracking an HMD (FIG. 13). The array in FIG. 13 utilizes 4 sets of discs/facets in order to account for surgeon head movement and to provide a wide range of visible angles.

The movement range through which the HMD was detectable or visible by the camera for an array with 1 set of discs or facets attached to the HMD vs. an array with 4 sets of discs or facets attached to the HMD was as follows for the configuration shown in FIG. 13:

Array with 1 Set of Discs or Facets Attached to the HMD:
Up-down (superior-inferior) visible/tracked HMD movement range: 110° (relative to camera, starting from neutral head/neck position: approximately up 55°, neutral 0°, down 55°).
Left-right visible/tracked HMD movement range: 110° (relative to camera, starting from neutral head/neck position: approximately left 55°, neutral 0°, right 55°).
Array with 4 Set of Discs or Facets Attached to the HMD:
Up-down (superior-inferior) visible/tracked HMD movement range: 170° (relative to camera, starting from neutral head/neck position: approximately up 85°, neutral 0°, down 85°).
Left-right visible/tracked HMD movement range: 290° (relative to camera, starting from neutral head/neck position: approximately left 145°, neutral 0°, right 145°).

Example 2: Tracking of HMDs Using Multiple Fiducial Markers, Sub-Arrays and/or Arrays A multi-faceted or multi-faced array can be an array where fiducial markers, e.g. discs or spheres, can be arranged into multiple facets or faces; each facet or face can be a sub-array; each facet or face (or sub-array) can comprise multiple fiducial markers arranged in the facet or face. Multiple facets can comprise completely separate fiducial markers; multiple facets can also share one or more select fiducial markers, with other, different one or more fiducial markers not being shared. A camera, e.g. a navigation camera, may, for example, track only one facet or face at a time. A multi-faceted or multi-faced array can be advantageous when the clinical application requires that an HMD can be moved beyond the visible or detectable movement range or visibility range of the camera for a single facet or face, e.g. for a given or predetermined camera position and/or head/neck position.

Each facet or face can be assigned a normal relative to the facet or face. The facet normal can be a vector that can, for example, point in the same direction as viewing direction of an HMD, which can allow the system to determine in which direction a facet integrated or attached to an HMD is facing.

When multiple facets or faces are integrated or attached to an HMD, each facet or face (or sub-array) can be integrated or attached in a predetermined position and/or orientation in relationship to the field of view or viewing direction of the HMD.

In this case, the facet normal(s) can be a vector(s) that can, for example, point in the same direction as the predetermined position and/or orientation in relationship to the field of view or view angle(s) or perspective view of the HMD. Thus, with knowledge of the predetermined position and/or orientation in relationship to the field of view or view angle or perspective view of the HMD and knowledge of the vector, the system can determine in which direction a facet integrated or attached to an HMD is facing and the system can determine the position and/or orientation of the HMD along with its perspective view and/or view angle.

In any of the embodiments throughout the specification, a camera can comprise an image capture system, a video system, an image sensor, an imaging system, a navigation system, a 3D scanner, a laser scanner, a Lidar scanner or any other system or technique capable of acquiring images of the human body and/or an HMD. In any of the embodiments throughout the specification, a camera can detect light within the visible light range, a camera can also detect light within a non-visible light wave range, e.g. infrared light or ultraviolet light, or combinations thereof. In any of the embodiments throughout the specification, camera can be integrated or attached to an HMD, separate from an HMD, attached to a surgeon, attached to a patient, attached to an anatomic structure, attached to an OR table, integrated or attached to a structure in the operating room, e.g. OR lights, integrated or attached to an imaging system, e.g. an x-ray imaging system, a C-arm, a 3D C-arm, a CT scanner, an MRI scanner, a PET-CT scanner, integrated or attached to a robot, e.g. a robotic arm and/or an end-effector, or a combination thereof.

All publications, patent applications and patents mentioned herein are hereby incorporated by reference in their entirety as if each individual publication or patent was specifically and individually indicated to be incorporated by reference.

The invention claimed is:

1. A system for guiding a physical surgical tool, instrument, implant or device in a surgical procedure of a patient, the system comprising:
    a head mounted display,
    at least one computer processor,
    at least one camera,
    a first fiducial marker, a first sub-array of fiducial markers or a first array of fiducial markers having a first location, first orientation, or first location and orientation on an outside surface of the head mounted display, and
    a second fiducial marker, a second sub-array of fiducial markers or a second array of fiducial markers having a second location, orientation, or location and orientation on the outside surface of the head mounted display,
    wherein the first and the second location, the first and the second orientation, or the first and the second location and orientation are different,
    wherein the first fiducial marker, first sub-array of fiducial markers or first array of fiducial markers has a different geometry than the second fiducial marker, second sub-array of fiducial markers or second array of fiducial markers,
    wherein a disk, shield or barrier is positioned between the first fiducial marker and the second fiducial marker, or between at least a portion of the first sub-array of fiducial markers or first array of fiducial markers and at least a portion of the second sub-array of fiducial markers or second array of fiducial markers, wherein the system is configured to track the first fiducial marker, first sub-array of fiducial markers or first array of fiducial markers within a first movement range of the head mounted display with the at least one camera and to track an anatomic structure of the patient with the at least one camera, wherein the system is configured to track the second fiducial marker, second sub-array of fiducial markers or second array of fiducial markers within a second movement range of the head mounted display with the at least one camera and to track the anatomic structure of the patient with the at least one camera, wherein the disk, shield or barrier is configured to occlude a line of sight between the at least one camera and the first fiducial marker, first sub-array of fiducial markers or first array of fiducial markers within the second movement range of the head mounted display or to occlude a line of sight between the at least one camera and the second fiducial marker, second sub-array of fiducial markers or second array of fiducial markers within the first movement range of the head mounted display, wherein the system is configured to generate a stereoscopic display, by the optical head mounted display, of a virtual surgical guide displayed in relationship to the tracked anatomic structure, wherein the system is configured to adjust in real time the stereoscopic display of the virtual surgical guide responsive to (i) tracking data of the tracked first fiducial marker, first sub-array of fiducial markers or first array of fiducial markers acquired within the first movement range and of the tracked anatomic structure, and (ii) responsive to the tracking data of the tracked second fiducial marker, second sub-array of fiducial markers or second array of fiducial markers within the second movement range and of the tracked anatomic structure, and wherein the first movement range and the second movement range are different.

2. The system of claim 1, wherein the first tracked movement range and the second tracked movement range determine a tracked composite movement range of the head mounted display, wherein the tracked composite movement range is greater than the first movement range or the second movement range.

3. The system of claim 1, wherein the first fiducial marker, first sub-array or first array has a first dimension, shape, geometric pattern or combination thereof, wherein the second fiducial marker, second sub-array or second array has a second dimension, shape, geometric pattern or combination thereof, and wherein the first dimension, shape, geometric pattern or combination thereof is different from the second dimension, shape, geometric pattern or combination thereof.

4. The system of claim 3, wherein the system is configured to recognize the first dimension, shape, geometric pattern or combination thereof and track it as part of the first fiducial marker, first sub-array of fiducial markers or first array of fiducial markers, wherein the system is configured to recognize the second dimension, shape, geometric pattern or combination thereof and track it as part of the second fiducial marker, second sub-array of fiducial markers or second array of fiducial markers.

5. The system of claim 1, wherein the first movement range is overlapping with the second movement range.

6. The system of claim 1, wherein the first movement range and the second movement range are not overlapping.

7. The system of claim 1, wherein the movement of the head mounted display comprises a movement in x direction, y direction, z direction, a rotation, or a combination thereof.

8. The system of claim 1, wherein the first movement range of the first fiducial marker, first sub-array or first array is different from the second movement range of the second fiducial marker, second sub-array or second array in at least a x direction, a y direction, a z direction, a rotation, or a combination thereof.

9. The system of claim 1, wherein the first movement range comprises a range of −110 to +110 degrees, or value or range therebetween in up or down, left or right, or a combination thereof of the head mounted display in relationship to an initial or a predetermined viewing direction of the head mounted display or in relationship to a neutral position of a surgeon's head or neck, a predetermined position of the surgeon's head or neck, the anatomic structure of the patient, a fiducial marker attached to the patient, a sub-array of fiducial markers attached to the patient, an array of fiducial makers attached to the patient, an operating room (OR) table, a fixed structure in an operating room, the at least one camera, or a combination thereof, or wherein the first movement range comprises a range of −600 to +600 mm, or value or range therebetween in up or down, left or right, or a combination thereof of the head mounted display in relationship to an initial or a predetermined viewing direction of the head mounted display or in relationship to a neutral position of the surgeon's head or neck, a predetermined position of the surgeon's head or neck, the anatomic structure of the patient, a fiducial marker attached to the patient, a sub-array of fiducial markers attached to the patient, an array of fiducial makers attached to the patient, an OR table, a fixed structure in the operating room, the at least one camera, or a combination thereof; and wherein the second movement range comprises a range of −110 to +110 degrees, or value or range therebetween in up or down, left or right, or a combination thereof of the head mounted display in relationship to an initial or a predetermined viewing direction of the head mounted display or in relationship to a neutral position of the surgeon's head or neck, a predetermined position of the surgeon's head or neck, the anatomic structure of the patient, a fiducial marker attached to the patient, a sub-array of fiducial markers attached to the patient, an array of fiducial makers attached to the patient, an OR table, a fixed structure in the operating room, the at least one camera, or a combination thereof, or wherein the second movement range comprises a range of −600 to +600 mm, or value or range therebetween in up or down, left or right, or a combination thereof of the head mounted display in relationship to an initial or a predetermined viewing direction of the head mounted display or in relationship to a neutral position of the surgeon's head or neck, a predetermined position of the surgeon's head or neck, the anatomic structure of the patient, a fiducial marker attached to the patient, a sub-array of fiducial markers attached to the patient, an array of fiducial makers attached to the patient, an OR table, a fixed structure in the operating room, the at least one camera, or a combination thereof.

10. The system of claim 1, wherein the at least one camera is configured to detect visible light, infrared light, or visible light and infrared light.

11. The system of claim 1, wherein the at least one camera is part of a surgical navigation system, or wherein the at least one camera is part of a surgical robot, or wherein the at least one camera is part of a surgical navigation system and a surgical robot.

12. The system of claim 1, wherein the at least one camera is integrated or attached to the head mounted display, or wherein the at least one camera is separate from the head mounted display.

13. The system of claim 1, wherein (i) the at least one camera is integrated or attached to a first head mounted display, and wherein the at least one camera is configured to track the first fiducial marker, first sub-array of fiducial markers or first array of fiducial markers, or (ii) wherein the at least one camera is configured to track the second fiducial marker, second sub-array of fiducial markers or second array of fiducial markers, or (iii) wherein the at least one camera is configured to track the first fiducial marker, first sub-array of fiducial markers or first array of fiducial markers and wherein the at least one camera is configured to track the second fiducial marker, second sub-array of fiducial markers or second array of fiducial markers, or (iv) wherein the at least one camera is external to the optical head mounted display.

14. The system of claim 1, wherein the first fiducial marker, the second fiducial marker, or the first fiducial marker and the second fiducial marker comprise at least one optical marker, geometric pattern, bar code, QR code, retroreflective marker, active marker, passive marker, RF marker, infrared marker, LED or a combination thereof.

15. The system of claim 1, wherein the virtual surgical guide comprises a virtual axis, a virtual plane, a three-dimensional digital representation of at least a portion of a tool, an instrument and/or a device, a graphical representation comprising positional and/or angular targeting information for a tool, an instrument, and/or a device, or a combination thereof.

16. The system of claim 1, wherein the system is configured to adjust in real time the stereoscopic display responsive to movement of the head mounted display within the first and second movement ranges and movement of the patient, or wherein the system is configured to adjust in real time the stereoscopic display responsive to movement of the head mounted display within the first and second movement ranges and movement of the anatomic structure of the patient.

17. The system of claim 1, wherein the system is configured to track the anatomic structure of the patient using the at least one camera, 3D scanner, or combination thereof.

18. The system of claim 17, wherein the at least one camera, 3D scanner, or combination thereof is configured to track an optical marker, geometric pattern, bar code, QR code, retroreflective marker, active marker, passive marker, RF marker, infrared marker, LED or a combination thereof.

19. The system of claim 1, wherein the first fiducial marker, first sub-array of fiducial markers or first array of fiducial markers and the second fiducial marker, second sub-array of fiducial markers or second array of fiducial markers are attached to or integrated into the outside surface of the head mounted display.

20. The system of claim 1, wherein the virtual surgical guide is a virtual display of at least a portion of a physical tool, physical instrument, physical guide, physical implant, physical device, 3D model of at least one anatomic structure or combination thereof, displayed by the head mounted display.

\* \* \* \* \*